United States Patent [19]
Qiu et al.

[11] Patent Number: 6,037,117
[45] Date of Patent: Mar. 14, 2000

[54] **METHODS USING THE *STAPHYLOCOCCUS AUREUS* GLYCYL TRNA SYNTHETASE CRYSTALLINE STRUCTURE**

[75] Inventors: Xiayang Qiu, Audubon, Pa.; Neal Frederick Osborne, Rusper; Christine Mary Richardson, Buntingford, both of United Kingdom; Cheryl A. Janson, Bryn Mawr, Pa.

[73] Assignees: Smithkline Beecham Corporation, Philadelphia, Pa.; Smithkline Beecham plc, Middlesex, United Kingdom

[21] Appl. No.: 08/792,295

[22] Filed: Jan. 31, 1997

[51] Int. Cl.[7] .............................. C12Q 1/70; C12N 9/00; A61K 38/00
[52] U.S. Cl. ................. 435/4; 435/183; 514/12; 702/19; 702/22
[58] Field of Search .......................... 435/4, 183; 514/12; 702/19, 22

[56] References Cited

PUBLICATIONS

Niyomporn, et al., "Biosynthesis of the Peptidoglycan of Bacterial Cell Walls", *J. Biol. Chem.*, vol. 243, No. 4, pp. 773–778, (1968).

Niyomporn, et al., "Glycyl–tRNA Synthetase (*Staphylococcus aureus*)", *Meth. Enzymol.*, vol. 17, pp. 966–970, (1971).

Belrhali, et al., "Crystal Structures at 2.5 Angstrom Resolution of Seryl–tRNA Synthetase Complexed with two Analogs of Seryl Adenylate", *Science*, vol. 263(5152), pp. 1432–1436, (1994).

Ueda, et al., "X–ray Crystallographic Conformational Study of 5'–O–[N–(L–alanyl)–sulfamoyl]adenosine, A Substrate Analog for Alanyl–tRNA Synthetase.", *Biochim. Biophys. Acta*, vol. 1080(2), pp. 126–134, (1991).

Logan, et al., "Crystal Structure of Glycyl–tRNA Synthetase from Thermus Thermophilus", *EMBO J.*, vol. 17(17), pp. 4156–4167, (1995).

*Primary Examiner*—Lisa J. Hobbs
*Attorney, Agent, or Firm*—Edward R. Gimmi; William T. King; Charles M. Kinzig

[57] ABSTRACT

A novel Staphylococcus glycyl tRNA synthetase crystalline structure is identified. Also disclosed are methods of identifying inhibitors of these synthetases and/or active sites, and inhibitors identified by these methods.

3 Claims, 135 Drawing Sheets

FIGURE 1A

CRYST1  81.490  123.070  127.480  90.00  90.00  90.00 P212121

| Atom | | Residue AA | No. | X | Y | Z |
|---|---|---|---|---|---|---|
| ATOM | 1 CB | MET | 1 | 26.350 | -12.380 | 34.911 |
| ATOM | 2 CG | MET | 1 | 24.811 | -12.477 | 34.478 |
| ATOM | 3 SD | MET | 1 | 23.347 | -11.804 | 35.520 |
| ATOM | 4 CE | MET | 1 | 21.876 | -12.705 | 34.649 |
| ATOM | 5 C | MET | 1 | 26.118 | -14.451 | 36.395 |
| ATOM | 6 O | MET | 1 | 26.546 | -15.494 | 35.876 |
| ATOM | 7 N | MET | 1 | 28.315 | -13.256 | 36.258 |
| ATOM | 8 CA | MET | 1 | 26.817 | -13.111 | 36.214 |
| ATOM | 9 N | ALA | 2 | 25.034 | -14.389 | 37.149 |
| ATOM | 10 CA | ALA | 2 | 24.247 | -15.561 | 37.439 |
| ATOM | 11 CB | ALA | 2 | 23.187 | -15.245 | 38.486 |
| ATOM | 12 C | ALA | 2 | 23.607 | -16.202 | 36.224 |
| ATOM | 13 O | ALA | 2 | 22.791 | -15.594 | 35.498 |
| ATOM | 14 N | LYS | 3 | 24.002 | -17.452 | 36.030 |
| ATOM | 15 CA | LYS | 3 | 23.489 | -18.270 | 34.951 |
| ATOM | 16 CB | LYS | 3 | 24.354 | -19.536 | 34.808 |
| ATOM | 17 CG | LYS | 3 | 25.391 | -19.766 | 35.943 |
| ATOM | 18 CD | LYS | 3 | 24.770 | -20.353 | 37.203 |
| ATOM | 19 CE | LYS | 3 | 24.117 | -21.724 | 36.938 |
| ATOM | 20 NZ | LYS | 3 | 25.025 | -22.916 | 36.909 |
| ATOM | 21 C | LYS | 3 | 22.027 | -18.617 | 35.291 |
| ATOM | 22 O | LYS | 3 | 21.081 | -17.944 | 34.832 |
| ATOM | 23 N | ASP | 4 | 21.862 | -19.612 | 36.159 |
| ATOM | 24 CA | ASP | 4 | 20.556 | -20.075 | 36.589 |
| ATOM | 25 CB | ASP | 4 | 20.728 | -21.507 | 37.118 |
| ATOM | 26 CG | ASP | 4 | 19.521 | -22.413 | 36.846 |
| ATOM | 27 OD1 | ASP | 4 | 18.386 | -21.911 | 36.666 |
| ATOM | 28 OD2 | ASP | 4 | 19.699 | -23.658 | 36.831 |
| ATOM | 29 C | ASP | 4 | 20.101 | -19.140 | 37.713 |
| ATOM | 30 O | ASP | 4 | 20.924 | -18.423 | 38.267 |
| ATOM | 31 N | MET | 5 | 18.796 | -19.036 | 37.961 |
| ATOM | 32 CA | MET | 5 | 18.316 | -18.246 | 39.102 |
| ATOM | 33 CB | MET | 5 | 16.894 | -17.692 | 38.923 |
| ATOM | 34 CG | MET | 5 | 16.331 | -16.937 | 40.192 |
| ATOM | 35 SD | MET | 5 | 16.671 | -15.076 | 40.424 |
| ATOM | 36 CE | MET | 5 | 18.427 | -15.020 | 40.792 |
| ATOM | 37 C | MET | 5 | 18.299 | -19.266 | 40.229 |
| ATOM | 38 O | MET | 5 | 18.686 | -18.964 | 41.342 |
| ATOM | 39 N | ASP | 6 | 17.901 | -20.494 | 39.898 |
| ATOM | 40 CA | ASP | 6 | 17.840 | -21.624 | 40.845 |
| ATOM | 41 CB | ASP | 6 | 17.325 | -22.908 | 40.162 |
| ATOM | 42 CG | ASP | 6 | 15.983 | -22.708 | 39.428 |
| ATOM | 43 OD1 | ASP | 6 | 15.734 | -23.447 | 38.440 |
| ATOM | 44 OD2 | ASP | 6 | 15.179 | -21.822 | 39.825 |
| ATOM | 45 C | ASP | 6 | 19.188 | -21.939 | 41.477 |
| ATOM | 46 O | ASP | 6 | 19.256 | -22.359 | 42.619 |

FIGURE 1B

|  | Atom | Residue AA | No. | X | Y | Z |
|---|---|---|---|---|---|---|
| ATOM | 47 N | THR | 7 | 20.260 | -21.803 | 40.714 |
| ATOM | 48 CA | THR | 7 | 21.565 | -22.060 | 41.269 |
| ATOM | 49 CB | THR | 7 | 22.663 | -21.995 | 40.227 |
| ATOM | 50 OG1 | THR | 7 | 22.642 | -23.198 | 39.458 |
| ATOM | 51 CG2 | THR | 7 | 24.019 | -21.856 | 40.870 |
| ATOM | 52 C | THR | 7 | 21.798 | -20.993 | 42.295 |
| ATOM | 53 O | THR | 7 | 22.185 | -21.299 | 43.413 |
| ATOM | 54 N | ILE | 8 | 21.500 | -19.749 | 41.943 |
| ATOM | 55 CA | ILE | 8 | 21.696 | -18.639 | 42.866 |
| ATOM | 56 CB | ILE | 8 | 21.549 | -17.273 | 42.140 |
| ATOM | 57 CG2 | ILE | 8 | 20.921 | -16.219 | 43.062 |
| ATOM | 58 CG1 | ILE | 8 | 22.919 | -16.817 | 41.620 |
| ATOM | 59 CD1 | ILE | 8 | 23.573 | -17.809 | 40.738 |
| ATOM | 60 C | ILE | 8 | 20.885 | -18.713 | 44.177 |
| ATOM | 61 O | ILE | 8 | 21.457 | -18.595 | 45.248 |
| ATOM | 62 N | VAL | 9 | 19.573 | -18.904 | 44.112 |
| ATOM | 63 CA | VAL | 9 | 18.793 | -19.020 | 45.334 |
| ATOM | 64 CB | VAL | 9 | 17.321 | -19.355 | 45.049 |
| ATOM | 65 CG1 | VAL | 9 | 16.688 | -20.054 | 46.220 |
| ATOM | 66 CG2 | VAL | 9 | 16.570 | -18.094 | 44.777 |
| ATOM | 67 C | VAL | 9 | 19.418 | -20.121 | 46.179 |
| ATOM | 68 O | VAL | 9 | 19.635 | -19.953 | 47.371 |
| ATOM | 69 N | SER | 10 | 19.786 | -21.217 | 45.543 |
| ATOM | 70 CA | SER | 10 | 20.378 | -22.318 | 46.263 |
| ATOM | 71 CB | SER | 10 | 20.691 | -23.455 | 45.305 |
| ATOM | 72 OG | SER | 10 | 21.227 | -24.561 | 46.002 |
| ATOM | 73 C | SER | 10 | 21.625 | -21.906 | 47.035 |
| ATOM | 74 O | SER | 10 | 21.703 | -22.107 | 48.245 |
| ATOM | 75 N | LEU | 11 | 22.609 | -21.335 | 46.358 |
| ATOM | 76 CA | LEU | 11 | 23.799 | -20.914 | 47.068 |
| ATOM | 77 CB | LEU | 11 | 24.862 | -20.386 | 46.126 |
| ATOM | 78 CG | LEU | 11 | 26.081 | -19.873 | 46.870 |
| ATOM | 79 CD1 | LEU | 11 | 27.237 | -20.847 | 46.751 |
| ATOM | 80 CD2 | LEU | 11 | 26.450 | -18.536 | 46.332 |
| ATOM | 81 C | LEU | 11 | 23.426 | -19.840 | 48.083 |
| ATOM | 82 O | LEU | 11 | 24.173 | -19.592 | 49.001 |
| ATOM | 83 N | ALA | 12 | 22.276 | -19.193 | 47.936 |
| ATOM | 84 CA | ALA | 12 | 21.890 | -18.190 | 48.913 |
| ATOM | 85 CB | ALA | 12 | 20.821 | -17.273 | 48.373 |
| ATOM | 86 C | ALA | 12 | 21.402 | -18.919 | 50.152 |
| ATOM | 87 O | ALA | 12 | 22.089 | -18.916 | 51.172 |
| ATOM | 88 N | LYS | 13 | 20.255 | -19.587 | 50.054 |
| ATOM | 89 CA | LYS | 13 | 19.678 | -20.322 | 51.175 |
| ATOM | 90 CB | LYS | 13 | 18.550 | -21.230 | 50.674 |
| ATOM | 91 CG | LYS | 13 | 18.195 | -22.440 | 51.579 |
| ATOM | 92 CD | LYS | 13 | 17.663 | -22.031 | 53.001 |
| ATOM | 93 CE | LYS | 13 | 17.204 | -23.232 | 53.925 |
| ATOM | 94 NZ | LYS | 13 | 16.360 | -22.851 | 55.146 |

FIGURE 1C

|  | Atom | Residue AA | No. | X | Y | Z |
|---|---|---|---|---|---|---|
| ATOM | 95 C | LYS | 13 | 20.715 | -21.120 | 51.948 |
| ATOM | 96 O | LYS | 13 | 21.181 | -20.719 | 52.994 |
| ATOM | 97 N | HIS | 14 | 21.156 | -22.208 | 51.375 |
| ATOM | 98 CA | HIS | 14 | 22.114 | -23.042 | 52.041 |
| ATOM | 99 CB | HIS | 14 | 22.538 | -24.157 | 51.100 |
| ATOM | 100 CG | HIS | 14 | 23.990 | -24.505 | 51.204 |
| ATOM | 101 CD2 | HIS | 14 | 24.619 | -25.594 | 51.705 |
| ATOM | 102 ND1 | HIS | 14 | 24.984 | -23.651 | 50.775 |
| ATOM | 103 CE1 | HIS | 14 | 26.164 | -24.200 | 51.002 |
| ATOM | 104 NE2 | HIS | 14 | 25.969 | -25.380 | 51.567 |
| ATOM | 105 C | HIS | 14 | 23.365 | -22.400 | 52.607 |
| ATOM | 106 O | HIS | 14 | 23.961 | -22.940 | 53.523 |
| ATOM | 107 N | ARG | 15 | 23.847 | -21.332 | 52.001 |
| ATOM | 108 CA | ARG | 15 | 25.083 | -20.732 | 52.476 |
| ATOM | 109 CB | ARG | 15 | 25.868 | -20.210 | 51.281 |
| ATOM | 110 CG | ARG | 15 | 27.246 | -19.755 | 51.556 |
| ATOM | 111 CD | ARG | 15 | 27.815 | -20.598 | 52.606 |
| ATOM | 112 NE | ARG | 15 | 27.934 | -21.979 | 52.186 |
| ATOM | 113 CZ | ARG | 15 | 29.072 | -22.505 | 51.742 |
| ATOM | 114 NH1 | ARG | 15 | 30.158 | -21.736 | 51.650 |
| ATOM | 115 NH2 | ARG | 15 | 29.167 | -23.814 | 51.509 |
| ATOM | 116 C | ARG | 15 | 24.864 | -19.672 | 53.550 |
| ATOM | 117 O | ARG | 15 | 25.800 | -19.110 | 54.107 |
| ATOM | 118 N | GLY | 16 | 23.612 | -19.457 | 53.892 |
| ATOM | 119 CA | GLY | 16 | 23.331 | -18.494 | 54.914 |
| ATOM | 120 C | GLY | 16 | 23.402 | -17.119 | 54.343 |
| ATOM | 121 O | GLY | 16 | 24.202 | -16.306 | 54.757 |
| ATOM | 122 N | PHE | 17 | 22.609 | -16.881 | 53.322 |
| ATOM | 123 CA | PHE | 17 | 22.555 | -15.568 | 52.729 |
| ATOM | 124 CB | PHE | 17 | 22.958 | -15.571 | 51.247 |
| ATOM | 125 CG | PHE | 17 | 24.379 | -15.114 | 50.971 |
| ATOM | 126 CD1 | PHE | 17 | 25.416 | -16.024 | 50.928 |
| ATOM | 127 CD2 | PHE | 17 | 24.648 | -13.801 | 50.639 |
| ATOM | 128 CE1 | PHE | 17 | 26.686 | -15.638 | 50.549 |
| ATOM | 129 CE2 | PHE | 17 | 25.916 | -13.410 | 50.259 |
| ATOM | 130 CZ | PHE | 17 | 26.932 | -14.330 | 50.213 |
| ATOM | 131 C | PHE | 17 | 21.106 | -15.210 | 52.888 |
| ATOM | 132 O | PHE | 17 | 20.815 | -14.133 | 53.325 |
| ATOM | 133 N | VAL | 18 | 20.193 | -16.121 | 52.573 |
| ATOM | 134 CA | VAL | 18 | 18.759 | -15.853 | 52.719 |
| ATOM | 135 CB | VAL | 18 | 18.139 | -15.144 | 51.447 |
| ATOM | 136 CG1 | VAL | 18 | 16.727 | -14.687 | 51.706 |
| ATOM | 137 CG2 | VAL | 18 | 18.922 | -13.930 | 51.076 |
| ATOM | 138 C | VAL | 18 | 18.031 | -17.178 | 52.993 |
| ATOM | 139 O | VAL | 18 | 18.306 | -18.173 | 52.333 |
| ATOM | 140 N | PHE | 19 | 17.178 | -17.201 | 54.019 |
| ATOM | 141 CA | PHE | 19 | 16.400 | -18.381 | 54.385 |
| ATOM | 142 CB | PHE | 19 | 16.522 | -18.726 | 55.874 |

FIGURE 1D

| Atom | | Residue AA | No. | X | Y | Z |
|---|---|---|---|---|---|---|
| ATOM | 143 | CG | PHE | 19 | 17.925 | -18.879 | 56.371 |
| ATOM | 144 | CD1 | PHE | 19 | 18.727 | -19.903 | 55.905 |
| ATOM | 145 | CD2 | PHE | 19 | 18.454 | -17.987 | 57.313 |
| ATOM | 146 | CE1 | PHE | 19 | 20.044 | -20.036 | 56.370 |
| ATOM | 147 | CE2 | PHE | 19 | 19.769 | -18.112 | 57.780 |
| ATOM | 148 | CZ | PHE | 19 | 20.560 | -19.126 | 57.314 |
| ATOM | 149 | C | PHE | 19 | 14.963 | -17.980 | 54.166 |
| ATOM | 150 | O | PHE | 19 | 14.613 | -16.820 | 54.312 |
| ATOM | 151 | N | PRO | 20 | 14.096 | -18.933 | 53.854 |
| ATOM | 152 | CD | PRO | 20 | 14.351 | -20.360 | 53.647 |
| ATOM | 153 | CA | PRO | 20 | 12.688 | -18.616 | 53.636 |
| ATOM | 154 | CB | PRO | 20 | 12.157 | -19.884 | 52.993 |
| ATOM | 155 | CG | PRO | 20 | 12.966 | -20.921 | 53.627 |
| ATOM | 156 | C | PRO | 20 | 11.945 | -18.286 | 54.946 |
| ATOM | 157 | O | PRO | 20 | 12.056 | -19.012 | 55.967 |
| ATOM | 158 | N | GLY | 21 | 11.173 | -17.195 | 54.901 |
| ATOM | 159 | CA | GLY | 21 | 10.395 | -16.728 | 56.054 |
| ATOM | 160 | C | GLY | 21 | 9.426 | -17.743 | 56.632 |
| ATOM | 161 | O | GLY | 21 | 8.875 | -18.560 | 55.891 |
| ATOM | 162 | N | SER | 22 | 9.212 | -17.681 | 57.949 |
| ATOM | 163 | CA | SER | 22 | 8.332 | -18.625 | 58.653 |
| ATOM | 164 | CB | SER | 22 | 6.865 | -18.230 | 58.524 |
| ATOM | 165 | OG | SER | 22 | 6.634 | -16.942 | 59.028 |
| ATOM | 166 | C | SER | 22 | 8.515 | -20.037 | 58.103 |
| ATOM | 167 | O | SER | 22 | 7.577 | -20.839 | 58.134 |
| ATOM | 168 | N | ASP | 23 | 9.735 | -20.343 | 57.662 |
| ATOM | 169 | CA | ASP | 23 | 10.027 | -21.631 | 57.086 |
| ATOM | 170 | CB | ASP | 23 | 11.538 | -21.811 | 56.903 |
| ATOM | 171 | CG | ASP | 23 | 11.894 | -23.096 | 56.102 |
| ATOM | 172 | OD1 | ASP | 23 | 10.954 | -23.716 | 55.556 |
| ATOM | 173 | OD2 | ASP | 23 | 13.097 | -23.487 | 56.015 |
| ATOM | 174 | C | ASP | 23 | 9.439 | -22.821 | 57.836 |
| ATOM | 175 | O | ASP | 23 | 8.398 | -23.314 | 57.460 |
| ATOM | 176 | N | ILE | 24 | 10.081 | -23.229 | 58.929 |
| ATOM | 177 | CA | ILE | 24 | 9.682 | -24.396 | 59.735 |
| ATOM | 178 | CB | ILE | 24 | 10.444 | -24.472 | 61.115 |
| ATOM | 179 | CG2 | ILE | 24 | 11.963 | -24.390 | 60.922 |
| ATOM | 180 | CG1 | ILE | 24 | 9.990 | -23.347 | 62.047 |
| ATOM | 181 | CD1 | ILE | 24 | 10.372 | -23.563 | 63.462 |
| ATOM | 182 | C | ILE | 24 | 8.190 | -24.610 | 60.006 |
| ATOM | 183 | O | ILE | 24 | 7.766 | -25.743 | 60.221 |
| ATOM | 184 | N | TYR | 25 | 7.402 | -23.544 | 60.068 |
| ATOM | 185 | CA | TYR | 25 | 5.981 | -23.714 | 60.301 |
| ATOM | 186 | CB | TYR | 25 | 5.379 | -22.480 | 60.949 |
| ATOM | 187 | CG | TYR | 25 | 5.544 | -22.499 | 62.434 |
| ATOM | 188 | CD1 | TYR | 25 | 6.799 | -22.700 | 63.006 |
| ATOM | 189 | CE1 | TYR | 25 | 6.962 | -22.794 | 64.391 |
| ATOM | 190 | CD2 | TYR | 25 | 4.445 | -22.380 | 63.281 |

FIGURE 1E

| Atom | | Residue AA | No. | X | Y | Z |
|---|---|---|---|---|---|---|
| ATOM | 191 CE2 | TYR | 25 | 4.600 | -22.471 | 64.691 |
| ATOM | 192 CZ | TYR | 25 | 5.864 | -22.686 | 65.232 |
| ATOM | 193 OH | TYR | 25 | 6.045 | -22.851 | 66.582 |
| ATOM | 194 C | TYR | 25 | 5.299 | -24.014 | 58.984 |
| ATOM | 195 O | TYR | 25 | 4.448 | -24.900 | 58.901 |
| ATOM | 196 N | GLY | 26 | 5.716 | -23.307 | 57.940 |
| ATOM | 197 CA | GLY | 26 | 5.140 | -23.506 | 56.623 |
| ATOM | 198 C | GLY | 26 | 5.567 | -22.393 | 55.691 |
| ATOM | 199 O | GLY | 26 | 5.667 | -22.592 | 54.484 |
| ATOM | 200 N | GLY | 27 | 5.830 | -21.219 | 56.250 |
| ATOM | 201 CA | GLY | 27 | 6.234 | -20.099 | 55.426 |
| ATOM | 202 C | GLY | 27 | 5.149 | -19.048 | 55.222 |
| ATOM | 203 O | GLY | 27 | 4.103 | -19.032 | 55.904 |
| ATOM | 204 N | LEU | 28 | 5.440 | -18.122 | 54.318 |
| ATOM | 205 CA | LEU | 28 | 4.527 | -17.049 | 54.000 |
| ATOM | 206 CB | LEU | 28 | 4.649 | -15.907 | 54.997 |
| ATOM | 207 CG | LEU | 28 | 3.573 | -14.853 | 54.798 |
| ATOM | 208 CD1 | LEU | 28 | 2.225 | -15.479 | 55.117 |
| ATOM | 209 CD2 | LEU | 28 | 3.825 | -13.645 | 55.672 |
| ATOM | 210 C | LEU | 28 | 4.941 | -16.566 | 52.637 |
| ATOM | 211 O | LEU | 28 | 6.138 | -16.434 | 52.352 |
| ATOM | 212 N | SER | 29 | 3.943 | -16.336 | 51.791 |
| ATOM | 213 CA | SER | 29 | 4.132 | -15.884 | 50.419 |
| ATOM | 214 CB | SER | 29 | 2.822 | -15.310 | 49.884 |
| ATOM | 215 OG | SER | 29 | 2.174 | -14.539 | 50.873 |
| ATOM | 216 C | SER | 29 | 5.260 | -14.893 | 50.195 |
| ATOM | 217 O | SER | 29 | 5.212 | -13.759 | 50.697 |
| ATOM | 218 N | ASN | 30 | 6.278 | -15.374 | 49.472 |
| ATOM | 219 CA | ASN | 30 | 7.472 | -14.608 | 49.084 |
| ATOM | 220 CB | ASN | 30 | 7.240 | -13.845 | 47.764 |
| ATOM | 221 CG | ASN | 30 | 8.408 | -13.978 | 46.762 |
| ATOM | 222 OD1 | ASN | 30 | 9.582 | -13.744 | 47.077 |
| ATOM | 223 ND2 | ASN | 30 | 8.068 | -14.354 | 45.544 |
| ATOM | 224 C | ASN | 30 | 7.885 | -13.610 | 50.141 |
| ATOM | 225 O | ASN | 30 | 7.792 | -12.382 | 49.935 |
| ATOM | 226 N | THR | 31 | 8.282 | -14.138 | 51.289 |
| ATOM | 227 CA | THR | 31 | 8.724 | -13.305 | 52.397 |
| ATOM | 228 CB | THR | 31 | 7.581 | -13.166 | 53.499 |
| ATOM | 229 OG1 | THR | 31 | 6.866 | -14.407 | 53.620 |
| ATOM | 230 CG2 | THR | 31 | 6.546 | -12.046 | 53.105 |
| ATOM | 231 C | THR | 31 | 10.004 | -14.010 | 52.837 |
| ATOM | 232 O | THR | 31 | 10.014 | -15.229 | 52.967 |
| ATOM | 233 N | TRP | 32 | 11.100 | -13.261 | 52.941 |
| ATOM | 234 CA | TRP | 32 | 12.420 | -13.826 | 53.260 |
| ATOM | 235 CB | TRP | 32 | 13.374 | -13.621 | 52.049 |
| ATOM | 236 CG | TRP | 32 | 12.858 | -14.222 | 50.781 |
| ATOM | 237 CD2 | TRP | 32 | 13.242 | -15.480 | 50.224 |
| ATOM | 238 CE2 | TRP | 32 | 12.297 | -15.808 | 49.244 |

FIGURE 1F

|  |  | Residue |  |  |  |  |
|---|---|---|---|---|---|---|
| Atom |  | AA | No. | X | Y | Z |
| ATOM | 239 CE3 | TRP | 32 | 14.284 | -16.378 | 50.480 |
| ATOM | 240 CD1 | TRP | 32 | 11.758 | -13.824 | 50.089 |
| ATOM | 241 NE1 | TRP | 32 | 11.403 | -14.776 | 49.178 |
| ATOM | 242 CZ2 | TRP | 32 | 12.353 | -16.998 | 48.526 |
| ATOM | 243 CZ3 | TRP | 32 | 14.342 | -17.564 | 49.763 |
| ATOM | 244 CH2 | TRP | 32 | 13.382 | -17.862 | 48.802 |
| ATOM | 245 C | TRP | 32 | 13.129 | -13.325 | 54.514 |
| ATOM | 246 O | TRP | 32 | 13.014 | -12.162 | 54.909 |
| ATOM | 247 N | ASP | 33 | 13.896 | -14.212 | 55.120 |
| ATOM | 248 CA | ASP | 33 | 14.655 | -13.846 | 56.294 |
| ATOM | 249 CB | ASP | 33 | 14.490 | -14.902 | 57.419 |
| ATOM | 250 CG | ASP | 33 | 13.100 | -14.879 | 58.095 |
| ATOM | 251 OD1 | ASP | 33 | 12.677 | -15.927 | 58.596 |
| ATOM | 252 OD2 | ASP | 33 | 12.426 | -13.841 | 58.177 |
| ATOM | 253 C | ASP | 33 | 16.115 | -13.759 | 55.833 |
| ATOM | 254 O | ASP | 33 | 16.592 | -14.639 | 55.129 |
| ATOM | 255 N | TYR | 34 | 16.779 | -12.653 | 56.134 |
| ATOM | 256 CA | TYR | 34 | 18.173 | -12.491 | 55.782 |
| ATOM | 257 CB | TYR | 34 | 18.556 | -11.025 | 55.693 |
| ATOM | 258 CG | TYR | 34 | 18.090 | -10.383 | 54.406 |
| ATOM | 259 CD1 | TYR | 34 | 16.730 | -10.343 | 54.078 |
| ATOM | 260 CE1 | TYR | 34 | 16.298 | -9.794 | 52.868 |
| ATOM | 261 CD2 | TYR | 34 | 19.008 | -9.852 | 53.488 |
| ATOM | 262 CE2 | TYR | 34 | 18.581 | -9.306 | 52.274 |
| ATOM | 263 CZ | TYR | 34 | 17.228 | -9.283 | 51.973 |
| ATOM | 264 OH | TYR | 34 | 16.793 | -8.777 | 50.771 |
| ATOM | 265 C | TYR | 34 | 19.039 | -13.173 | 56.799 |
| ATOM | 266 O | TYR | 34 | 19.142 | -12.739 | 57.906 |
| ATOM | 267 N | GLY | 35 | 19.663 | -14.257 | 56.397 |
| ATOM | 268 CA | GLY | 35 | 20.514 | -15.015 | 57.277 |
| ATOM | 269 C | GLY | 35 | 21.759 | -14.243 | 57.594 |
| ATOM | 270 O | GLY | 35 | 21.944 | -13.150 | 57.080 |
| ATOM | 271 N | PRO | 36 | 22.679 | -14.857 | 58.352 |
| ATOM | 272 CD | PRO | 36 | 22.544 | -16.305 | 58.584 |
| ATOM | 273 CA | PRO | 36 | 23.979 | -14.389 | 58.847 |
| ATOM | 274 CB | PRO | 36 | 24.696 | -15.686 | 59.173 |
| ATOM | 275 CG | PRO | 36 | 23.589 | -16.541 | 59.627 |
| ATOM | 276 C | PRO | 36 | 24.776 | -13.572 | 57.858 |
| ATOM | 277 O | PRO | 36 | 25.316 | -12.515 | 58.190 |
| ATOM | 278 N | LEU | 37 | 24.885 | -14.088 | 56.645 |
| ATOM | 279 CA | LEU | 37 | 25.609 | -13.401 | 55.612 |
| ATOM | 280 CB | LEU | 37 | 26.161 | -14.416 | 54.643 |
| ATOM | 281 CG | LEU | 37 | 27.296 | -15.166 | 55.304 |
| ATOM | 282 CD1 | LEU | 37 | 27.910 | -16.256 | 54.414 |
| ATOM | 283 CD2 | LEU | 37 | 28.307 | -14.112 | 55.634 |
| ATOM | 284 C | LEU | 37 | 24.739 | -12.363 | 54.916 |
| ATOM | 285 O | LEU | 37 | 25.207 | -11.263 | 54.611 |
| ATOM | 286 N | GLY | 38 | 23.457 | -12.677 | 54.747 |

FIGURE 1G

|  |  | Residue |  |  |  |  |
|---|---|---|---|---|---|---|
| | Atom | AA | No. | X | Y | Z |
| ATOM | 287 CA | GLY | 38 | 22.541 | -11.756 | 54.096 |
| ATOM | 288 C | GLY | 38 | 22.460 | -10.375 | 54.712 |
| ATOM | 289 O | GLY | 38 | 22.414 | -9.374 | 54.013 |
| ATOM | 290 N | VAL | 39 | 22.384 | -10.317 | 56.030 |
| ATOM | 291 CA | VAL | 39 | 22.326 | -9.038 | 56.717 |
| ATOM | 292 CB | VAL | 39 | 22.351 | -9.176 | 58.228 |
| ATOM | 293 CG1 | VAL | 39 | 20.981 | -9.035 | 58.780 |
| ATOM | 294 CG2 | VAL | 39 | 23.018 | -10.479 | 58.633 |
| ATOM | 295 C | VAL | 39 | 23.542 | -8.214 | 56.389 |
| ATOM | 296 O | VAL | 39 | 23.435 | -7.082 | 55.942 |
| ATOM | 297 N | GLU | 40 | 24.710 | -8.786 | 56.621 |
| ATOM | 298 CA | GLU | 40 | 25.927 | -8.047 | 56.388 |
| ATOM | 299 CB | GLU | 40 | 27.155 | -8.941 | 56.634 |
| ATOM | 300 CG | GLU | 40 | 28.157 | -8.438 | 57.729 |
| ATOM | 301 CD | GLU | 40 | 27.575 | -8.403 | 59.130 |
| ATOM | 302 OE1 | GLU | 40 | 26.981 | -9.419 | 59.589 |
| ATOM | 303 OE2 | GLU | 40 | 27.737 | -7.338 | 59.764 |
| ATOM | 304 C | GLU | 40 | 25.892 | -7.423 | 54.999 |
| ATOM | 305 O | GLU | 40 | 25.870 | -6.199 | 54.882 |
| ATOM | 306 N | LEU | 41 | 25.720 | -8.249 | 53.970 |
| ATOM | 307 CA | LEU | 41 | 25.670 | -7.749 | 52.585 |
| ATOM | 308 CB | LEU | 41 | 25.342 | -8.867 | 51.592 |
| ATOM | 309 CG | LEU | 41 | 25.321 | -8.483 | 50.136 |
| ATOM | 310 CD1 | LEU | 41 | 26.712 | -8.450 | 49.640 |
| ATOM | 311 CD2 | LEU | 41 | 24.549 | -9.491 | 49.384 |
| ATOM | 312 C | LEU | 41 | 24.628 | -6.655 | 52.450 |
| ATOM | 313 O | LEU | 41 | 24.960 | -5.554 | 52.039 |
| ATOM | 314 N | LYS | 42 | 23.391 | -6.931 | 52.863 |
| ATOM | 315 CA | LYS | 42 | 22.329 | -5.948 | 52.751 |
| ATOM | 316 CB | LYS | 42 | 21.015 | -6.493 | 53.267 |
| ATOM | 317 CG | LYS | 42 | 19.843 | -5.583 | 53.001 |
| ATOM | 318 CD | LYS | 42 | 18.600 | -6.227 | 53.529 |
| ATOM | 319 CE | LYS | 42 | 17.370 | -5.407 | 53.309 |
| ATOM | 320 NZ | LYS | 42 | 16.185 | -6.037 | 54.010 |
| ATOM | 321 C | LYS | 42 | 22.690 | -4.693 | 53.491 |
| ATOM | 322 O | LYS | 42 | 22.268 | -3.613 | 53.113 |
| ATOM | 323 N | ASN | 43 | 23.527 | -4.828 | 54.512 |
| ATOM | 324 CA | ASN | 43 | 23.952 | -3.685 | 55.305 |
| ATOM | 325 CB | ASN | 43 | 24.139 | -4.060 | 56.761 |
| ATOM | 326 CG | ASN | 43 | 22.882 | -3.835 | 57.551 |
| ATOM | 327 OD1 | ASN | 43 | 22.251 | -4.778 | 58.037 |
| ATOM | 328 ND2 | ASN | 43 | 22.459 | -2.575 | 57.622 |
| ATOM | 329 C | ASN | 43 | 25.146 | -2.943 | 54.757 |
| ATOM | 330 O | ASN | 43 | 25.280 | -1.745 | 54.992 |
| ATOM | 331 N | ASN | 44 | 26.012 | -3.646 | 54.031 |
| ATOM | 332 CA | ASN | 44 | 27.149 | -3.009 | 53.385 |
| ATOM | 333 CB | ASN | 44 | 28.123 | -4.056 | 52.875 |
| ATOM | 334 CG | ASN | 44 | 28.853 | -4.765 | 53.986 |

FIGURE 1H

|  |  | Residue |  |  |  |  |
|---|---|---|---|---|---|---|
| Atom |  | AA | No. | X | Y | Z |
| ATOM | 335 OD1 | ASN | 44 | 28.318 | -5.648 | 54.638 |
| ATOM | 336 ND2 | ASN | 44 | 30.100 | -4.397 | 54.190 |
| ATOM | 337 C | ASN | 44 | 26.542 | -2.221 | 52.199 |
| ATOM | 338 O | ASN | 44 | 27.041 | -1.173 | 51.797 |
| ATOM | 339 N | VAL | 45 | 25.456 | -2.745 | 51.642 |
| ATOM | 340 CA | VAL | 45 | 24.747 | -2.100 | 50.560 |
| ATOM | 341 CB | VAL | 45 | 23.605 | -2.990 | 50.066 |
| ATOM | 342 CG1 | VAL | 45 | 22.660 | -2.220 | 49.192 |
| ATOM | 343 CG2 | VAL | 45 | 24.144 | -4.142 | 49.325 |
| ATOM | 344 C | VAL | 45 | 24.133 | -0.878 | 51.194 |
| ATOM | 345 O | VAL | 45 | 24.420 | 0.249 | 50.796 |
| ATOM | 346 N | LYS | 46 | 23.368 | -1.138 | 52.260 |
| ATOM | 347 CA | LYS | 46 | 22.631 | -0.137 | 53.038 |
| ATOM | 348 CB | LYS | 46 | 21.782 | -0.828 | 54.104 |
| ATOM | 349 CG | LYS | 46 | 20.396 | -0.228 | 54.280 |
| ATOM | 350 CD | LYS | 46 | 19.305 | -1.261 | 54.686 |
| ATOM | 351 CE | LYS | 46 | 19.424 | -1.791 | 56.132 |
| ATOM | 352 NZ | LYS | 46 | 18.507 | -2.934 | 56.442 |
| ATOM | 353 C | LYS | 46 | 23.476 | 0.956 | 53.668 |
| ATOM | 354 O | LYS | 46 | 22.975 | 2.023 | 53.988 |
| ATOM | 355 N | ALA | 47 | 24.772 | 0.720 | 53.788 |
| ATOM | 356 CA | ALA | 47 | 25.646 | 1.716 | 54.378 |
| ATOM | 357 CB | ALA | 47 | 26.625 | 1.062 | 55.318 |
| ATOM | 358 C | ALA | 47 | 26.382 | 2.562 | 53.375 |
| ATOM | 359 O | ALA | 47 | 26.532 | 3.753 | 53.591 |
| ATOM | 360 N | ALA | 48 | 26.845 | 1.954 | 52.284 |
| ATOM | 361 CA | ALA | 48 | 27.577 | 2.671 | 51.234 |
| ATOM | 362 CB | ALA | 48 | 28.007 | 1.732 | 50.185 |
| ATOM | 363 C | ALA | 48 | 26.686 | 3.723 | 50.643 |
| ATOM | 364 O | ALA | 48 | 27.129 | 4.763 | 50.217 |
| ATOM | 365 N | TRP | 49 | 25.406 | 3.428 | 50.648 |
| ATOM | 366 CA | TRP | 49 | 24.405 | 4.333 | 50.166 |
| ATOM | 367 CB | TRP | 49 | 23.063 | 3.659 | 50.250 |
| ATOM | 368 CG | TRP | 49 | 22.062 | 4.385 | 49.517 |
| ATOM | 369 CD2 | TRP | 49 | 21.258 | 5.458 | 49.997 |
| ATOM | 370 CE2 | TRP | 49 | 20.429 | 5.860 | 48.932 |
| ATOM | 371 CE3 | TRP | 49 | 21.150 | 6.115 | 51.218 |
| ATOM | 372 CD1 | TRP | 49 | 21.710 | 4.185 | 48.228 |
| ATOM | 373 NE1 | TRP | 49 | 20.728 | 5.065 | 47.862 |
| ATOM | 374 CZ2 | TRP | 49 | 19.502 | 6.887 | 49.052 |
| ATOM | 375 CZ3 | TRP | 49 | 20.223 | 7.137 | 51.335 |
| ATOM | 376 CH2 | TRP | 49 | 19.412 | 7.511 | 50.259 |
| ATOM | 377 C | TRP | 49 | 24.368 | 5.564 | 51.036 |
| ATOM | 378 O | TRP | 49 | 24.502 | 6.656 | 50.568 |
| ATOM | 379 N | TRP | 50 | 24.107 | 5.376 | 52.312 |
| ATOM | 380 CA | TRP | 50 | 24.058 | 6.482 | 53.258 |
| ATOM | 381 CB | TRP | 50 | 23.893 | 5.950 | 54.718 |
| ATOM | 382 CG | TRP | 50 | 23.295 | 6.983 | 55.719 |

FIGURE 1I

| Atom | | AA | Residue No. | X | Y | Z |
|---|---|---|---|---|---|---|
| ATOM | 383 CD2 | TRP | 50 | 21.900 | 7.182 | 56.026 |
| ATOM | 384 CE2 | TRP | 50 | 21.798 | 8.374 | 56.766 |
| ATOM | 385 CE3 | TRP | 50 | 20.728 | 6.478 | 55.717 |
| ATOM | 386 CD1 | TRP | 50 | 23.958 | 8.023 | 56.328 |
| ATOM | 387 NE1 | TRP | 50 | 23.062 | 8.864 | 56.944 |
| ATOM | 388 CZ2 | TRP | 50 | 20.584 | 8.878 | 57.186 |
| ATOM | 389 CZ3 | TRP | 50 | 19.523 | 6.981 | 56.133 |
| ATOM | 390 CH2 | TRP | 50 | 19.457 | 8.170 | 56.857 |
| ATOM | 391 C | TRP | 50 | 25.349 | 7.289 | 53.146 |
| ATOM | 392 O | TRP | 50 | 25.341 | 8.514 | 53.020 |
| ATOM | 393 N | GLN | 51 | 26.453 | 6.565 | 53.178 |
| ATOM | 394 CA | GLN | 51 | 27.789 | 7.120 | 53.107 |
| ATOM | 395 CB | GLN | 51 | 28.767 | 5.999 | 52.753 |
| ATOM | 396 CG | GLN | 51 | 30.017 | 5.934 | 53.599 |
| ATOM | 397 CD | GLN | 51 | 30.966 | 7.076 | 53.304 |
| ATOM | 398 OE1 | GLN | 51 | 31.789 | 6.988 | 52.384 |
| ATOM | 399 NE2 | GLN | 51 | 30.871 | 8.154 | 54.094 |
| ATOM | 400 C | GLN | 51 | 27.868 | 8.201 | 52.061 |
| ATOM | 401 O | GLN | 51 | 27.957 | 9.380 | 52.385 |
| ATOM | 402 N | LYS | 52 | 27.710 | 7.790 | 50.813 |
| ATOM | 403 CA | LYS | 52 | 27.787 | 8.682 | 49.678 |
| ATOM | 404 CB | LYS | 52 | 28.082 | 7.855 | 48.430 |
| ATOM | 405 CG | LYS | 52 | 29.264 | 6.882 | 48.547 |
| ATOM | 406 CD | LYS | 52 | 30.571 | 7.611 | 48.753 |
| ATOM | 407 CE | LYS | 52 | 31.775 | 6.684 | 48.554 |
| ATOM | 408 NZ | LYS | 52 | 33.122 | 7.263 | 48.979 |
| ATOM | 409 C | LYS | 52 | 26.559 | 9.582 | 49.444 |
| ATOM | 410 O | LYS | 52 | 26.686 | 10.779 | 49.268 |
| ATOM | 411 N | PHE | 53 | 25.365 | 9.026 | 49.485 |
| ATOM | 412 CA | PHE | 53 | 24.170 | 9.815 | 49.228 |
| ATOM | 413 CB | PHE | 53 | 22.956 | 8.915 | 48.980 |
| ATOM | 414 CG | PHE | 53 | 22.735 | 8.598 | 47.536 |
| ATOM | 415 CD1 | PHE | 53 | 23.262 | 7.438 | 46.955 |
| ATOM | 416 CD2 | PHE | 53 | 22.039 | 9.477 | 46.729 |
| ATOM | 417 CE1 | PHE | 53 | 23.097 | 7.166 | 45.580 |
| ATOM | 418 CE2 | PHE | 53 | 21.863 | 9.210 | 45.343 |
| ATOM | 419 CZ | PHE | 53 | 22.394 | 8.056 | 44.779 |
| ATOM | 420 C | PHE | 53 | 23.792 | 10.848 | 50.241 |
| ATOM | 421 O | PHE | 53 | 22.996 | 11.719 | 49.928 |
| ATOM | 422 N | ILE | 54 | 24.328 | 10.765 | 51.455 |
| ATOM | 423 CA | ILE | 54 | 23.948 | 11.717 | 52.499 |
| ATOM | 424 CB | ILE | 54 | 23.057 | 11.068 | 53.537 |
| ATOM | 425 CG2 | ILE | 54 | 22.448 | 12.129 | 54.395 |
| ATOM | 426 CG1 | ILE | 54 | 21.987 | 10.196 | 52.885 |
| ATOM | 427 CD1 | ILE | 54 | 20.908 | 10.938 | 52.190 |
| ATOM | 428 C | ILE | 54 | 25.096 | 12.277 | 53.295 |
| ATOM | 429 O | ILE | 54 | 25.168 | 13.476 | 53.572 |
| ATOM | 430 N | THR | 55 | 25.953 | 11.378 | 53.737 |

FIGURE 1J

|  |  |  | Residue |  |  |  |
|---|---|---|---|---|---|---|
| Atom |  | AA | No. | X | Y | Z |
| ATOM | 431 CA | THR | 55 | 27.055 | 11.801 | 54.550 |
| ATOM | 432 CB | THR | 55 | 27.824 | 10.601 | 55.221 |
| ATOM | 433 OG1 | THR | 55 | 26.985 | 9.953 | 56.205 |
| ATOM | 434 CG2 | THR | 55 | 29.082 | 11.094 | 55.939 |
| ATOM | 435 C | THR | 55 | 27.948 | 12.740 | 53.784 |
| ATOM | 436 O | THR | 55 | 28.197 | 13.840 | 54.239 |
| ATOM | 437 N | GLN | 56 | 28.351 | 12.373 | 52.583 |
| ATOM | 438 CA | GLN | 56 | 29.228 | 13.256 | 51.824 |
| ATOM | 439 CB | GLN | 56 | 30.174 | 12.429 | 50.972 |
| ATOM | 440 CG | GLN | 56 | 31.130 | 11.609 | 51.808 |
| ATOM | 441 CD | GLN | 56 | 31.537 | 10.306 | 51.140 |
| ATOM | 442 OE1 | GLN | 56 | 30.731 | 9.368 | 51.040 |
| ATOM | 443 NE2 | GLN | 56 | 32.793 | 10.238 | 50.675 |
| ATOM | 444 C | GLN | 56 | 28.576 | 14.382 | 51.000 |
| ATOM | 445 O | GLN | 56 | 29.151 | 15.465 | 50.882 |
| ATOM | 446 N | SER | 57 | 27.389 | 14.150 | 50.449 |
| ATOM | 447 CA | SER | 57 | 26.709 | 15.170 | 49.650 |
| ATOM | 448 CB | SER | 57 | 25.711 | 14.497 | 48.716 |
| ATOM | 449 OG | SER | 57 | 24.838 | 13.677 | 49.478 |
| ATOM | 450 C | SER | 57 | 25.971 | 16.216 | 50.501 |
| ATOM | 451 O | SER | 57 | 24.784 | 16.037 | 50.830 |
| ATOM | 452 N | PRO | 58 | 26.602 | 17.388 | 50.724 |
| ATOM | 453 CD | PRO | 58 | 27.830 | 17.822 | 50.047 |
| ATOM | 454 CA | PRO | 58 | 26.064 | 18.500 | 51.516 |
| ATOM | 455 CB | PRO | 58 | 27.001 | 19.649 | 51.145 |
| ATOM | 456 CG | PRO | 58 | 28.262 | 18.973 | 50.899 |
| ATOM | 457 C | PRO | 58 | 24.610 | 18.850 | 51.204 |
| ATOM | 458 O | PRO | 58 | 23.921 | 19.487 | 51.987 |
| ATOM | 459 N | PHE | 59 | 24.147 | 18.427 | 50.046 |
| ATOM | 460 CA | PHE | 59 | 22.790 | 18.712 | 49.648 |
| ATOM | 461 CB | PHE | 59 | 22.512 | 18.125 | 48.261 |
| ATOM | 462 CG | PHE | 59 | 23.365 | 18.695 | 47.166 |
| ATOM | 463 CD1 | PHE | 59 | 23.265 | 20.049 | 46.817 |
| ATOM | 464 CD2 | PHE | 59 | 24.271 | 17.877 | 46.471 |
| ATOM | 465 CE1 | PHE | 59 | 24.065 | 20.598 | 45.786 |
| ATOM | 466 CE2 | PHE | 59 | 25.083 | 18.408 | 45.432 |
| ATOM | 467 CZ | PHE | 59 | 24.979 | 19.772 | 45.090 |
| ATOM | 468 C | PHE | 59 | 21.777 | 18.100 | 50.573 |
| ATOM | 469 O | PHE | 59 | 20.842 | 18.748 | 51.010 |
| ATOM | 470 N | ASN | 60 | 21.990 | 16.837 | 50.883 |
| ATOM | 471 CA | ASN | 60 | 21.014 | 16.103 | 51.657 |
| ATOM | 472 CB | ASN | 60 | 20.626 | 14.834 | 50.891 |
| ATOM | 473 CG | ASN | 60 | 21.203 | 14.797 | 49.504 |
| ATOM | 474 OD1 | ASN | 60 | 20.471 | 14.831 | 48.535 |
| ATOM | 475 ND2 | ASN | 60 | 22.520 | 14.756 | 49.401 |
| ATOM | 476 C | ASN | 60 | 21.263 | 15.748 | 53.125 |
| ATOM | 477 O | ASN | 60 | 22.412 | 15.705 | 53.612 |
| ATOM | 478 N | VAL | 61 | 20.137 | 15.448 | 53.786 |

FIGURE 1K

| Atom | | Residue AA | No. | X | Y | Z |
|---|---|---|---|---|---|---|
| ATOM | 479 CA | VAL | 61 | 20.050 | 15.062 | 55.191 |
| ATOM | 480 CB | VAL | 61 | 19.325 | 16.133 | 56.042 |
| ATOM | 481 CG1 | VAL | 61 | 20.133 | 17.428 | 56.083 |
| ATOM | 482 CG2 | VAL | 61 | 17.917 | 16.393 | 55.489 |
| ATOM | 483 C | VAL | 61 | 19.188 | 13.819 | 55.219 |
| ATOM | 484 O | VAL | 61 | 18.393 | 13.581 | 54.308 |
| ATOM | 485 N | GLY | 62 | 19.333 | 13.031 | 56.270 |
| ATOM | 486 CA | GLY | 62 | 18.548 | 11.823 | 56.356 |
| ATOM | 487 C | GLY | 62 | 17.512 | 11.965 | 57.433 |
| ATOM | 488 O | GLY | 62 | 17.489 | 12.969 | 58.127 |
| ATOM | 489 N | ILE | 63 | 16.575 | 11.033 | 57.463 |
| ATOM | 490 CA | ILE | 63 | 15.550 | 10.995 | 58.466 |
| ATOM | 491 CB | ILE | 63 | 14.349 | 11.946 | 58.174 |
| ATOM | 492 CG2 | ILE | 63 | 14.787 | 13.200 | 57.537 |
| ATOM | 493 CG1 | ILE | 63 | 13.332 | 11.325 | 57.258 |
| ATOM | 494 CD1 | ILE | 63 | 11.997 | 12.008 | 57.376 |
| ATOM | 495 C | ILE | 63 | 15.108 | 9.534 | 58.638 |
| ATOM | 496 O | ILE | 63 | 15.733 | 8.612 | 58.103 |
| ATOM | 497 N | ASP | 64 | 14.122 | 9.315 | 59.499 |
| ATOM | 498 CA | ASP | 64 | 13.569 | 7.982 | 59.756 |
| ATOM | 499 CB | ASP | 64 | 14.337 | 7.254 | 60.873 |
| ATOM | 500 CG | ASP | 64 | 13.965 | 5.755 | 60.993 |
| ATOM | 501 OD1 | ASP | 64 | 12.750 | 5.425 | 61.080 |
| ATOM | 502 OD2 | ASP | 64 | 14.902 | 4.909 | 61.015 |
| ATOM | 503 C | ASP | 64 | 12.127 | 8.201 | 60.177 |
| ATOM | 504 O | ASP | 64 | 11.844 | 8.551 | 61.306 |
| ATOM | 505 N | ALA | 65 | 11.224 | 8.061 | 59.231 |
| ATOM | 506 CA | ALA | 65 | 9.829 | 8.260 | 59.502 |
| ATOM | 507 CB | ALA | 65 | 9.116 | 8.703 | 58.245 |
| ATOM | 508 C | ALA | 65 | 9.226 | 6.987 | 60.042 |
| ATOM | 509 O | ALA | 65 | 9.854 | 5.921 | 60.011 |
| ATOM | 510 N | ALA | 66 | 7.961 | 7.099 | 60.435 |
| ATOM | 511 CA | ALA | 66 | 7.210 | 6.011 | 61.034 |
| ATOM | 512 CB | ALA | 66 | 6.237 | 6.590 | 62.041 |
| ATOM | 513 C | ALA | 66 | 6.460 | 5.143 | 60.057 |
| ATOM | 514 O | ALA | 66 | 5.709 | 5.649 | 59.259 |
| ATOM | 515 N | ILE | 67 | 6.623 | 3.835 | 60.135 |
| ATOM | 516 CA | ILE | 67 | 5.884 | 2.985 | 59.239 |
| ATOM | 517 CB | ILE | 67 | 6.176 | 1.565 | 59.503 |
| ATOM | 518 CG2 | ILE | 67 | 5.240 | 0.684 | 58.732 |
| ATOM | 519 CG1 | ILE | 67 | 7.606 | 1.271 | 59.113 |
| ATOM | 520 CD1 | ILE | 67 | 7.961 | -0.169 | 59.370 |
| ATOM | 521 C | ILE | 67 | 4.399 | 3.220 | 59.449 |
| ATOM | 522 O | ILE | 67 | 3.589 | 3.012 | 58.548 |
| ATOM | 523 N | LEU | 68 | 4.033 | 3.640 | 60.653 |
| ATOM | 524 CA | LEU | 68 | 2.626 | 3.929 | 60.960 |
| ATOM | 525 CB | LEU | 68 | 2.245 | 3.425 | 62.371 |
| ATOM | 526 CG | LEU | 68 | 1.955 | 1.956 | 62.706 |

FIGURE 1L

| Atom | | AA | Residue No. | X | Y | Z |
|---|---|---|---|---|---|---|
| ATOM | 527 CD1 | LEU | 68 | 0.723 | 1.474 | 61.960 |
| ATOM | 528 CD2 | LEU | 68 | 3.140 | 1.089 | 62.380 |
| ATOM | 529 C | LEU | 68 | 2.355 | 5.445 | 60.866 |
| ATOM | 530 O | LEU | 68 | 3.007 | 6.250 | 61.537 |
| ATOM | 531 N | MET | 69 | 1.415 | 5.837 | 60.013 |
| ATOM | 532 CA | MET | 69 | 1.076 | 7.247 | 59.897 |
| ATOM | 533 CB | MET | 69 | 2.046 | 7.998 | 58.976 |
| ATOM | 534 CG | MET | 69 | 2.394 | 7.364 | 57.607 |
| ATOM | 535 SD | MET | 69 | 3.550 | 8.460 | 56.676 |
| ATOM | 536 CE | MET | 69 | 5.227 | 7.677 | 56.906 |
| ATOM | 537 C | MET | 69 | -0.376 | 7.550 | 59.548 |
| ATOM | 538 O | MET | 69 | -1.117 | 6.698 | 59.012 |
| ATOM | 539 N | ASN | 70 | -0.784 | 8.742 | 59.982 |
| ATOM | 540 CA | ASN | 70 | -2.130 | 9.303 | 59.796 |
| ATOM | 541 CB | ASN | 70 | -2.079 | 10.813 | 60.084 |
| ATOM | 542 CG | ASN | 70 | -3.446 | 11.459 | 60.126 |
| ATOM | 543 OD1 | ASN | 70 | -3.672 | 12.468 | 59.458 |
| ATOM | 544 ND2 | ASN | 70 | -4.352 | 10.909 | 60.930 |
| ATOM | 545 C | ASN | 70 | -2.683 | 9.034 | 58.393 |
| ATOM | 546 O | ASN | 70 | -2.240 | 9.636 | 57.415 |
| ATOM | 547 N | PRO | 71 | -3.724 | 8.186 | 58.303 |
| ATOM | 548 CD | PRO | 71 | -4.508 | 7.660 | 59.438 |
| ATOM | 549 CA | PRO | 71 | -4.352 | 7.823 | 57.032 |
| ATOM | 550 CB | PRO | 71 | -5.636 | 7.108 | 57.461 |
| ATOM | 551 CG | PRO | 71 | -5.301 | 6.534 | 58.788 |
| ATOM | 552 C | PRO | 71 | -4.667 | 9.014 | 56.147 |
| ATOM | 553 O | PRO | 71 | -4.613 | 8.874 | 54.925 |
| ATOM | 554 N | ALA | 72 | -4.996 | 10.175 | 56.739 |
| ATOM | 555 CA | ALA | 72 | -5.318 | 11.387 | 55.950 |
| ATOM | 556 CB | ALA | 72 | -5.513 | 12.622 | 56.853 |
| ATOM | 557 C | ALA | 72 | -4.254 | 11.655 | 54.870 |
| ATOM | 558 O | ALA | 72 | -4.574 | 12.137 | 53.780 |
| ATOM | 559 N | VAL | 73 | -3.004 | 11.295 | 55.158 |
| ATOM | 560 CA | VAL | 73 | -1.921 | 11.451 | 54.205 |
| ATOM | 561 CB | VAL | 73 | -0.613 | 10.960 | 54.778 |
| ATOM | 562 CG1 | VAL | 73 | 0.309 | 10.493 | 53.664 |
| ATOM | 563 CG2 | VAL | 73 | 0.035 | 12.069 | 55.581 |
| ATOM | 564 C | VAL | 73 | -2.220 | 10.619 | 52.994 |
| ATOM | 565 O | VAL | 73 | -2.253 | 11.119 | 51.893 |
| ATOM | 566 N | TRP | 74 | -2.490 | 9.350 | 53.209 |
| ATOM | 567 CA | TRP | 74 | -2.777 | 8.448 | 52.114 |
| ATOM | 568 CB | TRP | 74 | -3.016 | 7.041 | 52.657 |
| ATOM | 569 CG | TRP | 74 | -1.766 | 6.497 | 53.316 |
| ATOM | 570 CD2 | TRP | 74 | -0.485 | 6.359 | 52.704 |
| ATOM | 571 CE2 | TRP | 74 | 0.410 | 5.912 | 53.695 |
| ATOM | 572 CE3 | TRP | 74 | -0.002 | 6.578 | 51.413 |
| ATOM | 573 CD1 | TRP | 74 | -1.605 | 6.120 | 54.634 |
| ATOM | 574 NE1 | TRP | 74 | -0.297 | 5.771 | 54.864 |

FIGURE 1M

| Atom | | Residue AA | No. | X | Y | Z |
|---|---|---|---|---|---|---|
| ATOM | 575 | CZ2 | TRP | 74 | 1.767 | 5.684 | 53.426 |
| ATOM | 576 | CZ3 | TRP | 74 | 1.344 | 6.352 | 51.152 |
| ATOM | 577 | CH2 | TRP | 74 | 2.213 | 5.910 | 52.150 |
| ATOM | 578 | C | TRP | 74 | -3.873 | 8.890 | 51.145 |
| ATOM | 579 | O | TRP | 74 | -4.086 | 8.258 | 50.106 |
| ATOM | 580 | N | GLU | 75 | -4.561 | 9.977 | 51.476 |
| ATOM | 581 | CA | GLU | 75 | -5.594 | 10.516 | 50.603 |
| ATOM | 582 | CB | GLU | 75 | -6.708 | 11.126 | 51.407 |
| ATOM | 583 | CG | GLU | 75 | -7.369 | 10.156 | 52.327 |
| ATOM | 584 | CD | GLU | 75 | -8.386 | 10.851 | 53.197 |
| ATOM | 585 | OE1 | GLU | 75 | -7.981 | 11.819 | 53.903 |
| ATOM | 586 | OE2 | GLU | 75 | -9.590 | 10.467 | 53.157 |
| ATOM | 587 | C | GLU | 75 | -4.950 | 11.590 | 49.766 |
| ATOM | 588 | O | GLU | 75 | -5.175 | 11.656 | 48.572 |
| ATOM | 589 | N | ALA | 76 | -4.145 | 12.437 | 50.398 |
| ATOM | 590 | CA | ALA | 76 | -3.438 | 13.489 | 49.671 |
| ATOM | 591 | CB | ALA | 76 | -2.752 | 14.437 | 50.615 |
| ATOM | 592 | C | ALA | 76 | -2.398 | 12.829 | 48.778 |
| ATOM | 593 | O | ALA | 76 | -1.732 | 13.513 | 47.991 |
| ATOM | 594 | N | SER | 77 | -2.180 | 11.527 | 49.000 |
| ATOM | 595 | CA | SER | 77 | -1.247 | 10.741 | 48.189 |
| ATOM | 596 | CB | SER | 77 | -0.497 | 9.705 | 49.043 |
| ATOM | 597 | OG | SER | 77 | -1.305 | 8.578 | 49.336 |
| ATOM | 598 | C | SER | 77 | -2.042 | 10.042 | 47.070 |
| ATOM | 599 | O | SER | 77 | -1.475 | 9.643 | 46.042 |
| ATOM | 600 | N | GLY | 78 | -3.356 | 9.910 | 47.281 |
| ATOM | 601 | CA | GLY | 78 | -4.221 | 9.263 | 46.309 |
| ATOM | 602 | C | GLY | 78 | -4.087 | 7.750 | 46.354 |
| ATOM | 603 | O | GLY | 78 | -4.821 | 7.032 | 45.671 |
| ATOM | 604 | N | HIS | 79 | -3.141 | 7.252 | 47.152 |
| ATOM | 605 | CA | HIS | 79 | -2.938 | 5.808 | 47.299 |
| ATOM | 606 | CB | HIS | 79 | -1.827 | 5.515 | 48.309 |
| ATOM | 607 | CG | HIS | 79 | -0.463 | 5.491 | 47.709 |
| ATOM | 608 | CD2 | HIS | 79 | 0.639 | 4.776 | 48.038 |
| ATOM | 609 | ND1 | HIS | 79 | -0.105 | 6.282 | 46.636 |
| ATOM | 610 | CE1 | HIS | 79 | 1.163 | 6.058 | 46.331 |
| ATOM | 611 | NE2 | HIS | 79 | 1.639 | 5.150 | 47.166 |
| ATOM | 612 | C | HIS | 79 | -4.229 | 5.130 | 47.773 |
| ATOM | 613 | O | HIS | 79 | -4.436 | 3.934 | 47.550 |
| ATOM | 614 | N | LEU | 80 | -5.063 | 5.897 | 48.465 |
| ATOM | 615 | CA | LEU | 80 | -6.321 | 5.403 | 48.944 |
| ATOM | 616 | CB | LEU | 80 | -7.165 | 6.589 | 49.390 |
| ATOM | 617 | CG | LEU | 80 | -7.708 | 6.553 | 50.822 |
| ATOM | 618 | CD1 | LEU | 80 | -8.834 | 5.530 | 50.941 |
| ATOM | 619 | CD2 | LEU | 80 | -6.568 | 6.271 | 51.811 |
| ATOM | 620 | C | LEU | 80 | -7.019 | 4.668 | 47.794 |
| ATOM | 621 | O | LEU | 80 | -7.624 | 3.613 | 47.998 |
| ATOM | 622 | N | ASN | 81 | -6.879 | 5.207 | 46.579 |

FIGURE 1N

| Atom | | AA | Residue No. | X | Y | Z |
|---|---|---|---|---|---|---|
| ATOM | 623 CA | ASN | 81 | -7.492 | 4.640 | 45.360 |
| ATOM | 624 CB | ASN | 81 | -8.777 | 5.431 | 44.972 |
| ATOM | 625 CG | ASN | 81 | -8.722 | 6.943 | 45.344 |
| ATOM | 626 OD1 | ASN | 81 | -7.917 | 7.730 | 44.807 |
| ATOM | 627 ND2 | ASN | 81 | -9.613 | 7.344 | 46.249 |
| ATOM | 628 C | ASN | 81 | -6.578 | 4.493 | 44.113 |
| ATOM | 629 O | ASN | 81 | -6.494 | 3.431 | 43.506 |
| ATOM | 630 N | ASN | 82 | -5.942 | 5.580 | 43.707 |
| ATOM | 631 CA | ASN | 82 | -5.068 | 5.568 | 42.552 |
| ATOM | 632 CB | ASN | 82 | -4.433 | 6.947 | 42.351 |
| ATOM | 633 CG | ASN | 82 | -5.485 | 8.078 | 42.232 |
| ATOM | 634 OD1 | ASN | 82 | -5.215 | 9.234 | 42.603 |
| ATOM | 635 ND2 | ASN | 82 | -6.686 | 7.748 | 41.715 |
| ATOM | 636 C | ASN | 82 | -3.996 | 4.498 | 42.698 |
| ATOM | 637 O | ASN | 82 | -3.502 | 3.973 | 41.688 |
| ATOM | 638 N | PHE | 83 | -3.594 | 4.201 | 43.943 |
| ATOM | 639 CA | PHE | 83 | -2.591 | 3.132 | 44.163 |
| ATOM | 640 CB | PHE | 83 | -2.036 | 3.070 | 45.607 |
| ATOM | 641 CG | PHE | 83 | -1.194 | 1.824 | 45.882 |
| ATOM | 642 CD1 | PHE | 83 | -1.806 | 0.613 | 46.273 |
| ATOM | 643 CD2 | PHE | 83 | 0.193 | 1.834 | 45.654 |
| ATOM | 644 CE1 | PHE | 83 | -1.056 | -0.551 | 46.413 |
| ATOM | 645 CE2 | PHE | 83 | 0.952 | 0.665 | 45.798 |
| ATOM | 646 CZ | PHE | 83 | 0.327 | -0.530 | 46.175 |
| ATOM | 647 C | PHE | 83 | -3.330 | 1.826 | 43.851 |
| ATOM | 648 O | PHE | 83 | -4.176 | 1.339 | 44.640 |
| ATOM | 649 N | ASN | 84 | -2.946 | 1.217 | 42.740 |
| ATOM | 650 CA | ASN | 84 | -3.626 | 0.017 | 42.332 |
| ATOM | 651 CB | ASN | 84 | -4.925 | 0.438 | 41.633 |
| ATOM | 652 CG | ASN | 84 | -6.162 | 0.142 | 42.452 |
| ATOM | 653 OD1 | ASN | 84 | -6.967 | -0.687 | 42.064 |
| ATOM | 654 ND2 | ASN | 84 | -6.354 | 0.857 | 43.548 |
| ATOM | 655 C | ASN | 84 | -2.841 | -0.940 | 41.410 |
| ATOM | 656 O | ASN | 84 | -1.686 | -0.686 | 40.950 |
| ATOM | 657 N | ALA | 85 | -3.488 | -2.091 | 41.230 |
| ATOM | 658 CA | ALA | 85 | -3.061 | -3.174 | 40.353 |
| ATOM | 659 CB | ALA | 85 | -2.431 | -4.353 | 41.159 |
| ATOM | 660 C | ALA | 85 | -4.465 | -3.530 | 39.809 |
| ATOM | 661 O | ALA | 85 | -5.319 | -4.028 | 40.565 |
| ATOM | 662 N | PRO | 86 | -4.808 | -2.982 | 38.622 |
| ATOM | 663 CD | PRO | 86 | -4.138 | -1.832 | 37.973 |
| ATOM | 664 CA | PRO | 86 | -6.109 | -3.244 | 37.990 |
| ATOM | 665 CB | PRO | 86 | -6.079 | -2.334 | 36.737 |
| ATOM | 666 CG | PRO | 86 | -5.301 | -1.135 | 37.230 |
| ATOM | 667 C | PRO | 86 | -6.290 | -4.744 | 37.643 |
| ATOM | 668 O | PRO | 86 | -5.261 | -5.408 | 37.279 |
| ATOM | 669 OT | PRO | 86 | -7.457 | -5.236 | 37.815 |
| ATOM | 670 CB | ALA | 150 | -9.259 | -1.337 | 39.891 |

FIGURE 10

|      | Atom | AA | Residue No. | X | Y | Z |
|---|---|---|---|---|---|---|
| ATOM | 671 C   | ALA | 150 | -8.591 | -3.142 | 41.644 |
| ATOM | 672 O   | ALA | 150 | -9.636 | -3.252 | 42.345 |
| ATOM | 673 N   | ALA | 150 | -9.441 | -3.796 | 39.273 |
| ATOM | 674 CA  | ALA | 150 | -8.680 | -2.785 | 40.107 |
| ATOM | 675 N   | ALA | 151 | -7.356 | -3.292 | 42.155 |
| ATOM | 676 CA  | ALA | 151 | -7.122 | -3.646 | 43.556 |
| ATOM | 677 CB  | ALA | 151 | -6.622 | -5.100 | 43.644 |
| ATOM | 678 C   | ALA | 151 | -6.136 | -2.710 | 44.285 |
| ATOM | 679 O   | ALA | 151 | -5.024 | -2.462 | 43.786 |
| ATOM | 680 N   | ASN | 152 | -6.555 | -2.182 | 45.454 |
| ATOM | 681 CA  | ASN | 152 | -5.706 | -1.297 | 46.305 |
| ATOM | 682 CB  | ASN | 152 | -6.514 | -0.173 | 46.981 |
| ATOM | 683 CG  | ASN | 152 | -5.635 | 0.751  | 47.810 |
| ATOM | 684 OD1 | ASN | 152 | -5.959 | 1.085  | 48.952 |
| ATOM | 685 ND2 | ASN | 152 | -4.493 | 1.128  | 47.254 |
| ATOM | 686 C   | ASN | 152 | -4.947 | -2.156 | 47.354 |
| ATOM | 687 O   | ASN | 152 | -5.446 | -2.513 | 48.448 |
| ATOM | 688 N   | LEU | 153 | -3.712 | -2.451 | 46.973 |
| ATOM | 689 CA  | LEU | 153 | -2.785 | -3.304 | 47.705 |
| ATOM | 690 CB  | LEU | 153 | -1.719 | -3.766 | 46.681 |
| ATOM | 691 CG  | LEU | 153 | -1.890 | -3.530 | 45.152 |
| ATOM | 692 CD1 | LEU | 153 | -0.510 | -3.491 | 44.449 |
| ATOM | 693 CD2 | LEU | 153 | -2.832 | -4.590 | 44.526 |
| ATOM | 694 C   | LEU | 153 | -2.087 | -2.754 | 48.976 |
| ATOM | 695 O   | LEU | 153 | -1.036 | -3.258 | 49.356 |
| ATOM | 696 N   | MET | 154 | -2.621 | -1.718 | 49.617 |
| ATOM | 697 CA  | MET | 154 | -1.970 | -1.165 | 50.822 |
| ATOM | 698 CB  | MET | 154 | -2.513 | 0.226  | 51.150 |
| ATOM | 699 CG  | MET | 154 | -2.319 | 1.275  | 50.056 |
| ATOM | 700 SD  | MET | 154 | -3.018 | 2.859  | 50.539 |
| ATOM | 701 CE  | MET | 154 | -1.966 | 3.276  | 51.958 |
| ATOM | 702 C   | MET | 154 | -2.312 | -2.109 | 51.953 |
| ATOM | 703 O   | MET | 154 | -3.446 | -2.614 | 51.993 |
| ATOM | 704 N   | PHE | 155 | -1.377 | -2.357 | 52.872 |
| ATOM | 705 CA  | PHE | 155 | -1.674 | -3.301 | 53.967 |
| ATOM | 706 CB  | PHE | 155 | -0.390 | -3.952 | 54.475 |
| ATOM | 707 CG  | PHE | 155 | -0.278 | -5.410 | 54.136 |
| ATOM | 708 CD1 | PHE | 155 | -1.360 | -6.269 | 54.346 |
| ATOM | 709 CD2 | PHE | 155 | 0.914  | -5.935 | 53.644 |
| ATOM | 710 CE1 | PHE | 155 | -1.246 | -7.634 | 54.074 |
| ATOM | 711 CE2 | PHE | 155 | 1.038  | -7.301 | 53.367 |
| ATOM | 712 CZ  | PHE | 155 | -0.040 | -8.149 | 53.583 |
| ATOM | 713 C   | PHE | 155 | -2.587 | -2.796 | 55.118 |
| ATOM | 714 O   | PHE | 155 | -2.234 | -1.901 | 55.919 |
| ATOM | 715 N   | ALA | 156 | -3.746 | -3.431 | 55.229 |
| ATOM | 716 CA  | ALA | 156 | -4.754 | -3.024 | 56.201 |
| ATOM | 717 CB  | ALA | 156 | -6.131 | -3.500 | 55.713 |
| ATOM | 718 C   | ALA | 156 | -4.586 | -3.355 | 57.691 |

FIGURE 1P

|  | Atom | Residue AA | No. | X | Y | Z |
|---|---|---|---|---|---|---|
| ATOM | 719 O | ALA | 156 | -4.446 | -4.528 | 58.060 |
| ATOM | 720 N | THR | 157 | -4.655 | -2.331 | 58.544 |
| ATOM | 721 CA | THR | 157 | -4.576 | -2.559 | 59.985 |
| ATOM | 722 CB | THR | 157 | -3.161 | -2.315 | 60.576 |
| ATOM | 723 OG1 | THR | 157 | -3.015 | -3.127 | 61.750 |
| ATOM | 724 CG2 | THR | 157 | -2.965 | -0.849 | 61.002 |
| ATOM | 725 C | THR | 157 | -5.609 | -1.753 | 60.785 |
| ATOM | 726 O | THR | 157 | -6.201 | -0.782 | 60.276 |
| ATOM | 727 N | ALA | 158 | -5.830 | -2.195 | 62.029 |
| ATOM | 728 CA | ALA | 158 | -6.769 | -1.560 | 62.961 |
| ATOM | 729 CB | ALA | 158 | -7.998 | -2.460 | 63.209 |
| ATOM | 730 C | ALA | 158 | -6.041 | -1.283 | 64.271 |
| ATOM | 731 O | ALA | 158 | -5.348 | -2.168 | 64.802 |
| ATOM | 732 N | GLN | 159 | -6.209 | -0.055 | 64.773 |
| ATOM | 733 CA | GLN | 159 | -5.572 | 0.386 | 66.009 |
| ATOM | 734 CB | GLN | 159 | -4.699 | 1.594 | 65.713 |
| ATOM | 735 CG | GLN | 159 | -3.917 | 2.123 | 66.912 |
| ATOM | 736 CD | GLN | 159 | -3.217 | 3.446 | 66.583 |
| ATOM | 737 OE1 | GLN | 159 | -2.010 | 3.633 | 66.841 |
| ATOM | 738 NE2 | GLN | 159 | -3.975 | 4.371 | 65.971 |
| ATOM | 739 C | GLN | 159 | -6.582 | 0.728 | 67.106 |
| ATOM | 740 O | GLN | 159 | -7.052 | 1.870 | 67.189 |
| ATOM | 741 N | GLY | 160 | -6.899 | -0.270 | 67.939 |
| ATOM | 742 CA | GLY | 160 | -7.860 | -0.112 | 69.032 |
| ATOM | 743 C | GLY | 160 | -8.879 | -1.268 | 69.132 |
| ATOM | 744 O | GLY | 160 | -8.686 | -2.263 | 69.872 |
| ATOM | 745 N | ALA | 161 | -9.992 | -1.112 | 68.409 |
| ATOM | 746 CA | ALA | 161 | -11.069 | -2.115 | 68.343 |
| ATOM | 747 CB | ALA | 161 | -11.548 | -2.514 | 69.770 |
| ATOM | 748 C | ALA | 161 | -12.268 | -1.686 | 67.420 |
| ATOM | 749 O | ALA | 161 | -12.526 | -2.435 | 66.435 |
| ATOM | 750 OT | ALA | 161 | -12.912 | -0.607 | 67.623 |
| ATOM | 751 CB | ALA | 164 | -15.791 | -0.318 | 63.377 |
| ATOM | 752 C | ALA | 164 | -13.539 | -0.063 | 62.220 |
| ATOM | 753 O | ALA | 164 | -12.340 | -0.348 | 61.945 |
| ATOM | 754 N | ALA | 164 | -13.735 | -0.946 | 64.603 |
| ATOM | 755 CA | ALA | 164 | -14.368 | -0.892 | 63.239 |
| ATOM | 756 N | ALA | 165 | -14.204 | 0.928 | 61.627 |
| ATOM | 757 CA | ALA | 165 | -13.566 | 1.841 | 60.681 |
| ATOM | 758 CB | ALA | 165 | -14.528 | 2.161 | 59.486 |
| ATOM | 759 C | ALA | 165 | -13.263 | 3.109 | 61.507 |
| ATOM | 760 O | ALA | 165 | -14.156 | 3.586 | 62.236 |
| ATOM | 761 N | THR | 166 | -11.995 | 3.555 | 61.451 |
| ATOM | 762 CA | THR | 166 | -11.415 | 4.749 | 62.133 |
| ATOM | 763 CB | THR | 166 | -12.276 | 5.348 | 63.292 |
| ATOM | 764 OG1 | THR | 166 | -12.832 | 4.292 | 64.097 |
| ATOM | 765 CG2 | THR | 166 | -13.364 | 6.322 | 62.755 |
| ATOM | 766 C | THR | 166 | -10.075 | 4.320 | 62.723 |

FIGURE 1Q

| Atom | | AA | Residue No. | X | Y | Z |
|---|---|---|---|---|---|---|
| ATOM | 767 O | THR | 166 | -9.100 | 5.117 | 62.816 |
| ATOM | 768 N | ASN | 167 | -10.096 | 3.066 | 63.194 |
| ATOM | 769 CA | ASN | 167 | -8.925 | 2.363 | 63.754 |
| ATOM | 770 CB | ASN | 167 | -9.349 | 1.045 | 64.460 |
| ATOM | 771 CG | ASN | 167 | -10.650 | 1.196 | 65.306 |
| ATOM | 772 OD1 | ASN | 167 | -11.764 | 1.178 | 64.763 |
| ATOM | 773 ND2 | ASN | 167 | -10.504 | 1.358 | 66.618 |
| ATOM | 774 C | ASN | 167 | -8.132 | 2.046 | 62.478 |
| ATOM | 775 O | ASN | 167 | -6.896 | 1.920 | 62.501 |
| ATOM | 776 N | ALA | 168 | -8.897 | 1.945 | 61.380 |
| ATOM | 777 CA | ALA | 168 | -8.418 | 1.696 | 60.021 |
| ATOM | 778 CB | ALA | 168 | -9.616 | 1.798 | 59.028 |
| ATOM | 779 C | ALA | 168 | -7.271 | 2.633 | 59.587 |
| ATOM | 780 O | ALA | 168 | -7.488 | 3.781 | 59.163 |
| ATOM | 781 N | ILE | 169 | -6.050 | 2.155 | 59.777 |
| ATOM | 782 CA | ILE | 169 | -4.854 | 2.890 | 59.390 |
| ATOM | 783 CB | ILE | 169 | -4.118 | 3.465 | 60.612 |
| ATOM | 784 CG2 | ILE | 169 | -5.110 | 4.230 | 61.493 |
| ATOM | 785 CG1 | ILE | 169 | -3.444 | 2.346 | 61.407 |
| ATOM | 786 CD1 | ILE | 169 | -2.450 | 2.854 | 62.410 |
| ATOM | 787 C | ILE | 169 | -4.012 | 1.811 | 58.692 |
| ATOM | 788 O | ILE | 169 | -4.293 | 0.611 | 58.860 |
| ATOM | 789 N | PHE | 170 | -3.027 | 2.184 | 57.877 |
| ATOM | 790 CA | PHE | 170 | -2.260 | 1.141 | 57.196 |
| ATOM | 791 CB | PHE | 170 | -2.618 | 1.071 | 55.736 |
| ATOM | 792 CG | PHE | 170 | -4.039 | 1.336 | 55.480 |
| ATOM | 793 CD1 | PHE | 170 | -5.004 | 0.444 | 55.921 |
| ATOM | 794 CD2 | PHE | 170 | -4.437 | 2.525 | 54.868 |
| ATOM | 795 CE1 | PHE | 170 | -6.357 | 0.735 | 55.764 |
| ATOM | 796 CE2 | PHE | 170 | -5.784 | 2.822 | 54.706 |
| ATOM | 797 CZ | PHE | 170 | -6.747 | 1.925 | 55.156 |
| ATOM | 798 C | PHE | 170 | -0.803 | 1.368 | 57.252 |
| ATOM | 799 O | PHE | 170 | -0.319 | 2.397 | 57.769 |
| ATOM | 800 N | LEU | 171 | -0.105 | 0.412 | 56.658 |
| ATOM | 801 CA | LEU | 171 | 1.337 | 0.463 | 56.587 |
| ATOM | 802 CB | LEU | 171 | 1.928 | -0.943 | 56.681 |
| ATOM | 803 CG | LEU | 171 | 1.151 | -2.044 | 57.392 |
| ATOM | 804 CD1 | LEU | 171 | 2.139 | -3.163 | 57.661 |
| ATOM | 805 CD2 | LEU | 171 | 0.499 | -1.564 | 58.675 |
| ATOM | 806 C | LEU | 171 | 1.707 | 1.130 | 55.253 |
| ATOM | 807 O | LEU | 171 | 1.005 | 0.965 | 54.244 |
| ATOM | 808 N | ARG | 172 | 2.796 | 1.896 | 55.274 |
| ATOM | 809 CA | ARG | 172 | 3.307 | 2.617 | 54.110 |
| ATOM | 810 CB | ARG | 172 | 4.472 | 3.541 | 54.524 |
| ATOM | 811 CG | ARG | 172 | 5.796 | 2.853 | 54.938 |
| ATOM | 812 CD | ARG | 172 | 6.824 | 3.914 | 55.311 |
| ATOM | 813 NE | ARG | 172 | 8.011 | 3.399 | 56.007 |
| ATOM | 814 CZ | ARG | 172 | 9.012 | 4.167 | 56.470 |

FIGURE 1R

| Atom | | Residue AA | No. | X | Y | Z |
|---|---|---|---|---|---|---|
| ATOM | 815 NH1 | ARG | 172 | 8.971 | 5.495 | 56.319 |
| ATOM | 816 NH2 | ARG | 172 | 10.073 | 3.615 | 57.078 |
| ATOM | 817 C | ARG | 172 | 3.772 | 1.747 | 52.950 |
| ATOM | 818 O | ARG | 172 | 4.615 | 0.866 | 53.131 |
| ATOM | 819 N | PRO | 173 | 3.197 | 1.950 | 51.751 |
| ATOM | 820 CD | PRO | 173 | 1.946 | 2.643 | 51.435 |
| ATOM | 821 CA | PRO | 173 | 3.616 | 1.158 | 50.600 |
| ATOM | 822 CB | PRO | 173 | 2.377 | 1.190 | 49.705 |
| ATOM | 823 CG | PRO | 173 | 1.285 | 1.650 | 50.579 |
| ATOM | 824 C | PRO | 173 | 4.770 | 1.941 | 49.949 |
| ATOM | 825 O | PRO | 173 | 5.507 | 1.442 | 49.097 |
| ATOM | 826 N | GLU | 174 | 4.941 | 3.175 | 50.398 |
| ATOM | 827 CA | GLU | 174 | 5.955 | 4.038 | 49.859 |
| ATOM | 828 CB | GLU | 174 | 5.335 | 4.880 | 48.750 |
| ATOM | 829 CG | GLU | 174 | 6.198 | 6.021 | 48.222 |
| ATOM | 830 CD | GLU | 174 | 5.581 | 6.686 | 46.986 |
| ATOM | 831 OE1 | GLU | 174 | 6.341 | 7.002 | 46.036 |
| ATOM | 832 OE2 | GLU | 174 | 4.332 | 6.862 | 46.949 |
| ATOM | 833 C | GLU | 174 | 6.562 | 4.919 | 50.930 |
| ATOM | 834 O | GLU | 174 | 5.886 | 5.710 | 51.594 |
| ATOM | 835 N | THR | 175 | 7.867 | 4.809 | 51.026 |
| ATOM | 836 CA | THR | 175 | 8.681 | 5.539 | 51.970 |
| ATOM | 837 CB | THR | 175 | 10.062 | 4.953 | 51.871 |
| ATOM | 838 OG1 | THR | 175 | 9.955 | 3.542 | 52.095 |
| ATOM | 839 CG2 | THR | 175 | 11.017 | 5.588 | 52.852 |
| ATOM | 840 C | THR | 175 | 8.763 | 7.071 | 51.819 |
| ATOM | 841 O | THR | 175 | 9.172 | 7.785 | 52.738 |
| ATOM | 842 N | ALA | 176 | 8.323 | 7.579 | 50.677 |
| ATOM | 843 CA | ALA | 176 | 8.401 | 9.011 | 50.388 |
| ATOM | 844 CB | ALA | 176 | 8.128 | 9.238 | 48.939 |
| ATOM | 845 C | ALA | 176 | 7.507 | 9.896 | 51.198 |
| ATOM | 846 O | ALA | 176 | 7.902 | 10.976 | 51.618 |
| ATOM | 847 N | GLN | 177 | 6.272 | 9.460 | 51.346 |
| ATOM | 848 CA | GLN | 177 | 5.312 | 10.229 | 52.087 |
| ATOM | 849 CB | GLN | 177 | 4.037 | 9.418 | 52.272 |
| ATOM | 850 CG | GLN | 177 | 3.291 | 9.241 | 50.961 |
| ATOM | 851 CD | GLN | 177 | 3.356 | 10.512 | 50.128 |
| ATOM | 852 OE1 | GLN | 177 | 2.918 | 11.583 | 50.571 |
| ATOM | 853 NE2 | GLN | 177 | 3.979 | 10.419 | 48.953 |
| ATOM | 854 C | GLN | 177 | 5.889 | 10.686 | 53.404 |
| ATOM | 855 O | GLN | 177 | 5.796 | 11.862 | 53.753 |
| ATOM | 856 N | GLY | 178 | 6.584 | 9.773 | 54.069 |
| ATOM | 857 CA | GLY | 178 | 7.212 | 10.088 | 55.338 |
| ATOM | 858 C | GLY | 178 | 8.171 | 11.254 | 55.195 |
| ATOM | 859 O | GLY | 178 | 8.404 | 11.988 | 56.149 |
| ATOM | 860 N | ILE | 179 | 8.744 | 11.424 | 54.010 |
| ATOM | 861 CA | ILE | 179 | 9.650 | 12.536 | 53.800 |
| ATOM | 862 CB | ILE | 179 | 10.609 | 12.326 | 52.608 |

FIGURE 1S

|  |  | Residue |  |  |  |  |
|---|---|---|---|---|---|---|
| Atom |  | AA | No. | X | Y | Z |
| ATOM | 863 CG2 | ILE | 179 | 11.754 | 13.330 | 52.692 |
| ATOM | 864 CG1 | ILE | 179 | 11.174 | 10.910 | 52.615 |
| ATOM | 865 CD1 | ILE | 179 | 12.222 | 10.657 | 51.550 |
| ATOM | 866 C | ILE | 179 | 8.839 | 13.791 | 53.532 |
| ATOM | 867 O | ILE | 179 | 9.010 | 14.803 | 54.211 |
| ATOM | 868 N | PHE | 180 | 7.911 | 13.710 | 52.585 |
| ATOM | 869 CA | PHE | 180 | 7.108 | 14.875 | 52.216 |
| ATOM | 870 CB | PHE | 180 | 6.062 | 14.494 | 51.184 |
| ATOM | 871 CG | PHE | 180 | 6.653 | 14.170 | 49.878 |
| ATOM | 872 CD1 | PHE | 180 | 6.156 | 13.139 | 49.108 |
| ATOM | 873 CD2 | PHE | 180 | 7.779 | 14.860 | 49.440 |
| ATOM | 874 CE1 | PHE | 180 | 6.787 | 12.788 | 47.894 |
| ATOM | 875 CE2 | PHE | 180 | 8.411 | 14.521 | 48.244 |
| ATOM | 876 CZ | PHE | 180 | 7.916 | 13.482 | 47.466 |
| ATOM | 877 C | PHE | 180 | 6.474 | 15.597 | 53.370 |
| ATOM | 878 O | PHE | 180 | 6.536 | 16.835 | 53.466 |
| ATOM | 879 N | VAL | 181 | 5.859 | 14.814 | 54.242 |
| ATOM | 880 CA | VAL | 181 | 5.215 | 15.363 | 55.420 |
| ATOM | 881 CB | VAL | 181 | 4.461 | 14.261 | 56.210 |
| ATOM | 882 CG1 | VAL | 181 | 3.239 | 13.833 | 55.442 |
| ATOM | 883 CG2 | VAL | 181 | 5.364 | 13.047 | 56.447 |
| ATOM | 884 C | VAL | 181 | 6.248 | 16.034 | 56.330 |
| ATOM | 885 O | VAL | 181 | 5.918 | 16.952 | 57.093 |
| ATOM | 886 N | ASN | 182 | 7.496 | 15.583 | 56.229 |
| ATOM | 887 CA | ASN | 182 | 8.565 | 16.121 | 57.047 |
| ATOM | 888 CB | ASN | 182 | 9.427 | 14.992 | 57.652 |
| ATOM | 889 CG | ASN | 182 | 8.758 | 14.312 | 58.860 |
| ATOM | 890 OD1 | ASN | 182 | 9.156 | 14.505 | 60.017 |
| ATOM | 891 ND2 | ASN | 182 | 7.740 | 13.518 | 58.587 |
| ATOM | 892 C | ASN | 182 | 9.427 | 17.086 | 56.277 |
| ATOM | 893 O | ASN | 182 | 10.598 | 17.277 | 56.607 |
| ATOM | 894 N | TYR | 183 | 8.851 | 17.722 | 55.268 |
| ATOM | 895 CA | TYR | 183 | 9.627 | 18.671 | 54.477 |
| ATOM | 896 CB | TYR | 183 | 8.911 | 19.044 | 53.144 |
| ATOM | 897 CG | TYR | 183 | 9.484 | 20.289 | 52.430 |
| ATOM | 898 CD1 | TYR | 183 | 8.692 | 21.428 | 52.219 |
| ATOM | 899 CE1 | TYR | 183 | 9.223 | 22.602 | 51.646 |
| ATOM | 900 CD2 | TYR | 183 | 10.839 | 20.352 | 52.032 |
| ATOM | 901 CE2 | TYR | 183 | 11.382 | 21.532 | 51.451 |
| ATOM | 902 CZ | TYR | 183 | 10.569 | 22.649 | 51.271 |
| ATOM | 903 OH | TYR | 183 | 11.118 | 23.814 | 50.768 |
| ATOM | 904 C | TYR | 183 | 9.927 | 19.920 | 55.285 |
| ATOM | 905 O | TYR | 183 | 11.085 | 20.213 | 55.620 |
| ATOM | 906 N | ALA | 184 | 8.863 | 20.642 | 55.604 |
| ATOM | 907 CA | ALA | 184 | 8.981 | 21.884 | 56.336 |
| ATOM | 908 CB | ALA | 184 | 7.597 | 22.407 | 56.705 |
| ATOM | 909 C | ALA | 184 | 9.884 | 21.753 | 57.570 |
| ATOM | 910 O | ALA | 184 | 10.780 | 22.585 | 57.797 |

FIGURE 1T

|  |  |  | Residue |  |  |  |
|---|---|---|---|---|---|---|
|  | Atom |  | AA | No. | X | Y | Z |
| ATOM | 911 | N | ASN | 185 | 9.707 | 20.661 | 58.312 |
| ATOM | 912 | CA | ASN | 185 | 10.498 | 20.406 | 59.522 |
| ATOM | 913 | CB | ASN | 185 | 10.141 | 19.035 | 60.144 |
| ATOM | 914 | CG | ASN | 185 | 8.661 | 18.902 | 60.536 |
| ATOM | 915 | OD1 | ASN | 185 | 7.936 | 19.888 | 60.615 |
| ATOM | 916 | ND2 | ASN | 185 | 8.218 | 17.668 | 60.788 |
| ATOM | 917 | C | ASN | 185 | 12.012 | 20.460 | 59.254 |
| ATOM | 918 | O | ASN | 185 | 12.697 | 21.360 | 59.736 |
| ATOM | 919 | N | VAL | 186 | 12.514 | 19.514 | 58.455 |
| ATOM | 920 | CA | VAL | 186 | 13.938 | 19.428 | 58.130 |
| ATOM | 921 | CB | VAL | 186 | 14.208 | 18.429 | 57.009 |
| ATOM | 922 | CG1 | VAL | 186 | 15.686 | 18.432 | 56.670 |
| ATOM | 923 | CG2 | VAL | 186 | 13.734 | 17.047 | 57.408 |
| ATOM | 924 | C | VAL | 186 | 14.404 | 20.761 | 57.644 |
| ATOM | 925 | O | VAL | 186 | 15.520 | 21.193 | 57.919 |
| ATOM | 926 | N | GLN | 187 | 13.529 | 21.387 | 56.877 |
| ATOM | 927 | CA | GLN | 187 | 13.802 | 22.686 | 56.340 |
| ATOM | 928 | CB | GLN | 187 | 12.521 | 23.248 | 55.702 |
| ATOM | 929 | CG | GLN | 187 | 12.374 | 24.776 | 55.692 |
| ATOM | 930 | CD | GLN | 187 | 13.573 | 25.509 | 55.070 |
| ATOM | 931 | OE1 | GLN | 187 | 14.430 | 24.899 | 54.416 |
| ATOM | 932 | NE2 | GLN | 187 | 13.649 | 26.825 | 55.301 |
| ATOM | 933 | C | GLN | 187 | 14.310 | 23.566 | 57.473 |
| ATOM | 934 | O | GLN | 187 | 15.514 | 23.881 | 57.542 |
| ATOM | 935 | N | ALA | 188 | 13.402 | 23.846 | 58.409 |
| ATOM | 936 | CA | ALA | 188 | 13.678 | 24.704 | 59.554 |
| ATOM | 937 | CB | ALA | 188 | 12.389 | 24.980 | 60.304 |
| ATOM | 938 | C | ALA | 188 | 14.752 | 24.181 | 60.514 |
| ATOM | 939 | O | ALA | 188 | 15.821 | 24.814 | 60.672 |
| ATOM | 940 | N | SER | 189 | 14.468 | 23.031 | 61.140 |
| ATOM | 941 | CA | SER | 189 | 15.379 | 22.402 | 62.101 |
| ATOM | 942 | CB | SER | 189 | 14.836 | 21.038 | 62.519 |
| ATOM | 943 | OG | SER | 189 | 14.642 | 20.216 | 61.390 |
| ATOM | 944 | C | SER | 189 | 16.806 | 22.262 | 61.562 |
| ATOM | 945 | O | SER | 189 | 17.758 | 22.122 | 62.341 |
| ATOM | 946 | N | MET | 190 | 16.936 | 22.296 | 60.232 |
| ATOM | 947 | CA | MET | 190 | 18.229 | 22.187 | 59.575 |
| ATOM | 948 | CB | MET | 190 | 18.214 | 21.026 | 58.594 |
| ATOM | 949 | CG | MET | 190 | 17.992 | 19.714 | 59.275 |
| ATOM | 950 | SD | MET | 190 | 19.144 | 19.446 | 60.655 |
| ATOM | 951 | CE | MET | 190 | 20.815 | 19.750 | 59.914 |
| ATOM | 952 | C | MET | 190 | 18.697 | 23.468 | 58.883 |
| ATOM | 953 | O | MET | 190 | 19.888 | 23.575 | 58.517 |
| ATOM | 954 | N | ALA | 191 | 17.761 | 24.409 | 58.687 |
| ATOM | 955 | CA | ALA | 191 | 18.024 | 25.716 | 58.053 |
| ATOM | 956 | CB | ALA | 191 | 19.055 | 26.516 | 58.901 |
| ATOM | 957 | C | ALA | 191 | 18.493 | 25.603 | 56.588 |
| ATOM | 958 | O | ALA | 191 | 19.533 | 26.178 | 56.177 |

FIGURE 1U

|  |  | Residue |  |  |  |  |
|---|---|---|---|---|---|---|
| Atom |  | AA | No. | X | Y | Z |
| ATOM | 959 N | LYS | 192 | 17.664 | 24.948 | 55.785 |
| ATOM | 960 CA | LYS | 192 | 18.024 | 24.702 | 54.403 |
| ATOM | 961 CB | LYS | 192 | 17.410 | 23.372 | 53.953 |
| ATOM | 962 CG | LYS | 192 | 17.860 | 22.145 | 54.741 |
| ATOM | 963 CD | LYS | 192 | 19.175 | 21.541 | 54.224 |
| ATOM | 964 CE | LYS | 192 | 20.365 | 22.496 | 54.321 |
| ATOM | 965 NZ | LYS | 192 | 21.668 | 21.845 | 54.012 |
| ATOM | 966 C | LYS | 192 | 17.746 | 25.762 | 53.347 |
| ATOM | 967 O | LYS | 192 | 16.751 | 26.480 | 53.417 |
| ATOM | 968 N | LYS | 193 | 18.660 | 25.863 | 52.384 |
| ATOM | 969 CA | LYS | 193 | 18.493 | 26.759 | 51.246 |
| ATOM | 970 CB | LYS | 193 | 19.819 | 27.416 | 50.854 |
| ATOM | 971 CG | LYS | 193 | 20.350 | 28.415 | 51.904 |
| ATOM | 972 CD | LYS | 193 | 19.270 | 29.448 | 52.337 |
| ATOM | 973 CE | LYS | 193 | 19.493 | 29.995 | 53.791 |
| ATOM | 974 NZ | LYS | 193 | 18.215 | 30.335 | 54.589 |
| ATOM | 975 C | LYS | 193 | 18.037 | 25.741 | 50.212 |
| ATOM | 976 O | LYS | 193 | 18.547 | 24.621 | 50.226 |
| ATOM | 977 N | LEU | 194 | 17.150 | 26.129 | 49.291 |
| ATOM | 978 CA | LEU | 194 | 16.572 | 25.180 | 48.334 |
| ATOM | 979 CB | LEU | 194 | 15.740 | 25.839 | 47.260 |
| ATOM | 980 CG | LEU | 194 | 14.288 | 25.380 | 47.517 |
| ATOM | 981 CD1 | LEU | 194 | 13.330 | 25.989 | 46.517 |
| ATOM | 982 CD2 | LEU | 194 | 14.145 | 23.865 | 47.484 |
| ATOM | 983 C | LEU | 194 | 17.327 | 23.992 | 47.793 |
| ATOM | 984 O | LEU | 194 | 16.748 | 22.911 | 47.688 |
| ATOM | 985 N | PRO | 195 | 18.570 | 24.175 | 47.322 |
| ATOM | 986 CD | PRO | 195 | 19.383 | 25.384 | 47.093 |
| ATOM | 987 CA | PRO | 195 | 19.246 | 22.951 | 46.838 |
| ATOM | 988 CB | PRO | 195 | 20.523 | 23.497 | 46.197 |
| ATOM | 989 CG | PRO | 195 | 20.771 | 24.802 | 47.016 |
| ATOM | 990 C | PRO | 195 | 19.550 | 22.026 | 48.067 |
| ATOM | 991 O | PRO | 195 | 20.548 | 22.207 | 48.781 |
| ATOM | 992 N | PHE | 196 | 18.642 | 21.100 | 48.357 |
| ATOM | 993 CA | PHE | 196 | 18.833 | 20.206 | 49.477 |
| ATOM | 994 CB | PHE | 196 | 18.543 | 20.946 | 50.782 |
| ATOM | 995 CG | PHE | 196 | 17.093 | 20.973 | 51.169 |
| ATOM | 996 CD1 | PHE | 196 | 16.507 | 19.879 | 50.931 |
| ATOM | 998 CE1 | PHE | 196 | 15.187 | 19.903 | 52.164 |
| ATOM | 999 CE2 | PHE | 196 | 14.980 | 22.133 | 51.309 |
| ATOM | 1000 CZ | PHE | 196 | 14.417 | 21.030 | 51.925 |
| ATOM | 1001 C | PHE | 196 | 17.938 | 18.981 | 49.339 |
| ATOM | 1002 O | PHE | 196 | 16.794 | 19.101 | 48.894 |
| ATOM | 1003 N | GLY | 197 | 18.453 | 17.816 | 49.742 |
| ATOM | 1004 CA | GLY | 197 | 17.692 | 16.578 | 49.651 |
| ATOM | 1005 C | GLY | 197 | 17.358 | 16.022 | 51.019 |
| ATOM | 1006 O | GLY | 197 | 17.786 | 16.583 | 52.016 |

FIGURE 1V

| Atom | | Residue AA | No. | X | Y | Z |
|---|---|---|---|---|---|---|
| ATOM | 1007 N | ILE | 198 | 16.606 | 14.927 | 51.078 |
| ATOM | 1008 CA | ILE | 198 | 16.225 | 14.303 | 52.356 |
| ATOM | 1009 CB | ILE | 198 | 14.857 | 14.824 | 52.866 |
| ATOM | 1010 CG2 | ILE | 198 | 14.576 | 14.286 | 54.243 |
| ATOM | 1011 CG1 | ILE | 198 | 14.831 | 16.338 | 52.959 |
| ATOM | 1012 CD1 | ILE | 198 | 13.487 | 16.856 | 53.414 |
| ATOM | 1013 C | ILE | 198 | 16.090 | 12.767 | 52.226 |
| ATOM | 1014 O | ILE | 198 | 14.975 | 12.240 | 52.060 |
| ATOM | 1015 N | GLY | 199 | 17.199 | 12.041 | 52.343 |
| ATOM | 1016 CA | GLY | 199 | 17.132 | 10.590 | 52.203 |
| ATOM | 1017 C | GLY | 199 | 16.592 | 9.851 | 53.408 |
| ATOM | 1018 O | GLY | 199 | 16.372 | 10.456 | 54.439 |
| ATOM | 1019 N | GLN | 200 | 16.337 | 8.559 | 53.275 |
| ATOM | 1020 CA | GLN | 200 | 15.856 | 7.775 | 54.396 |
| ATOM | 1021 CB | GLN | 200 | 14.608 | 8.408 | 55.022 |
| ATOM | 1022 CG | GLN | 200 | 13.341 | 8.367 | 54.181 |
| ATOM | 1023 CD | GLN | 200 | 12.085 | 7.886 | 54.966 |
| ATOM | 1024 OE1 | GLN | 200 | 10.978 | 8.413 | 54.792 |
| ATOM | 1025 NE2 | GLN | 200 | 12.256 | 6.863 | 55.803 |
| ATOM | 1026 C | GLN | 200 | 15.573 | 6.321 | 54.039 |
| ATOM | 1027 O | GLN | 200 | 14.670 | 6.037 | 53.263 |
| ATOM | 1028 N | ILE | 201 | 16.335 | 5.388 | 54.600 |
| ATOM | 1029 CA | ILE | 201 | 16.114 | 3.962 | 54.330 |
| ATOM | 1030 CB | ILE | 201 | 17.283 | 3.157 | 54.793 |
| ATOM | 1031 CG2 | ILE | 201 | 17.009 | 1.685 | 54.662 |
| ATOM | 1032 CG1 | ILE | 201 | 18.492 | 3.575 | 54.002 |
| ATOM | 1033 CD1 | ILE | 201 | 19.711 | 2.913 | 54.456 |
| ATOM | 1034 C | ILE | 201 | 14.904 | 3.481 | 55.100 |
| ATOM | 1035 O | ILE | 201 | 14.591 | 4.007 | 56.166 |
| ATOM | 1036 N | GLY | 202 | 14.226 | 2.460 | 54.615 |
| ATOM | 1037 CA | GLY | 202 | 13.078 | 2.040 | 55.378 |
| ATOM | 1038 C | GLY | 202 | 12.239 | 0.888 | 54.893 |
| ATOM | 1039 O | GLY | 202 | 12.474 | 0.311 | 53.830 |
| ATOM | 1040 N | LYS | 203 | 11.243 | 0.569 | 55.713 |
| ATOM | 1041 CA | LYS | 203 | 10.331 | -0.509 | 55.437 |
| ATOM | 1042 CB | LYS | 203 | 9.987 | -1.241 | 56.740 |
| ATOM | 1043 CG | LYS | 203 | 10.196 | -2.740 | 56.698 |
| ATOM | 1044 CD | LYS | 203 | 11.657 | -3.080 | 56.855 |
| ATOM | 1045 CE | LYS | 203 | 12.006 | -4.469 | 56.326 |
| ATOM | 1046 NZ | LYS | 203 | 11.232 | -5.556 | 56.899 |
| ATOM | 1047 C | LYS | 203 | 9.064 | 0.017 | 54.733 |
| ATOM | 1048 O | LYS | 203 | 8.487 | 1.039 | 55.129 |
| ATOM | 1049 N | SER | 204 | 8.709 | -0.638 | 53.626 |
| ATOM | 1050 CA | SER | 204 | 7.510 | -0.317 | 52.852 |
| ATOM | 1051 CB | SER | 204 | 7.870 | 0.339 | 51.497 |
| ATOM | 1052 OG | SER | 204 | 8.096 | 1.758 | 51.576 |
| ATOM | 1053 C | SER | 204 | 6.851 | -1.687 | 52.670 |
| ATOM | 1054 O | SER | 204 | 7.545 | -2.691 | 52.669 |

FIGURE 1W

| Atom | | AA | Residue No. | X | Y | Z |
|---|---|---|---|---|---|---|
| ATOM | 1055 N | PHE | 205 | 5.528 | -1.739 | 52.590 |
| ATOM | 1056 CA | PHE | 205 | 4.830 | -3.015 | 52.460 |
| ATOM | 1057 CB | PHE | 205 | 4.150 | -3.443 | 53.784 |
| ATOM | 1058 CG | PHE | 205 | 5.052 | -3.437 | 55.008 |
| ATOM | 1059 CD1 | PHE | 205 | 5.324 | -2.258 | 55.693 |
| ATOM | 1060 CD2 | PHE | 205 | 5.596 | -4.611 | 55.490 |
| ATOM | 1061 CE1 | PHE | 205 | 6.114 | -2.251 | 56.819 |
| ATOM | 1062 CE2 | PHE | 205 | 6.388 | -4.599 | 56.618 |
| ATOM | 1063 CZ | PHE | 205 | 6.647 | -3.417 | 57.282 |
| ATOM | 1064 C | PHE | 205 | 3.748 | -2.957 | 51.384 |
| ATOM | 1065 O | PHE | 205 | 2.905 | -2.067 | 51.374 |
| ATOM | 1066 N | ARG | 206 | 3.716 | -3.980 | 50.545 |
| ATOM | 1067 CA | ARG | 206 | 2.750 | -4.082 | 49.455 |
| ATOM | 1068 CB | ARG | 206 | 3.479 | -4.007 | 48.122 |
| ATOM | 1069 CG | ARG | 206 | 3.246 | -2.730 | 47.369 |
| ATOM | 1070 CD | ARG | 206 | 4.122 | -1.569 | 47.856 |
| ATOM | 1071 NE | ARG | 206 | 5.071 | -1.073 | 46.834 |
| ATOM | 1072 CZ | ARG | 206 | 4.798 | -0.830 | 45.534 |
| ATOM | 1073 NH1 | ARG | 206 | 3.575 | -1.030 | 45.015 |
| ATOM | 1074 NH2 | ARG | 206 | 5.765 | -1.360 | 44.731 |
| ATOM | 1075 C | ARG | 206 | 1.978 | -5.398 | 49.503 |
| ATOM | 1076 O | ARG | 206 | 2.574 | -6.489 | 49.485 |
| ATOM | 1077 N | ASN | 207 | 0.656 | -5.299 | 49.564 |
| ATOM | 1078 CA | ASN | 207 | 0.206 | -6.481 | 49.585 |
| ATOM | 1079 CB | ASN | 207 | -1.603 | -6.104 | 50.082 |
| ATOM | 1080 CG | ASN | 207 | -2.454 | -7.317 | 50.461 |
| ATOM | 1081 OD1 | ASN | 207 | -2.051 | -8.483 | 50.308 |
| ATOM | 1082 ND2 | ASN | 207 | -3.647 | -7.036 | 50.980 |
| ATOM | 1083 C | ASN | 207 | -0.276 | -6.966 | 48.134 |
| ATOM | 1084 O | ASN | 207 | -1.221 | -6.643 | 47.401 |
| ATOM | 1085 N | GLU | 208 | 0.743 | -7.731 | 47.731 |
| ATOM | 1086 CA | GLU | 208 | 0.888 | -8.258 | 46.356 |
| ATOM | 1087 CB | GLU | 208 | 2.298 | -8.843 | 46.164 |
| ATOM | 1088 CG | GLU | 208 | 2.966 | -8.376 | 44.889 |
| ATOM | 1089 CD | GLU | 208 | 2.847 | -6.871 | 44.637 |
| ATOM | 1090 OE1 | GLU | 208 | 3.887 | -6.191 | 44.762 |
| ATOM | 1091 OE2 | GLU | 208 | 1.741 | -6.362 | 44.299 |
| ATOM | 1092 C | GLU | 208 | -0.174 | -9.223 | 45.783 |
| ATOM | 1093 O | GLU | 208 | -1.329 | -9.263 | 46.256 |
| ATOM | 1094 N | ILE | 209 | 0.196 | -9.936 | 44.712 |
| ATOM | 1095 CA | ILE | 209 | -0.728 | -10.881 | 44.079 |
| ATOM | 1096 CB | ILE | 209 | -1.254 | -10.373 | 42.687 |
| ATOM | 1097 CG2 | ILE | 209 | -2.408 | -9.335 | 42.885 |
| ATOM | 1098 CG1 | ILE | 209 | -0.097 | -9.886 | 41.782 |
| ATOM | 1099 CD1 | ILE | 209 | 0.434 | -8.495 | 42.078 |
| ATOM | 1100 C | ILE | 209 | -0.086 | -12.256 | 43.928 |
| ATOM | 1101 O | ILE | 209 | -0.404 | -13.216 | 44.680 |
| ATOM | 1102 N | THR | 210 | 0.860 | -12.320 | 42.992 |

FIGURE 1X

|  |  | Residue |  |  |  |
|---|---|---|---|---|---|
| Atom |  | AA No. | X | Y | Z |
| ATOM | 1103 CA | THR 210 | 1.601 | -13.541 | 42.709 |
| ATOM | 1104 CB | THR 210 | 1.236 | -14.054 | 41.280 |
| ATOM | 1105 OG1 | THR 210 | 1.976 | -15.244 | 40.986 |
| ATOM | 1106 CG2 | THR 210 | 1.473 | -12.960 | 40.209 |
| ATOM | 1107 C | THR 210 | 3.113 | -13.234 | 42.891 |
| ATOM | 1108 O | THR 210 | 3.912 | -13.364 | 41.942 |
| ATOM | 1109 N | PRO 211 | 3.515 | -12.825 | 44.132 |
| ATOM | 1110 CD | PRO 211 | 2.756 | -12.743 | 45.404 |
| ATOM | 1111 CA | PRO 211 | 4.915 | -12.503 | 44.388 |
| ATOM | 1112 CB | PRO 211 | 5.024 | -12.682 | 45.898 |
| ATOM | 1113 CG | PRO 211 | 3.755 | -12.095 | 46.353 |
| ATOM | 1114 C | PRO 211 | 5.938 | -13.271 | 43.558 |
| ATOM | 1115 O | PRO 211 | 6.085 | -14.506 | 43.654 |
| ATOM | 1116 N | GLY 212 | 6.490 | -12.508 | 42.617 |
| ATOM | 1117 CA | GLY 212 | 7.501 | -12.991 | 41.701 |
| ATOM | 1118 C | GLY 212 | 8.781 | -13.409 | 42.394 |
| ATOM | 1119 O | GLY 212 | 9.524 | -12.585 | 42.957 |
| ATOM | 1120 N | ASN 213 | 8.990 | -14.723 | 42.350 |
| ATOM | 1121 CA | ASN 213 | 10.124 | -15.434 | 42.945 |
| ATOM | 1122 CB | ASN 213 | 10.594 | -16.565 | 42.002 |
| ATOM | 1123 CG | ASN 213 | 10.700 | -16.119 | 40.514 |
| ATOM | 1124 OD1 | ASN 213 | 9.786 | -15.478 | 39.971 |
| ATOM | 1125 ND2 | ASN 213 | 11.823 | -16.465 | 39.858 |
| ATOM | 1126 C | ASN 213 | 11.305 | -14.613 | 43.517 |
| ATOM | 1127 O | ASN 213 | 11.668 | -13.565 | 42.996 |
| ATOM | 1128 N | PHE 214 | 11.831 | -15.082 | 44.648 |
| ATOM | 1129 CA | PHE 214 | 12.930 | -14.444 | 45.340 |
| ATOM | 1130 CB | PHE 214 | 14.247 | -14.698 | 44.622 |
| ATOM | 1131 CG | PHE 214 | 15.379 | -15.038 | 45.546 |
| ATOM | 1132 CD1 | PHE 214 | 16.688 | -14.759 | 45.203 |
| ATOM | 1133 CD2 | PHE 214 | 15.137 | -15.671 | 46.748 |
| ATOM | 1134 CE1 | PHE 214 | 17.725 | -15.107 | 46.037 |
| ATOM | 1135 CE2 | PHE 214 | 16.168 | -16.025 | 47.591 |
| ATOM | 1136 CZ | PHE 214 | 17.459 | -15.744 | 47.236 |
| ATOM | 1137 C | PHE 214 | 12.762 | -12.970 | 45.612 |
| ATOM | 1138 O | PHE 214 | 11.724 | -12.359 | 45.328 |
| ATOM | 1139 N | ILE 215 | 13.850 | -12.408 | 46.119 |
| ATOM | 1140 CA | ILE 215 | 13.943 | -11.009 | 46.497 |
| ATOM | 1141 CB | ILE 215 | 15.411 | -10.603 | 46.832 |
| ATOM | 1142 CG2 | ILE 215 | 15.430 | -9.446 | 47.791 |
| ATOM | 1143 CG1 | ILE 215 | 16.156 | -11.732 | 47.522 |
| ATOM | 1144 CD1 | ILE 215 | 17.555 | -11.356 | 47.885 |
| ATOM | 1145 C | ILE 215 | 13.369 | -9.985 | 45.494 |
| ATOM | 1146 O | ILE 215 | 13.156 | -8.815 | 45.865 |
| ATOM | 1147 N | PHE 216 | 13.129 | -10.373 | 44.238 |
| ATOM | 1148 CA | PHE 216 | 12.590 | -9.384 | 43.311 |
| ATOM | 1149 CB | PHE 216 | 12.766 | -9.728 | 41.810 |
| ATOM | 1150 CG | PHE 216 | 12.693 | -11.233 | 41.452 |

FIGURE 1Y

| Atom | | AA | Residue No. | X | Y | Z |
|---|---|---|---|---|---|---|
| ATOM | 1151 CD1 | PHE | 216 | 11.571 | -11.762 | 40.765 |
| ATOM | 1152 CD2 | PHE | 216 | 13.816 | -12.076 | 41.622 |
| ATOM | 1153 CE1 | PHE | 216 | 11.579 | -13.076 | 40.244 |
| ATOM | 1154 CE2 | PHE | 216 | 13.827 | -13.408 | 41.095 |
| ATOM | 1155 CZ | PHE | 216 | 12.713 | -13.890 | 40.409 |
| ATOM | 1156 C | PHE | 216 | 11.174 | -8.954 | 43.655 |
| ATOM | 1157 O | PHE | 216 | 10.867 | -7.753 | 43.624 |
| ATOM | 1158 N | ARG | 217 | 10.311 | -9.898 | 44.010 |
| ATOM | 1159 CA | ARG | 217 | 8.961 | -9.483 | 44.380 |
| ATOM | 1160 CB | ARG | 217 | 7.932 | -9.752 | 43.273 |
| ATOM | 1161 CG | ARG | 217 | 7.030 | -8.552 | 42.961 |
| ATOM | 1162 CD | ARG | 217 | 5.864 | -8.929 | 42.050 |
| ATOM | 1163 NE | ARG | 217 | 4.737 | -9.519 | 42.785 |
| ATOM | 1164 CZ | ARG | 217 | 3.574 | -9.900 | 42.235 |
| ATOM | 1165 NH1 | ARG | 217 | 3.363 | -9.770 | 40.927 |
| ATOM | 1166 NH2 | ARG | 217 | 2.591 | -10.372 | 42.997 |
| ATOM | 1167 C | ARG | 217 | 8.523 | -10.098 | 45.710 |
| ATOM | 1168 O | ARG | 217 | 7.943 | -11.195 | 45.758 |
| ATOM | 1169 N | THR | 218 | 8.772 | -9.337 | 46.778 |
| ATOM | 1170 CA | THR | 218 | 8.472 | -9.725 | 48.149 |
| ATOM | 1171 CB | THR | 218 | 9.711 | -9.500 | 49.071 |
| ATOM | 1172 OG1 | THR | 218 | 10.388 | -8.300 | 48.671 |
| ATOM | 1173 CG2 | THR | 218 | 10.689 | -10.687 | 49.019 |
| ATOM | 1174 C | THR | 218 | 7.346 | -8.848 | 48.648 |
| ATOM | 1175 O | THR | 218 | 7.290 | -7.657 | 48.326 |
| ATOM | 1176 N | ARG | 219 | 6.473 | -9.430 | 49.461 |
| ATOM | 1177 CA | ARG | 219 | 5.336 | -8.701 | 50.023 |
| ATOM | 1178 CB | ARG | 219 | 4.425 | -9.658 | 50.798 |
| ATOM | 1179 CG | ARG | 219 | 4.364 | -11.050 | 50.203 |
| ATOM | 1180 CD | ARG | 219 | 3.026 | -11.722 | 50.457 |
| ATOM | 1181 NE | ARG | 219 | 1.853 | -10.948 | 49.978 |
| ATOM | 1182 CZ | ARG | 219 | 1.079 | -11.238 | 48.904 |
| ATOM | 1183 NH1 | ARG | 219 | 1.309 | -12.292 | 48.103 |
| ATOM | 1184 NH2 | ARG | 219 | -0.019 | -10.520 | 48.676 |
| ATOM | 1185 C | ARG | 219 | 5.824 | -7.607 | 50.962 |
| ATOM | 1186 O | ARG | 219 | 5.088 | -6.691 | 51.282 |
| ATOM | 1187 N | GLU | 220 | 7.072 | -7.707 | 51.392 |
| ATOM | 1188 CA | GLU | 220 | 7.645 | -6.746 | 52.314 |
| ATOM | 1189 CB | GLU | 220 | 7.668 | -7.366 | 53.702 |
| ATOM | 1190 CG | GLU | 220 | 8.390 | -6.579 | 54.764 |
| ATOM | 1191 CD | GLU | 220 | 8.699 | -7.428 | 55.954 |
| ATOM | 1192 OE1 | GLU | 220 | 9.880 | -7.505 | 56.326 |
| ATOM | 1193 OE2 | GLU | 220 | 7.765 | -8.047 | 56.491 |
| ATOM | 1194 C | GLU | 220 | 9.057 | -6.481 | 51.837 |
| ATOM | 1195 O | GLU | 220 | 9.751 | -7.430 | 51.491 |
| ATOM | 1196 N | PHE | 221 | 9.504 | -5.218 | 51.894 |
| ATOM | 1197 CA | PHE | 221 | 10.836 | -4.815 | 51.400 |
| ATOM | 1198 CB | PHE | 221 | 10.783 | -4.649 | 49.875 |

FIGURE 1Z

| Atom | | AA | Residue No. | X | Y | Z |
|---|---|---|---|---|---|---|
| ATOM | 1199 CG | PHE | 221 | 9.708 | -3.696 | 49.419 |
| ATOM | 1200 CD1 | PHE | 221 | 9.956 | -2.330 | 49.346 |
| ATOM | 1201 CD2 | PHE | 221 | 8.407 | -4.164 | 49.142 |
| ATOM | 1202 CE1 | PHE | 221 | 8.926 | -1.445 | 49.012 |
| ATOM | 1203 CE2 | PHE | 221 | 7.360 | -3.282 | 48.805 |
| ATOM | 1204 CZ | PHE | 221 | 7.619 | -1.928 | 48.743 |
| ATOM | 1205 C | PHE | 221 | 11.326 | -3.494 | 51.951 |
| ATOM | 1206 O | PHE | 221 | 10.551 | -2.673 | 52.440 |
| ATOM | 1207 N | GLU | 222 | 12.597 | -3.237 | 51.700 |
| ATOM | 1208 CA | GLU | 222 | 13.231 | -2.009 | 52.125 |
| ATOM | 1209 CB | GLU | 222 | 14.496 | -2.323 | 52.913 |
| ATOM | 1210 CG | GLU | 222 | 14.301 | -2.519 | 54.371 |
| ATOM | 1211 CD | GLU | 222 | 15.604 | -2.573 | 55.101 |
| ATOM | 1212 OE1 | GLU | 222 | 16.104 | -1.520 | 55.524 |
| ATOM | 1213 OE2 | GLU | 222 | 16.136 | -3.676 | 55.248 |
| ATOM | 1214 C | GLU | 222 | 13.595 | -1.132 | 50.922 |
| ATOM | 1215 O | GLU | 222 | 14.251 | -1.607 | 49.988 |
| ATOM | 1216 N | GLN | 223 | 13.206 | 0.141 | 50.983 |
| ATOM | 1217 CA | GLN | 223 | 13.480 | 1.112 | 49.938 |
| ATOM | 1218 CB | GLN | 223 | 12.461 | 2.215 | 50.000 |
| ATOM | 1219 CG | GLN | 223 | 11.053 | 1.686 | 50.096 |
| ATOM | 1220 CD | GLN | 223 | 10.275 | 1.809 | 48.803 |
| ATOM | 1221 OE1 | GLN | 223 | 10.824 | 1.639 | 47.716 |
| ATOM | 1222 NE2 | GLN | 223 | 8.980 | 2.098 | 48.919 |
| ATOM | 1223 C | GLN | 223 | 14.863 | 1.698 | 50.093 |
| ATOM | 1224 O | GLN | 223 | 15.811 | 0.967 | 50.328 |
| ATOM | 1225 N | MET | 224 | 14.990 | 3.003 | 49.922 |
| ATOM | 1226 CA | MET | 224 | 16.271 | 3.663 | 50.050 |
| ATOM | 1227 CB | MET | 224 | 17.370 | 2.824 | 49.450 |
| ATOM | 1228 CG | MET | 224 | 18.506 | 2.649 | 50.353 |
| ATOM | 1229 SD | MET | 224 | 19.018 | 1.020 | 50.206 |
| ATOM | 1230 CE | MET | 224 | 20.692 | 1.255 | 49.950 |
| ATOM | 1231 C | MET | 224 | 16.185 | 4.930 | 49.267 |
| ATOM | 1232 O | MET | 224 | 17.081 | 5.242 | 48.507 |
| ATOM | 1233 N | GLU | 225 | 15.128 | 5.689 | 49.512 |
| ATOM | 1234 CA | GLU | 225 | 14.827 | 6.937 | 48.806 |
| ATOM | 1235 CB | GLU | 225 | 13.335 | 7.143 | 48.845 |
| ATOM | 1236 CG | GLU | 225 | 12.636 | 5.820 | 48.712 |
| ATOM | 1237 CD | GLU | 225 | 11.176 | 5.961 | 48.533 |
| ATOM | 1238 OE1 | GLU | 225 | 10.626 | 6.903 | 49.127 |
| ATOM | 1239 OE2 | GLU | 225 | 10.582 | 5.139 | 47.798 |
| ATOM | 1240 C | GLU | 225 | 15.517 | 8.213 | 49.247 |
| ATOM | 1241 O | GLU | 225 | 16.087 | 8.285 | 50.326 |
| ATOM | 1242 N | LEU | 226 | 15.447 | 9.225 | 48.394 |
| ATOM | 1243 CA | LEU | 226 | 16.054 | 10.521 | 48.660 |
| ATOM | 1244 CB | LEU | 226 | 17.509 | 10.555 | 48.197 |
| ATOM | 1245 CG | LEU | 226 | 18.235 | 11.898 | 48.160 |
| ATOM | 1246 CD1 | LEU | 226 | 19.699 | 11.670 | 48.286 |

FIGURE 1AA

| Atom | | AA | Residue No. | X | Y | Z |
|---|---|---|---|---|---|---|
| ATOM | 1247 | CD2 | LEU 226 | 17.964 | 12.641 | 46.880 |
| ATOM | 1248 | C | LEU 226 | 15.291 | 11.466 | 47.808 |
| ATOM | 1249 | O | LEU 226 | 15.174 | 11.231 | 46.630 |
| ATOM | 1250 | N | GLU 227 | 14.742 | 12.513 | 48.394 |
| ATOM | 1251 | CA | GLU 227 | 14.000 | 13.483 | 47.615 |
| ATOM | 1252 | CB | GLU 227 | 12.660 | 13.794 | 48.251 |
| ATOM | 1253 | CG | GLU 227 | 11.498 | 13.457 | 47.369 |
| ATOM | 1254 | CD | GLU 227 | 11.245 | 11.977 | 47.307 |
| ATOM | 1255 | OE1 | GLU 227 | 10.089 | 11.573 | 47.435 |
| ATOM | 1256 | OE2 | GLU 227 | 12.197 | 11.202 | 47.142 |
| ATOM | 1257 | C | GLU 227 | 14.822 | 14.729 | 47.564 |
| ATOM | 1258 | O | GLU 227 | 15.109 | 15.318 | 48.606 |
| ATOM | 1259 | N | PHE 228 | 15.244 | 15.103 | 46.359 |
| ATOM | 1260 | CA | PHE 228 | 16.065 | 16.300 | 46.146 |
| ATOM | 1261 | CB | PHE 228 | 17.058 | 16.061 | 45.000 |
| ATOM | 1262 | CG | PHE 228 | 18.128 | 17.085 | 44.898 |
| ATOM | 1263 | CD1 | PHE 228 | 17.895 | 18.296 | 44.284 |
| ATOM | 1264 | CD2 | PHE 228 | 19.387 | 16.828 | 45.389 |
| ATOM | 1265 | CE1 | PHE 228 | 18.911 | 19.232 | 44.162 |
| ATOM | 1266 | CE2 | PHE 228 | 20.413 | 17.761 | 45.268 |
| ATOM | 1267 | CZ | PHE 228 | 20.176 | 18.957 | 44.657 |
| ATOM | 1268 | C | PHE 228 | 15.108 | 17.444 | 45.799 |
| ATOM | 1269 | O | PHE 228 | 14.272 | 17.295 | 44.888 |
| ATOM | 1270 | N | PHE 229 | 15.149 | 18.519 | 46.599 |
| ATOM | 1271 | CA | PHE 229 | 14.303 | 19.689 | 46.363 |
| ATOM | 1272 | CB | PHE 229 | 13.751 | 20.236 | 47.662 |
| ATOM | 1273 | CG | PHE 229 | 12.793 | 19.311 | 48.281 |
| ATOM | 1274 | CD1 | PHE 229 | 13.240 | 18.169 | 48.897 |
| ATOM | 1275 | CD2 | PHE 229 | 11.443 | 19.469 | 48.084 |
| ATOM | 1276 | CE1 | PHE 229 | 12.354 | 17.193 | 49.289 |
| ATOM | 1277 | CE2 | PHE 229 | 10.550 | 18.491 | 48.477 |
| ATOM | 1278 | CZ | PHE 229 | 11.003 | 17.354 | 49.074 |
| ATOM | 1279 | C | PHE 229 | 15.104 | 20.664 | 45.530 |
| ATOM | 1280 | O | PHE 229 | 16.285 | 20.968 | 45.823 |
| ATOM | 1281 | N | CYS 230 | 14.444 | 21.105 | 44.460 |
| ATOM | 1282 | CA | CYS 230 | 15.054 | 21.928 | 43.436 |
| ATOM | 1283 | CB | CYS 230 | 15.089 | 21.104 | 42.153 |
| ATOM | 1284 | SG | CYS 230 | 16.294 | 21.646 | 40.991 |
| ATOM | 1285 | C | CYS 230 | 14.309 | 23.197 | 43.145 |
| ATOM | 1286 | O | CYS 230 | 13.074 | 23.187 | 43.119 |
| ATOM | 1287 | N | LYS 231 | 15.057 | 24.283 | 42.937 |
| ATOM | 1288 | CA | LYS 231 | 14.452 | 25.558 | 42.581 |
| ATOM | 1289 | CB | LYS 231 | 15.534 | 26.631 | 42.445 |
| ATOM | 1290 | CG | LYS 231 | 15.016 | 28.025 | 42.003 |
| ATOM | 1291 | CD | LYS 231 | 14.816 | 28.184 | 40.448 |
| ATOM | 1292 | CE | LYS 231 | 16.157 | 28.234 | 39.633 |
| ATOM | 1293 | NZ | LYS 231 | 16.027 | 28.079 | 38.130 |
| ATOM | 1294 | C | LYS 231 | 13.816 | 25.234 | 41.215 |

FIGURE 1BB

| Atom | | Residue AA | No. | X | Y | Z |
|---|---|---|---|---|---|---|
| ATOM | 1295 | O | LYS | 231 | 14.515 | 24.775 | 40.303 |
| ATOM | 1296 | N | PRO | 232 | 12.505 | 25.506 | 41.045 |
| ATOM | 1297 | CD | PRO | 232 | 11.797 | 26.323 | 42.045 |
| ATOM | 1298 | CA | PRO | 232 | 11.633 | 25.288 | 39.876 |
| ATOM | 1299 | CB | PRO | 232 | 10.518 | 26.304 | 40.095 |
| ATOM | 1300 | CG | PRO | 232 | 10.348 | 26.258 | 41.552 |
| ATOM | 1301 | C | PRO | 232 | 12.137 | 25.323 | 38.428 |
| ATOM | 1302 | O | PRO | 232 | 11.339 | 25.088 | 37.519 |
| ATOM | 1303 | N | GLY | 233 | 13.419 | 25.625 | 38.194 |
| ATOM | 1304 | CA | GLY | 233 | 13.933 | 25.674 | 36.832 |
| ATOM | 1305 | C | GLY | 233 | 14.897 | 24.556 | 36.506 |
| ATOM | 1306 | O | GLY | 233 | 14.862 | 23.975 | 35.431 |
| ATOM | 1307 | N | GLU | 234 | 15.671 | 24.159 | 37.491 |
| ATOM | 1308 | CA | GLU | 234 | 16.655 | 23.123 | 37.282 |
| ATOM | 1309 | CB | GLU | 234 | 17.792 | 23.356 | 38.247 |
| ATOM | 1310 | CG | GLU | 234 | 18.166 | 24.817 | 38.305 |
| ATOM | 1311 | CD | GLU | 234 | 18.391 | 25.329 | 39.738 |
| ATOM | 1312 | OE1 | GLU | 234 | 18.085 | 24.599 | 40.723 |
| ATOM | 1313 | OE2 | GLU | 234 | 18.880 | 26.480 | 39.881 |
| ATOM | 1314 | C | GLU | 234 | 16.188 | 21.663 | 37.346 |
| ATOM | 1315 | O | GLU | 234 | 17.020 | 20.743 | 37.325 |
| ATOM | 1316 | N | GLU | 235 | 14.876 | 21.436 | 37.376 |
| ATOM | 1317 | CA | GLU | 235 | 14.336 | 20.074 | 37.433 |
| ATOM | 1318 | CB | GLU | 235 | 12.833 | 20.031 | 37.058 |
| ATOM | 1319 | CG | GLU | 235 | 12.421 | 20.559 | 35.639 |
| ATOM | 1320 | CD | GLU | 235 | 12.479 | 22.105 | 35.479 |
| ATOM | 1321 | OE1 | GLU | 235 | 12.218 | 22.621 | 34.351 |
| ATOM | 1322 | OE2 | GLU | 235 | 12.772 | 22.796 | 36.486 |
| ATOM | 1323 | C | GLU | 235 | 15.155 | 19.071 | 36.607 |
| ATOM | 1324 | O | GLU | 235 | 15.538 | 18.025 | 37.103 |
| ATOM | 1325 | N | ILE | 236 | 15.547 | 19.463 | 35.401 |
| ATOM | 1326 | CA | ILE | 236 | 16.316 | 18.588 | 34.534 |
| ATOM | 1327 | CB | ILE | 236 | 16.147 | 18.903 | 33.037 |
| ATOM | 1328 | CG2 | ILE | 236 | 14.757 | 18.479 | 32.572 |
| ATOM | 1329 | CG1 | ILE | 236 | 16.514 | 20.369 | 32.716 |
| ATOM | 1330 | CD1 | ILE | 236 | 15.435 | 21.446 | 32.982 |
| ATOM | 1331 | C | ILE | 236 | 17.784 | 18.526 | 34.840 |
| ATOM | 1332 | O | ILE | 236 | 18.383 | 17.480 | 34.680 |
| ATOM | 1333 | N | GLU | 237 | 18.379 | 19.633 | 35.258 |
| ATOM | 1334 | CA | GLU | 237 | 19.805 | 19.626 | 35.590 |
| ATOM | 1335 | CB | GLU | 237 | 20.240 | 20.953 | 36.221 |
| ATOM | 1336 | CG | GLU | 237 | 20.463 | 22.051 | 35.248 |
| ATOM | 1337 | CD | GLU | 237 | 19.412 | 22.033 | 34.153 |
| ATOM | 1338 | OE1 | GLU | 237 | 18.259 | 22.473 | 34.424 |
| ATOM | 1339 | OE2 | GLU | 237 | 19.731 | 21.551 | 33.027 |
| ATOM | 1340 | C | GLU | 237 | 19.976 | 18.560 | 36.637 |
| ATOM | 1341 | O | GLU | 237 | 20.854 | 17.691 | 36.558 |
| ATOM | 1342 | N | TRP | 238 | 19.091 | 18.615 | 37.616 |

FIGURE 1CC

| Atom | | Residue AA | No. | X | Y | Z |
|---|---|---|---|---|---|---|
| ATOM | 1343 | CA | TRP | 238 | 19.183 | 17.676 | 38.662 |
| ATOM | 1344 | CB | TRP | 238 | 18.478 | 18.199 | 39.890 |
| ATOM | 1345 | CG | TRP | 238 | 19.248 | 19.380 | 40.414 |
| ATOM | 1346 | CD2 | TRP | 238 | 20.565 | 19.364 | 40.981 |
| ATOM | 1347 | CE2 | TRP | 238 | 20.940 | 20.703 | 41.209 |
| ATOM | 1348 | CE3 | TRP | 238 | 21.466 | 18.349 | 41.308 |
| ATOM | 1349 | CD1 | TRP | 238 | 18.886 | 20.691 | 40.340 |
| ATOM | 1350 | NE1 | TRP | 238 | 19.896 | 21.495 | 40.812 |
| ATOM | 1351 | CZ2 | TRP | 238 | 22.172 | 21.049 | 41.744 |
| ATOM | 1352 | CZ3 | TRP | 238 | 22.687 | 18.696 | 41.838 |
| ATOM | 1353 | CH2 | TRP | 238 | 23.030 | 20.033 | 42.050 |
| ATOM | 1354 | C | TRP | 238 | 18.721 | 16.361 | 38.144 |
| ATOM | 1355 | O | TRP | 238 | 19.518 | 15.436 | 38.117 |
| ATOM | 1356 | N | GLN | 239 | 17.555 | 16.327 | 37.522 |
| ATOM | 1357 | CA | GLN | 239 | 17.040 | 15.074 | 36.995 |
| ATOM | 1358 | CB | GLN | 239 | 15.904 | 15.346 | 36.031 |
| ATOM | 1359 | CG | GLN | 239 | 15.656 | 14.255 | 35.009 |
| ATOM | 1360 | CD | GLN | 239 | 15.320 | 12.921 | 35.619 |
| ATOM | 1361 | OE1 | GLN | 239 | 15.860 | 11.884 | 35.228 |
| ATOM | 1362 | NE2 | GLN | 239 | 14.417 | 12.932 | 36.571 |
| ATOM | 1363 | C | GLN | 239 | 18.101 | 14.194 | 36.341 |
| ATOM | 1364 | O | GLN | 239 | 17.953 | 12.982 | 36.241 |
| ATOM | 1365 | N | ASN | 240 | 19.187 | 14.795 | 35.901 |
| ATOM | 1366 | CA | ASN | 240 | 20.232 | 14.002 | 35.303 |
| ATOM | 1367 | CB | ASN | 240 | 20.692 | 14.591 | 33.970 |
| ATOM | 1368 | CG | ASN | 240 | 19.662 | 14.399 | 32.858 |
| ATOM | 1369 | OD1 | ASN | 240 | 19.467 | 15.285 | 32.021 |
| ATOM | 1370 | ND2 | ASN | 240 | 18.994 | 13.241 | 32.848 |
| ATOM | 1371 | C | ASN | 240 | 21.405 | 13.861 | 36.222 |
| ATOM | 1372 | O | ASN | 240 | 22.094 | 12.852 | 36.175 |
| ATOM | 1373 | N | TYR | 241 | 21.648 | 14.869 | 37.049 |
| ATOM | 1374 | CA | TYR | 241 | 22.772 | 14.821 | 37.970 |
| ATOM | 1375 | CB | TYR | 241 | 22.748 | 16.017 | 38.922 |
| ATOM | 1376 | CG | TYR | 241 | 23.771 | 15.895 | 40.018 |
| ATOM | 1377 | CD1 | TYR | 241 | 23.390 | 15.596 | 41.327 |
| ATOM | 1378 | CE1 | TYR | 241 | 24.339 | 15.400 | 42.319 |
| ATOM | 1379 | CD2 | TYR | 241 | 25.127 | 15.998 | 39.736 |
| ATOM | 1380 | CE2 | TYR | 241 | 26.085 | 15.798 | 40.722 |
| ATOM | 1381 | CZ | TYR | 241 | 25.687 | 15.498 | 42.002 |
| ATOM | 1382 | OH | TYR | 241 | 26.655 | 15.252 | 42.934 |
| ATOM | 1383 | C | TYR | 241 | 22.732 | 13.522 | 38.760 |
| ATOM | 1384 | O | TYR | 241 | 23.714 | 12.786 | 38.876 |
| ATOM | 1385 | N | TRP | 242 | 21.561 | 13.221 | 39.268 |
| ATOM | 1386 | CA | TRP | 242 | 21.390 | 12.013 | 40.037 |
| ATOM | 1387 | CB | TRP | 242 | 20.100 | 12.115 | 40.879 |
| ATOM | 1388 | CG | TRP | 242 | 20.209 | 13.205 | 41.905 |
| ATOM | 1389 | CD2 | TRP | 242 | 21.014 | 13.180 | 43.087 |
| ATOM | 1390 | CE2 | TRP | 242 | 20.955 | 14.458 | 43.658 |

FIGURE 1DD

| Atom | | AA | Residue No. | X | Y | Z |
|---|---|---|---|---|---|---|
| ATOM | 1391 CE3 | TRP | 242 | 21.788 | 12.201 | 43.711 |
| ATOM | 1392 CD1 | TRP | 242 | 19.686 | 14.456 | 41.822 |
| ATOM | 1393 NE1 | TRP | 242 | 20.137 | 15.220 | 42.862 |
| ATOM | 1394 CZ2 | TRP | 242 | 21.651 | 14.794 | 44.837 |
| ATOM | 1395 CZ3 | TRP | 242 | 22.482 | 12.533 | 44.883 |
| ATOM | 1396 CH2 | TRP | 242 | 22.408 | 13.819 | 45.432 |
| ATOM | 1397 C | TRP | 242 | 21.454 | 10.739 | 39.176 |
| ATOM | 1398 O | TRP | 242 | 21.989 | 9.731 | 39.620 |
| ATOM | 1399 N | ALA | 243 | 20.946 | 10.798 | 37.940 |
| ATOM | 1400 CA | ALA | 243 | 20.968 | 9.642 | 37.027 |
| ATOM | 1401 CB | ALA | 243 | 20.304 | 9.991 | 35.648 |
| ATOM | 1402 C | ALA | 243 | 22.426 | 9.229 | 36.846 |
| ATOM | 1403 O | ALA | 243 | 22.793 | 8.073 | 37.062 |
| ATOM | 1404 N | THR | 244 | 23.261 | 10.216 | 36.556 |
| ATOM | 1405 CA | THR | 244 | 24.688 | 9.995 | 36.366 |
| ATOM | 1406 CB | THR | 244 | 25.408 | 11.328 | 35.976 |
| ATOM | 1407 OG1 | THR | 244 | 24.783 | 11.914 | 34.822 |
| ATOM | 1408 CG2 | THR | 244 | 26.874 | 11.081 | 35.690 |
| ATOM | 1409 C | THR | 244 | 25.296 | 9.462 | 37.677 |
| ATOM | 1410 O | THR | 244 | 26.005 | 8.448 | 37.696 |
| ATOM | 1411 N | PHE | 245 | 24.940 | 10.123 | 38.776 |
| ATOM | 1412 CA | PHE | 245 | 25.424 | 9.796 | 40.111 |
| ATOM | 1413 CB | PHE | 245 | 24.855 | 10.805 | 41.081 |
| ATOM | 1414 CG | PHE | 245 | 25.399 | 10.671 | 42.438 |
| ATOM | 1415 CD1 | PHE | 245 | 26.781 | 10.635 | 42.638 |
| ATOM | 1416 CD2 | PHE | 245 | 24.544 | 10.550 | 43.525 |
| ATOM | 1417 CE1 | PHE | 245 | 27.309 | 10.479 | 43.915 |
| ATOM | 1418 CE2 | PHE | 245 | 25.042 | 10.395 | 44.807 |
| ATOM | 1419 CZ | PHE | 245 | 26.432 | 10.358 | 45.007 |
| ATOM | 1420 C | PHE | 245 | 25.070 | 8.405 | 40.595 |
| ATOM | 1421 O | PHE | 245 | 25.924 | 7.669 | 41.070 |
| ATOM | 1422 N | ALA | 246 | 23.776 | 8.116 | 40.544 |
| ATOM | 1423 CA | ALA | 246 | 23.191 | 6.848 | 40.944 |
| ATOM | 1424 CB | ALA | 246 | 21.685 | 6.886 | 40.740 |
| ATOM | 1425 C | ALA | 246 | 23.790 | 5.743 | 40.110 |
| ATOM | 1426 O | ALA | 246 | 24.143 | 4.686 | 40.619 |
| ATOM | 1427 N | SER | 247 | 23.927 | 6.002 | 38.820 |
| ATOM | 1428 CA | SER | 247 | 24.474 | 5.011 | 37.918 |
| ATOM | 1429 CB | SER | 247 | 24.133 | 5.368 | 36.486 |
| ATOM | 1430 OG | SER | 247 | 22.720 | 5.425 | 36.368 |
| ATOM | 1431 C | SER | 247 | 25.953 | 4.870 | 38.120 |
| ATOM | 1432 O | SER | 247 | 26.490 | 3.772 | 38.096 |
| ATOM | 1433 N | ASP | 248 | 26.616 | 5.988 | 38.339 |
| ATOM | 1434 CA | ASP | 248 | 28.047 | 5.938 | 38.602 |
| ATOM | 1435 CB | ASP | 248 | 28.613 | 7.352 | 38.842 |
| ATOM | 1436 CG | ASP | 248 | 29.437 | 7.878 | 37.666 |
| ATOM | 1437 OD1 | ASP | 248 | 30.252 | 7.128 | 37.070 |
| ATOM | 1438 OD2 | ASP | 248 | 29.279 | 9.078 | 37.367 |

FIGURE 1EE

| Atom | | AA | Residue No. | X | Y | Z |
|---|---|---|---|---|---|---|
| ATOM | 1439 C | ASP | 248 | 28.208 | 5.094 | 39.887 |
| ATOM | 1440 O | ASP | 248 | 29.075 | 4.217 | 39.984 |
| ATOM | 1441 N | TRP | 249 | 27.328 | 5.333 | 40.851 |
| ATOM | 1442 CA | TRP | 249 | 27.371 | 4.604 | 42.098 |
| ATOM | 1443 CB | TRP | 249 | 26.151 | 4.970 | 42.941 |
| ATOM | 1444 CG | TRP | 249 | 26.263 | 4.536 | 44.351 |
| ATOM | 1445 CD2 | TRP | 249 | 25.592 | 3.424 | 44.977 |
| ATOM | 1446 CE2 | TRP | 249 | 26.070 | 3.342 | 46.290 |
| ATOM | 1447 CE3 | TRP | 249 | 24.647 | 2.481 | 44.548 |
| ATOM | 1448 CD1 | TRP | 249 | 27.080 | 5.070 | 45.288 |
| ATOM | 1449 NE1 | TRP | 249 | 26.976 | 4.358 | 46.453 |
| ATOM | 1450 CZ2 | TRP | 249 | 25.637 | 2.353 | 47.187 |
| ATOM | 1451 CZ3 | TRP | 249 | 24.218 | 1.490 | 45.446 |
| ATOM | 1452 CH2 | TRP | 249 | 24.714 | 1.440 | 46.741 |
| ATOM | 1453 C | TRP | 249 | 27.395 | 3.096 | 41.836 |
| ATOM | 1454 O | TRP | 249 | 28.339 | 2.403 | 42.185 |
| ATOM | 1455 N | LEU | 250 | 26.376 | 2.599 | 41.161 |
| ATOM | 1456 CA | LEU | 250 | 26.306 | 1.183 | 40.899 |
| ATOM | 1457 CB | LEU | 250 | 25.200 | 0.878 | 39.905 |
| ATOM | 1458 CG | LEU | 250 | 23.877 | 0.851 | 40.643 |
| ATOM | 1459 CD1 | LEU | 250 | 22.761 | 1.285 | 39.763 |
| ATOM | 1460 CD2 | LEU | 250 | 23.638 | -0.519 | 41.155 |
| ATOM | 1461 C | LEU | 250 | 27.615 | 0.563 | 40.475 |
| ATOM | 1462 O | LEU | 250 | 28.200 | -0.209 | 41.213 |
| ATOM | 1463 N | THR | 251 | 28.144 | 0.965 | 39.340 |
| ATOM | 1464 CA | THR | 251 | 29.382 | 0.352 | 38.908 |
| ATOM | 1465 CB | THR | 251 | 29.783 | 0.720 | 37.422 |
| ATOM | 1466 OG1 | THR | 251 | 30.107 | 2.119 | 37.309 |
| ATOM | 1467 CG2 | THR | 251 | 28.639 | 0.356 | 36.440 |
| ATOM | 1468 C | THR | 251 | 30.535 | 0.588 | 39.881 |
| ATOM | 1469 O | THR | 251 | 31.386 | -0.284 | 40.009 |
| ATOM | 1470 N | SER | 252 | 30.519 | 1.695 | 40.630 |
| ATOM | 1471 CA | SER | 252 | 31.610 | 1.992 | 41.581 |
| ATOM | 1472 CB | SER | 252 | 31.506 | 3.410 | 42.142 |
| ATOM | 1473 OG | SER | 252 | 30.281 | 3.623 | 42.819 |
| ATOM | 1474 C | SER | 252 | 31.693 | 0.986 | 42.715 |
| ATOM | 1475 O | SER | 252 | 32.787 | 0.727 | 43.233 |
| ATOM | 1476 N | ALA | 253 | 30.523 | 0.455 | 43.105 |
| ATOM | 1477 CA | ALA | 253 | 30.412 | -0.588 | 44.138 |
| ATOM | 1478 CB | ALA | 253 | 29.017 | -0.561 | 44.821 |
| ATOM | 1479 C | ALA | 253 | 30.678 | -1.939 | 43.412 |
| ATOM | 1480 O | ALA | 253 | 30.624 | -3.014 | 44.036 |
| ATOM | 1481 N | ASN | 254 | 30.981 | -1.835 | 42.098 |
| ATOM | 1482 CA | ASN | 254 | 31.346 | -2.936 | 41.163 |
| ATOM | 1483 CB | ASN | 254 | 32.108 | -4.041 | 41.905 |
| ATOM | 1484 CG | ASN | 254 | 33.538 | -4.152 | 41.470 |
| ATOM | 1485 OD1 | ASN | 254 | 34.057 | -5.259 | 41.294 |
| ATOM | 1486 ND2 | ASN | 254 | 34.205 | -3.007 | 41.315 |

FIGURE 1FF

|  | Atom | AA | Residue No. | X | Y | Z |
|---|---|---|---|---|---|---|
| ATOM | 1487 C | ASN | 254 | 30.320 | -3.598 | 40.228 |
| ATOM | 1488 O | ASN | 254 | 30.503 | -4.758 | 39.828 |
| ATOM | 1489 N | MET | 255 | 29.292 | -2.875 | 39.804 |
| ATOM | 1490 CA | MET | 255 | 28.303 | -3.529 | 38.966 |
| ATOM | 1491 CB | MET | 255 | 26.905 | -3.196 | 39.424 |
| ATOM | 1492 CG | MET | 255 | 25.957 | -4.284 | 39.099 |
| ATOM | 1493 SD | MET | 255 | 24.359 | -3.711 | 39.469 |
| ATOM | 1494 CE | MET | 255 | 24.212 | -2.604 | 38.133 |
| ATOM | 1495 C | MET | 255 | 28.409 | -3.350 | 37.462 |
| ATOM | 1496 O | MET | 255 | 27.691 | -2.546 | 36.866 |
| ATOM | 1497 N | SER | 256 | 29.250 | -4.181 | 36.856 |
| ATOM | 1498 CA | SER | 256 | 29.501 | -4.194 | 35.420 |
| ATOM | 1499 CB | SER | 256 | 29.735 | -5.635 | 34.949 |
| ATOM | 1500 OG | SER | 256 | 28.661 | -6.486 | 35.311 |
| ATOM | 1501 C | SER | 256 | 28.445 | -3.541 | 34.536 |
| ATOM | 1502 O | SER | 256 | 27.298 | -3.996 | 34.457 |
| ATOM | 1503 N | SER | 257 | 28.872 | -2.497 | 33.833 |
| ATOM | 1504 CA | SER | 257 | 28.010 | -1.743 | 32.922 |
| ATOM | 1505 CB | SER | 257 | 28.822 | -0.671 | 32.163 |
| ATOM | 1506 OG | SER | 257 | 30.083 | -1.164 | 31.734 |
| ATOM | 1507 C | SER | 257 | 27.312 | -2.660 | 31.933 |
| ATOM | 1508 O | SER | 257 | 26.105 | -2.582 | 31.752 |
| ATOM | 1509 N | GLU | 258 | 28.077 | -3.600 | 31.393 |
| ATOM | 1510 CA | GLU | 258 | 27.596 | -4.553 | 30.408 |
| ATOM | 1511 CB | GLU | 258 | 28.780 | -5.371 | 29.845 |
| ATOM | 1512 CG | GLU | 258 | 29.612 | -4.612 | 28.722 |
| ATOM | 1513 CD | GLU | 258 | 31.114 | -4.221 | 29.084 |
| ATOM | 1514 OE1 | GLU | 258 | 31.696 | -4.773 | 30.091 |
| ATOM | 1515 OE2 | GLU | 258 | 31.706 | -3.368 | 28.323 |
| ATOM | 1516 C | GLU | 258 | 26.454 | -5.449 | 30.886 |
| ATOM | 1517 O | GLU | 258 | 26.151 | -6.464 | 30.257 |
| ATOM | 1518 N | ASN | 259 | 25.804 | -5.063 | 31.980 |
| ATOM | 1519 CA | ASN | 259 | 24.685 | -5.822 | 32.492 |
| ATOM | 1520 CB | ASN | 259 | 25.123 | -6.641 | 33.671 |
| ATOM | 1521 CG | ASN | 259 | 24.896 | -8.098 | 33.451 |
| ATOM | 1522 OD1 | ASN | 259 | 23.878 | -8.482 | 32.891 |
| ATOM | 1523 ND2 | ASN | 259 | 25.845 | -8.930 | 33.879 |
| ATOM | 1524 C | ASN | 259 | 23.503 | -4.965 | 32.877 |
| ATOM | 1525 O | ASN | 259 | 22.448 | -5.485 | 33.212 |
| ATOM | 1526 N | MET | 260 | 23.659 | -3.652 | 32.712 |
| ATOM | 1527 CA | MET | 260 | 22.638 | -2.642 | 33.046 |
| ATOM | 1528 CB | MET | 260 | 23.008 | -1.993 | 34.401 |
| ATOM | 1529 CG | MET | 260 | 24.510 | -1.716 | 34.529 |
| ATOM | 1530 SD | MET | 260 | 25.009 | -0.529 | 35.750 |
| ATOM | 1531 CE | MET | 260 | 23.922 | 0.714 | 35.447 |
| ATOM | 1532 C | MET | 260 | 22.532 | -1.519 | 31.982 |
| ATOM | 1533 O | MET | 260 | 23.546 | -1.092 | 31.419 |
| ATOM | 1534 N | ARG | 261 | 21.322 | -0.989 | 31.782 |

FIGURE 1GG

|      |      |     | Residue |        |        |        |
|------|------|-----|---------|--------|--------|--------|
|      | Atom | AA  | No.     | X      | Y      | Z      |
| ATOM | 1535 CA  | ARG | 261 | 21.064 | 0.104  | 30.826 |
| ATOM | 1536 CB  | ARG | 261 | 20.359 | -0.454 | 29.603 |
| ATOM | 1537 CG  | ARG | 261 | 18.869 | -0.802 | 29.811 |
| ATOM | 1538 CD  | ARG | 261 | 18.265 | -1.409 | 28.535 |
| ATOM | 1539 NE  | ARG | 261 | 16.822 | -1.660 | 28.586 |
| ATOM | 1540 CZ  | ARG | 261 | 16.263 | -2.831 | 28.299 |
| ATOM | 1541 NH1 | ARG | 261 | 14.949 | -2.998 | 28.338 |
| ATOM | 1542 NH2 | ARG | 261 | 17.026 | -3.856 | 27.993 |
| ATOM | 1543 C   | ARG | 261 | 20.105 | 1.087  | 31.469 |
| ATOM | 1544 O   | ARG | 261 | 19.618 | 0.838  | 32.550 |
| ATOM | 1545 N   | LEU | 262 | 19.789 | 2.190  | 30.820 |
| ATOM | 1546 CA  | LEU | 262 | 18.811 | 3.091  | 31.422 |
| ATOM | 1547 CB  | LEU | 262 | 19.395 | 4.453  | 31.775 |
| ATOM | 1548 CG  | LEU | 262 | 20.861 | 4.672  | 32.107 |
| ATOM | 1549 CD1 | LEU | 262 | 20.945 | 6.044  | 32.733 |
| ATOM | 1550 CD2 | LEU | 262 | 21.427 | 3.621  | 33.025 |
| ATOM | 1551 C   | LEU | 262 | 17.647 | 3.299  | 30.469 |
| ATOM | 1552 O   | LEU | 262 | 17.708 | 4.155  | 29.601 |
| ATOM | 1553 N   | ARG | 263 | 16.589 | 2.513  | 30.632 |
| ATOM | 1554 CA  | ARG | 263 | 15.392 | 2.596  | 29.785 |
| ATOM | 1555 CB  | ARG | 263 | 14.568 | 1.304  | 29.912 |
| ATOM | 1556 CG  | ARG | 263 | 13.254 | 1.283  | 29.177 |
| ATOM | 1557 CD  | ARG | 263 | 12.112 | 1.303  | 30.156 |
| ATOM | 1558 NE  | ARG | 263 | 10.949 | 1.973  | 29.589 |
| ATOM | 1559 CZ  | ARG | 263 | 9.709  | 1.930  | 30.084 |
| ATOM | 1560 NH1 | ARG | 263 | 8.742  | 2.585  | 29.455 |
| ATOM | 1561 NH2 | ARG | 263 | 9.425  | 1.288  | 31.212 |
| ATOM | 1562 C   | ARG | 263 | 14.538 | 3.814  | 30.096 |
| ATOM | 1563 O   | ARG | 263 | 13.363 | 3.698  | 30.386 |
| ATOM | 1564 N   | ASP | 264 | 15.167 | 4.978  | 30.063 |
| ATOM | 1565 CA  | ASP | 264 | 14.534 | 6.278  | 30.306 |
| ATOM | 1566 CB  | ASP | 264 | 15.381 | 7.336  | 29.593 |
| ATOM | 1567 CG  | ASP | 264 | 14.935 | 8.744  | 29.864 |
| ATOM | 1568 OD1 | ASP | 264 | 14.001 | 8.997  | 30.664 |
| ATOM | 1569 OD2 | ASP | 264 | 15.557 | 9.616  | 29.244 |
| ATOM | 1570 C   | ASP | 264 | 13.145 | 6.209  | 29.683 |
| ATOM | 1571 O   | ASP | 264 | 13.039 | 6.187  | 28.457 |
| ATOM | 1572 N   | HIS | 265 | 12.078 | 6.244  | 30.486 |
| ATOM | 1573 CA  | HIS | 265 | 10.772 | 6.058  | 29.864 |
| ATOM | 1574 CB  | HIS | 265 | 10.021 | 4.881  | 30.468 |
| ATOM | 1575 CG  | HIS | 265 | 9.525  | 5.088  | 31.858 |
| ATOM | 1576 CD2 | HIS | 265 | 8.478  | 5.804  | 32.330 |
| ATOM | 1577 ND1 | HIS | 265 | 10.011 | 4.364  | 32.927 |
| ATOM | 1578 CE1 | HIS | 265 | 9.273  | 4.614  | 33.991 |
| ATOM | 1579 NE2 | HIS | 265 | 8.337  | 5.485  | 33.657 |
| ATOM | 1580 C   | HIS | 265 | 9.796  | 7.072  | 29.344 |
| ATOM | 1581 O   | HIS | 265 | 9.833  | 8.264  | 29.635 |
| ATOM | 1582 N   | ASP | 266 | 8.931  | 6.497  | 28.518 |

FIGURE 1HH

|  | Atom | Residue AA | No. | X | Y | Z |
|---|---|---|---|---|---|---|
| ATOM | 1583 CA | ASP | 266 | 7.868 | 7.143 | 27.745 |
| ATOM | 1584 CB | ASP | 266 | 7.461 | 6.200 | 26.581 |
| ATOM | 1585 CG | ASP | 266 | 6.823 | 4.857 | 27.074 |
| ATOM | 1586 OD1 | ASP | 266 | 7.497 | 4.090 | 27.825 |
| ATOM | 1587 OD2 | ASP | 266 | 5.659 | 4.572 | 26.681 |
| ATOM | 1588 C | ASP | 266 | 6.580 | 7.648 | 28.415 |
| ATOM | 1589 O | ASP | 266 | 6.234 | 7.257 | 29.548 |
| ATOM | 1590 N | ALA | 267 | 5.811 | 8.379 | 27.595 |
| ATOM | 1591 CA | ALA | 267 | 4.533 | 8.973 | 27.973 |
| ATOM | 1592 CB | ALA | 267 | 4.179 | 10.130 | 27.011 |
| ATOM | 1593 C | ALA | 267 | 3.385 | 7.956 | 28.051 |
| ATOM | 1594 O | ALA | 267 | 2.212 | 8.309 | 27.841 |
| ATOM | 1595 N | ASP | 268 | 3.732 | 6.681 | 28.231 |
| ATOM | 1596 CA | ASP | 268 | 2.706 | 5.653 | 28.406 |
| ATOM | 1597 CB | ASP | 268 | 3.244 | 4.222 | 28.094 |
| ATOM | 1598 CG | ASP | 268 | 2.406 | 3.065 | 28.771 |
| ATOM | 1599 OD1 | ASP | 268 | 3.040 | 2.068 | 29.218 |
| ATOM | 1600 OD2 | ASP | 268 | 1.142 | 3.135 | 28.851 |
| ATOM | 1601 C | ASP | 268 | 2.458 | 5.789 | 29.890 |
| ATOM | 1602 O | ASP | 268 | 1.449 | 6.362 | 30.329 |
| ATOM | 1603 N | GLU | 269 | 3.500 | 5.379 | 30.619 |
| ATOM | 1604 CA | GLU | 269 | 3.534 | 5.364 | 32.073 |
| ATOM | 1605 CB | GLU | 269 | 4.167 | 4.038 | 32.568 |
| ATOM | 1606 CG | GLU | 269 | 5.695 | 3.891 | 32.399 |
| ATOM | 1607 CD | GLU | 269 | 6.132 | 3.584 | 30.986 |
| ATOM | 1608 OE1 | GLU | 269 | 6.450 | 4.541 | 30.257 |
| ATOM | 1609 OE2 | GLU | 269 | 6.187 | 2.388 | 30.628 |
| ATOM | 1610 C | GLU | 269 | 4.230 | 6.592 | 32.704 |
| ATOM | 1611 O | GLU | 269 | 4.494 | 6.613 | 33.929 |
| ATOM | 1612 N | LEU | 270 | 4.595 | 7.577 | 31.877 |
| ATOM | 1613 CA | LEU | 270 | 5.217 | 8.782 | 32.425 |
| ATOM | 1614 CB | LEU | 270 | 5.771 | 9.720 | 31.361 |
| ATOM | 1615 CG | LEU | 270 | 6.348 | 10.967 | 32.019 |
| ATOM | 1616 CD1 | LEU | 270 | 7.645 | 11.375 | 31.344 |
| ATOM | 1617 CD2 | LEU | 270 | 5.321 | 12.068 | 31.962 |
| ATOM | 1618 C | LEU | 270 | 4.039 | 9.405 | 33.108 |
| ATOM | 1619 O | LEU | 270 | 2.893 | 9.329 | 32.620 |
| ATOM | 1620 N | SER | 271 | 4.298 | 9.973 | 34.268 |
| ATOM | 1621 CA | SER | 271 | 3.186 | 10.511 | 34.995 |
| ATOM | 1622 CB | SER | 271 | 3.398 | 10.425 | 36.510 |
| ATOM | 1623 OG | SER | 271 | 2.333 | 9.690 | 37.127 |
| ATOM | 1624 C | SER | 271 | 2.775 | 11.877 | 34.575 |
| ATOM | 1625 O | SER | 271 | 3.579 | 12.646 | 34.058 |
| ATOM | 1626 N | ALA | 272 | 1.469 | 12.097 | 34.723 |
| ATOM | 1627 CA | ALA | 272 | 0.793 | 13.356 | 34.430 |
| ATOM | 1628 CB | ALA | 272 | -0.648 | 13.297 | 35.010 |
| ATOM | 1629 C | ALA | 272 | 1.587 | 14.523 | 35.070 |
| ATOM | 1630 O | ALA | 272 | 1.733 | 15.609 | 34.460 |

FIGURE III

|  | Atom | Residue AA | No. | X | Y | Z |
|---|---|---|---|---|---|---|
| ATOM | 1631 N | TYR | 273 | 2.073 | 14.276 | 36.300 |
| ATOM | 1632 CA | TYR | 273 | 2.863 | 15.239 | 37.086 |
| ATOM | 1633 CB | TYR | 273 | 2.734 | 14.953 | 38.590 |
| ATOM | 1634 CG | TYR | 273 | 3.112 | 13.532 | 39.053 |
| ATOM | 1635 CD1 | TYR | 273 | 2.118 | 12.519 | 39.164 |
| ATOM | 1636 CE1 | TYR | 273 | 2.421 | 11.236 | 39.679 |
| ATOM | 1637 CD2 | TYR | 273 | 4.436 | 13.218 | 39.466 |
| ATOM | 1638 CE2 | TYR | 273 | 4.750 | 11.934 | 39.980 |
| ATOM | 1639 CZ | TYR | 273 | 3.728 | 10.950 | 40.085 |
| ATOM | 1640 OH | TYR | 273 | 3.981 | 9.691 | 40.606 |
| ATOM | 1641 C | TYR | 273 | 4.328 | 15.206 | 36.703 |
| ATOM | 1642 O | TYR | 273 | 5.019 | 16.228 | 36.747 |
| ATOM | 1643 N | SER | 274 | 4.791 | 13.993 | 36.415 |
| ATOM | 1644 CA | SER | 274 | 6.159 | 13.749 | 36.021 |
| ATOM | 1645 CB | SER | 274 | 6.424 | 12.245 | 35.965 |
| ATOM | 1646 OG | SER | 274 | 7.731 | 11.964 | 35.479 |
| ATOM | 1647 C | SER | 274 | 6.384 | 14.354 | 34.648 |
| ATOM | 1648 O | SER | 274 | 5.480 | 14.928 | 34.030 |
| ATOM | 1649 N | ASN | 275 | 7.605 | 14.193 | 34.175 |
| ATOM | 1650 CA | ASN | 275 | 8.027 | 14.699 | 32.884 |
| ATOM | 1651 CB | ASN | 275 | 7.801 | 16.211 | 32.812 |
| ATOM | 1652 CG | ASN | 275 | 8.227 | 16.921 | 34.088 |
| ATOM | 1653 OD1 | ASN | 275 | 7.437 | 17.071 | 35.011 |
| ATOM | 1654 ND2 | ASN | 275 | 9.498 | 17.308 | 34.165 |
| ATOM | 1655 C | ASN | 275 | 9.509 | 14.370 | 32.873 |
| ATOM | 1656 O | ASN | 275 | 10.368 | 15.226 | 32.592 |
| ATOM | 1657 N | ALA | 276 | 9.790 | 13.133 | 33.285 |
| ATOM | 1658 CA | ALA | 276 | 11.142 | 12.564 | 33.385 |
| ATOM | 1659 CB | ALA | 276 | 12.163 | 13.575 | 33.945 |
| ATOM | 1660 C | ALA | 276 | 11.013 | 11.412 | 34.343 |
| ATOM | 1661 O | ALA | 276 | 10.428 | 11.542 | 35.423 |
| ATOM | 1662 N | THR | 277 | 11.565 | 10.289 | 33.940 |
| ATOM | 1663 CA | THR | 277 | 11.493 | 9.111 | 34.748 |
| ATOM | 1664 CB | THR | 277 | 9.994 | 8.708 | 35.025 |
| ATOM | 1665 OG1 | THR | 277 | 9.948 | 7.375 | 35.533 |
| ATOM | 1666 CG2 | THR | 277 | 9.079 | 8.855 | 33.787 |
| ATOM | 1667 C | THR | 277 | 12.306 | 8.032 | 34.048 |
| ATOM | 1668 O | THR | 277 | 11.783 | 7.170 | 33.317 |
| ATOM | 1669 N | THR | 278 | 13.617 | 8.169 | 34.208 |
| ATOM | 1670 CA | THR | 278 | 14.572 | 7.244 | 33.620 |
| ATOM | 1671 CB | THR | 278 | 15.908 | 7.965 | 33.266 |
| ATOM | 1672 OG1 | THR | 278 | 17.000 | 7.053 | 33.372 |
| ATOM | 1673 CG2 | THR | 278 | 16.151 | 9.155 | 34.157 |
| ATOM | 1674 C | THR | 278 | 14.837 | 6.109 | 34.593 |
| ATOM | 1675 O | THR | 278 | 15.385 | 6.352 | 35.651 |
| ATOM | 1676 N | ASP | 279 | 14.349 | 4.904 | 34.318 |
| ATOM | 1677 CA | ASP | 279 | 14.639 | 3.772 | 35.201 |
| ATOM | 1678 CB | ASP | 279 | 13.700 | 2.601 | 34.934 |

FIGURE 1JJ

| Atom | | Residue AA | No. | X | Y | Z |
|---|---|---|---|---|---|---|
| ATOM | 1679 | CG | ASP | 279 | 12.310 | 2.839 | 35.416 |
| ATOM | 1680 | OD1 | ASP | 279 | 12.056 | 3.903 | 36.011 |
| ATOM | 1681 | OD2 | ASP | 279 | 11.468 | 1.941 | 35.206 |
| ATOM | 1682 | C | ASP | 279 | 16.046 | 3.310 | 34.823 |
| ATOM | 1683 | O | ASP | 279 | 16.563 | 3.722 | 33.782 |
| ATOM | 1684 | N | ILE | 280 | 16.687 | 2.515 | 35.677 |
| ATOM | 1685 | CA | ILE | 280 | 18.005 | 1.953 | 35.391 |
| ATOM | 1686 | CB | ILE | 280 | 19.051 | 2.331 | 36.438 |
| ATOM | 1687 | CG2 | ILE | 280 | 20.359 | 1.707 | 36.079 |
| ATOM | 1688 | CG1 | ILE | 280 | 19.200 | 3.848 | 36.516 |
| ATOM | 1689 | CD1 | ILE | 280 | 20.356 | 4.316 | 37.324 |
| ATOM | 1690 | C | ILE | 280 | 17.638 | 0.505 | 35.534 |
| ATOM | 1691 | O | ILE | 280 | 16.909 | 0.171 | 36.450 |
| ATOM | 1692 | N | GLU | 281 | 18.072 | -0.361 | 34.638 |
| ATOM | 1693 | CA | GLU | 281 | 17.658 | -1.752 | 34.749 |
| ATOM | 1694 | CB | GLU | 281 | 16.801 | -2.159 | 33.538 |
| ATOM | 1695 | CG | GLU | 281 | 15.723 | -1.142 | 33.081 |
| ATOM | 1696 | CD | GLU | 281 | 14.796 | -1.672 | 31.972 |
| ATOM | 1697 | OE1 | GLU | 281 | 13.717 | -1.103 | 31.749 |
| ATOM | 1698 | OE2 | GLU | 281 | 15.129 | -2.669 | 31.321 |
| ATOM | 1699 | C | GLU | 281 | 18.802 | -2.720 | 34.885 |
| ATOM | 1700 | O | GLU | 281 | 19.942 | -2.384 | 34.625 |
| ATOM | 1701 | N | TYR | 282 | 18.488 | -3.934 | 35.297 |
| ATOM | 1702 | CA | TYR | 282 | 19.495 | -4.957 | 35.434 |
| ATOM | 1703 | CB | TYR | 282 | 19.728 | -5.369 | 36.899 |
| ATOM | 1704 | CG | TYR | 282 | 20.931 | -6.287 | 37.093 |
| ATOM | 1705 | CD1 | TYR | 282 | 20.804 | -7.658 | 37.012 |
| ATOM | 1706 | CE1 | TYR | 282 | 21.903 | -8.483 | 37.070 |
| ATOM | 1707 | CD2 | TYR | 282 | 22.210 | -5.767 | 37.255 |
| ATOM | 1708 | CE2 | TYR | 282 | 23.320 | -6.586 | 37.314 |
| ATOM | 1709 | CZ | TYR | 282 | 23.155 | -7.940 | 37.210 |
| ATOM | 1710 | OH | TYR | 282 | 24.250 | -8.754 | 37.187 |
| ATOM | 1711 | C | TYR | 282 | 19.072 | -6.167 | 34.631 |
| ATOM | 1712 | O | TYR | 282 | 17.890 | -6.474 | 34.467 |
| ATOM | 1713 | N | ALA | 283 | 20.073 | -6.830 | 34.097 |
| ATOM | 1714 | CA | ALA | 283 | 19.886 | -8.018 | 33.314 |
| ATOM | 1715 | CB | ALA | 283 | 21.008 | -8.113 | 32.286 |
| ATOM | 1716 | C | ALA | 283 | 19.913 | -9.213 | 34.257 |
| ATOM | 1717 | O | ALA | 283 | 20.888 | -9.962 | 34.318 |
| ATOM | 1718 | N | PHE | 284 | 18.858 | -9.357 | 35.037 |
| ATOM | 1719 | CA | PHE | 284 | 18.780 | -10.462 | 35.974 |
| ATOM | 1720 | CB | PHE | 284 | 17.571 | -10.285 | 36.878 |
| ATOM | 1721 | CG | PHE | 284 | 17.664 | -9.124 | 37.805 |
| ATOM | 1722 | CD1 | PHE | 284 | 18.755 | -8.970 | 38.631 |
| ATOM | 1723 | CD2 | PHE | 284 | 16.648 | -8.193 | 37.861 |
| ATOM | 1724 | CE1 | PHE | 284 | 18.838 | -7.906 | 39.500 |
| ATOM | 1725 | CE2 | PHE | 284 | 16.721 | -7.123 | 38.729 |
| ATOM | 1726 | CZ | PHE | 284 | 17.824 | -6.981 | 39.553 |

FIGURE 1KK

|  | | Residue | | | |
|---|---|---|---|---|---|
| Atom | AA | No. | X | Y | Z |
| ATOM 1727 C | PHE | 284 | 18.626 | -11.761 | 35.212 |
| ATOM 1728 O | PHE | 284 | 18.194 | -11.757 | 34.085 |
| ATOM 1729 N | PRO | 285 | 18.909 | -12.900 | 35.844 |
| ATOM 1730 CD | PRO | 285 | 19.370 | -13.126 | 37.225 |
| ATOM 1731 CA | PRO | 285 | 18.765 | -14.172 | 35.127 |
| ATOM 1732 CB | PRO | 285 | 19.022 | -15.213 | 36.221 |
| ATOM 1733 CG | PRO | 285 | 19.971 | -14.510 | 37.137 |
| ATOM 1734 C | PRO | 285 | 17.360 | -14.323 | 34.569 |
| ATOM 1735 O | PRO | 285 | 17.158 | -14.859 | 33.492 |
| ATOM 1736 N | PHE | 286 | 16.387 | -13.820 | 35.303 |
| ATOM 1737 CA | PHE | 286 | 15.001 | -13.912 | 34.866 |
| ATOM 1738 CB | PHE | 286 | 14.048 | -13.963 | 36.073 |
| ATOM 1739 CG | PHE | 286 | 14.215 | -12.813 | 37.011 |
| ATOM 1740 CD1 | PHE | 286 | 13.475 | -11.664 | 36.845 |
| ATOM 1741 CD2 | PHE | 286 | 15.201 | -12.838 | 37.978 |
| ATOM 1742 CE1 | PHE | 286 | 13.726 | -10.561 | 37.611 |
| ATOM 1743 CE2 | PHE | 286 | 15.455 | -11.740 | 38.744 |
| ATOM 1744 CZ | PHE | 286 | 14.719 | -10.595 | 38.559 |
| ATOM 1745 C | PHE | 286 | 14.584 | -12.778 | 33.926 |
| ATOM 1746 O | PHE | 286 | 13.399 | -12.627 | 33.640 |
| ATOM 1747 N | GLY | 287 | 15.526 | -11.958 | 33.477 |
| ATOM 1748 CA | GLY | 287 | 15.159 | -10.887 | 32.572 |
| ATOM 1749 C | GLY | 287 | 15.624 | -9.493 | 32.930 |
| ATOM 1750 O | GLY | 287 | 16.579 | -9.296 | 33.686 |
| ATOM 1751 N | TRP | 288 | 14.998 | -8.510 | 32.302 |
| ATOM 1752 CA | TRP | 288 | 15.347 | -7.135 | 32.576 |
| ATOM 1753 CB | TRP | 288 | 15.071 | -6.246 | 31.366 |
| ATOM 1754 CG | TRP | 288 | 16.130 | -6.372 | 30.352 |
| ATOM 1755 CD2 | TRP | 288 | 17.318 | -5.559 | 30.229 |
| ATOM 1756 CE2 | TRP | 288 | 18.104 | -6.118 | 29.195 |
| ATOM 1757 CE3 | TRP | 288 | 17.795 | -4.420 | 30.892 |
| ATOM 1758 CD1 | TRP | 288 | 16.233 | -7.351 | 29.405 |
| ATOM 1759 NE1 | TRP | 288 | 17.424 | -7.208 | 28.710 |
| ATOM 1760 CZ2 | TRP | 288 | 19.345 | -5.569 | 28.809 |
| ATOM 1761 CZ3 | TRP | 288 | 19.044 | -3.876 | 30.502 |
| ATOM 1762 CH2 | TRP | 288 | 19.791 | -4.452 | 29.477 |
| ATOM 1763 C | TRP | 288 | 14.485 | -6.727 | 33.737 |
| ATOM 1764 O | TRP | 288 | 13.378 | -7.256 | 33.907 |
| ATOM 1765 N | GLY | 289 | 15.006 | -5.820 | 34.556 |
| ATOM 1766 CA | GLY | 289 | 14.263 | -5.333 | 35.708 |
| ATOM 1767 C | GLY | 289 | 14.839 | -4.017 | 36.189 |
| ATOM 1768 O | GLY | 289 | 15.984 | -3.701 | 35.884 |
| ATOM 1769 N | GLU | 290 | 14.061 | -3.246 | 36.935 |
| ATOM 1770 CA | GLU | 290 | 14.561 | -1.978 | 37.402 |
| ATOM 1771 CB | GLU | 290 | 13.425 | -0.977 | 37.537 |
| ATOM 1772 CG | GLU | 290 | 12.391 | -1.284 | 38.611 |
| ATOM 1773 CD | GLU | 290 | 11.205 | -0.284 | 38.607 |
| ATOM 1774 OE1 | GLU | 290 | 10.212 | -0.542 | 37.867 |

FIGURE 1LL

| Atom | | AA | Residue No. | X | Y | Z |
|---|---|---|---|---|---|---|
| ATOM | 1775 OE2 | GLU | 290 | 11.260 | 0.749 | 39.338 |
| ATOM | 1776 C | GLU | 290 | 15.324 | -2.075 | 38.700 |
| ATOM | 1777 O | GLU | 290 | 15.162 | -3.026 | 39.450 |
| ATOM | 1778 N | LEU | 291 | 16.258 | -1.155 | 38.882 |
| ATOM | 1779 CA | LEU | 291 | 17.030 | -1.073 | 40.100 |
| ATOM | 1780 CB | LEU | 291 | 18.528 | -0.882 | 39.824 |
| ATOM | 1781 CG | LEU | 291 | 19.369 | -2.096 | 39.455 |
| ATOM | 1782 CD1 | LEU | 291 | 20.739 | -1.973 | 40.076 |
| ATOM | 1783 CD2 | LEU | 291 | 18.683 | -3.342 | 39.925 |
| ATOM | 1784 C | LEU | 291 | 16.466 | 0.189 | 40.699 |
| ATOM | 1785 O | LEU | 291 | 15.445 | 0.171 | 41.387 |
| ATOM | 1786 N | TRP | 292 | 17.096 | 1.296 | 40.335 |
| ATOM | 1787 CA | TRP | 292 | 16.708 | 2.612 | 40.786 |
| ATOM | 1788 CB | TRP | 292 | 17.849 | 3.558 | 40.488 |
| ATOM | 1789 CG | TRP | 292 | 18.441 | 4.205 | 41.645 |
| ATOM | 1790 CD2 | TRP | 292 | 19.746 | 3.991 | 42.135 |
| ATOM | 1791 CE2 | TRP | 292 | 19.943 | 4.895 | 43.205 |
| ATOM | 1792 CE3 | TRP | 292 | 20.785 | 3.130 | 41.772 |
| ATOM | 1793 CD1 | TRP | 292 | 17.896 | 5.193 | 42.408 |
| ATOM | 1794 NE1 | TRP | 292 | 18.787 | 5.615 | 43.357 |
| ATOM | 1795 CZ2 | TRP | 292 | 21.137 | 4.960 | 43.910 |
| ATOM | 1796 CZ3 | TRP | 292 | 21.971 | 3.194 | 42.474 |
| ATOM | 1797 CH2 | TRP | 292 | 22.140 | 4.103 | 43.530 |
| ATOM | 1798 C | TRP | 292 | 15.463 | 3.096 | 40.035 |
| ATOM | 1799 O | TRP | 292 | 14.832 | 2.348 | 39.304 |
| ATOM | 1800 N | GLY | 293 | 15.149 | 4.372 | 40.197 |
| ATOM | 1801 CA | GLY | 293 | 14.017 | 4.961 | 39.521 |
| ATOM | 1802 C | GLY | 293 | 14.083 | 6.468 | 39.675 |
| ATOM | 1803 O | GLY | 293 | 13.268 | 7.029 | 40.398 |
| ATOM | 1804 N | ILE | 294 | 15.061 | 7.121 | 39.043 |
| ATOM | 1805 CA | ILE | 294 | 15.203 | 8.573 | 39.129 |
| ATOM | 1806 CB | ILE | 294 | 16.519 | 9.044 | 38.513 |
| ATOM | 1807 CG2 | ILE | 294 | 16.741 | 10.486 | 38.784 |
| ATOM | 1808 CG1 | ILE | 294 | 17.696 | 8.287 | 39.095 |
| ATOM | 1809 CD1 | ILE | 294 | 17.975 | 6.992 | 38.390 |
| ATOM | 1810 C | ILE | 294 | 14.039 | 9.178 | 38.348 |
| ATOM | 1811 O | ILE | 294 | 13.725 | 8.715 | 37.247 |
| ATOM | 1812 N | ALA | 295 | 13.392 | 10.201 | 38.897 |
| ATOM | 1813 CA | ALA | 295 | 12.241 | 10.786 | 38.216 |
| ATOM | 1814 CB | ALA | 295 | 11.018 | 9.921 | 38.432 |
| ATOM | 1815 C | ALA | 295 | 11.936 | 12.199 | 38.655 |
| ATOM | 1816 O | ALA | 295 | 12.083 | 12.512 | 39.826 |
| ATOM | 1817 N | SER | 296 | 11.496 | 13.038 | 37.709 |
| ATOM | 1818 CA | SER | 296 | 11.145 | 14.447 | 37.973 |
| ATOM | 1819 CB | SER | 296 | 11.615 | 15.375 | 36.833 |
| ATOM | 1820 OG | SER | 296 | 11.480 | 16.759 | 37.157 |
| ATOM | 1821 C | SER | 296 | 9.629 | 14.528 | 38.132 |
| ATOM | 1822 O | SER | 296 | 8.871 | 14.319 | 37.177 |

FIGURE 1MM

|  |  | Residue |  |  |  |
|---|---|---|---|---|---|
| Atom | AA | No. | X | Y | Z |
| ATOM 1823 N | ARG | 297 | 9.206 | 14.779 | 39.366 |
| ATOM 1824 CA | ARG | 297 | 7.788 | 14.867 | 39.709 |
| ATOM 1825 CB | ARG | 297 | 7.520 | 14.064 | 40.992 |
| ATOM 1826 CG | ARG | 297 | 8.285 | 12.757 | 41.123 |
| ATOM 1827 CD | ARG | 297 | 8.166 | 12.209 | 42.539 |
| ATOM 1828 NE | ARG | 297 | 6.771 | 12.005 | 42.935 |
| ATOM 1829 CZ | ARG | 297 | 6.197 | 10.821 | 43.126 |
| ATOM 1830 NH1 | ARG | 297 | 6.901 | 9.720 | 42.958 |
| ATOM 1831 NH2 | ARG | 297 | 4.913 | 10.735 | 43.479 |
| ATOM 1832 C | ARG | 297 | 7.342 | 16.333 | 39.927 |
| ATOM 1833 O | ARG | 297 | 6.193 | 16.585 | 40.372 |
| ATOM 1834 N | THR | 298 | 8.236 | 17.277 | 39.590 |
| ATOM 1835 CA | THR | 298 | 7.991 | 18.713 | 39.753 |
| ATOM 1836 CB | THR | 298 | 6.844 | 19.232 | 38.828 |
| ATOM 1837 OG1 | THR | 298 | 5.579 | 18.626 | 39.159 |
| ATOM 1838 CG2 | THR | 298 | 7.192 | 18.933 | 37.396 |
| ATOM 1839 C | THR | 298 | 7.710 | 19.050 | 41.217 |
| ATOM 1840 O | THR | 298 | 8.589 | 18.896 | 42.072 |
| ATOM 1841 N | ASP | 299 | 6.507 | 19.531 | 41.509 |
| ATOM 1842 CA | ASP | 299 | 6.170 | 19.833 | 42.891 |
| ATOM 1843 CB | ASP | 299 | 5.839 | 21.319 | 43.116 |
| ATOM 1844 CG | ASP | 299 | 4.999 | 21.929 | 42.004 |
| ATOM 1845 OD1 | ASP | 299 | 5.489 | 22.940 | 41.421 |
| ATOM 1846 OD2 | ASP | 299 | 3.854 | 21.435 | 41.761 |
| ATOM 1847 C | ASP | 299 | 5.091 | 18.882 | 43.418 |
| ATOM 1848 O | ASP | 299 | 5.273 | 18.278 | 44.478 |
| ATOM 1849 N | PHE | 300 | 4.012 | 18.713 | 42.656 |
| ATOM 1850 CA | PHE | 300 | 2.904 | 17.791 | 42.977 |
| ATOM 1851 CB | PHE | 300 | 3.029 | 16.527 | 42.114 |
| ATOM 1852 CG | PHE | 300 | 1.930 | 15.519 | 42.337 |
| ATOM 1853 CD1 | PHE | 300 | 0.590 | 15.893 | 42.203 |
| ATOM 1854 CD2 | PHE | 300 | 2.234 | 14.185 | 42.636 |
| ATOM 1855 CE1 | PHE | 300 | -0.440 | 14.953 | 42.357 |
| ATOM 1856 CE2 | PHE | 300 | 1.213 | 13.237 | 42.793 |
| ATOM 1857 CZ | PHE | 300 | -0.127 | 13.625 | 42.651 |
| ATOM 1858 C | PHE | 300 | 2.648 | 17.342 | 44.429 |
| ATOM 1859 O | PHE | 300 | 1.565 | 17.594 | 44.973 |
| ATOM 1860 N | ASP | 301 | 3.599 | 16.585 | 44.996 |
| ATOM 1861 CA | ASP | 301 | 3.513 | 16.052 | 46.360 |
| ATOM 1862 CB | ASP | 301 | 4.661 | 15.114 | 46.604 |
| ATOM 1863 CG | ASP | 301 | 4.748 | 14.082 | 45.564 |
| ATOM 1864 OD1 | ASP | 301 | 5.578 | 14.293 | 44.651 |
| ATOM 1865 OD2 | ASP | 301 | 3.952 | 13.107 | 45.651 |
| ATOM 1866 C | ASP | 301 | 3.479 | 17.094 | 47.461 |
| ATOM 1867 O | ASP | 301 | 2.508 | 17.113 | 48.228 |
| ATOM 1868 N | LEU | 302 | 4.524 | 17.932 | 47.575 |
| ATOM 1869 CA | LEU | 302 | 4.518 | 18.976 | 48.604 |
| ATOM 1870 CB | LEU | 302 | 5.638 | 19.988 | 48.429 |

FIGURE 1NN

|  |  | Residue |  |  |  |
|---|---|---|---|---|---|
| Atom |  | AA No. | X | Y | Z |
| ATOM | 1871 CG | LEU 302 | 7.086 | 19.562 | 48.585 |
| ATOM | 1872 CD1 | LEU 302 | 7.187 | 18.570 | 49.750 |
| ATOM | 1873 CD2 | LEU 302 | 7.571 | 18.947 | 47.269 |
| ATOM | 1874 C | LEU 302 | 3.211 | 19.698 | 48.402 |
| ATOM | 1875 O | LEU 302 | 2.411 | 19.807 | 49.325 |
| ATOM | 1876 N | ALA 303 | 2.955 | 20.061 | 47.145 |
| ATOM | 1877 CA | ALA 303 | 1.728 | 20.759 | 46.734 |
| ATOM | 1878 CB | ALA 303 | 1.864 | 21.285 | 45.295 |
| ATOM | 1879 C | ALA 303 | 0.407 | 19.985 | 46.888 |
| ATOM | 1880 O | ALA 303 | -0.654 | 20.579 | 46.735 |
| ATOM | 1881 N | ALA 304 | 0.466 | 18.673 | 47.118 |
| ATOM | 1882 CA | ALA 304 | -0.741 | 17.864 | 47.325 |
| ATOM | 1883 CB | ALA 304 | -0.491 | 16.424 | 46.897 |
| ATOM | 1884 C | ALA 304 | -1.068 | 17.929 | 48.826 |
| ATOM | 1885 O | ALA 304 | -2.226 | 17.908 | 49.245 |
| ATOM | 1886 N | HIS 305 | -0.010 | 18.038 | 49.618 |
| ATOM | 1887 CA | HIS 305 | -0.096 | 18.131 | 51.056 |
| ATOM | 1888 CB | HIS 305 | 1.240 | 17.731 | 51.647 |
| ATOM | 1889 CG | HIS 305 | 1.541 | 16.276 | 51.497 |
| ATOM | 1890 CD2 | HIS 305 | 2.718 | 15.616 | 51.377 |
| ATOM | 1891 ND1 | HIS 305 | 0.555 | 15.311 | 51.488 |
| ATOM | 1892 CE1 | HIS 305 | 1.110 | 14.116 | 51.376 |
| ATOM | 1893 NE2 | HIS 305 | 2.423 | 14.273 | 51.307 |
| ATOM | 1894 C | HIS 305 | -0.401 | 19.567 | 51.402 |
| ATOM | 1895 O | HIS 305 | -1.396 | 19.859 | 52.059 |
| ATOM | 1896 N | ALA 306 | 0.467 | 20.455 | 50.925 |
| ATOM | 1897 CA | ALA 306 | 0.341 | 21.894 | 51.117 |
| ATOM | 1898 CB | ALA 306 | 1.293 | 22.651 | 50.181 |
| ATOM | 1899 C | ALA 306 | -1.077 | 22.347 | 50.851 |
| ATOM | 1900 O | ALA 306 | -1.523 | 23.352 | 51.412 |
| ATOM | 1901 N | GLU 307 | -1.764 | 21.642 | 49.956 |
| ATOM | 1902 CA | GLU 307 | -3.127 | 22.002 | 49.629 |
| ATOM | 1903 CB | GLU 307 | -3.392 | 21.901 | 48.126 |
| ATOM | 1904 CG | GLU 307 | -4.834 | 22.345 | 47.677 |
| ATOM | 1905 CD | GLU 307 | -5.836 | 21.173 | 47.397 |
| ATOM | 1906 OE1 | GLU 307 | -5.879 | 20.722 | 46.204 |
| ATOM | 1907 OE2 | GLU 307 | -6.582 | 20.746 | 48.352 |
| ATOM | 1908 C | GLU 307 | -4.111 | 21.138 | 50.360 |
| ATOM | 1909 O | GLU 307 | -4.858 | 21.631 | 51.201 |
| ATOM | 1910 N | HIS 308 | -4.109 | 19.851 | 50.039 |
| ATOM | 1911 CA | HIS 308 | -5.047 | 18.920 | 50.631 |
| ATOM | 1912 CB | HIS 308 | -4.795 | 17.532 | 50.054 |
| ATOM | 1913 CG | HIS 308 | -5.713 | 16.467 | 50.570 |
| ATOM | 1914 CD2 | HIS 308 | -6.942 | 16.068 | 50.158 |
| ATOM | 1915 ND1 | HIS 308 | -5.353 | 15.608 | 51.591 |
| ATOM | 1916 CE1 | HIS 308 | -6.316 | 14.720 | 51.780 |
| ATOM | 1917 NE2 | HIS 308 | -7.292 | 14.977 | 50.921 |
| ATOM | 1918 C | HIS 308 | -5.021 | 18.916 | 52.165 |

FIGURE 100

| Atom | | Residue | | X | Y | Z |
|---|---|---|---|---|---|---|
| | | AA | No. | | | |
| ATOM | 1919 O | HIS | 308 | -6.006 | 18.487 | 52.792 |
| ATOM | 1920 N | SER | 309 | -3.935 | 19.419 | 52.770 |
| ATOM | 1921 CA | SER | 309 | -3.837 | 19.463 | 54.235 |
| ATOM | 1922 CB | SER | 309 | -3.303 | 18.135 | 54.800 |
| ATOM | 1923 OG | SER | 309 | -4.244 | 17.071 | 54.627 |
| ATOM | 1924 C | SER | 309 | -3.147 | 20.678 | 54.889 |
| ATOM | 1925 O | SER | 309 | -1.968 | 20.649 | 55.312 |
| ATOM | 1926 N | GLY | 310 | -3.945 | 21.741 | 54.948 |
| ATOM | 1927 CA | GLY | 310 | -3.594 | 23.016 | 55.560 |
| ATOM | 1928 C | GLY | 310 | -2.275 | 23.765 | 55.432 |
| ATOM | 1929 O | GLY | 310 | -2.265 | 24.976 | 55.103 |
| ATOM | 1930 N | GLU | 311 | -1.184 | 23.067 | 55.742 |
| ATOM | 1931 CA | GLU | 311 | 0.154 | 23.640 | 55.753 |
| ATOM | 1932 CB | GLU | 311 | 1.178 | 22.509 | 55.827 |
| ATOM | 1933 CG | GLU | 311 | 2.379 | 22.844 | 56.726 |
| ATOM | 1934 CD | GLU | 311 | 2.018 | 22.932 | 58.228 |
| ATOM | 1935 OE1 | GLU | 311 | 2.977 | 22.925 | 59.059 |
| ATOM | 1936 OE2 | GLU | 311 | 0.794 | 22.993 | 58.584 |
| ATOM | 1937 C | GLU | 311 | 0.649 | 24.782 | 54.810 |
| ATOM | 1938 O | GLU | 311 | 0.638 | 25.955 | 55.215 |
| ATOM | 1939 N | ASP | 312 | 1.100 | 24.412 | 53.600 |
| ATOM | 1940 CA | ASP | 312 | 1.694 | 25.267 | 52.539 |
| ATOM | 1941 CB | ASP | 312 | 1.387 | 26.772 | 52.687 |
| ATOM | 1942 CG | ASP | 312 | 2.566 | 27.583 | 53.262 |
| ATOM | 1943 OD1 | ASP | 312 | 2.605 | 27.795 | 54.504 |
| ATOM | 1944 OD2 | ASP | 312 | 3.434 | 28.032 | 52.474 |
| ATOM | 1945 C | ASP | 312 | 3.207 | 24.968 | 52.614 |
| ATOM | 1946 O | ASP | 312 | 3.770 | 24.785 | 53.701 |
| ATOM | 1947 N | PHE | 313 | 3.870 | 24.872 | 51.471 |
| ATOM | 1948 CA | PHE | 313 | 5.293 | 24.519 | 51.514 |
| ATOM | 1949 CB | PHE | 313 | 5.443 | 23.014 | 51.214 |
| ATOM | 1950 CG | PHE | 313 | 4.750 | 22.077 | 52.228 |
| ATOM | 1951 CD1 | PHE | 313 | 3.450 | 21.600 | 52.005 |
| ATOM | 1952 CD2 | PHE | 313 | 5.450 | 21.578 | 53.336 |
| ATOM | 1953 CE1 | PHE | 313 | 2.875 | 20.655 | 52.841 |
| ATOM | 1954 CE2 | PHE | 313 | 4.874 | 20.626 | 54.178 |
| ATOM | 1955 CZ | PHE | 313 | 3.590 | 20.169 | 53.923 |
| ATOM | 1956 C | PHE | 313 | 6.240 | 25.316 | 50.593 |
| ATOM | 1957 O | PHE | 313 | 7.373 | 24.895 | 50.332 |
| ATOM | 1958 N | ALA | 314 | 5.788 | 26.475 | 50.132 |
| ATOM | 1959 CA | ALA | 314 | 6.581 | 27.302 | 49.237 |
| ATOM | 1960 CB | ALA | 314 | 5.733 | 28.433 | 48.718 |
| ATOM | 1961 C | ALA | 314 | 7.843 | 27.856 | 49.873 |
| ATOM | 1962 O | ALA | 314 | 7.819 | 28.339 | 51.011 |
| ATOM | 1963 N | TYR | 315 | 8.949 | 27.764 | 49.140 |
| ATOM | 1964 CA | TYR | 315 | 10.230 | 28.303 | 49.598 |
| ATOM | 1965 CB | TYR | 315 | 11.361 | 27.706 | 48.778 |
| ATOM | 1966 CG | TYR | 315 | 12.711 | 28.236 | 49.132 |

FIGURE 1PP

| Atom | | Residue AA | No. | X | Y | Z |
|---|---|---|---|---|---|---|
| ATOM | 1967 CD1 | TYR | 315 | 13.248 | 29.317 | 48.468 |
| ATOM | 1968 CE1 | TYR | 315 | 14.548 | 29.778 | 48.744 |
| ATOM | 1969 CD2 | TYR | 315 | 13.484 | 27.621 | 50.089 |
| ATOM | 1970 CE2 | TYR | 315 | 14.792 | 28.067 | 50.380 |
| ATOM | 1971 CZ | TYR | 315 | 15.320 | 29.147 | 49.697 |
| ATOM | 1972 OH | TYR | 315 | 16.618 | 29.567 | 49.931 |
| ATOM | 1973 C | TYR | 315 | 10.136 | 29.806 | 49.336 |
| ATOM | 1974 O | TYR | 315 | 9.267 | 30.236 | 48.583 |
| ATOM | 1975 N | ALA | 316 | 11.006 | 30.615 | 49.925 |
| ATOM | 1976 CA | ALA | 316 | 10.906 | 32.056 | 49.678 |
| ATOM | 1977 CB | ALA | 316 | 10.104 | 32.733 | 50.794 |
| ATOM | 1978 C | ALA | 316 | 12.262 | 32.707 | 49.555 |
| ATOM | 1979 O | ALA | 316 | 12.939 | 32.884 | 50.584 |
| ATOM | 1980 N | ASP | 317 | 12.645 | 33.053 | 48.315 |
| ATOM | 1981 CA | ASP | 317 | 13.934 | 33.687 | 48.045 |
| ATOM | 1982 CB | ASP | 317 | 14.968 | 33.187 | 49.070 |
| ATOM | 1983 CG | ASP | 317 | 16.282 | 33.868 | 48.964 |
| ATOM | 1984 OD1 | ASP | 317 | 17.136 | 33.395 | 48.183 |
| ATOM | 1985 OD2 | ASP | 317 | 16.479 | 34.845 | 49.702 |
| ATOM | 1986 C | ASP | 317 | 14.522 | 33.472 | 46.637 |
| ATOM | 1987 O | ASP | 317 | 15.109 | 32.411 | 46.374 |
| ATOM | 1988 N | PRO | 318 | 14.323 | 34.427 | 45.688 |
| ATOM | 1989 CD | PRO | 318 | 13.500 | 35.646 | 45.723 |
| ATOM | 1990 CA | PRO | 318 | 14.896 | 34.284 | 44.344 |
| ATOM | 1991 CB | PRO | 318 | 13.818 | 34.910 | 43.467 |
| ATOM | 1992 CG | PRO | 318 | 13.475 | 36.131 | 44.264 |
| ATOM | 1993 C | PRO | 318 | 16.104 | 35.246 | 44.525 |
| ATOM | 1994 O | PRO | 318 | 16.187 | 36.299 | 43.861 |
| ATOM | 1995 N | ALA | 319 | 16.918 | 34.921 | 45.553 |
| ATOM | 1996 CA | ALA | 319 | 18.107 | 35.668 | 46.029 |
| ATOM | 1997 CB | ALA | 319 | 18.826 | 36.472 | 44.882 |
| ATOM | 1998 C | ALA | 319 | 17.622 | 36.636 | 47.119 |
| ATOM | 1999 O | ALA | 319 | 18.305 | 36.892 | 48.122 |
| ATOM | 2000 N | THR | 320 | 16.422 | 37.157 | 46.909 |
| ATOM | 2001 CA | THR | 320 | 15.789 | 38.113 | 47.813 |
| ATOM | 2002 CB | THR | 320 | 15.256 | 39.312 | 46.962 |
| ATOM | 2003 OG1 | THR | 320 | 14.538 | 38.800 | 45.807 |
| ATOM | 2004 CG2 | THR | 320 | 16.431 | 40.213 | 46.511 |
| ATOM | 2005 C | THR | 320 | 14.623 | 37.380 | 48.500 |
| ATOM | 2006 O | THR | 320 | 14.794 | 36.730 | 49.543 |
| ATOM | 2007 N | ASN | 321 | 13.438 | 37.528 | 47.901 |
| ATOM | 2008 CA | ASN | 321 | 12.206 | 36.864 | 48.329 |
| ATOM | 2009 CB | ASN | 321 | 11.566 | 37.502 | 49.608 |
| ATOM | 2010 CG | ASN | 321 | 11.175 | 36.431 | 50.694 |
| ATOM | 2011 OD1 | ASN | 321 | 9.999 | 36.022 | 50.816 |
| ATOM | 2012 ND2 | ASN | 321 | 12.177 | 35.970 | 51.456 |
| ATOM | 2013 C | ASN | 321 | 11.233 | 36.794 | 47.107 |
| ATOM | 2014 O | ASN | 321 | 11.143 | 37.744 | 46.294 |

FIGURE 1QQ

|  | Residue | | | | |
|---|---|---|---|---|---|
| Atom | AA | No. | X | Y | Z |
| ATOM 2015 N | ALA | 322 | 10.833 | 35.538 | 46.851 |
| ATOM 2016 CA | ALA | 322 | 9.886 | 35.084 | 45.812 |
| ATOM 2017 CB | ALA | 322 | 10.557 | 34.849 | 44.439 |
| ATOM 2018 C | ALA | 322 | 9.430 | 33.745 | 46.391 |
| ATOM 2019 O | ALA | 322 | 10.261 | 32.954 | 46.890 |
| ATOM 2020 N | ALA | 323 | 8.116 | 33.540 | 46.384 |
| ATOM 2021 CA | ALA | 323 | 7.520 | 32.324 | 46.914 |
| ATOM 2022 CB | ALA | 323 | 6.292 | 32.672 | 47.834 |
| ATOM 2023 C | ALA | 323 | 7.130 | 31.383 | 45.754 |
| ATOM 2024 O | ALA | 323 | 6.478 | 31.787 | 44.800 |
| ATOM 2025 N | TYR | 324 | 7.595 | 30.141 | 45.841 |
| ATOM 2026 CA | TYR | 324 | 7.355 | 29.105 | 44.847 |
| ATOM 2027 CB | TYR | 324 | 8.306 | 29.297 | 43.688 |
| ATOM 2028 CG | TYR | 324 | 9.749 | 29.510 | 44.094 |
| ATOM 2029 CD1 | TYR | 324 | 10.196 | 30.775 | 44.465 |
| ATOM 2030 CE1 | TYR | 324 | 11.537 | 31.020 | 44.724 |
| ATOM 2031 CD2 | TYR | 324 | 10.684 | 28.478 | 44.005 |
| ATOM 2032 CE2 | TYR | 324 | 12.031 | 28.705 | 44.256 |
| ATOM 2033 CZ | TYR | 324 | 12.454 | 29.992 | 44.612 |
| ATOM 2034 OH | TYR | 324 | 13.789 | 30.301 | 44.809 |
| ATOM 2035 C | TYR | 324 | 7.659 | 27.741 | 45.453 |
| ATOM 2036 O | TYR | 324 | 8.797 | 27.481 | 45.867 |
| ATOM 2037 N | ILE | 325 | 6.657 | 26.871 | 45.522 |
| ATOM 2038 CA | ILE | 325 | 6.866 | 25.535 | 46.077 |
| ATOM 2039 CB | ILE | 325 | 5.586 | 24.729 | 46.045 |
| ATOM 2040 CG2 | ILE | 325 | 4.990 | 24.748 | 44.649 |
| ATOM 2041 CG1 | ILE | 325 | 5.859 | 23.306 | 46.495 |
| ATOM 2042 CD1 | ILE | 325 | 4.604 | 22.592 | 46.833 |
| ATOM 2043 C | ILE | 325 | 7.952 | 24.845 | 45.252 |
| ATOM 2044 O | ILE | 325 | 7.991 | 24.992 | 44.016 |
| ATOM 2045 N | PRO | 326 | 8.879 | 24.128 | 45.924 |
| ATOM 2046 CD | PRO | 326 | 9.070 | 24.042 | 47.385 |
| ATOM 2047 CA | PRO | 326 | 9.977 | 23.437 | 45.223 |
| ATOM 2048 CB | PRO | 326 | 10.910 | 22.994 | 46.372 |
| ATOM 2049 CG | PRO | 326 | 10.579 | 23.959 | 47.489 |
| ATOM 2050 C | PRO | 326 | 9.617 | 22.261 | 44.293 |
| ATOM 2051 O | PRO | 326 | 8.501 | 21.695 | 44.308 |
| ATOM 2052 N | TYR | 327 | 10.607 | 21.905 | 43.491 |
| ATOM 2053 CA | TYR | 327 | 10.475 | 20.814 | 42.560 |
| ATOM 2054 CB | TYR | 327 | 11.029 | 21.237 | 41.204 |
| ATOM 2055 CG | TYR | 327 | 10.027 | 21.756 | 40.195 |
| ATOM 2056 CD1 | TYR | 327 | 10.174 | 21.447 | 38.828 |
| ATOM 2057 CE1 | TYR | 327 | 9.303 | 21.967 | 37.883 |
| ATOM 2058 CD2 | TYR | 327 | 8.965 | 22.598 | 40.590 |
| ATOM 2059 CE2 | TYR | 327 | 8.082 | 23.126 | 39.648 |
| ATOM 2060 CZ | TYR | 327 | 8.256 | 22.812 | 38.294 |
| ATOM 2061 OH | TYR | 327 | 7.397 | 23.371 | 37.362 |
| ATOM 2062 C | TYR | 327 | 11.382 | 19.728 | 43.074 |

FIGURE 1RR

| Atom | | Residue AA | No. | X | Y | Z |
|---|---|---|---|---|---|---|
| ATOM | 2063 O | TYR | 327 | 12.514 | 20.034 | 43.438 |
| ATOM | 2064 N | CYS | 328 | 10.923 | 18.478 | 43.116 |
| ATOM | 2065 CA | CYS | 328 | 11.818 | 17.414 | 43.561 |
| ATOM | 2066 CB | CYS | 328 | 11.314 | 16.699 | 44.816 |
| ATOM | 2067 SG | CYS | 328 | 10.065 | 15.451 | 44.552 |
| ATOM | 2068 C | CYS | 328 | 12.123 | 16.413 | 42.455 |
| ATOM | 2069 O | CYS | 328 | 11.555 | 16.475 | 41.351 |
| ATOM | 2070 N | ILE | 329 | 13.069 | 15.527 | 42.743 |
| ATOM | 2071 CA | ILE | 329 | 13.512 | 14.486 | 41.819 |
| ATOM | 2072 CB | ILE | 329 | 14.893 | 14.853 | 41.235 |
| ATOM | 2073 CG2 | ILE | 329 | 15.558 | 13.660 | 40.655 |
| ATOM | 2074 CG1 | ILE | 329 | 14.766 | 15.948 | 40.191 |
| ATOM | 2075 CD1 | ILE | 329 | 14.855 | 17.328 | 40.746 |
| ATOM | 2076 C | ILE | 329 | 13.667 | 13.280 | 42.732 |
| ATOM | 2077 O | ILE | 329 | 14.456 | 13.339 | 43.643 |
| ATOM | 2078 N | GLU | 330 | 12.945 | 12.193 | 42.536 |
| ATOM | 2079 CA | GLU | 330 | 13.135 | 11.123 | 43.481 |
| ATOM | 2080 CB | GLU | 330 | 11.811 | 10.733 | 44.128 |
| ATOM | 2081 CG | GLU | 330 | 10.940 | 9.803 | 43.354 |
| ATOM | 2082 CD | GLU | 330 | 9.806 | 9.249 | 44.179 |
| ATOM | 2083 OE1 | GLU | 330 | 9.784 | 8.026 | 44.433 |
| ATOM | 2084 OE2 | GLU | 330 | 8.930 | 10.041 | 44.563 |
| ATOM | 2085 C | GLU | 330 | 13.907 | 9.910 | 43.026 |
| ATOM | 2086 O | GLU | 330 | 13.355 | 9.017 | 42.433 |
| ATOM | 2087 N | PRO | 331 | 15.222 | 9.891 | 43.225 |
| ATOM | 2088 CD | PRO | 331 | 16.137 | 11.017 | 43.425 |
| ATOM | 2089 CA | PRO | 331 | 15.955 | 8.704 | 42.793 |
| ATOM | 2090 CB | PRO | 331 | 17.404 | 9.189 | 42.790 |
| ATOM | 2091 CG | PRO | 331 | 17.417 | 10.331 | 43.721 |
| ATOM | 2092 C | PRO | 331 | 15.746 | 7.502 | 43.724 |
| ATOM | 2093 O | PRO | 331 | 16.674 | 7.072 | 44.412 |
| ATOM | 2094 N | SER | 332 | 14.529 | 6.954 | 43.725 |
| ATOM | 2095 CA | SER | 332 | 14.141 | 5.801 | 44.558 |
| ATOM | 2096 CB | SER | 332 | 12.663 | 5.457 | 44.335 |
| ATOM | 2097 OG | SER | 332 | 12.375 | 4.105 | 44.611 |
| ATOM | 2098 C | SER | 332 | 15.000 | 4.581 | 44.297 |
| ATOM | 2099 O | SER | 332 | 15.668 | 4.512 | 43.289 |
| ATOM | 2100 N | LEU | 333 | 14.943 | 3.591 | 45.181 |
| ATOM | 2101 CA | LEU | 333 | 15.747 | 2.372 | 45.027 |
| ATOM | 2102 CB | LEU | 333 | 17.147 | 2.552 | 45.646 |
| ATOM | 2103 CG | LEU | 333 | 18.249 | 1.616 | 45.133 |
| ATOM | 2104 CD1 | LEU | 333 | 18.199 | 1.532 | 43.645 |
| ATOM | 2105 CD2 | LEU | 333 | 19.617 | 2.065 | 45.564 |
| ATOM | 2106 C | LEU | 333 | 15.043 | 1.126 | 45.594 |
| ATOM | 2107 O | LEU | 333 | 13.803 | 1.017 | 45.567 |
| ATOM | 2108 N | GLY | 334 | 15.827 | 0.171 | 46.065 |
| ATOM | 2109 CA | GLY | 334 | 15.250 | -1.037 | 46.595 |
| ATOM | 2110 C | GLY | 334 | 16.440 | -1.718 | 47.194 |

FIGURE 1SS

|  Atom |  | Residue |  |  |  |
|---|---|---|---|---|---|
|  |  | AA | No. | X | Y | Z |
| ATOM | 2111 | O | GLY | 334 | 17.310 | -2.206 | 46.480 |
| ATOM | 2112 | N | ALA | 335 | 16.535 | -1.689 | 48.509 |
| ATOM | 2113 | CA | ALA | 335 | 17.674 | -2.295 | 49.156 |
| ATOM | 2114 | CB | ALA | 335 | 17.639 | -2.008 | 50.620 |
| ATOM | 2115 | C | ALA | 335 | 17.639 | -3.774 | 48.897 |
| ATOM | 2116 | O | ALA | 335 | 18.650 | -4.383 | 48.561 |
| ATOM | 2117 | N | ASP | 336 | 16.442 | -4.334 | 49.007 |
| ATOM | 2118 | CA | ASP | 336 | 16.280 | -5.750 | 48.781 |
| ATOM | 2119 | CB | ASP | 336 | 14.814 | -6.192 | 48.973 |
| ATOM | 2120 | CG | ASP | 336 | 14.438 | -6.480 | 50.470 |
| ATOM | 2121 | OD1 | ASP | 336 | 14.333 | -7.675 | 50.870 |
| ATOM | 2122 | OD2 | ASP | 336 | 14.174 | -5.512 | 51.225 |
| ATOM | 2123 | C | ASP | 336 | 16.824 | -6.050 | 47.379 |
| ATOM | 2124 | O | ASP | 336 | 17.803 | -6.786 | 47.267 |
| ATOM | 2125 | N | ARG | 337 | 16.296 | -5.378 | 46.343 |
| ATOM | 2126 | CA | ARG | 337 | 16.744 | -5.561 | 44.936 |
| ATOM | 2127 | CB | ARG | 337 | 15.916 | -4.737 | 43.957 |
| ATOM | 2128 | CG | ARG | 337 | 14.513 | -5.233 | 43.711 |
| ATOM | 2129 | CD | ARG | 337 | 14.111 | -5.006 | 42.230 |
| ATOM | 2130 | NE | ARG | 337 | 12.699 | -4.631 | 42.080 |
| ATOM | 2131 | CZ | ARG | 337 | 12.236 | -3.377 | 42.170 |
| ATOM | 2132 | NH1 | ARG | 337 | 13.073 | -2.349 | 42.389 |
| ATOM | 2133 | NH2 | ARG | 337 | 10.919 | -3.156 | 42.147 |
| ATOM | 2134 | C | ARG | 337 | 18.207 | -5.259 | 44.655 |
| ATOM | 2135 | O | ARG | 337 | 18.920 | -6.130 | 44.188 |
| ATOM | 2136 | N | VAL | 338 | 18.648 | -4.033 | 44.912 |
| ATOM | 2137 | CA | VAL | 338 | 20.032 | -3.666 | 44.676 |
| ATOM | 2138 | CB | VAL | 338 | 20.424 | -2.330 | 45.346 |
| ATOM | 2139 | CG1 | VAL | 338 | 21.871 | -1.970 | 45.067 |
| ATOM | 2140 | CG2 | VAL | 338 | 19.570 | -1.251 | 44.841 |
| ATOM | 2141 | C | VAL | 338 | 20.957 | -4.758 | 45.176 |
| ATOM | 2142 | O | VAL | 338 | 22.036 | -4.918 | 44.632 |
| ATOM | 2143 | N | THR | 339 | 20.543 | -5.538 | 46.179 |
| ATOM | 2144 | CA | THR | 339 | 21.418 | -6.596 | 46.680 |
| ATOM | 2145 | CB | THR | 339 | 21.220 | -6.915 | 48.193 |
| ATOM | 2146 | OG1 | THR | 339 | 20.013 | -7.635 | 48.403 |
| ATOM | 2147 | CG2 | THR | 339 | 21.138 | -5.644 | 48.990 |
| ATOM | 2148 | C | THR | 339 | 21.349 | -7.830 | 45.809 |
| ATOM | 2149 | O | THR | 339 | 22.365 | -8.481 | 45.585 |
| ATOM | 2150 | N | LEU | 340 | 20.178 | -8.106 | 45.246 |
| ATOM | 2151 | CA | LEU | 340 | 20.029 | -9.253 | 44.366 |
| ATOM | 2152 | CB | LEU | 340 | 18.582 | -9.411 | 43.928 |
| ATOM | 2153 | CG | LEU | 340 | 18.267 | -10.709 | 43.191 |
| ATOM | 2154 | CD1 | LEU | 340 | 18.944 | -11.865 | 43.863 |
| ATOM | 2155 | CD2 | LEU | 340 | 16.778 | -10.936 | 43.124 |
| ATOM | 2156 | C | LEU | 340 | 20.948 | -9.037 | 43.164 |
| ATOM | 2157 | O | LEU | 340 | 21.635 | -9.952 | 42.715 |
| ATOM | 2158 | N | ALA | 341 | 21.002 | -7.800 | 42.683 |

FIGURE 1TT

|  |  | Residue |  |  |  |
|---|---|---|---|---|---|
| Atom |  | AA No. | X | Y | Z |
| ATOM 2159 | CA | ALA 341 | 21.854 | -7.444 | 41.565 |
| ATOM 2160 | CB | ALA 341 | 21.843 | -5.961 | 41.337 |
| ATOM 2161 | C | ALA 341 | 23.224 | -7.879 | 41.960 |
| ATOM 2162 | O | ALA 341 | 23.667 | -8.950 | 41.611 |
| ATOM 2163 | N | PHE 342 | 23.841 | -7.079 | 42.798 |
| ATOM 2164 | CA | PHE 342 | 25.175 | -7.352 | 43.306 |
| ATOM 2165 | CB | PHE 342 | 25.425 | -6.519 | 44.577 |
| ATOM 2166 | CG | PHE 342 | 25.659 | -5.052 | 44.326 |
| ATOM 2167 | CD1 | PHE 342 | 24.662 | -4.125 | 44.571 |
| ATOM 2168 | CD2 | PHE 342 | 26.903 | -4.598 | 43.916 |
| ATOM 2169 | CE1 | PHE 342 | 24.897 | -2.772 | 44.422 |
| ATOM 2170 | CE2 | PHE 342 | 27.155 | -3.251 | 43.761 |
| ATOM 2171 | CZ | PHE 342 | 26.154 | -2.334 | 44.016 |
| ATOM 2172 | C | PHE 342 | 25.471 | -8.842 | 43.583 |
| ATOM 2173 | O | PHE 342 | 26.602 | -9.282 | 43.398 |
| ATOM 2174 | N | LEU 343 | 24.472 | -9.604 | 44.028 |
| ATOM 2175 | CA | LEU 343 | 24.671 | -11.021 | 44.310 |
| ATOM 2176 | CB | LEU 343 | 23.483 | -11.619 | 45.083 |
| ATOM 2177 | CG | LEU 343 | 23.668 | -12.770 | 46.087 |
| ATOM 2178 | CD1 | LEU 343 | 22.353 | -13.475 | 46.298 |
| ATOM 2179 | CD2 | LEU 343 | 24.675 | -13.772 | 45.631 |
| ATOM 2180 | C | LEU 343 | 24.833 | -11.728 | 42.966 |
| ATOM 2181 | O | LEU 343 | 25.859 | -12.370 | 42.726 |
| ATOM 2182 | N | CYS 344 | 23.838 | -11.577 | 42.082 |
| ATOM 2183 | CA | CYS 344 | 23.842 | -12.191 | 40.751 |
| ATOM 2184 | CB | CYS 344 | 22.588 | -11.787 | 40.006 |
| ATOM 2185 | SG | CYS 344 | 21.156 | -12.665 | 40.492 |
| ATOM 2186 | C | CYS 344 | 25.048 | -11.775 | 39.911 |
| ATOM 2187 | O | CYS 344 | 25.808 | -12.598 | 39.401 |
| ATOM 2188 | N | ASP 345 | 25.199 | -10.473 | 39.775 |
| ATOM 2189 | CA | ASP 345 | 26.261 | -9.863 | 39.024 |
| ATOM 2190 | CB | ASP 345 | 26.220 | -8.386 | 39.301 |
| ATOM 2191 | CG | ASP 345 | 26.975 | -7.610 | 38.300 |
| ATOM 2192 | OD1 | ASP 345 | 28.168 | -7.318 | 38.566 |
| ATOM 2193 | OD2 | ASP 345 | 26.375 | -7.298 | 37.247 |
| ATOM 2194 | C | ASP 345 | 27.603 | -10.391 | 39.441 |
| ATOM 2195 | O | ASP 345 | 28.558 | -10.396 | 38.663 |
| ATOM 2196 | N | ALA 346 | 27.675 | -10.811 | 40.695 |
| ATOM 2197 | CA | ALA 346 | 28.904 | -11.332 | 41.275 |
| ATOM 2198 | CB | ALA 346 | 29.060 | -10.839 | 42.708 |
| ATOM 2199 | C | ALA 346 | 29.027 | -12.844 | 41.216 |
| ATOM 2200 | O | ALA 346 | 30.127 | -13.375 | 41.325 |
| ATOM 2201 | N | TYR 347 | 27.910 | -13.537 | 41.068 |
| ATOM 2202 | CA | TYR 347 | 27.966 | -14.968 | 40.978 |
| ATOM 2203 | CB | TYR 347 | 26.615 | -15.555 | 40.687 |
| ATOM 2204 | CG | TYR 347 | 26.713 | -17.037 | 40.698 |
| ATOM 2205 | CD1 | TYR 347 | 26.688 | -17.777 | 39.527 |
| ATOM 2206 | CE1 | TYR 347 | 26.839 | -19.146 | 39.558 |

FIGURE 1UU

|  |  |  | Residue |  |  |  |
|---|---|---|---|---|---|---|
|  | Atom |  | AA | No. | X | Y | Z |

| | | | | | | | |
|---|---|---|---|---|---|---|---|
| ATOM | 2207 | CD2 | TYR | 347 | 26.889 | -17.703 | 41.890 |
| ATOM | 2208 | CE2 | TYR | 347 | 27.039 | -19.058 | 41.932 |
| ATOM | 2209 | CZ  | TYR | 347 | 27.012 | -19.777 | 40.770 |
| ATOM | 2210 | OH  | TYR | 347 | 27.151 | -21.135 | 40.859 |
| ATOM | 2211 | C   | TYR | 347 | 28.857 | -15.284 | 39.818 |
| ATOM | 2212 | O   | TYR | 347 | 29.067 | -14.435 | 38.965 |
| ATOM | 2213 | N   | ASP | 348 | 29.346 | -16.510 | 39.744 |
| ATOM | 2214 | CA  | ASP | 348 | 30.235 | -16.926 | 38.652 |
| ATOM | 2215 | CB  | ASP | 348 | 31.536 | -16.108 | 38.693 |
| ATOM | 2216 | CG  | ASP | 348 | 32.523 | -16.496 | 37.602 |
| ATOM | 2217 | OD1 | ASP | 348 | 32.410 | -16.026 | 36.429 |
| ATOM | 2218 | OD2 | ASP | 348 | 33.449 | -17.256 | 37.933 |
| ATOM | 2219 | C   | ASP | 348 | 30.529 | -18.396 | 38.847 |
| ATOM | 2220 | O   | ASP | 348 | 30.116 | -18.959 | 39.846 |
| ATOM | 2221 | N   | GLU | 349 | 31.134 | -19.040 | 37.863 |
| ATOM | 2222 | CA  | GLU | 349 | 31.501 | -20.447 | 37.964 |
| ATOM | 2223 | CB  | GLU | 349 | 30.478 | -21.373 | 37.285 |
| ATOM | 2224 | CG  | GLU | 349 | 29.083 | -21.371 | 37.982 |
| ATOM | 2225 | CD  | GLU | 349 | 27.975 | -22.187 | 37.270 |
| ATOM | 2226 | OE1 | GLU | 349 | 27.469 | -23.164 | 37.878 |
| ATOM | 2227 | OE2 | GLU | 349 | 27.565 | -21.827 | 36.137 |
| ATOM | 2228 | C   | GLU | 349 | 32.807 | -20.407 | 37.235 |
| ATOM | 2229 | O   | GLU | 349 | 32.882 | -19.877 | 36.136 |
| ATOM | 2230 | N   | GLU | 350 | 33.865 | -20.813 | 37.917 |
| ATOM | 2231 | CA  | GLU | 350 | 35.202 | -20.768 | 37.358 |
| ATOM | 2232 | CB  | GLU | 350 | 36.158 | -20.041 | 38.307 |
| ATOM | 2233 | CG  | GLU | 350 | 36.464 | -18.652 | 37.855 |
| ATOM | 2234 | CD  | GLU | 350 | 37.859 | -18.210 | 38.202 |
| ATOM | 2235 | OE1 | GLU | 350 | 38.028 | -17.011 | 38.508 |
| ATOM | 2236 | OE2 | GLU | 350 | 38.792 | -19.044 | 38.143 |
| ATOM | 2237 | C   | GLU | 350 | 35.847 | -22.069 | 36.934 |
| ATOM | 2238 | O   | GLU | 350 | 35.198 | -23.134 | 36.814 |
| ATOM | 2239 | N   | GLY | 351 | 37.145 | -21.905 | 36.665 |
| ATOM | 2240 | CA  | GLY | 351 | 38.073 | -22.949 | 36.249 |
| ATOM | 2241 | C   | GLY | 351 | 37.632 | -24.094 | 35.356 |
| ATOM | 2242 | O   | GLY | 351 | 38.037 | -24.177 | 34.182 |
| ATOM | 2243 | N   | VAL | 352 | 36.843 | -24.980 | 35.971 |
| ATOM | 2244 | CA  | VAL | 352 | 36.286 | -26.212 | 35.397 |
| ATOM | 2245 | CB  | VAL | 352 | 35.570 | -25.956 | 34.034 |
| ATOM | 2246 | CG1 | VAL | 352 | 35.077 | -27.297 | 33.405 |
| ATOM | 2247 | CG2 | VAL | 352 | 34.389 | -24.952 | 34.255 |
| ATOM | 2248 | C   | VAL | 352 | 37.269 | -27.423 | 35.370 |
| ATOM | 2249 | O   | VAL | 352 | 38.458 | -27.285 | 34.969 |
| ATOM | 2250 | OT  | VAL | 352 | 36.854 | -28.503 | 35.871 |
| ATOM | 2251 | CB  | ALA | 356 | 39.926 | -30.567 | 35.981 |
| ATOM | 2252 | C   | ALA | 356 | 39.381 | -29.620 | 38.330 |
| ATOM | 2253 | O   | ALA | 356 | 38.988 | -29.716 | 39.523 |
| ATOM | 2254 | N   | ALA | 356 | 37.664 | -30.912 | 37.046 |

FIGURE IVV

| Atom | | Residue AA | No. | X | Y | Z |
|---|---|---|---|---|---|---|
| ATOM | 2255 CA | ALA | 356 | 39.134 | -30.788 | 37.329 |
| ATOM | 2256 N | ALA | 357 | 39.924 | -28.506 | 37.797 |
| ATOM | 2257 CA | ALA | 357 | 40.255 | -27.273 | 38.542 |
| ATOM | 2258 CB | ALA | 357 | 41.542 | -26.613 | 37.895 |
| ATOM | 2259 C | ALA | 357 | 39.066 | -26.244 | 38.635 |
| ATOM | 2260 O | ALA | 357 | 39.256 | -25.031 | 38.459 |
| ATOM | 2261 N | ALA | 358 | 37.864 | -26.735 | 38.963 |
| ATOM | 2262 CA | ALA | 358 | 36.673 | -25.885 | 39.061 |
| ATOM | 2263 CB | ALA | 358 | 35.416 | -26.755 | 39.155 |
| ATOM | 2264 C | ALA | 358 | 36.736 | -24.865 | 40.217 |
| ATOM | 2265 O | ALA | 358 | 37.792 | -24.708 | 40.861 |
| ATOM | 2266 N | ARG | 359 | 35.613 | -24.176 | 40.466 |
| ATOM | 2267 CA | ARG | 359 | 35.519 | -23.169 | 41.527 |
| ATOM | 2268 CB | ARG | 359 | 36.722 | -22.204 | 41.437 |
| ATOM | 2269 CG | ARG | 359 | 36.587 | -20.902 | 42.218 |
| ATOM | 2270 CD | ARG | 359 | 37.928 | -20.201 | 42.416 |
| ATOM | 2271 NE | ARG | 359 | 37.823 | -18.763 | 42.184 |
| ATOM | 2272 CZ | ARG | 359 | 38.575 | -17.824 | 42.752 |
| ATOM | 2273 NH1 | ARG | 359 | 39.528 | -18.153 | 43.600 |
| ATOM | 2274 NH2 | ARG | 359 | 38.346 | -16.542 | 42.489 |
| ATOM | 2275 C | ARG | 359 | 34.248 | -22.362 | 41.362 |
| ATOM | 2276 O | ARG | 359 | 33.836 | -22.172 | 40.246 |
| ATOM | 2277 N | THR | 360 | 33.579 | -21.989 | 42.454 |
| ATOM | 2278 CA | THR | 360 | 32.401 | -21.102 | 42.408 |
| ATOM | 2279 CB | THR | 360 | 31.155 | -21.592 | 43.179 |
| ATOM | 2280 OG1 | THR | 360 | 30.459 | -22.601 | 42.430 |
| ATOM | 2281 CG2 | THR | 360 | 30.212 | -20.421 | 43.430 |
| ATOM | 2282 C | THR | 360 | 32.919 | -19.919 | 43.188 |
| ATOM | 2283 O | THR | 360 | 33.452 | -20.088 | 44.288 |
| ATOM | 2284 N | VAL | 361 | 32.806 | -18.733 | 42.621 |
| ATOM | 2285 CA | VAL | 361 | 33.288 | -17.544 | 43.292 |
| ATOM | 2286 CB | VAL | 361 | 34.433 | -16.878 | 42.515 |
| ATOM | 2287 CG1 | VAL | 361 | 35.342 | -16.123 | 43.445 |
| ATOM | 2288 CG2 | VAL | 361 | 35.183 | -17.876 | 41.743 |
| ATOM | 2289 C | VAL | 361 | 32.142 | -16.572 | 43.304 |
| ATOM | 2290 O | VAL | 361 | 31.098 | -16.853 | 42.742 |
| ATOM | 2291 N | LEU | 362 | 32.292 | -15.506 | 44.068 |
| ATOM | 2292 CA | LEU | 362 | 31.333 | -14.421 | 44.109 |
| ATOM | 2293 CB | LEU | 362 | 30.454 | -14.409 | 45.360 |
| ATOM | 2294 CG | LEU | 362 | 29.303 | -15.419 | 45.481 |
| ATOM | 2295 CD1 | LEU | 362 | 28.180 | -14.852 | 46.308 |
| ATOM | 2296 CD2 | LEU | 362 | 28.760 | -15.760 | 44.134 |
| ATOM | 2297 C | LEU | 362 | 32.371 | -13.355 | 44.171 |
| ATOM | 2298 O | LEU | 362 | 33.378 | -13.512 | 44.843 |
| ATOM | 2299 N | HIS | 363 | 32.248 | -12.363 | 43.321 |
| ATOM | 2300 CA | HIS | 363 | 33.251 | -11.321 | 43.318 |
| ATOM | 2301 CB | HIS | 363 | 33.851 | -11.130 | 41.905 |
| ATOM | 2302 CG | HIS | 363 | 34.677 | -12.289 | 41.388 |

FIGURE 1WW

|  | Atom |  | Residue |  | X | Y | Z |
|---|---|---|---|---|---|---|---|
|  |  |  | AA | No. |  |  |  |
| ATOM | 2303 | CD2 | HIS | 363 | 36.018 | -12.493 | 41.375 |
| ATOM | 2304 | ND1 | HIS | 363 | 34.129 | -13.370 | 40.722 |
| ATOM | 2305 | CE1 | HIS | 363 | 35.092 | -14.185 | 40.327 |
| ATOM | 2306 | NE2 | HIS | 363 | 36.248 | -13.675 | 40.712 |
| ATOM | 2307 | C | HIS | 363 | 32.619 | -10.025 | 43.820 |
| ATOM | 2308 | O | HIS | 363 | 32.205 | -9.186 | 43.023 |
| ATOM | 2309 | N | PHE | 364 | 32.496 | -9.898 | 45.146 |
| ATOM | 2310 | CA | PHE | 364 | 31.911 | -8.712 | 45.800 |
| ATOM | 2311 | CB | PHE | 364 | 31.427 | -9.057 | 47.227 |
| ATOM | 2312 | CG | PHE | 364 | 30.232 | -9.974 | 47.296 |
| ATOM | 2313 | CD1 | PHE | 364 | 30.348 | -11.230 | 47.824 |
| ATOM | 2314 | CD2 | PHE | 364 | 28.979 | -9.546 | 46.928 |
| ATOM | 2315 | CE1 | PHE | 364 | 29.241 | -12.031 | 47.986 |
| ATOM | 2316 | CE2 | PHE | 364 | 27.869 | -10.357 | 47.097 |
| ATOM | 2317 | CZ | PHE | 364 | 28.004 | -11.590 | 47.624 |
| ATOM | 2318 | C | PHE | 364 | 32.985 | -7.629 | 45.946 |
| ATOM | 2319 | O | PHE | 364 | 34.147 | -7.933 | 46.209 |
| ATOM | 2320 | N | HIS | 365 | 32.630 | -6.374 | 45.731 |
| ATOM | 2321 | CA | HIS | 365 | 33.616 | -5.325 | 45.949 |
| ATOM | 2322 | CB | HIS | 365 | 32.993 | -3.980 | 45.598 |
| ATOM | 2323 | CG | HIS | 365 | 33.803 | -2.811 | 46.035 |
| ATOM | 2324 | CD2 | HIS | 365 | 35.066 | -2.437 | 45.723 |
| ATOM | 2325 | ND1 | HIS | 365 | 33.336 | -1.877 | 46.927 |
| ATOM | 2326 | CE1 | HIS | 365 | 34.279 | -0.981 | 47.152 |
| ATOM | 2327 | NE2 | HIS | 365 | 35.337 | -1.297 | 46.434 |
| ATOM | 2328 | C | HIS | 365 | 33.871 | -5.431 | 47.468 |
| ATOM | 2329 | O | HIS | 365 | 32.929 | -5.642 | 48.222 |
| ATOM | 2330 | N | PRO | 366 | 35.121 | -5.295 | 47.946 |
| ATOM | 2331 | CD | PRO | 366 | 36.362 | -4.966 | 47.237 |
| ATOM | 2332 | CA | PRO | 366 | 35.382 | -5.399 | 49.391 |
| ATOM | 2333 | CB | PRO | 366 | 36.734 | -4.748 | 49.523 |
| ATOM | 2334 | CG | PRO | 366 | 37.405 | -5.200 | 48.303 |
| ATOM | 2335 | C | PRO | 366 | 34.359 | -4.708 | 50.283 |
| ATOM | 2336 | O | PRO | 366 | 33.693 | -5.351 | 51.077 |
| ATOM | 2337 | N | ALA | 367 | 34.180 | -3.409 | 50.092 |
| ATOM | 2338 | CA | ALA | 367 | 33.226 | -2.629 | 50.866 |
| ATOM | 2339 | CB | ALA | 367 | 33.407 | -1.165 | 50.557 |
| ATOM | 2340 | C | ALA | 367 | 31.775 | -3.028 | 50.648 |
| ATOM | 2341 | O | ALA | 367 | 30.883 | -2.215 | 50.818 |
| ATOM | 2342 | N | LEU | 368 | 31.544 | -4.270 | 50.254 |
| ATOM | 2343 | CA | LEU | 368 | 30.209 | -4.788 | 50.012 |
| ATOM | 2344 | CB | LEU | 368 | 29.817 | -4.588 | 48.552 |
| ATOM | 2345 | CG | LEU | 368 | 28.578 | -3.808 | 48.134 |
| ATOM | 2346 | CD1 | LEU | 368 | 27.370 | -4.520 | 48.543 |
| ATOM | 2347 | CD2 | LEU | 368 | 28.591 | -2.430 | 48.688 |
| ATOM | 2348 | C | LEU | 368 | 30.220 | -6.282 | 50.335 |
| ATOM | 2349 | O | LEU | 368 | 29.171 | -6.911 | 50.464 |
| ATOM | 2350 | N | ALA | 369 | 31.411 | -6.853 | 50.454 |

FIGURE IXX

|  |  | Residue |  |  |  |
|---|---|---|---|---|---|
| Atom | AA | No. | X | Y | Z |
| ATOM 2351 CA | ALA | 369 | 31.560 | -8.269 | 50.766 |
| ATOM 2352 CB | ALA | 369 | 32.989 | -8.662 | 50.606 |
| ATOM 2353 C | ALA | 369 | 31.143 | -8.495 | 52.198 |
| ATOM 2354 O | ALA | 369 | 31.469 | -7.695 | 53.059 |
| ATOM 2355 N | PRO | 370 | 30.447 | -9.600 | 52.488 |
| ATOM 2356 CD | PRO | 370 | 30.119 | -10.765 | 51.660 |
| ATOM 2357 CA | PRO | 370 | 30.038 | -9.836 | 53.872 |
| ATOM 2358 CB | PRO | 370 | 29.336 | -11.201 | 53.781 |
| ATOM 2359 CG | PRO | 370 | 30.060 | -11.876 | 52.689 |
| ATOM 2360 C | PRO | 370 | 31.231 | -9.799 | 54.880 |
| ATOM 2361 O | PRO | 370 | 31.186 | -9.064 | 55.891 |
| ATOM 2362 N | TYR | 371 | 32.277 | -10.585 | 54.613 |
| ATOM 2363 CA | TYR | 371 | 33.463 | -10.598 | 55.471 |
| ATOM 2364 CB | TYR | 371 | 33.934 | -12.015 | 55.768 |
| ATOM 2365 CG | TYR | 371 | 33.016 | -12.805 | 56.649 |
| ATOM 2366 CD1 | TYR | 371 | 33.096 | -12.717 | 58.026 |
| ATOM 2367 CE1 | TYR | 371 | 32.251 | -13.464 | 58.847 |
| ATOM 2368 CD2 | TYR | 371 | 32.080 | -13.653 | 56.106 |
| ATOM 2369 CE2 | TYR | 371 | 31.241 | -14.402 | 56.909 |
| ATOM 2370 CZ | TYR | 371 | 31.323 | -14.309 | 58.276 |
| ATOM 2371 OH | TYR | 371 | 30.478 | -15.083 | 59.049 |
| ATOM 2372 C | TYR | 371 | 34.556 | -9.865 | 54.718 |
| ATOM 2373 O | TYR | 371 | 34.562 | -9.898 | 53.501 |
| ATOM 2374 N | LYS | 372 | 35.490 | -9.236 | 55.418 |
| ATOM 2375 CA | LYS | 372 | 36.532 | -8.497 | 54.747 |
| ATOM 2376 CB | LYS | 372 | 36.777 | -7.195 | 55.462 |
| ATOM 2377 CG | LYS | 372 | 35.570 | -6.331 | 55.487 |
| ATOM 2378 CD | LYS | 372 | 35.193 | -5.952 | 54.103 |
| ATOM 2379 CE | LYS | 372 | 33.713 | -6.084 | 53.903 |
| ATOM 2380 NZ | LYS | 372 | 32.904 | -5.224 | 54.803 |
| ATOM 2381 C | LYS | 372 | 37.802 | -9.258 | 54.627 |
| ATOM 2382 O | LYS | 372 | 38.680 | -8.892 | 53.877 |
| ATOM 2383 N | ALA | 373 | 37.912 | -10.315 | 55.394 |
| ATOM 2384 CA | ALA | 373 | 39.103 | -11.138 | 55.361 |
| ATOM 2385 CB | ALA | 373 | 40.283 | -10.443 | 56.058 |
| ATOM 2386 C | ALA | 373 | 38.690 | -12.359 | 56.125 |
| ATOM 2387 O | ALA | 373 | 37.514 | -12.493 | 56.462 |
| ATOM 2388 N | ALA | 374 | 39.635 | -13.257 | 56.366 |
| ATOM 2389 CA | ALA | 374 | 39.364 | -14.461 | 57.125 |
| ATOM 2390 CB | ALA | 374 | 38.708 | -15.498 | 56.259 |
| ATOM 2391 C | ALA | 374 | 40.693 | -14.960 | 57.650 |
| ATOM 2392 O | ALA | 374 | 41.696 | -14.905 | 56.931 |
| ATOM 2393 N | ILE | 375 | 40.734 | -15.312 | 58.936 |
| ATOM 2394 CA | ILE | 375 | 41.955 | -15.826 | 59.524 |
| ATOM 2395 CB | ILE | 375 | 42.247 | -15.237 | 60.884 |
| ATOM 2396 CG2 | ILE | 375 | 43.723 | -15.121 | 61.045 |
| ATOM 2397 CG1 | ILE | 375 | 41.658 | -13.848 | 61.000 |
| ATOM 2398 CD1 | ILE | 375 | 42.374 | -12.866 | 60.198 |

FIGURE 1YY

| Atom | | Residue AA | No. | X | Y | Z |
|---|---|---|---|---|---|---|
| ATOM | 2399 | C | ILE | 375 | 41.771 | -17.324 | 59.644 |
| ATOM | 2400 | O | ILE | 375 | 40.902 | -17.797 | 60.348 |
| ATOM | 2401 | N | LEU | 376 | 42.474 | -18.053 | 58.799 |
| ATOM | 2402 | CA | LEU | 376 | 42.431 | -19.507 | 58.792 |
| ATOM | 2403 | CB | LEU | 376 | 42.522 | -20.048 | 57.355 |
| ATOM | 2404 | CG | LEU | 376 | 41.466 | -19.777 | 56.289 |
| ATOM | 2405 | CD1 | LEU | 376 | 40.203 | -20.509 | 56.594 |
| ATOM | 2406 | CD2 | LEU | 376 | 41.212 | -18.321 | 56.206 |
| ATOM | 2407 | C | LEU | 376 | 43.730 | -19.827 | 59.493 |
| ATOM | 2408 | O | LEU | 376 | 44.752 | -19.206 | 59.197 |
| ATOM | 2409 | N | PRO | 377 | 43.712 | -20.712 | 60.489 |
| ATOM | 2410 | CD | PRO | 377 | 42.659 | -21.453 | 61.189 |
| ATOM | 2411 | CA | PRO | 377 | 45.007 | -20.962 | 61.100 |
| ATOM | 2412 | CB | PRO | 377 | 44.653 | -21.858 | 62.272 |
| ATOM | 2413 | CG | PRO | 377 | 43.442 | -22.571 | 61.788 |
| ATOM | 2414 | C | PRO | 377 | 45.763 | -21.700 | 60.047 |
| ATOM | 2415 | O | PRO | 377 | 46.073 | -21.150 | 59.004 |
| ATOM | 2416 | N | LEU | 378 | 46.018 | -22.965 | 60.309 |
| ATOM | 2417 | CA | LEU | 378 | 46.711 | -23.850 | 59.390 |
| ATOM | 2418 | CB | LEU | 378 | 48.238 | -23.695 | 59.477 |
| ATOM | 2419 | CG | LEU | 378 | 49.124 | -24.377 | 58.414 |
| ATOM | 2420 | CD1 | LEU | 378 | 48.721 | -25.823 | 58.128 |
| ATOM | 2421 | CD2 | LEU | 378 | 49.088 | -23.596 | 57.147 |
| ATOM | 2422 | C | LEU | 378 | 46.315 | -25.172 | 59.996 |
| ATOM | 2423 | O | LEU | 378 | 45.710 | -26.029 | 59.332 |
| ATOM | 2424 | N | SER | 379 | 46.616 | -25.276 | 61.299 |
| ATOM | 2425 | CA | SER | 379 | 46.356 | -26.460 | 62.118 |
| ATOM | 2426 | CB | SER | 379 | 47.671 | -27.174 | 62.427 |
| ATOM | 2427 | OG | SER | 379 | 47.432 | -28.504 | 62.821 |
| ATOM | 2428 | C | SER | 379 | 45.758 | -25.987 | 63.415 |
| ATOM | 2429 | O | SER | 379 | 46.160 | -24.934 | 63.914 |
| ATOM | 2430 | N | ALA | 380 | 44.848 | -26.785 | 63.975 |
| ATOM | 2431 | CA | ALA | 380 | 44.192 | -26.455 | 65.232 |
| ATOM | 2432 | CB | ALA | 380 | 43.411 | -27.663 | 65.762 |
| ATOM | 2433 | C | ALA | 380 | 45.232 | -25.964 | 66.255 |
| ATOM | 2434 | O | ALA | 380 | 44.918 | -25.167 | 67.142 |
| ATOM | 2435 | N | ALA | 381 | 46.481 | -26.391 | 66.077 |
| ATOM | 2436 | CA | ALA | 381 | 47.582 | -25.980 | 66.941 |
| ATOM | 2437 | CB | ALA | 381 | 48.875 | -26.610 | 66.461 |
| ATOM | 2438 | C | ALA | 381 | 47.709 | -24.451 | 66.956 |
| ATOM | 2439 | O | ALA | 381 | 47.575 | -23.817 | 67.998 |
| ATOM | 2440 | N | LEU | 382 | 47.897 | -23.845 | 65.795 |
| ATOM | 2441 | CA | LEU | 382 | 48.018 | -22.399 | 65.765 |
| ATOM | 2442 | CB | LEU | 382 | 48.704 | -21.913 | 64.470 |
| ATOM | 2443 | CG | LEU | 382 | 50.038 | -22.469 | 63.945 |
| ATOM | 2444 | CD1 | LEU | 382 | 50.986 | -22.774 | 65.117 |
| ATOM | 2445 | CD2 | LEU | 382 | 49.767 | -23.719 | 63.097 |
| ATOM | 2446 | C | LEU | 382 | 46.668 | -21.694 | 65.932 |

FIGURE 1ZZ

|  |  | Residue |  |  |  |
|---|---|---|---|---|---|
| Atom | AA | No. | X | Y | Z |
| ATOM 2447 O | LEU | 382 | 46.529 | -20.548 | 65.500 |
| ATOM 2448 N | SER | 383 | 45.674 | -22.365 | 66.522 |
| ATOM 2449 CA | SER | 383 | 44.359 | -21.748 | 66.725 |
| ATOM 2450 CB | SER | 383 | 43.393 | -22.689 | 67.442 |
| ATOM 2451 OG | SER | 383 | 42.847 | -23.643 | 66.551 |
| ATOM 2452 C | SER | 383 | 44.602 | -20.516 | 67.566 |
| ATOM 2453 O | SER | 383 | 44.196 | -19.400 | 67.225 |
| ATOM 2454 N | GLY | 384 | 45.257 | -20.718 | 68.692 |
| ATOM 2455 CA | GLY | 384 | 45.605 | -19.571 | 69.493 |
| ATOM 2456 C | GLY | 384 | 46.709 | -18.939 | 68.651 |
| ATOM 2457 O | GLY | 384 | 47.477 | -19.670 | 67.996 |
| ATOM 2458 N | ALA | 385 | 46.773 | -17.603 | 68.664 |
| ATOM 2459 CA | ALA | 385 | 47.735 | -16.765 | 67.910 |
| ATOM 2460 CB | ALA | 385 | 49.022 | -17.517 | 67.502 |
| ATOM 2461 C | ALA | 385 | 46.983 | -16.279 | 66.692 |
| ATOM 2462 O | ALA | 385 | 47.015 | -15.097 | 66.368 |
| ATOM 2463 N | ALA | 386 | 46.261 | -17.188 | 66.054 |
| ATOM 2464 CA | ALA | 386 | 45.460 | -16.820 | 64.913 |
| ATOM 2465 CB | ALA | 386 | 44.984 | -18.064 | 64.193 |
| ATOM 2466 C | ALA | 386 | 44.278 | -16.004 | 65.473 |
| ATOM 2467 O | ALA | 386 | 43.918 | -14.947 | 64.937 |
| ATOM 2468 N | ILE | 387 | 43.749 | -16.429 | 66.614 |
| ATOM 2469 CA | ILE | 387 | 42.634 | -15.720 | 67.200 |
| ATOM 2470 CB | ILE | 387 | 42.149 | -16.394 | 68.437 |
| ATOM 2471 CG2 | ILE | 387 | 40.886 | -15.709 | 68.922 |
| ATOM 2472 CG1 | ILE | 387 | 41.850 | -17.859 | 68.123 |
| ATOM 2473 CD1 | ILE | 387 | 41.715 | -18.777 | 69.334 |
| ATOM 2474 C | ILE | 387 | 43.068 | -14.339 | 67.553 |
| ATOM 2475 O | ILE | 387 | 42.259 | -13.432 | 67.630 |
| ATOM 2476 N | ALA | 388 | 44.372 | -14.182 | 67.716 |
| ATOM 2477 CA | ALA | 388 | 44.958 | -12.894 | 68.063 |
| ATOM 2478 CB | ALA | 388 | 46.423 | -13.076 | 68.488 |
| ATOM 2479 C | ALA | 388 | 44.827 | -11.844 | 66.941 |
| ATOM 2480 O | ALA | 388 | 44.355 | -10.708 | 67.183 |
| ATOM 2481 N | ILE | 389 | 45.259 | -12.193 | 65.729 |
| ATOM 2482 CA | ILE | 389 | 45.122 | -11.255 | 64.626 |
| ATOM 2483 CB | ILE | 389 | 45.777 | -11.729 | 63.339 |
| ATOM 2484 CG2 | ILE | 389 | 46.949 | -10.841 | 63.015 |
| ATOM 2485 CG1 | ILE | 389 | 46.076 | -13.222 | 63.406 |
| ATOM 2486 CD1 | ILE | 389 | 47.212 | -13.660 | 62.521 |
| ATOM 2487 C | ILE | 389 | 43.637 | -11.078 | 64.378 |
| ATOM 2488 O | ILE | 389 | 43.177 | -9.991 | 64.009 |
| ATOM 2489 N | PHE | 390 | 42.880 | -12.142 | 64.613 |
| ATOM 2490 CA | PHE | 390 | 41.458 | -12.065 | 64.423 |
| ATOM 2491 CB | PHE | 390 | 40.756 | -13.281 | 64.990 |
| ATOM 2492 CG | PHE | 390 | 39.298 | -13.081 | 65.118 |
| ATOM 2493 CD1 | PHE | 390 | 38.781 | -12.387 | 66.191 |
| ATOM 2494 CD2 | PHE | 390 | 38.441 | -13.469 | 64.117 |

FIGURE 1AAA

|  | | Residue | | | |
|---|---|---|---|---|---|
| Atom | AA | No. | X | Y | Z |
| ATOM 2495 CE1 | PHE | 390 | 37.434 | -12.071 | 66.264 |
| ATOM 2496 CE2 | PHE | 390 | 37.085 | -13.151 | 64.190 |
| ATOM 2497 CZ | PHE | 390 | 36.590 | -12.448 | 65.267 |
| ATOM 2498 C | PHE | 390 | 40.936 | -10.825 | 65.113 |
| ATOM 2499 O | PHE | 390 | 40.362 | -9.962 | 64.478 |
| ATOM 2500 N | GLU | 391 | 41.176 | -10.735 | 66.412 |
| ATOM 2501 CA | GLU | 391 | 40.713 | -9.606 | 67.220 |
| ATOM 2502 CB | GLU | 391 | 41.049 | -9.820 | 68.684 |
| ATOM 2503 CG | GLU | 391 | 40.226 | -10.892 | 69.351 |
| ATOM 2504 CD | GLU | 391 | 40.769 | -11.295 | 70.721 |
| ATOM 2505 OE1 | GLU | 391 | 41.947 | -10.967 | 71.044 |
| ATOM 2506 OE2 | GLU | 391 | 40.001 | -11.960 | 71.464 |
| ATOM 2507 C | GLU | 391 | 41.230 | -8.237 | 66.829 |
| ATOM 2508 O | GLU | 391 | 40.448 | -7.279 | 66.719 |
| ATOM 2509 N | GLN | 392 | 42.550 | -8.124 | 66.687 |
| ATOM 2510 CA | GLN | 392 | 43.178 | -6.852 | 66.315 |
| ATOM 2511 CB | GLN | 392 | 44.630 | -7.108 | 65.875 |
| ATOM 2512 CG | GLN | 392 | 45.429 | -5.866 | 65.377 |
| ATOM 2513 CD | GLN | 392 | 46.524 | -6.219 | 64.315 |
| ATOM 2514 OE1 | GLN | 392 | 46.652 | -5.532 | 63.269 |
| ATOM 2515 NE2 | GLN | 392 | 47.303 | -7.299 | 64.579 |
| ATOM 2516 C | GLN | 392 | 42.396 | -6.156 | 65.196 |
| ATOM 2517 O | GLN | 392 | 42.256 | -4.938 | 65.191 |
| ATOM 2518 N | LEU | 393 | 41.848 | -6.964 | 64.295 |
| ATOM 2519 CA | LEU | 393 | 41.101 | -6.474 | 63.163 |
| ATOM 2520 CB | LEU | 393 | 41.378 | -7.344 | 61.937 |
| ATOM 2521 CG | LEU | 393 | 42.877 | -7.450 | 61.629 |
| ATOM 2522 CD1 | LEU | 393 | 43.114 | -8.526 | 60.642 |
| ATOM 2523 CD2 | LEU | 393 | 43.469 | -6.139 | 61.131 |
| ATOM 2524 C | LEU | 393 | 39.625 | -6.355 | 63.409 |
| ATOM 2525 O | LEU | 393 | 39.025 | -5.422 | 62.920 |
| ATOM 2526 N | SER | 394 | 39.043 | -7.261 | 64.189 |
| ATOM 2527 CA | SER | 394 | 37.608 | -7.239 | 64.475 |
| ATOM 2528 CB | SER | 394 | 37.277 | -8.224 | 65.574 |
| ATOM 2529 OG | SER | 394 | 37.910 | -9.458 | 65.333 |
| ATOM 2530 C | SER | 394 | 37.159 | -5.855 | 64.898 |
| ATOM 2531 O | SER | 394 | 36.024 | -5.440 | 64.668 |
| ATOM 2532 N | SER | 395 | 38.098 | -5.122 | 65.469 |
| ATOM 2533 CA | SER | 395 | 37.888 | -3.769 | 65.951 |
| ATOM 2534 CB | SER | 395 | 39.243 | -3.199 | 66.349 |
| ATOM 2535 OG | SER | 395 | 40.244 | -3.708 | 65.484 |
| ATOM 2536 C | SER | 395 | 37.280 | -2.886 | 64.906 |
| ATOM 2537 O | SER | 395 | 36.723 | -1.841 | 65.208 |
| ATOM 2538 N | LYS | 396 | 37.432 | -3.301 | 63.662 |
| ATOM 2539 CA | LYS | 396 | 36.940 | -2.531 | 62.537 |
| ATOM 2540 CB | LYS | 396 | 38.097 | -1.690 | 61.974 |
| ATOM 2541 CG | LYS | 396 | 38.359 | -0.366 | 62.721 |
| ATOM 2542 CD | LYS | 396 | 39.205 | -0.492 | 64.001 |

FIGURE 1BBB

|  |  | Residue |  |  |  |
|---|---|---|---|---|---|
| Atom |  | AA No. | X | Y | Z |
| ATOM 2543 | CE | LYS 396 | 40.693 | -0.523 | 63.711 |
| ATOM 2544 | NZ | LYS 396 | 41.053 | -1.693 | 62.889 |
| ATOM 2545 | C | LYS 396 | 36.243 | -3.280 | 61.385 |
| ATOM 2546 | O | LYS 396 | 35.223 | -2.815 | 60.865 |
| ATOM 2547 | N | PHE 397 | 36.776 | -4.434 | 60.993 |
| ATOM 2548 | CA | PHE 397 | 36.231 | -5.197 | 59.859 |
| ATOM 2549 | CB | PHE 397 | 37.376 | -5.564 | 58.892 |
| ATOM 2550 | CG | PHE 397 | 38.309 | -4.424 | 58.575 |
| ATOM 2551 | CD1 | PHE 397 | 37.810 | -3.160 | 58.270 |
| ATOM 2552 | CD2 | PHE 397 | 39.676 | -4.615 | 58.623 |
| ATOM 2553 | CE1 | PHE 397 | 38.658 | -2.113 | 58.028 |
| ATOM 2554 | CE2 | PHE 397 | 40.535 | -3.572 | 58.383 |
| ATOM 2555 | CZ | PHE 397 | 40.032 | -2.313 | 58.086 |
| ATOM 2556 | C | PHE 397 | 35.456 | -6.472 | 60.173 |
| ATOM 2557 | O | PHE 397 | 35.856 | -7.246 | 61.010 |
| ATOM 2558 | N | SER 398 | 34.412 | -6.749 | 59.414 |
| ATOM 2559 | CA | SER 398 | 33.626 | -7.953 | 59.640 |
| ATOM 2560 | CB | SER 398 | 32.318 | -7.889 | 58.839 |
| ATOM 2561 | OG | SER 398 | 31.964 | -6.561 | 58.468 |
| ATOM 2562 | C | SER 398 | 34.396 | -9.174 | 59.178 |
| ATOM 2563 | O | SER 398 | 34.072 | -9.726 | 58.150 |
| ATOM 2564 | N | ILE 399 | 35.392 | -9.628 | 59.921 |
| ATOM 2565 | CA | ILE 399 | 36.160 | -10.787 | 59.482 |
| ATOM 2566 | CB | ILE 399 | 37.658 | -10.544 | 59.661 |
| ATOM 2567 | CG2 | ILE 399 | 37.992 | -9.121 | 59.291 |
| ATOM 2568 | CG1 | ILE 399 | 38.089 | -10.836 | 61.089 |
| ATOM 2569 | CD1 | ILE 399 | 39.554 | -10.631 | 61.313 |
| ATOM 2570 | C | ILE 399 | 35.766 | -12.148 | 60.069 |
| ATOM 2571 | O | ILE 399 | 35.197 | -12.230 | 61.143 |
| ATOM 2572 | N | ASP 400 | 36.034 | -13.212 | 59.325 |
| ATOM 2573 | CA | ASP 400 | 35.723 | -14.577 | 59.747 |
| ATOM 2574 | CB | ASP 400 | 35.226 | -15.378 | 58.521 |
| ATOM 2575 | CG | ASP 400 | 34.501 | -16.702 | 58.873 |
| ATOM 2576 | OD1 | ASP 400 | 34.906 | -17.450 | 59.779 |
| ATOM 2577 | OD2 | ASP 400 | 33.527 | -17.046 | 58.175 |
| ATOM 2578 | C | ASP 400 | 37.016 | -15.195 | 60.289 |
| ATOM 2579 | O | ASP 400 | 38.094 | -14.617 | 60.193 |
| ATOM 2580 | N | PHE 401 | 36.871 | -16.337 | 60.938 |
| ATOM 2581 | CA | PHE 401 | 37.975 | -17.113 | 61.476 |
| ATOM 2582 | CB | PHE 401 | 38.140 | -16.855 | 62.990 |
| ATOM 2583 | CG | PHE 401 | 39.299 | -17.595 | 63.624 |
| ATOM 2584 | CD1 | PHE 401 | 40.558 | -17.019 | 63.678 |
| ATOM 2585 | CD2 | PHE 401 | 39.138 | -18.887 | 64.123 |
| ATOM 2586 | CE1 | PHE 401 | 41.642 | -17.724 | 64.211 |
| ATOM 2587 | CE2 | PHE 401 | 40.212 | -19.593 | 64.657 |
| ATOM 2588 | CZ | PHE 401 | 41.465 | -19.014 | 64.699 |
| ATOM 2589 | C | PHE 401 | 37.555 | -18.574 | 61.203 |
| ATOM 2590 | O | PHE 401 | 36.422 | -18.969 | 61.498 |

FIGURE 1CCC

| Atom | | Residue AA | No. | X | Y | Z |
|---|---|---|---|---|---|---|
| ATOM | 2591 N | ASP | 402 | 38.422 | -19.345 | 60.556 |
| ATOM | 2592 CA | ASP | 402 | 38.099 | -20.730 | 60.283 |
| ATOM | 2593 CB | ASP | 402 | 37.442 | -20.893 | 58.926 |
| ATOM | 2594 CG | ASP | 402 | 36.662 | -22.167 | 58.824 |
| ATOM | 2595 OD1 | ASP | 402 | 35.913 | -22.318 | 57.845 |
| ATOM | 2596 OD2 | ASP | 402 | 36.776 | -23.012 | 59.740 |
| ATOM | 2597 C | ASP | 402 | 39.302 | -21.634 | 60.384 |
| ATOM | 2598 O | ASP | 402 | 40.323 | -21.430 | 59.746 |
| ATOM | 2599 N | GLU | 403 | 39.152 | -22.640 | 61.222 |
| ATOM | 2600 CA | GLU | 403 | 40.197 | -23.599 | 61.457 |
| ATOM | 2601 CB | GLU | 403 | 40.547 | -23.628 | 62.943 |
| ATOM | 2602 CG | GLU | 403 | 39.325 | -23.670 | 63.866 |
| ATOM | 2603 CD | GLU | 403 | 39.684 | -23.753 | 65.355 |
| ATOM | 2604 OE1 | GLU | 403 | 39.179 | -24.686 | 66.017 |
| ATOM | 2605 OE2 | GLU | 403 | 40.449 | -22.896 | 65.865 |
| ATOM | 2606 C | GLU | 403 | 39.713 | -24.960 | 61.020 |
| ATOM | 2607 O | GLU | 403 | 40.466 | -25.746 | 60.434 |
| ATOM | 2608 N | SER | 404 | 38.446 | -25.240 | 61.301 |
| ATOM | 2609 CA | SER | 404 | 37.869 | -26.538 | 60.943 |
| ATOM | 2610 CB | SER | 404 | 36.371 | -26.583 | 61.320 |
| ATOM | 2611 OG | SER | 404 | 35.874 | -27.921 | 61.503 |
| ATOM | 2612 C | SER | 404 | 38.068 | -26.846 | 59.458 |
| ATOM | 2613 O | SER | 404 | 37.861 | -25.973 | 58.604 |
| ATOM | 2614 N | GLN | 405 | 38.470 | -28.089 | 59.183 |
| ATOM | 2615 CA | GLN | 405 | 38.726 | -28.602 | 57.834 |
| ATOM | 2616 CB | GLN | 405 | 37.820 | -27.926 | 56.784 |
| ATOM | 2617 CG | GLN | 405 | 36.316 | -27.963 | 57.090 |
| ATOM | 2618 CD | GLN | 405 | 35.883 | -29.281 | 57.733 |
| ATOM | 2619 OE1 | GLN | 405 | 35.090 | -29.285 | 58.678 |
| ATOM | 2620 NE2 | GLN | 405 | 36.415 | -30.406 | 57.233 |
| ATOM | 2621 C | GLN | 405 | 40.206 | -28.529 | 57.407 |
| ATOM | 2622 O | GLN | 405 | 41.101 | -28.370 | 58.243 |
| ATOM | 2623 N | SER | 406 | 40.459 | -28.728 | 56.117 |
| ATOM | 2624 CA | SER | 406 | 41.813 | -28.699 | 55.591 |
| ATOM | 2625 CB | SER | 406 | 41.866 | -29.375 | 54.202 |
| ATOM | 2626 OG | SER | 406 | 41.045 | -28.705 | 53.257 |
| ATOM | 2627 C | SER | 406 | 42.319 | -27.252 | 55.541 |
| ATOM | 2628 O | SER | 406 | 42.620 | -26.657 | 56.580 |
| ATOM | 2629 N | ILE | 407 | 42.419 | -26.711 | 54.323 |
| ATOM | 2630 CA | ILE | 407 | 42.864 | -25.341 | 54.057 |
| ATOM | 2631 CB | ILE | 407 | 44.420 | -25.169 | 54.156 |
| ATOM | 2632 CG2 | ILE | 407 | 45.082 | -25.129 | 52.793 |
| ATOM | 2633 CG1 | ILE | 407 | 44.762 | -23.866 | 54.873 |
| ATOM | 2634 CD1 | ILE | 407 | 44.063 | -22.656 | 54.346 |
| ATOM | 2635 C | ILE | 407 | 42.362 | -25.080 | 52.646 |
| ATOM | 2636 O | ILE | 407 | 41.743 | -24.056 | 52.383 |
| ATOM | 2637 N | GLY | 408 | 42.553 | -26.060 | 51.768 |
| ATOM | 2638 CA | GLY | 408 | 42.097 | -25.926 | 50.400 |

FIGURE 1DDD

| Atom | | Residue | | X | Y | Z |
|---|---|---|---|---|---|---|
| | | AA | No. | | | |
| ATOM | 2639 C | GLY | 408 | 40.582 | -25.970 | 50.402 |
| ATOM | 2640 O | GLY | 408 | 39.941 | -25.179 | 49.719 |
| ATOM | 2641 N | LYS | 409 | 40.014 | -26.874 | 51.195 |
| ATOM | 2642 CA | LYS | 409 | 38.578 | -27.006 | 51.282 |
| ATOM | 2643 CB | LYS | 409 | 38.221 | -28.276 | 52.038 |
| ATOM | 2644 CG | LYS | 409 | 37.477 | -29.335 | 51.226 |
| ATOM | 2645 CD | LYS | 409 | 36.001 | -28.948 | 50.956 |
| ATOM | 2646 CE | LYS | 409 | 35.238 | -30.090 | 50.222 |
| ATOM | 2647 NZ | LYS | 409 | 33.770 | -29.814 | 49.977 |
| ATOM | 2648 C | LYS | 409 | 38.052 | -25.788 | 52.010 |
| ATOM | 2649 O | LYS | 409 | 36.909 | -25.379 | 51.796 |
| ATOM | 2650 N | ARG | 410 | 38.913 | -25.201 | 52.844 |
| ATOM | 2651 CA | ARG | 410 | 38.589 | -24.005 | 53.637 |
| ATOM | 2652 CB | ARG | 410 | 39.655 | -23.740 | 54.730 |
| ATOM | 2653 CG | ARG | 410 | 39.163 | -23.950 | 56.214 |
| ATOM | 2654 CD | ARG | 410 | 40.214 | -24.538 | 57.168 |
| ATOM | 2655 NE | ARG | 410 | 41.167 | -23.547 | 57.640 |
| ATOM | 2656 CZ | ARG | 410 | 42.214 | -23.818 | 58.416 |
| ATOM | 2657 NH1 | ARG | 410 | 43.036 | -22.848 | 58.800 |
| ATOM | 2658 NH2 | ARG | 410 | 42.447 | -25.060 | 58.817 |
| ATOM | 2659 C | ARG | 410 | 38.501 | -22.836 | 52.698 |
| ATOM | 2660 O | ARG | 410 | 37.545 | -22.074 | 52.726 |
| ATOM | 2661 N | TYR | 411 | 39.499 | -22.723 | 51.843 |
| ATOM | 2662 CA | TYR | 411 | 39.533 | -21.684 | 50.845 |
| ATOM | 2663 CB | TYR | 411 | 40.747 | -21.882 | 49.958 |
| ATOM | 2664 CG | TYR | 411 | 42.044 | -21.421 | 50.545 |
| ATOM | 2665 CD1 | TYR | 411 | 43.228 | -22.116 | 50.290 |
| ATOM | 2666 CE1 | TYR | 411 | 44.476 | -21.641 | 50.733 |
| ATOM | 2667 CD2 | TYR | 411 | 42.123 | -20.248 | 51.268 |
| ATOM | 2668 CE2 | TYR | 411 | 43.367 | -19.760 | 51.717 |
| ATOM | 2669 CZ | TYR | 411 | 44.542 | -20.462 | 51.439 |
| ATOM | 2670 OH | TYR | 411 | 45.779 | -19.973 | 51.809 |
| ATOM | 2671 C | TYR | 411 | 38.244 | -21.775 | 50.000 |
| ATOM | 2672 O | TYR | 411 | 37.490 | -20.820 | 49.909 |
| ATOM | 2673 N | ARG | 412 | 37.953 | -22.939 | 49.438 |
| ATOM | 2674 CA | ARG | 412 | 36.759 | -23.088 | 48.626 |
| ATOM | 2675 CB | ARG | 412 | 36.429 | -24.581 | 48.347 |
| ATOM | 2676 CG | ARG | 412 | 35.053 | -24.859 | 47.579 |
| ATOM | 2677 CD | ARG | 412 | 34.181 | -26.099 | 48.110 |
| ATOM | 2678 NE | ARG | 412 | 33.519 | -25.933 | 49.436 |
| ATOM | 2679 CZ | ARG | 412 | 32.249 | -26.266 | 49.725 |
| ATOM | 2680 NH1 | ARG | 412 | 31.776 | -26.079 | 50.959 |
| ATOM | 2681 NH2 | ARG | 412 | 31.429 | -26.746 | 48.785 |
| ATOM | 2682 C | ARG | 412 | 35.562 | -22.424 | 49.283 |
| ATOM | 2683 O | ARG | 412 | 35.027 | -21.465 | 48.746 |
| ATOM | 2684 N | ARG | 413 | 35.177 | -22.883 | 50.464 |
| ATOM | 2685 CA | ARG | 413 | 33.995 | -22.338 | 51.116 |
| ATOM | 2686 CB | ARG | 413 | 33.813 | -22.948 | 52.517 |

FIGURE 1EEE

| Atom | | Residue AA | No. | X | Y | Z |
|---|---|---|---|---|---|---|
| ATOM | 2687 CG | ARG | 413 | 32.540 | -22.457 | 53.225 |
| ATOM | 2688 CD | ARG | 413 | 32.709 | -22.241 | 54.750 |
| ATOM | 2689 NE | ARG | 413 | 31.700 | -21.314 | 55.330 |
| ATOM | 2690 CZ | ARG | 413 | 30.378 | -21.561 | 55.459 |
| ATOM | 2691 NH1 | ARG | 413 | 29.839 | -22.724 | 55.053 |
| ATOM | 2692 NH2 | ARG | 413 | 29.569 | -20.637 | 55.990 |
| ATOM | 2693 C | ARG | 413 | 33.945 | -20.814 | 51.196 |
| ATOM | 2694 O | ARG | 413 | 32.872 | -20.212 | 51.123 |
| ATOM | 2695 N | ALA | 414 | 35.115 | -20.205 | 51.321 |
| ATOM | 2696 CA | ALA | 414 | 35.224 | -18.762 | 51.450 |
| ATOM | 2697 CB | ALA | 414 | 36.651 | -18.382 | 51.902 |
| ATOM | 2698 C | ALA | 414 | 34.832 | -18.024 | 50.173 |
| ATOM | 2699 O | ALA | 414 | 34.101 | -17.028 | 50.194 |
| ATOM | 2700 N | ASP | 415 | 35.305 | -18.529 | 49.050 |
| ATOM | 2701 CA | ASP | 415 | 35.009 | -17.923 | 47.770 |
| ATOM | 2702 CB | ASP | 415 | 35.813 | -18.607 | 46.675 |
| ATOM | 2703 CG | ASP | 415 | 37.307 | -18.467 | 46.900 |
| ATOM | 2704 OD1 | ASP | 415 | 37.700 | -17.360 | 47.335 |
| ATOM | 2705 OD2 | ASP | 415 | 38.075 | -19.446 | 46.694 |
| ATOM | 2706 C | ASP | 415 | 33.519 | -17.993 | 47.515 |
| ATOM | 2707 O | ASP | 415 | 32.897 | -16.964 | 47.334 |
| ATOM | 2708 N | GLU | 416 | 32.910 | -19.164 | 47.626 |
| ATOM | 2709 CA | GLU | 416 | 31.486 | -19.240 | 47.381 |
| ATOM | 2710 CB | GLU | 416 | 31.016 | -20.671 | 47.442 |
| ATOM | 2711 CG | GLU | 416 | 31.569 | -21.400 | 48.619 |
| ATOM | 2712 CD | GLU | 416 | 30.878 | -22.724 | 48.879 |
| ATOM | 2713 OE1 | GLU | 416 | 29.797 | -22.981 | 48.293 |
| ATOM | 2714 OE2 | GLU | 416 | 31.411 | -23.503 | 49.701 |
| ATOM | 2715 C | GLU | 416 | 30.613 | -18.338 | 48.256 |
| ATOM | 2716 O | GLU | 416 | 29.431 | -18.206 | 47.987 |
| ATOM | 2717 N | ILE | 417 | 31.162 | -17.770 | 49.333 |
| ATOM | 2718 CA | ILE | 417 | 30.382 | -16.843 | 50.185 |
| ATOM | 2719 CB | ILE | 417 | 30.587 | -17.002 | 51.748 |
| ATOM | 2720 CG2 | ILE | 417 | 30.668 | -18.484 | 52.159 |
| ATOM | 2721 CG1 | ILE | 417 | 31.815 | -16.208 | 52.215 |
| ATOM | 2722 CD1 | ILE | 417 | 32.057 | -16.280 | 53.689 |
| ATOM | 2723 C | ILE | 417 | 30.830 | -15.454 | 49.778 |
| ATOM | 2724 O | ILE | 417 | 30.209 | -14.463 | 50.133 |
| ATOM | 2725 N | GLY | 418 | 32.002 | -15.403 | 49.166 |
| ATOM | 2726 CA | GLY | 418 | 32.513 | -14.166 | 48.636 |
| ATOM | 2727 C | GLY | 418 | 33.395 | -13.262 | 49.434 |
| ATOM | 2728 O | GLY | 418 | 33.170 | -12.067 | 49.453 |
| ATOM | 2729 N | THR | 419 | 34.463 | -13.773 | 50.002 |
| ATOM | 2730 CA | THR | 419 | 35.292 | -12.883 | 50.772 |
| ATOM | 2731 CB | THR | 419 | 35.314 | -13.309 | 52.267 |
| ATOM | 2732 OG1 | THR | 419 | 35.857 | -14.625 | 52.421 |
| ATOM | 2733 CG2 | THR | 419 | 33.874 | -13.335 | 52.808 |
| ATOM | 2734 C | THR | 419 | 36.660 | -12.619 | 50.173 |

FIGURE 1FFF

|  | Residue | | | | |
|---|---|---|---|---|---|
| Atom | AA | No. | X | Y | Z |
| ATOM 2735 O | THR | 419 | 37.371 | -13.538 | 49.814 |
| ATOM 2736 N | PRO | 420 | 37.014 | -11.342 | 50.010 |
| ATOM 2737 CD | PRO | 420 | 36.044 | -10.301 | 50.376 |
| ATOM 2738 CA | PRO | 420 | 38.232 | -10.727 | 49.470 |
| ATOM 2739 CB | PRO | 420 | 38.076 | -9.271 | 49.867 |
| ATOM 2740 CG | PRO | 420 | 36.635 | -9.065 | 49.765 |
| ATOM 2741 C | PRO | 420 | 39.624 | -11.238 | 49.851 |
| ATOM 2742 O | PRO | 420 | 40.543 | -11.092 | 49.041 |
| ATOM 2743 N | TYR | 421 | 39.815 | -11.754 | 51.077 |
| ATOM 2744 CA | TYR | 421 | 41.136 | -12.267 | 51.516 |
| ATOM 2745 CB | TYR | 421 | 42.010 | -11.147 | 52.059 |
| ATOM 2746 CG | TYR | 421 | 42.172 | -10.022 | 51.105 |
| ATOM 2747 CD1 | TYR | 421 | 41.328 | -8.921 | 51.174 |
| ATOM 2748 CE1 | TYR | 421 | 41.415 | -7.905 | 50.275 |
| ATOM 2749 CD2 | TYR | 421 | 43.128 | -10.073 | 50.105 |
| ATOM 2750 CE2 | TYR | 421 | 43.238 | -9.062 | 49.198 |
| ATOM 2751 CZ | TYR | 421 | 42.371 | -7.977 | 49.286 |
| ATOM 2752 OH | TYR | 421 | 42.445 | -6.952 | 48.380 |
| ATOM 2753 C | TYR | 421 | 41.178 | -13.388 | 52.547 |
| ATOM 2754 O | TYR | 421 | 40.396 | -13.426 | 53.488 |
| ATOM 2755 N | CYS | 422 | 42.177 | -14.244 | 52.406 |
| ATOM 2756 CA | CYS | 422 | 42.362 | -15.338 | 53.322 |
| ATOM 2757 CB | CYS | 422 | 42.178 | -16.661 | 52.623 |
| ATOM 2758 SG | CYS | 422 | 40.482 | -16.979 | 52.303 |
| ATOM 2759 C | CYS | 422 | 43.735 | -15.277 | 53.935 |
| ATOM 2760 O | CYS | 422 | 44.733 | -15.599 | 53.287 |
| ATOM 2761 N | VAL | 423 | 43.781 | -14.814 | 55.180 |
| ATOM 2762 CA | VAL | 423 | 45.028 | -14.713 | 55.935 |
| ATOM 2763 CB | VAL | 423 | 44.989 | -13.569 | 56.960 |
| ATOM 2764 CG1 | VAL | 423 | 46.360 | -13.424 | 57.630 |
| ATOM 2765 CG2 | VAL | 423 | 44.570 | -12.280 | 56.285 |
| ATOM 2766 C | VAL | 423 | 45.287 | -16.018 | 56.684 |
| ATOM 2767 O | VAL | 423 | 44.627 | -16.322 | 57.683 |
| ATOM 2768 N | THR | 424 | 46.236 | -16.793 | 56.178 |
| ATOM 2769 CA | THR | 424 | 46.567 | -18.065 | 56.784 |
| ATOM 2770 CB | THR | 424 | 46.846 | -19.139 | 55.713 |
| ATOM 2771 OG1 | THR | 424 | 47.728 | -18.603 | 54.713 |
| ATOM 2772 CG2 | THR | 424 | 45.542 | -19.569 | 55.057 |
| ATOM 2773 C | THR | 424 | 47.743 | -17.938 | 57.734 |
| ATOM 2774 O | THR | 424 | 48.769 | -17.330 | 57.409 |
| ATOM 2775 N | PHE | 425 | 47.550 | -18.444 | 58.942 |
| ATOM 2776 CA | PHE | 425 | 48.584 | -18.414 | 59.943 |
| ATOM 2777 CB | PHE | 425 | 48.013 | -18.034 | 61.311 |
| ATOM 2778 CG | PHE | 425 | 49.072 | -17.767 | 62.350 |
| ATOM 2779 CD1 | PHE | 425 | 49.432 | -16.460 | 62.673 |
| ATOM 2780 CD2 | PHE | 425 | 49.771 | -18.817 | 62.941 |
| ATOM 2781 CE1 | PHE | 425 | 50.472 | -16.205 | 63.553 |
| ATOM 2782 CE2 | PHE | 425 | 50.812 | -18.564 | 63.822 |

FIGURE 1GGG

| Atom | | Residue AA | No. | X | Y | Z |
|---|---|---|---|---|---|---|
| ATOM | 2783 CZ | PHE | 425 | 51.163 | -17.255 | 64.125 |
| ATOM | 2784 C | PHE | 425 | 49.113 | -19.816 | 60.001 |
| ATOM | 2785 O | PHE | 425 | 48.387 | -20.743 | 60.306 |
| ATOM | 2786 N | ASP | 426 | 50.372 | -19.994 | 59.684 |
| ATOM | 2787 CA | ASP | 426 | 50.930 | -21.321 | 59.739 |
| ATOM | 2788 CB | ASP | 426 | 51.483 | -21.694 | 58.382 |
| ATOM | 2789 CG | ASP | 426 | 52.779 | -21.021 | 58.102 |
| ATOM | 2790 OD1 | ASP | 426 | 53.788 | -21.743 | 58.138 |
| ATOM | 2791 OD2 | ASP | 426 | 52.795 | -19.783 | 57.900 |
| ATOM | 2792 C | ASP | 426 | 52.053 | -21.292 | 60.728 |
| ATOM | 2793 O | ASP | 426 | 52.244 | -20.313 | 61.419 |
| ATOM | 2794 N | PHE | 427 | 52.887 | -22.310 | 60.672 |
| ATOM | 2795 CA | PHE | 427 | 54.015 | -22.410 | 61.564 |
| ATOM | 2796 CB | PHE | 427 | 54.616 | -23.796 | 61.442 |
| ATOM | 2797 CG | PHE | 427 | 53.644 | -24.892 | 61.802 |
| ATOM | 2798 CD1 | PHE | 427 | 53.860 | -25.700 | 62.910 |
| ATOM | 2799 CD2 | PHE | 427 | 52.514 | -25.121 | 61.031 |
| ATOM | 2800 CE1 | PHE | 427 | 52.960 | -26.728 | 63.239 |
| ATOM | 2801 CE2 | PHE | 427 | 51.608 | -26.145 | 61.353 |
| ATOM | 2802 CZ | PHE | 427 | 51.827 | -26.946 | 62.449 |
| ATOM | 2803 C | PHE | 427 | 55.033 | -21.297 | 61.331 |
| ATOM | 2804 O | PHE | 427 | 55.477 | -20.634 | 62.262 |
| ATOM | 2805 N | ASP | 428 | 55.402 | -21.057 | 60.094 |
| ATOM | 2806 CA | ASP | 428 | 56.334 | -19.981 | 59.859 |
| ATOM | 2807 CB | ASP | 428 | 56.855 | -19.989 | 58.434 |
| ATOM | 2808 CG | ASP | 428 | 57.649 | -21.239 | 58.121 |
| ATOM | 2809 OD1 | ASP | 428 | 57.157 | -22.354 | 58.439 |
| ATOM | 2810 OD2 | ASP | 428 | 58.765 | -21.108 | 57.561 |
| ATOM | 2811 C | ASP | 428 | 55.667 | -18.672 | 60.167 |
| ATOM | 2812 O | ASP | 428 | 56.341 | -17.726 | 60.517 |
| ATOM | 2813 N | SER | 429 | 54.347 | -18.619 | 60.089 |
| ATOM | 2814 CA | SER | 429 | 53.670 | -17.375 | 60.386 |
| ATOM | 2815 CB | SER | 429 | 52.154 | -17.542 | 60.337 |
| ATOM | 2816 OG | SER | 429 | 51.685 | -17.668 | 59.003 |
| ATOM | 2817 C | SER | 429 | 54.121 | -16.856 | 61.754 |
| ATOM | 2818 O | SER | 429 | 54.445 | -15.673 | 61.902 |
| ATOM | 2819 N | LEU | 430 | 54.187 | -17.734 | 62.752 |
| ATOM | 2820 CA | LEU | 430 | 54.644 | -17.287 | 64.066 |
| ATOM | 2821 CB | LEU | 430 | 54.304 | -18.264 | 65.219 |
| ATOM | 2822 CG | LEU | 430 | 54.560 | -19.767 | 65.427 |
| ATOM | 2823 CD1 | LEU | 430 | 53.561 | -20.590 | 64.657 |
| ATOM | 2824 CD2 | LEU | 430 | 55.984 | -20.161 | 65.132 |
| ATOM | 2825 C | LEU | 430 | 56.126 | -17.016 | 63.976 |
| ATOM | 2826 O | LEU | 430 | 56.543 | -15.894 | 64.196 |
| ATOM | 2827 N | ALA | 431 | 56.880 | -17.997 | 63.491 |
| ATOM | 2828 CA | ALA | 431 | 58.332 | -17.883 | 63.345 |
| ATOM | 2829 CB | ALA | 431 | 58.863 | -19.038 | 62.479 |
| ATOM | 2830 C | ALA | 431 | 58.794 | -16.533 | 62.766 |

FIGURE 1HHH

|  | Atom | Residue AA | No. | X | Y | Z |
|---|---|---|---|---|---|---|
| ATOM | 2831 O | ALA | 431 | 59.544 | -15.796 | 63.407 |
| ATOM | 2832 N | ASP | 432 | 58.355 | -16.221 | 61.553 |
| ATOM | 2833 CA | ASP | 432 | 58.742 | -14.987 | 60.914 |
| ATOM | 2834 CB | ASP | 432 | 58.832 | -15.158 | 59.379 |
| ATOM | 2835 CG | ASP | 432 | 57.465 | -15.189 | 58.678 |
| ATOM | 2836 OD1 | ASP | 432 | 56.435 | -15.545 | 59.295 |
| ATOM | 2837 OD2 | ASP | 432 | 57.426 | -14.848 | 57.474 |
| ATOM | 2838 C | ASP | 432 | 57.807 | -13.870 | 61.303 |
| ATOM | 2839 O | ASP | 432 | 58.091 | -12.728 | 61.055 |
| ATOM | 2840 N | ASN | 433 | 56.676 | -14.202 | 61.891 |
| ATOM | 2841 CA | ASN | 433 | 55.715 | -13.196 | 62.304 |
| ATOM | 2842 CB | ASN | 433 | 56.354 | -12.239 | 63.320 |
| ATOM | 2843 CG | ASN | 433 | 55.501 | -12.066 | 64.591 |
| ATOM | 2844 OD1 | ASN | 433 | 55.530 | -11.002 | 65.236 |
| ATOM | 2845 ND2 | ASN | 433 | 54.746 | -13.120 | 64.965 |
| ATOM | 2846 C | ASN | 433 | 55.051 | -12.441 | 61.144 |
| ATOM | 2847 O | ASN | 433 | 54.727 | -11.251 | 61.251 |
| ATOM | 2848 N | GLN | 434 | 54.795 | -13.163 | 60.056 |
| ATOM | 2849 CA | GLN | 434 | 54.142 | -12.619 | 58.872 |
| ATOM | 2850 CB | GLN | 434 | 55.152 | -12.317 | 57.775 |
| ATOM | 2851 CG | GLN | 434 | 56.102 | -11.215 | 58.134 |
| ATOM | 2852 CD | GLN | 434 | 56.985 | -10.787 | 56.982 |
| ATOM | 2853 OE1 | GLN | 434 | 58.193 | -10.518 | 57.170 |
| ATOM | 2854 NE2 | GLN | 434 | 56.395 | -10.698 | 55.777 |
| ATOM | 2855 C | GLN | 434 | 53.178 | -13.678 | 58.395 |
| ATOM | 2856 O | GLN | 434 | 53.330 | -14.847 | 58.735 |
| ATOM | 2857 N | VAL | 435 | 52.214 | -13.288 | 57.573 |
| ATOM | 2858 CA | VAL | 435 | 51.220 | -14.237 | 57.080 |
| ATOM | 2859 CB | VAL | 435 | 49.903 | -14.087 | 57.893 |
| ATOM | 2860 CG1 | VAL | 435 | 50.067 | -14.674 | 59.279 |
| ATOM | 2861 CG2 | VAL | 435 | 49.538 | -12.621 | 58.014 |
| ATOM | 2862 C | VAL | 435 | 50.933 | -14.185 | 55.558 |
| ATOM | 2863 O | VAL | 435 | 51.247 | -13.214 | 54.888 |
| ATOM | 2864 N | THR | 436 | 50.346 | -15.252 | 55.029 |
| ATOM | 2865 CA | THR | 436 | 50.006 | -15.352 | 53.619 |
| ATOM | 2866 CB | THR | 436 | 50.081 | -16.802 | 53.150 |
| ATOM | 2867 OG1 | THR | 436 | 49.883 | -17.675 | 54.262 |
| ATOM | 2868 CG2 | THR | 436 | 51.428 | -17.092 | 52.538 |
| ATOM | 2869 C | THR | 436 | 48.623 | -14.808 | 53.271 |
| ATOM | 2870 O | THR | 436 | 47.607 | -15.411 | 53.611 |
| ATOM | 2871 N | VAL | 437 | 48.601 | -13.653 | 52.613 |
| ATOM | 2872 CA | VAL | 437 | 47.374 | -12.991 | 52.178 |
| ATOM | 2873 CB | VAL | 437 | 47.519 | -11.447 | 52.204 |
| ATOM | 2874 CG1 | VAL | 437 | 46.230 | -10.787 | 51.755 |
| ATOM | 2875 CG2 | VAL | 437 | 47.891 | -10.978 | 53.577 |
| ATOM | 2876 C | VAL | 437 | 47.084 | -13.395 | 50.737 |
| ATOM | 2877 O | VAL | 437 | 47.748 | -12.927 | 49.816 |
| ATOM | 2878 N | ARG | 438 | 46.132 | -14.300 | 50.544 |

FIGURE 1III

|  | Atom | Residue AA | No. | X | Y | Z |
|---|---|---|---|---|---|---|
| ATOM | 2879 CA | ARG | 438 | 45.771 | -14.738 | 49.212 |
| ATOM | 2880 CB | ARG | 438 | 45.418 | -16.218 | 49.236 |
| ATOM | 2881 CG | ARG | 438 | 44.008 | -16.553 | 48.879 |
| ATOM | 2882 CD | ARG | 438 | 43.969 | -17.893 | 48.201 |
| ATOM | 2883 NE | ARG | 438 | 42.615 | -18.325 | 47.873 |
| ATOM | 2884 CZ | ARG | 438 | 42.324 | -19.323 | 47.042 |
| ATOM | 2885 NH1 | ARG | 438 | 43.302 | -19.993 | 46.445 |
| ATOM | 2886 NH2 | ARG | 438 | 41.056 | -19.669 | 46.821 |
| ATOM | 2887 C | ARG | 438 | 44.604 | -13.901 | 48.719 |
| ATOM | 2888 O | ARG | 438 | 43.750 | -13.513 | 49.525 |
| ATOM | 2889 N | ASP | 439 | 44.603 | -13.574 | 47.420 |
| ATOM | 2890 CA | ASP | 439 | 43.525 | -12.790 | 46.791 |
| ATOM | 2891 CB | ASP | 439 | 44.070 | -11.999 | 45.586 |
| ATOM | 2892 CG | ASP | 439 | 42.969 | -11.184 | 44.845 |
| ATOM | 2893 OD1 | ASP | 439 | 41.994 | -11.810 | 44.370 |
| ATOM | 2894 OD2 | ASP | 439 | 43.085 | -9.925 | 44.706 |
| ATOM | 2895 C | ASP | 439 | 42.414 | -13.723 | 46.317 |
| ATOM | 2896 O | ASP | 439 | 42.701 | -14.813 | 45.868 |
| ATOM | 2897 N | ARG | 440 | 41.164 | -13.286 | 46.362 |
| ATOM | 2898 CA | ARG | 440 | 40.086 | -14.142 | 45.902 |
| ATOM | 2899 CB | ARG | 440 | 38.712 | -13.526 | 46.199 |
| ATOM | 2900 CG | ARG | 440 | 37.527 | -14.337 | 45.597 |
| ATOM | 2901 CD | ARG | 440 | 36.295 | -13.498 | 45.438 |
| ATOM | 2902 NE | ARG | 440 | 36.663 | -12.123 | 45.150 |
| ATOM | 2903 CZ | ARG | 440 | 35.925 | -11.071 | 45.459 |
| ATOM | 2904 NH1 | ARG | 440 | 34.757 | -11.229 | 46.055 |
| ATOM | 2905 NH2 | ARG | 440 | 36.405 | -9.856 | 45.256 |
| ATOM | 2906 C | ARG | 440 | 40.183 | -14.492 | 44.402 |
| ATOM | 2907 O | ARG | 440 | 40.614 | -15.585 | 44.026 |
| ATOM | 2908 N | ASP | 441 | 39.732 | -13.571 | 43.549 |
| ATOM | 2909 CA | ASP | 441 | 39.750 | -13.770 | 42.108 |
| ATOM | 2910 CB | ASP | 441 | 39.335 | -12.484 | 41.335 |
| ATOM | 2911 CG | ASP | 441 | 39.027 | -11.240 | 42.245 |
| ATOM | 2912 OD1 | ASP | 441 | 39.889 | -10.347 | 42.391 |
| ATOM | 2913 OD2 | ASP | 441 | 37.897 | -11.086 | 42.735 |
| ATOM | 2914 C | ASP | 441 | 41.143 | -14.250 | 41.705 |
| ATOM | 2915 O | ASP | 441 | 41.312 | -15.387 | 41.316 |
| ATOM | 2916 N | SER | 442 | 42.141 | -13.416 | 41.974 |
| ATOM | 2917 CA | SER | 442 | 43.556 | -13.672 | 41.678 |
| ATOM | 2918 CB | SER | 442 | 44.409 | -12.531 | 42.275 |
| ATOM | 2919 OG | SER | 442 | 45.672 | -12.950 | 42.790 |
| ATOM | 2920 C | SER | 442 | 44.163 | -15.025 | 42.070 |
| ATOM | 2921 O | SER | 442 | 45.065 | -15.516 | 41.382 |
| ATOM | 2922 N | MET | 443 | 43.764 | -15.562 | 43.223 |
| ATOM | 2923 CA | MET | 443 | 44.282 | -16.840 | 43.708 |
| ATOM | 2924 CB | MET | 443 | 44.058 | -17.917 | 42.661 |
| ATOM | 2925 CG | MET | 443 | 42.621 | -18.111 | 42.320 |
| ATOM | 2926 SD | MET | 443 | 42.329 | -19.816 | 42.524 |

FIGURE 1JJJ

| Atom | | Residue AA | No. | X | Y | Z |
|---|---|---|---|---|---|---|
| ATOM | 2927 CE | MET | 443 | 40.905 | -20.019 | 41.597 |
| ATOM | 2928 C | MET | 443 | 45.759 | -16.805 | 44.093 |
| ATOM | 2929 O | MET | 443 | 46.307 | -17.793 | 44.593 |
| ATOM | 2930 N | GLU | 444 | 46.415 | -15.680 | 43.837 |
| ATOM | 2931 CA | GLU | 444 | 47.819 | -15.555 | 44.169 |
| ATOM | 2932 CB | GLU | 444 | 48.527 | -14.586 | 43.220 |
| ATOM | 2933 CG | GLU | 444 | 49.780 | -15.214 | 42.554 |
| ATOM | 2934 CD | GLU | 444 | 49.593 | -16.710 | 42.068 |
| ATOM | 2935 OE1 | GLU | 444 | 48.883 | -16.936 | 41.029 |
| ATOM | 2936 OE2 | GLU | 444 | 50.174 | -17.651 | 42.713 |
| ATOM | 2937 C | GLU | 444 | 47.872 | -15.073 | 45.585 |
| ATOM | 2938 O | GLU | 444 | 46.917 | -14.424 | 46.039 |
| ATOM | 2939 N | GLN | 445 | 48.952 | -15.421 | 46.292 |
| ATOM | 2940 CA | GLN | 445 | 49.124 | -15.039 | 47.699 |
| ATOM | 2941 CB | GLN | 445 | 48.738 | -16.197 | 48.612 |
| ATOM | 2942 CG | GLN | 445 | 49.290 | -17.534 | 48.199 |
| ATOM | 2943 CD | GLN | 445 | 48.754 | -18.647 | 49.057 |
| ATOM | 2944 OE1 | GLN | 445 | 49.528 | -19.385 | 49.643 |
| ATOM | 2945 NE2 | GLN | 445 | 47.426 | -18.768 | 49.154 |
| ATOM | 2946 C | GLN | 445 | 50.507 | -14.560 | 48.075 |
| ATOM | 2947 O | GLN | 445 | 51.498 | -15.184 | 47.724 |
| ATOM | 2948 N | VAL | 446 | 50.558 | -13.476 | 48.837 |
| ATOM | 2949 CA | VAL | 446 | 51.815 | -12.888 | 49.294 |
| ATOM | 2950 CB | VAL | 446 | 51.877 | -11.411 | 48.895 |
| ATOM | 2951 CG1 | VAL | 446 | 50.557 | -10.737 | 49.206 |
| ATOM | 2952 CG2 | VAL | 446 | 53.003 | -10.701 | 49.644 |
| ATOM | 2953 C | VAL | 446 | 51.943 | -12.966 | 50.821 |
| ATOM | 2954 O | VAL | 446 | 50.932 | -12.868 | 51.521 |
| ATOM | 2955 N | ARG | 447 | 53.156 | -13.163 | 51.345 |
| ATOM | 2956 CA | ARG | 447 | 53.338 | -13.204 | 52.802 |
| ATOM | 2957 CB | ARG | 447 | 54.431 | -14.209 | 53.209 |
| ATOM | 2958 CG | ARG | 447 | 54.635 | -14.312 | 54.721 |
| ATOM | 2959 CD | ARG | 447 | 55.613 | -15.414 | 55.152 |
| ATOM | 2960 NE | ARG | 447 | 55.053 | -16.769 | 55.064 |
| ATOM | 2961 CZ | ARG | 447 | 54.758 | -17.564 | 56.104 |
| ATOM | 2962 NH1 | ARG | 447 | 54.960 | -17.167 | 57.365 |
| ATOM | 2963 NH2 | ARG | 447 | 54.243 | -18.774 | 55.872 |
| ATOM | 2964 C | ARG | 447 | 53.691 | -11.789 | 53.278 |
| ATOM | 2965 O | ARG | 447 | 54.704 | -11.228 | 52.851 |
| ATOM | 2966 N | MET | 448 | 52.841 | -11.197 | 54.118 |
| ATOM | 2967 CA | MET | 448 | 53.075 | -9.849 | 54.624 |
| ATOM | 2968 CB | MET | 448 | 51.982 | -8.896 | 54.131 |
| ATOM | 2969 CG | MET | 448 | 50.585 | -9.289 | 54.480 |
| ATOM | 2970 SD | MET | 448 | 49.405 | -8.187 | 53.662 |
| ATOM | 2971 CE | MET | 448 | 50.057 | -6.557 | 54.214 |
| ATOM | 2972 C | MET | 448 | 53.214 | -9.767 | 56.143 |
| ATOM | 2973 O | MET | 448 | 52.792 | -10.663 | 56.866 |
| ATOM | 2974 N | PRO | 449 | 53.893 | -8.725 | 56.638 |

FIGURE 1KKK

|  | Residue | | | |  |
| Atom | AA | No. | X | Y | Z |
| ATOM 2975 CD | PRO | 449 | 54.571 | -7.706 | 55.820 |
| ATOM 2976 CA | PRO | 449 | 54.120 | -8.478 | 58.065 |
| ATOM 2977 CB | PRO | 449 | 54.839 | -7.138 | 58.062 |
| ATOM 2978 CG | PRO | 449 | 55.605 | -7.168 | 56.774 |
| ATOM 2979 C | PRO | 449 | 52.783 | -8.365 | 58.759 |
| ATOM 2980 O | PRO | 449 | 52.064 | -7.383 | 58.569 |
| ATOM 2981 N | ILE | 450 | 52.476 | -9.358 | 59.586 |
| ATOM 2982 CA | ILE | 450 | 51.204 | -9.429 | 60.294 |
| ATOM 2983 CB | ILE | 450 | 51.291 | -10.337 | 61.531 |
| ATOM 2984 CG2 | ILE | 450 | 49.949 | -10.403 | 62.205 |
| ATOM 2985 CG1 | ILE | 450 | 51.678 | -11.751 | 61.108 |
| ATOM 2986 CD1 | ILE | 450 | 51.636 | -12.769 | 62.209 |
| ATOM 2987 C | ILE | 450 | 50.649 | -8.073 | 60.676 |
| ATOM 2988 O | ILE | 450 | 49.446 | -7.819 | 60.593 |
| ATOM 2989 N | SER | 451 | 51.559 | -7.188 | 61.034 |
| ATOM 2990 CA | SER | 451 | 51.216 | -5.832 | 61.414 |
| ATOM 2991 CB | SER | 451 | 52.515 | -5.064 | 61.712 |
| ATOM 2992 OG | SER | 451 | 52.536 | -3.769 | 61.105 |
| ATOM 2993 C | SER | 451 | 50.407 | -5.095 | 60.332 |
| ATOM 2994 O | SER | 451 | 49.286 | -4.626 | 60.573 |
| ATOM 2995 N | GLU | 452 | 50.983 | -5.020 | 59.141 |
| ATOM 2996 CA | GLU | 452 | 50.380 | -4.313 | 58.029 |
| ATOM 2997 CB | GLU | 452 | 51.337 | -4.342 | 56.837 |
| ATOM 2998 CG | GLU | 452 | 52.761 | -3.815 | 57.217 |
| ATOM 2999 CD | GLU | 452 | 53.670 | -3.370 | 56.002 |
| ATOM 3000 OE1 | GLU | 452 | 53.998 | -4.223 | 55.110 |
| ATOM 3001 OE2 | GLU | 452 | 54.084 | -2.165 | 55.969 |
| ATOM 3002 C | GLU | 452 | 48.958 | -4.703 | 57.617 |
| ATOM 3003 O | GLU | 452 | 48.255 | -3.925 | 56.951 |
| ATOM 3004 N | LEU | 453 | 48.514 | -5.873 | 58.058 |
| ATOM 3005 CA | LEU | 453 | 47.173 | -6.347 | 57.742 |
| ATOM 3006 CB | LEU | 453 | 46.836 | -7.542 | 58.635 |
| ATOM 3007 CG | LEU | 453 | 47.393 | -8.928 | 58.290 |
| ATOM 3008 CD1 | LEU | 453 | 46.564 | -9.562 | 57.173 |
| ATOM 3009 CD2 | LEU | 453 | 48.875 | -8.848 | 57.927 |
| ATOM 3010 C | LEU | 453 | 46.122 | -5.245 | 57.932 |
| ATOM 3011 O | LEU | 453 | 45.138 | -5.172 | 57.194 |
| ATOM 3012 N | GLU | 454 | 46.359 | -4.383 | 58.917 |
| ATOM 3013 CA | GLU | 454 | 45.456 | -3.276 | 59.243 |
| ATOM 3014 CB | GLU | 454 | 45.946 | -2.492 | 60.476 |
| ATOM 3015 CG | GLU | 454 | 45.305 | -2.925 | 61.818 |
| ATOM 3016 CD | GLU | 454 | 44.315 | -1.903 | 62.398 |
| ATOM 3017 OE1 | GLU | 454 | 44.060 | -1.997 | 63.630 |
| ATOM 3018 OE2 | GLU | 454 | 43.801 | -1.031 | 61.638 |
| ATOM 3019 C | GLU | 454 | 45.370 | -2.328 | 58.090 |
| ATOM 3020 O | GLU | 454 | 44.301 | -2.156 | 57.505 |
| ATOM 3021 N | ALA | 455 | 46.510 | -1.724 | 57.769 |
| ATOM 3022 CA | ALA | 455 | 46.598 | -0.769 | 56.677 |

FIGURE 1LLL

| Atom | | Residue AA No. | X | Y | Z |
|---|---|---|---|---|---|
| ATOM | 3023 CB | ALA 455 | 48.043 | -0.336 | 56.492 |
| ATOM | 3024 C | ALA 455 | 46.043 | -1.366 | 55.372 |
| ATOM | 3025 O | ALA 455 | 45.217 | -0.718 | 54.692 |
| ATOM | 3026 N | PHE 456 | 46.470 | -2.599 | 55.057 |
| ATOM | 3027 CA | PHE 456 | 46.035 | -3.315 | 53.856 |
| ATOM | 3028 CB | PHE 456 | 46.591 | -4.746 | 53.864 |
| ATOM | 3029 CG | PHE 456 | 46.280 | -5.542 | 52.613 |
| ATOM | 3030 CD1 | PHE 456 | 47.296 | -6.125 | 51.877 |
| ATOM | 3031 CD2 | PHE 456 | 44.973 | -5.702 | 52.166 |
| ATOM | 3032 CE1 | PHE 456 | 47.019 | -6.846 | 50.720 |
| ATOM | 3033 CE2 | PHE 456 | 44.690 | -6.421 | 51.012 |
| ATOM | 3034 CZ | PHE 456 | 45.711 | -6.993 | 50.287 |
| ATOM | 3035 C | PHE 456 | 44.507 | -3.345 | 53.733 |
| ATOM | 3036 O | PHE 456 | 43.936 | -2.659 | 52.886 |
| ATOM | 3037 N | LEU 457 | 43.848 | -4.138 | 54.571 |
| ATOM | 3038 CA | LEU 457 | 42.394 | -4.265 | 54.532 |
| ATOM | 3039 CB | LEU 457 | 41.901 | -5.133 | 55.678 |
| ATOM | 3040 CG | LEU 457 | 42.297 | -6.579 | 55.536 |
| ATOM | 3041 CD1 | LEU 457 | 41.790 | -7.337 | 56.710 |
| ATOM | 3042 CD2 | LEU 457 | 41.714 | -7.117 | 54.256 |
| ATOM | 3043 C | LEU 457 | 41.628 | -2.952 | 54.539 |
| ATOM | 3044 O | LEU 457 | 40.470 | -2.930 | 54.138 |
| ATOM | 3045 N | THR 458 | 42.269 | -1.877 | 55.009 |
| ATOM | 3046 CA | THR 458 | 41.665 | -0.552 | 55.069 |
| ATOM | 3047 CB | THR 458 | 42.476 | 0.351 | 55.926 |
| ATOM | 3048 OG1 | THR 458 | 42.616 | -0.258 | 57.200 |
| ATOM | 3049 CG2 | THR 458 | 41.786 | 1.677 | 56.080 |
| ATOM | 3050 C | THR 458 | 41.587 | 0.108 | 53.710 |
| ATOM | 3051 O | THR 458 | 40.536 | 0.623 | 53.321 |
| ATOM | 3052 N | ALA 459 | 42.725 | 0.134 | 53.014 |
| ATOM | 3053 CA | ALA 459 | 42.847 | 0.728 | 51.674 |
| ATOM | 3054 CB | ALA 459 | 44.294 | 0.776 | 51.231 |
| ATOM | 3055 C | ALA 459 | 42.070 | -0.055 | 50.671 |
| ATOM | 3056 O | ALA 459 | 41.257 | 0.510 | 49.958 |
| ATOM | 3057 N | LYS 460 | 42.298 | -1.364 | 50.649 |
| ATOM | 3058 CA | LYS 460 | 41.626 | -2.251 | 49.722 |
| ATOM | 3059 CB | LYS 460 | 42.255 | -3.638 | 49.759 |
| ATOM | 3060 CG | LYS 460 | 42.538 | -4.191 | 48.384 |
| ATOM | 3061 CD | LYS 460 | 43.941 | -3.793 | 47.841 |
| ATOM | 3062 CE | LYS 460 | 44.026 | -3.698 | 46.253 |
| ATOM | 3063 NZ | LYS 460 | 43.888 | -4.962 | 45.401 |
| ATOM | 3064 C | LYS 460 | 40.149 | -2.370 | 49.996 |
| ATOM | 3065 O | LYS 460 | 39.558 | -3.375 | 49.660 |
| ATOM | 3066 N | THR 461 | 39.545 | -1.314 | 50.520 |
| ATOM | 3067 CA | THR 461 | 38.145 | -1.311 | 50.860 |
| ATOM | 3068 CB | THR 461 | 37.995 | -1.413 | 52.350 |
| ATOM | 3069 OG1 | THR 461 | 38.624 | -2.607 | 52.815 |
| ATOM | 3070 CG2 | THR 461 | 36.524 | -1.402 | 52.726 |

FIGURE 1MMM

| Atom | | Residue AA | No. | X | Y | Z |
|---|---|---|---|---|---|---|
| ATOM | 3071 C | THR | 461 | 37.449 | -0.029 | 50.465 |
| ATOM | 3072 O | THR | 461 | 36.322 | -0.068 | 49.976 |
| ATOM | 3073 N | ALA | 462 | 38.089 | 1.087 | 50.820 |
| ATOM | 3074 CA | ALA | 462 | 37.653 | 2.473 | 50.586 |
| ATOM | 3075 CB | ALA | 462 | 38.752 | 3.242 | 49.885 |
| ATOM | 3076 C | ALA | 462 | 36.302 | 2.777 | 49.927 |
| ATOM | 3077 O | ALA | 462 | 35.662 | 3.787 | 50.269 |
| ATOM | 3078 N | PHE | 463 | 35.918 | 1.961 | 48.944 |
| ATOM | 3079 CA | PHE | 463 | 34.645 | 2.111 | 48.225 |
| ATOM | 3080 CB | PHE | 463 | 33.463 | 2.190 | 49.195 |
| ATOM | 3081 CG | PHE | 463 | 32.130 | 2.120 | 48.519 |
| ATOM | 3082 CD1 | PHE | 463 | 31.717 | 0.935 | 47.895 |
| ATOM | 3083 CD2 | PHE | 463 | 31.291 | 3.223 | 48.511 |
| ATOM | 3084 CE1 | PHE | 463 | 30.484 | 0.836 | 47.270 |
| ATOM | 3085 CE2 | PHE | 463 | 30.069 | 3.155 | 47.902 |
| ATOM | 3086 CZ | PHE | 463 | 29.653 | 1.942 | 47.269 |
| ATOM | 3087 C | PHE | 463 | 34.649 | 3.321 | 47.279 |
| ATOM | 3088 O | PHE | 463 | 35.708 | 3.485 | 46.614 |
| ATOM | 3089 OT | PHE | 463 | 33.632 | 4.068 | 47.193 |
| ATOM | 3090 CB | MET | 1001 | 21.009 | 13.671 | 84.565 |
| ATOM | 3091 CG | MET | 1001 | 19.537 | 13.254 | 85.037 |
| ATOM | 3092 SD | MET | 1001 | 18.432 | 12.056 | 84.091 |
| ATOM | 3093 CE | MET | 1001 | 16.748 | 12.318 | 84.896 |
| ATOM | 3094 C | MET | 1001 | 20.000 | 15.514 | 83.107 |
| ATOM | 3095 O | MET | 1001 | 19.992 | 16.640 | 83.663 |
| ATOM | 3096 N | MET | 1001 | 22.497 | 15.237 | 83.191 |
| ATOM | 3097 CA | MET | 1001 | 21.161 | 14.532 | 83.261 |
| ATOM | 3098 N | ALA | 1002 | 19.018 | 15.059 | 82.342 |
| ATOM | 3099 CA | ALA | 1002 | 17.822 | 15.839 | 82.060 |
| ATOM | 3100 CB | ALA | 1002 | 16.957 | 15.132 | 81.009 |
| ATOM | 3101 C | ALA | 1002 | 16.979 | 16.198 | 83.284 |
| ATOM | 3102 O | ALA | 1002 | 16.456 | 15.324 | 84.005 |
| ATOM | 3103 N | LYS | 1003 | 16.892 | 17.503 | 83.507 |
| ATOM | 3104 CA | LYS | 1003 | 16.105 | 18.049 | 84.582 |
| ATOM | 3105 CB | LYS | 1003 | 16.406 | 19.549 | 84.712 |
| ATOM | 3106 CG | LYS | 1003 | 17.272 | 20.152 | 83.582 |
| ATOM | 3107 CD | LYS | 1003 | 16.474 | 20.468 | 82.305 |
| ATOM | 3108 CE | LYS | 1003 | 15.331 | 21.477 | 82.540 |
| ATOM | 3109 NZ | LYS | 1003 | 15.723 | 22.913 | 82.519 |
| ATOM | 3110 C | LYS | 1003 | 14.627 | 17.799 | 84.213 |
| ATOM | 3111 O | LYS | 1003 | 14.004 | 16.807 | 84.624 |
| ATOM | 3112 N | ASP | 1004 | 14.101 | 18.674 | 83.373 |
| ATOM | 3113 CA | ASP | 1004 | 12.729 | 18.589 | 82.925 |
| ATOM | 3114 CB | ASP | 1004 | 12.317 | 19.994 | 82.391 |
| ATOM | 3115 CG | ASP | 1004 | 10.824 | 20.364 | 82.673 |
| ATOM | 3116 OD1 | ASP | 1004 | 9.972 | 19.454 | 82.877 |
| ATOM | 3117 OD2 | ASP | 1004 | 10.494 | 21.586 | 82.682 |
| ATOM | 3118 C | ASP | 1004 | 12.696 | 17.539 | 81.791 |

FIGURE 1NNN

| Atom | Residue AA | No. | X | Y | Z |
|---|---|---|---|---|---|
| ATOM 3119 O | ASP | 1004 | 13.748 | 17.185 | 81.254 |
| ATOM 3120 N | MET | 1005 | 11.528 | 16.941 | 81.534 |
| ATOM 3121 CA | MET | 1005 | 11.387 | 16.036 | 80.382 |
| ATOM 3122 CB | MET | 1005 | 10.287 | 14.972 | 80.562 |
| ATOM 3123 CG | MET | 1005 | 10.034 | 14.109 | 79.283 |
| ATOM 3124 SD | MET | 1005 | 11.007 | 12.551 | 79.076 |
| ATOM 3125 CE | MET | 1005 | 12.685 | 13.162 | 78.685 |
| ATOM 3126 C | MET | 1005 | 10.982 | 16.995 | 79.248 |
| ATOM 3127 O | MET | 1005 | 11.500 | 16.901 | 78.142 |
| ATOM 3128 N | ASP | 1006 | 10.122 | 17.964 | 79.581 |
| ATOM 3129 CA | ASP | 1006 | 9.626 | 18.978 | 78.648 |
| ATOM 3130 CB | ASP | 1006 | 8.651 | 19.954 | 79.320 |
| ATOM 3131 CG | ASP | 1006 | 7.462 | 19.247 | 79.993 |
| ATOM 3132 OD1 | ASP | 1006 | 6.903 | 19.812 | 80.982 |
| ATOM 3133 OD2 | ASP | 1006 | 7.088 | 18.128 | 79.543 |
| ATOM 3134 C | ASP | 1006 | 10.755 | 19.779 | 78.064 |
| ATOM 3135 O | ASP | 1006 | 10.698 | 20.182 | 76.916 |
| ATOM 3136 N | THR | 1007 | 11.773 | 20.056 | 78.849 |
| ATOM 3137 CA | THR | 1007 | 12.865 | 20.810 | 78.296 |
| ATOM 3138 CB | THR | 1007 | 13.894 | 21.162 | 79.343 |
| ATOM 3139 OG1 | THR | 1007 | 13.382 | 22.216 | 80.180 |
| ATOM 3140 CG2 | THR | 1007 | 15.208 | 21.583 | 78.672 |
| ATOM 3141 C | THR | 1007 | 13.514 | 19.954 | 77.259 |
| ATOM 3142 O | THR | 1007 | 13.824 | 20.436 | 76.183 |
| ATOM 3143 N | ILE | 1008 | 13.671 | 18.672 | 77.579 |
| ATOM 3144 CA | ILE | 1008 | 14.304 | 17.724 | 76.666 |
| ATOM 3145 CB | ILE | 1008 | 14.726 | 16.407 | 77.393 |
| ATOM 3146 CG2 | ILE | 1008 | 14.560 | 15.200 | 76.483 |
| ATOM 3147 CG1 | ILE | 1008 | 16.183 | 16.527 | 77.877 |
| ATOM 3148 CD1 | ILE | 1008 | 16.429 | 17.695 | 78.780 |
| ATOM 3149 C | ILE | 1008 | 13.530 | 17.474 | 75.357 |
| ATOM 3150 O | ILE | 1008 | 14.107 | 17.599 | 74.275 |
| ATOM 3151 N | VAL | 1009 | 12.242 | 17.156 | 75.421 |
| ATOM 3152 CA | VAL | 1009 | 11.494 | 16.958 | 74.180 |
| ATOM 3153 CB | VAL | 1009 | 9.981 | 16.690 | 74.432 |
| ATOM 3154 CG1 | VAL | 1009 | 9.146 | 17.085 | 73.241 |
| ATOM 3155 CG2 | VAL | 1009 | 9.751 | 15.235 | 74.698 |
| ATOM 3156 C | VAL | 1009 | 11.662 | 18.215 | 73.331 |
| ATOM 3157 O | VAL | 1009 | 11.929 | 18.131 | 72.138 |
| ATOM 3158 N | SER | 1010 | 11.586 | 19.376 | 73.964 |
| ATOM 3159 CA | SER | 1010 | 11.724 | 20.621 | 73.231 |
| ATOM 3160 CB | SER | 1010 | 11.536 | 21.822 | 74.150 |
| ATOM 3161 OG | SER | 1010 | 11.625 | 23.039 | 73.420 |
| ATOM 3162 C | SER | 1010 | 13.046 | 20.727 | 72.479 |
| ATOM 3163 O | SER | 1010 | 13.065 | 20.964 | 71.281 |
| ATOM 3164 N | LEU | 1011 | 14.160 | 20.547 | 73.152 |
| ATOM 3165 CA | LEU | 1011 | 15.412 | 20.649 | 72.444 |
| ATOM 3166 CB | LEU | 1011 | 16.597 | 20.562 | 73.393 |

FIGURE 1000

|  | | Residue | | | |
|---|---|---|---|---|---|
| Atom | AA | No. | X | Y | Z |
| ATOM 3167 CG | LEU | 1011 | 17.933 | 20.560 | 72.656 |
| ATOM 3168 CD1 | LEU | 1011 | 18.599 | 21.935 | 72.688 |
| ATOM 3169 CD2 | LEU | 1011 | 18.810 | 19.472 | 73.268 |
| ATOM 3170 C | LEU | 1011 | 15.489 | 19.547 | 71.415 |
| ATOM 3171 O | LEU | 1011 | 16.263 | 19.633 | 70.487 |
| ATOM 3172 N | ALA | 1012 | 14.692 | 18.503 | 71.568 |
| ATOM 3173 CA | ALA | 1012 | 14.725 | 17.417 | 70.585 |
| ATOM 3174 CB | ALA | 1012 | 14.063 | 16.146 | 71.138 |
| ATOM 3175 C | ALA | 1012 | 14.000 | 17.883 | 69.328 |
| ATOM 3176 O | ALA | 1012 | 14.624 | 18.113 | 68.286 |
| ATOM 3177 N | LYS | 1013 | 12.682 | 18.035 | 69.435 |
| ATOM 3178 CA | LYS | 1013 | 11.867 | 18.496 | 68.322 |
| ATOM 3179 CB | LYS | 1013 | 10.461 | 18.911 | 68.825 |
| ATOM 3180 CG | LYS | 1013 | 9.662 | 19.879 | 67.893 |
| ATOM 3181 CD | LYS | 1013 | 9.374 | 19.302 | 66.461 |
| ATOM 3182 CE | LYS | 1013 | 8.556 | 20.273 | 65.562 |
| ATOM 3183 NZ | LYS | 1013 | 7.900 | 19.639 | 64.367 |
| ATOM 3184 C | LYS | 1013 | 12.549 | 19.639 | 67.557 |
| ATOM 3185 O | LYS | 1013 | 13.187 | 19.414 | 66.532 |
| ATOM 3186 N | HIS | 1014 | 12.513 | 20.829 | 68.129 |
| ATOM 3187 CA | HIS | 1014 | 13.065 | 21.981 | 67.492 |
| ATOM 3188 CB | HIS | 1014 | 13.011 | 23.161 | 68.446 |
| ATOM 3189 CG | HIS | 1014 | 14.227 | 24.041 | 68.371 |
| ATOM 3190 CD2 | HIS | 1014 | 14.422 | 25.256 | 67.796 |
| ATOM 3191 ND1 | HIS | 1014 | 15.461 | 23.658 | 68.870 |
| ATOM 3192 CE1 | HIS | 1014 | 16.359 | 24.592 | 68.602 |
| ATOM 3193 NE2 | HIS | 1014 | 15.755 | 25.572 | 67.952 |
| ATOM 3194 C | HIS | 1014 | 14.477 | 21.856 | 66.946 |
| ATOM 3195 O | HIS | 1014 | 14.849 | 22.587 | 66.027 |
| ATOM 3196 N | ARG | 1015 | 15.312 | 21.022 | 67.540 |
| ATOM 3197 CA | ARG | 1015 | 16.698 | 20.963 | 67.063 |
| ATOM 3198 CB | ARG | 1015 | 17.642 | 20.758 | 68.265 |
| ATOM 3199 CG | ARG | 1015 | 19.111 | 20.909 | 67.998 |
| ATOM 3200 CD | ARG | 1015 | 19.316 | 21.902 | 66.916 |
| ATOM 3201 NE | ARG | 1015 | 18.880 | 23.218 | 67.308 |
| ATOM 3202 CZ | ARG | 1015 | 19.718 | 24.138 | 67.762 |
| ATOM 3203 NH1 | ARG | 1015 | 21.015 | 23.850 | 67.877 |
| ATOM 3204 NH2 | ARG | 1015 | 19.280 | 25.364 | 68.035 |
| ATOM 3205 C | ARG | 1015 | 16.904 | 19.928 | 65.969 |
| ATOM 3206 O | ARG | 1015 | 17.977 | 19.790 | 65.402 |
| ATOM 3207 N | GLY | 1016 | 15.828 | 19.249 | 65.625 |
| ATOM 3208 CA | GLY | 1016 | 15.928 | 18.249 | 64.602 |
| ATOM 3209 C | GLY | 1016 | 16.545 | 16.999 | 65.179 |
| ATOM 3210 O | GLY | 1016 | 17.617 | 16.552 | 64.770 |
| ATOM 3211 N | PHE | 1017 | 15.900 | 16.473 | 66.204 |
| ATOM 3212 CA | PHE | 1017 | 16.360 | 15.239 | 66.814 |
| ATOM 3213 CB | PHE | 1017 | 16.721 | 15.414 | 68.301 |
| ATOM 3214 CG | PHE | 1017 | 18.206 | 15.551 | 68.582 |

FIGURE 1PPP

| Atom | | Residue AA | No. | X | Y | Z |
|---|---|---|---|---|---|---|
| ATOM | 3215 | CD1 | PHE 1017 | 18.815 | 16.795 | 68.632 |
| ATOM | 3216 | CD2 | PHE 1017 | 18.965 | 14.448 | 68.916 |
| ATOM | 3217 | CE1 | PHE 1017 | 20.165 | 16.936 | 69.025 |
| ATOM | 3218 | CE2 | PHE 1017 | 20.309 | 14.586 | 69.306 |
| ATOM | 3219 | CZ | PHE 1017 | 20.901 | 15.832 | 69.361 |
| ATOM | 3220 | C | PHE 1017 | 15.149 | 14.342 | 66.634 |
| ATOM | 3221 | O | PHE 1017 | 15.284 | 13.239 | 66.135 |
| ATOM | 3222 | N | VAL 1018 | 13.959 | 14.833 | 66.969 |
| ATOM | 3223 | CA | VAL 1018 | 12.747 | 14.028 | 66.805 |
| ATOM | 3224 | CB | VAL 1018 | 12.423 | 13.140 | 68.079 |
| ATOM | 3225 | CG1 | VAL 1018 | 11.304 | 12.166 | 67.786 |
| ATOM | 3226 | CG2 | VAL 1018 | 13.618 | 12.339 | 68.509 |
| ATOM | 3227 | C | VAL 1018 | 11.569 | 14.975 | 66.522 |
| ATOM | 3228 | O | VAL 1018 | 11.442 | 15.994 | 67.200 |
| ATOM | 3229 | N | PHE 1019 | 10.778 | 14.680 | 65.476 |
| ATOM | 3230 | CA | PHE 1019 | 9.600 | 15.475 | 65.096 |
| ATOM | 3231 | CB | PHE 1019 | 9.588 | 15.846 | 63.614 |
| ATOM | 3232 | CG | PHE 1019 | 10.804 | 16.555 | 63.147 |
| ATOM | 3233 | CD1 | PHE 1019 | 11.161 | 17.797 | 63.662 |
| ATOM | 3234 | CD2 | PHE 1019 | 11.621 | 15.969 | 62.192 |
| ATOM | 3235 | CE1 | PHE 1019 | 12.340 | 18.449 | 63.224 |
| ATOM | 3236 | CE2 | PHE 1019 | 12.804 | 16.614 | 61.749 |
| ATOM | 3237 | CZ | PHE 1019 | 13.160 | 17.856 | 62.270 |
| ATOM | 3238 | C | PHE 1019 | 8.429 | 14.552 | 65.285 |
| ATOM | 3239 | O | PHE 1019 | 8.550 | 13.346 | 65.077 |
| ATOM | 3240 | N | PRO 1020 | 7.257 | 15.104 | 65.591 |
| ATOM | 3241 | CD | PRO 1020 | 6.947 | 16.520 | 65.814 |
| ATOM | 3242 | CA | PRO 1020 | 6.075 | 14.271 | 65.790 |
| ATOM | 3243 | CB | PRO 1020 | 5.083 | 15.243 | 66.420 |
| ATOM | 3244 | CG | PRO 1020 | 5.446 | 16.527 | 65.807 |
| ATOM | 3245 | C | PRO 1020 | 5.547 | 13.666 | 64.497 |
| ATOM | 3246 | O | PRO 1020 | 5.394 | 14.358 | 63.481 |
| ATOM | 3247 | N | GLY 1021 | 5.255 | 12.369 | 64.558 |
| ATOM | 3248 | CA | GLY 1021 | 4.738 | 11.646 | 63.406 |
| ATOM | 3249 | C | GLY 1021 | 3.443 | 12.207 | 62.830 |
| ATOM | 3250 | O | GLY 1021 | 2.609 | 12.742 | 63.574 |
| ATOM | 3251 | N | SER 1022 | 3.270 | 12.067 | 61.513 |
| ATOM | 3252 | CA | SER 1022 | 2.086 | 12.569 | 60.826 |
| ATOM | 3253 | CB | SER 1022 | 0.917 | 11.609 | 61.012 |
| ATOM | 3254 | OG | SER 1022 | 1.244 | 10.319 | 60.533 |
| ATOM | 3255 | C | SER 1022 | 1.702 | 13.947 | 61.340 |
| ATOM | 3256 | O | SER 1022 | 0.540 | 14.339 | 61.266 |
| ATOM | 3257 | N | ASP 1023 | 2.702 | 14.701 | 61.781 |
| ATOM | 3258 | CA | ASP 1023 | 2.463 | 16.008 | 62.342 |
| ATOM | 3259 | CB | ASP 1023 | 3.792 | 16.756 | 62.551 |
| ATOM | 3260 | CG | ASP 1023 | 3.627 | 18.060 | 63.393 |
| ATOM | 3261 | OD1 | ASP 1023 | 2.512 | 18.240 | 63.973 |
| ATOM | 3262 | OD2 | ASP 1023 | 4.601 | 18.889 | 63.475 |

FIGURE 1QQQ

| Atom | | Residue | | X | Y | Z |
|---|---|---|---|---|---|---|
| | | AA | No. | | | |
| ATOM | 3263 C | ASP | 1023 | 1.465 | 16.884 | 61.581 |
| ATOM | 3264 O | ASP | 1023 | 0.292 | 16.941 | 61.932 |
| ATOM | 3265 N | ILE | 1024 | 1.927 | 17.503 | 60.500 |
| ATOM | 3266 CA | ILE | 1024 | 1.124 | 18.438 | 59.727 |
| ATOM | 3267 CB | ILE | 1024 | 1.800 | 18.824 | 58.403 |
| ATOM | 3268 CG2 | ILE | 1024 | 3.235 | 19.322 | 58.646 |
| ATOM | 3269 CG1 | ILE | 1024 | 1.803 | 17.621 | 57.467 |
| ATOM | 3270 CD1 | ILE | 1024 | 2.054 | 17.964 | 56.017 |
| ATOM | 3271 C | ILE | 1024 | -0.317 | 18.061 | 59.459 |
| ATOM | 3272 O | ILE | 1024 | -1.149 | 18.932 | 59.247 |
| ATOM | 3273 N | TYR | 1025 | -0.622 | 16.778 | 59.436 |
| ATOM | 3274 CA | TYR | 1025 | -2.005 | 16.392 | 59.187 |
| ATOM | 3275 CB | TYR | 1025 | -2.125 | 15.018 | 58.487 |
| ATOM | 3276 CG | TYR | 1025 | -2.003 | 15.118 | 56.982 |
| ATOM | 3277 CD1 | TYR | 1025 | -0.920 | 15.792 | 56.410 |
| ATOM | 3278 CE1 | TYR | 1025 | -0.802 | 15.945 | 55.046 |
| ATOM | 3279 CD2 | TYR | 1025 | -2.978 | 14.588 | 56.133 |
| ATOM | 3280 CE2 | TYR | 1025 | -2.869 | 14.734 | 54.748 |
| ATOM | 3281 CZ | TYR | 1025 | -1.770 | 15.420 | 54.214 |
| ATOM | 3282 OH | TYR | 1025 | -1.622 | 15.620 | 52.860 |
| ATOM | 3283 C | TYR | 1025 | -2.772 | 16.400 | 60.493 |
| ATOM | 3284 O | TYR | 1025 | -3.908 | 16.890 | 60.565 |
| ATOM | 3285 N | GLY | 1026 | -2.123 | 15.914 | 61.542 |
| ATOM | 3286 CA | GLY | 1026 | -2.768 | 15.850 | 62.839 |
| ATOM | 3287 C | GLY | 1026 | -1.974 | 14.958 | 63.760 |
| ATOM | 3288 O | GLY | 1026 | -2.016 | 15.130 | 64.978 |
| ATOM | 3289 N | GLY | 1027 | -1.264 | 13.992 | 63.179 |
| ATOM | 3290 CA | GLY | 1027 | -0.440 | 13.095 | 63.964 |
| ATOM | 3291 C | GLY | 1027 | -1.010 | 11.712 | 64.131 |
| ATOM | 3292 O | GLY | 1027 | -1.892 | 11.269 | 63.403 |
| ATOM | 3293 N | LEU | 1028 | -0.418 | 11.000 | 65.065 |
| ATOM | 3294 CA | LEU | 1028 | -0.837 | 9.661 | 65.400 |
| ATOM | 3295 CB | LEU | 1028 | -0.308 | 8.658 | 64.381 |
| ATOM | 3296 CG | LEU | 1028 | -0.895 | 7.267 | 64.617 |
| ATOM | 3297 CD1 | LEU | 1028 | -2.359 | 7.304 | 64.264 |
| ATOM | 3298 CD2 | LEU | 1028 | -0.191 | 6.220 | 63.800 |
| ATOM | 3299 C | LEU | 1028 | -0.281 | 9.367 | 66.806 |
| ATOM | 3300 O | LEU | 1028 | 0.860 | 9.758 | 67.144 |
| ATOM | 3301 N | SER | 1029 | -1.128 | 8.775 | 67.645 |
| ATOM | 3302 CA | SER | 1029 | -0.776 | 8.418 | 69.014 |
| ATOM | 3303 CB | SER | 1029 | -1.790 | 7.399 | 69.532 |
| ATOM | 3304 OG | SER | 1029 | -2.098 | 6.439 | 68.531 |
| ATOM | 3305 C | SER | 1029 | 0.666 | 7.909 | 69.250 |
| ATOM | 3306 O | SER | 1029 | 1.082 | 6.839 | 68.753 |
| ATOM | 3307 N | ASN | 1030 | 1.412 | 8.735 | 69.985 |
| ATOM | 3308 CA | ASN | 1030 | 2.797 | 8.475 | 70.367 |
| ATOM | 3309 CB | ASN | 1030 | 2.847 | 7.686 | 71.675 |
| ATOM | 3310 CG | ASN | 1030 | 3.887 | 8.247 | 72.679 |

FIGURE 1RRR

| Atom | | Residue | | X | Y | Z |
|---|---|---|---|---|---|---|
| | | AA | No. | | | |
| ATOM | 3311 OD1 | ASN | 1030 | 5.073 | 8.472 | 72.335 |
| ATOM | 3312 ND2 | ASN | 1030 | 3.430 | 8.503 | 73.920 |
| ATOM | 3313 C | ASN | 1030 | 3.580 | 7.738 | 69.319 |
| ATOM | 3314 O | ASN | 1030 | 3.973 | 6.594 | 69.505 |
| ATOM | 3315 N | THR | 1031 | 3.748 | 8.387 | 68.189 |
| ATOM | 3316 CA | THR | 1031 | 4.481 | 7.808 | 67.084 |
| ATOM | 3317 CB | THR | 1031 | 3.493 | 7.214 | 65.993 |
| ATOM | 3318 OG1 | THR | 1031 | 2.355 | 8.069 | 65.840 |
| ATOM | 3319 CG2 | THR | 1031 | 2.960 | 5.823 | 66.429 |
| ATOM | 3320 C | THR | 1031 | 5.384 | 8.969 | 66.621 |
| ATOM | 3321 O | THR | 1031 | 4.920 | 10.107 | 66.439 |
| ATOM | 3322 N | TRP | 1032 | 6.687 | 8.697 | 66.544 |
| ATOM | 3323 CA | TRP | 1032 | 7.702 | 9.716 | 66.214 |
| ATOM | 3324 CB | TRP | 1032 | 8.655 | 9.893 | 67.434 |
| ATOM | 3325 CG | TRP | 1032 | 7.926 | 10.244 | 68.681 |
| ATOM | 3326 CD2 | TRP | 1032 | 7.780 | 11.563 | 69.228 |
| ATOM | 3327 CE2 | TRP | 1032 | 6.765 | 11.495 | 70.209 |
| ATOM | 3328 CE3 | TRP | 1032 | 8.393 | 12.802 | 68.965 |
| ATOM | 3329 CD1 | TRP | 1032 | 7.055 | 9.439 | 69.376 |
| ATOM | 3330 NE1 | TRP | 1032 | 6.344 | 10.190 | 70.278 |
| ATOM | 3331 CZ2 | TRP | 1032 | 6.346 | 12.616 | 70.920 |
| ATOM | 3332 CZ3 | TRP | 1032 | 7.981 | 13.910 | 69.668 |
| ATOM | 3333 CH2 | TRP | 1032 | 6.962 | 13.811 | 70.637 |
| ATOM | 3334 C | TRP | 1032 | 8.554 | 9.538 | 64.942 |
| ATOM | 3335 O | TRP | 1032 | 8.884 | 8.415 | 64.510 |
| ATOM | 3336 N | ASP | 1033 | 8.925 | 10.668 | 64.364 |
| ATOM | 3337 CA | ASP | 1033 | 9.761 | 10.648 | 63.196 |
| ATOM | 3338 CB | ASP | 1033 | 9.198 | 11.566 | 62.089 |
| ATOM | 3339 CG | ASP | 1033 | 7.923 | 11.003 | 61.398 |
| ATOM | 3340 OD1 | ASP | 1033 | 7.109 | 11.826 | 60.932 |
| ATOM | 3341 OD2 | ASP | 1033 | 7.722 | 9.770 | 61.274 |
| ATOM | 3342 C | ASP | 1033 | 11.124 | 11.139 | 63.677 |
| ATOM | 3343 O | ASP | 1033 | 11.212 | 12.133 | 64.392 |
| ATOM | 3344 N | TYR | 1034 | 12.167 | 10.376 | 63.377 |
| ATOM | 3345 CA | TYR | 1034 | 13.519 | 10.756 | 63.749 |
| ATOM | 3346 CB | TYR | 1034 | 14.451 | 9.542 | 63.830 |
| ATOM | 3347 CG | TYR | 1034 | 14.262 | 8.753 | 65.100 |
| ATOM | 3348 CD1 | TYR | 1034 | 13.007 | 8.235 | 65.442 |
| ATOM | 3349 CE1 | TYR | 1034 | 12.803 | 7.565 | 66.655 |
| ATOM | 3350 CD2 | TYR | 1034 | 15.313 | 8.578 | 65.998 |
| ATOM | 3351 CE2 | TYR | 1034 | 15.114 | 7.907 | 67.221 |
| ATOM | 3352 CZ | TYR | 1034 | 13.855 | 7.405 | 67.538 |
| ATOM | 3353 OH | TYR | 1034 | 13.634 | 6.746 | 68.727 |
| ATOM | 3354 C | TYR | 1034 | 14.033 | 11.725 | 62.729 |
| ATOM | 3355 O | TYR | 1034 | 14.210 | 11.379 | 61.581 |
| ATOM | 3356 N | GLY | 1035 | 14.242 | 12.952 | 63.168 |
| ATOM | 3357 CA | GLY | 1035 | 14.738 | 13.995 | 62.304 |
| ATOM | 3358 C | GLY | 1035 | 16.183 | 13.774 | 61.969 |

FIGURE 1SSS

| Atom | | Residue AA | No. | X | Y | Z |
|---|---|---|---|---|---|---|
| ATOM | 3359 | O | GLY 1035 | 16.791 | 12.861 | 62.501 |
| ATOM | 3360 | N | PRO 1036 | 16.783 | 14.674 | 61.181 |
| ATOM | 3361 | CD | PRO 1036 | 16.112 | 15.961 | 60.949 |
| ATOM | 3362 | CA | PRO 1036 | 18.160 | 14.727 | 60.672 |
| ATOM | 3363 | CB | PRO 1036 | 18.328 | 16.187 | 60.325 |
| ATOM | 3364 | CG | PRO 1036 | 16.971 | 16.570 | 59.899 |
| ATOM | 3365 | C | PRO 1036 | 19.203 | 14.293 | 61.662 |
| ATOM | 3366 | O | PRO 1036 | 20.117 | 13.552 | 61.319 |
| ATOM | 3367 | N | LEU 1037 | 19.080 | 14.780 | 62.886 |
| ATOM | 3368 | CA | LEU 1037 | 20.013 | 14.430 | 63.922 |
| ATOM | 3369 | CB | LEU 1037 | 20.137 | 15.586 | 64.888 |
| ATOM | 3370 | CG | LEU 1037 | 20.931 | 16.710 | 64.230 |
| ATOM | 3371 | CD1 | LEU 1037 | 21.078 | 17.942 | 65.103 |
| ATOM | 3372 | CD2 | LEU 1037 | 22.288 | 16.152 | 63.923 |
| ATOM | 3373 | C | LEU 1037 | 19.626 | 13.138 | 64.628 |
| ATOM | 3374 | O | LEU 1037 | 20.491 | 12.327 | 64.981 |
| ATOM | 3375 | N | GLY 1038 | 18.320 | 12.913 | 64.753 |
| ATOM | 3376 | CA | GLY 1038 | 17.805 | 11.716 | 65.408 |
| ATOM | 3377 | C | GLY 1038 | 18.267 | 10.413 | 64.806 |
| ATOM | 3378 | O | GLY 1038 | 18.590 | 9. | 65.525 |
| ATOM | 3379 | N | VAL 1039 | 18.259 | 10.347 | 63.479 |
| ATOM | 3380 | CA | VAL 1039 | 18.714 | 9.159 | 62.750 |
| ATOM | 3381 | CB | VAL 1039 | 18.710 | 9.318 | 61.236 |
| ATOM | 3382 | CG1 | VAL 1039 | 17.493 | 8.695 | 60.667 |
| ATOM | 3383 | CG2 | VAL 1039 | 18.822 | 10.759 | 60.842 |
| ATOM | 3384 | C | VAL 1039 | 20.141 | 8.855 | 63.069 |
| ATOM | 3385 | O | VAL 1039 | 20.462 | 7.748 | 63.477 |
| ATOM | 3386 | N | GLU 1040 | 21.008 | 9.830 | 62.840 |
| ATOM | 3387 | CA | GLU 1040 | 22.420 | 9.644 | 63.122 |
| ATOM | 3388 | CB | GLU 1040 | 23.193 | 10.959 | 62.921 |
| ATOM | 3389 | CG | GLU 1040 | 24.292 | 10.919 | 61.809 |
| ATOM | 3390 | CD | GLU 1040 | 23.766 | 10.636 | 60.374 |
| ATOM | 3391 | OE1 | GLU 1040 | 22.823 | 11.326 | 59.912 |
| ATOM | 3392 | OE2 | GLU 1040 | 24.326 | 9.737 | 59.694 |
| ATOM | 3393 | C | GLU 1040 | 22.618 | 9.055 | 64.530 |
| ATOM | 3394 | O | GLU 1040 | 23.083 | 7.911 | 64.656 |
| ATOM | 3395 | N | LEU 1041 | 22.148 | 9.763 | 65.563 |
| ATOM | 3396 | CA | LEU 1041 | 22.267 | 9.264 | 66.945 |
| ATOM | 3397 | CB | LEU 1041 | 21.535 | 10.170 | 67.942 |
| ATOM | 3398 | CG | LEU 1041 | 21.648 | 9.783 | 69.408 |
| ATOM | 3399 | CD1 | LEU 1041 | 22.933 | 10.273 | 69.901 |
| ATOM | 3400 | CD2 | LEU 1041 | 20.541 | 10.395 | 70.188 |
| ATOM | 3401 | C | LEU 1041 | 21.718 | 7.831 | 67.066 |
| ATOM | 3402 | O | LEU 1041 | 22.452 | 6.922 | 67.486 |
| ATOM | 3403 | N | LYS 1042 | 20.467 | 7.614 | 66.638 |
| ATOM | 3404 | CA | LYS 1042 | 19.854 | 6.285 | 66.721 |
| ATOM | 3405 | CB | LYS 1042 | 18.446 | 6.272 | 66.159 |
| ATOM | 3406 | CG | LYS 1042 | 17.727 | 4.983 | 66.419 |

FIGURE 1TTT

| Atom | | Residue AA No. | X | Y | Z |
|---|---|---|---|---|---|
| ATOM | 3407 CD | LYS 1042 | 16.323 | 5.100 | 65.901 |
| ATOM | 3408 CE | LYS 1042 | 15.472 | 3.874 | 66.186 |
| ATOM | 3409 NZ | LYS 1042 | 14.131 | 3.905 | 65.508 |
| ATOM | 3410 C | LYS 1042 | 20.679 | 5.247 | 66.004 |
| ATOM | 3411 O | LYS 1042 | 20.679 | 4.078 | 66.387 |
| ATOM | 3412 N | ASN 1043 | 21.421 | 5.692 | 64.992 |
| ATOM | 3413 CA | ASN 1043 | 22.262 | 4.809 | 64.210 |
| ATOM | 3414 CB | ASN 1043 | 22.296 | 5.231 | 62.749 |
| ATOM | 3415 CG | ASN 1043 | 21.194 | 4.560 | 61.940 |
| ATOM | 3416 OD1 | ASN 1043 | 20.269 | 5.207 | 61.433 |
| ATOM | 3417 ND2 | ASN 1043 | 21.264 | 3.241 | 61.856 |
| ATOM | 3418 C | ASN 1043 | 23.639 | 4.612 | 64.779 |
| ATOM | 3419 O | ASN 1043 | 24.239 | 3.571 | 64.576 |
| ATOM | 3420 N | ASN 1044 | 24.139 | 5.593 | 65.509 |
| ATOM | 3421 CA | ASN 1044 | 25.434 | 5.438 | 66.140 |
| ATOM | 3422 CB | ASN 1044 | 25.948 | 6.764 | 66.691 |
| ATOM | 3423 CG | ASN 1044 | 26.359 | 7.736 | 65.605 |
| ATOM | 3424 OD1 | ASN 1044 | 25.509 | 8.362 | 64.982 |
| ATOM | 3425 ND2 | ASN 1044 | 27.670 | 7.899 | 65.401 |
| ATOM | 3426 C | ASN 1044 | 25.182 | 4.478 | 67.289 |
| ATOM | 3427 O | ASN 1044 | 26.061 | 3.715 | 67.696 |
| ATOM | 3428 N | VAL 1045 | 23.967 | 4.541 | 67.820 |
| ATOM | 3429 CA | VAL 1045 | 23.553 | 3.674 | 68.908 |
| ATOM | 3430 CB | VAL 1045 | 22.146 | 4.066 | 69.433 |
| ATOM | 3431 CG1 | VAL 1045 | 21.584 | 2.982 | 70.313 |
| ATOM | 3432 CG2 | VAL 1045 | 22.205 | 5.351 | 70.202 |
| ATOM | 3433 C | VAL 1045 | 23.464 | 2.300 | 68.280 |
| ATOM | 3434 O | VAL 1045 | 24.164 | 1.356 | 68.677 |
| ATOM | 3435 N | LYS 1046 | 22.691 | 2.261 | 67.203 |
| ATOM | 3436 CA | LYS 1046 | 22.408 | 1.049 | 66.460 |
| ATOM | 3437 CB | LYS 1046 | 21.339 | 1.354 | 65.406 |
| ATOM | 3438 CG | LYS 1046 | 20.245 | 0.275 | 65.273 |
| ATOM | 3439 CD | LYS 1046 | 18.847 | 0.821 | 64.882 |
| ATOM | 3440 CE | LYS 1046 | 18.769 | 1.322 | 63.435 |
| ATOM | 3441 NZ | LYS 1046 | 17.477 | 1.993 | 63.125 |
| ATOM | 3442 C | LYS 1046 | 23.614 | 0.360 | 65.841 |
| ATOM | 3443 O | LYS 1046 | 23.584 | -0.822 | 65.528 |
| ATOM | 3444 N | ALA 1047 | 24.704 | 1.080 | 65.711 |
| ATOM | 3445 CA | ALA 1047 | 25.880 | 0.483 | 65.122 |
| ATOM | 3446 CB | ALA 1047 | 26.516 | 1.460 | 64.160 |
| ATOM | 3447 C | ALA 1047 | 26.899 | -0.004 | 66.149 |
| ATOM | 3448 O | ALA 1047 | 27.506 | -1.050 | 65.963 |
| ATOM | 3449 N | ALA 1048 | 27.089 | 0.752 | 67.227 |
| ATOM | 3450 CA | ALA 1048 | 28.033 | 0.391 | 68.264 |
| ATOM | 3451 CB | ALA 1048 | 28.036 | 1.432 | 69.304 |
| ATOM | 3452 C | ALA 1048 | 27.605 | -0.930 | 68.837 |
| ATOM | 3453 O | ALA 1048 | 28.428 | -1.737 | 69.227 |
| ATOM | 3454 N | TRP 1049 | 26.302 | -1.149 | 68.845 |

FIGURE 1UUU

| Atom | | Residue AA No. | X | Y | Z |
|---|---|---|---|---|---|
| ATOM | 3455 CA | TRP 1049 | 25.731 | -2.376 | 69.337 |
| ATOM | 3456 CB | TRP 1049 | 24.226 | -2.294 | 69.247 |
| ATOM | 3457 CG | TRP 1049 | 23.570 | -3.354 | 69.978 |
| ATOM | 3458 CD2 | TRP 1049 | 23.235 | -4.654 | 69.503 |
| ATOM | 3459 CE2 | TRP 1049 | 22.637 | -5.340 | 70.556 |
| ATOM | 3460 CE3 | TRP 1049 | 23.374 | -5.305 | 68.287 |
| ATOM | 3461 CD1 | TRP 1049 | 23.171 | -3.304 | 71.253 |
| ATOM | 3462 NE1 | TRP 1049 | 22.607 | -4.490 | 71.622 |
| ATOM | 3463 CZ2 | TRP 1049 | 22.180 | -6.654 | 70.433 |
| ATOM | 3464 CZ3 | TRP 1049 | 22.911 | -6.619 | 68.167 |
| ATOM | 3465 CH2 | TRP 1049 | 22.327 | -7.269 | 69.229 |
| ATOM | 3466 C | TRP 1049 | 26.199 | -3.541 | 68.493 |
| ATOM | 3467 O | TRP 1049 | 26.765 | -4.500 | 68.993 |
| ATOM | 3468 N | TRP 1050 | 25.921 | -3.457 | 67.200 |
| ATOM | 3469 CA | TRP 1050 | 26.281 | -4.507 | 66.249 |
| ATOM | 3470 CB | TRP 1050 | 25.881 | -4.098 | 64.807 |
| ATOM | 3471 CG | TRP 1050 | 25.739 | -5.264 | 63.853 |
| ATOM | 3472 CD2 | TRP 1050 | 24.538 | -5.990 | 63.552 |
| ATOM | 3473 CE2 | TRP 1050 | 24.901 | -7.088 | 62.752 |
| ATOM | 3474 CE3 | TRP 1050 | 23.202 | -5.826 | 63.891 |
| ATOM | 3475 CD1 | TRP 1050 | 26.744 | -5.919 | 63.216 |
| ATOM | 3476 NE1 | TRP 1050 | 26.251 | -7.021 | 62.558 |
| ATOM | 3477 CZ2 | TRP 1050 | 23.982 | -8.014 | 62.299 |
| ATOM | 3478 CZ3 | TRP 1050 | 22.289 | -6.745 | 63.438 |
| ATOM | 3479 CH2 | TRP 1050 | 22.680 | -7.827 | 62.653 |
| ATOM | 3480 C | TRP 1050 | 27.778 | -4.745 | 66.340 |
| ATOM | 3481 O | TRP 1050 | 28.246 | -5.880 | 66.429 |
| ATOM | 3482 N | GLN 1051 | 28.509 | -3.641 | 66.369 |
| ATOM | 3483 CA | GLN 1051 | 29.951 | -3.628 | 66.423 |
| ATOM | 3484 CB | GLN 1051 | 30.418 | -2.223 | 66.755 |
| ATOM | 3485 CG | GLN 1051 | 31.529 | -1.714 | 65.899 |
| ATOM | 3486 CD | GLN 1051 | 32.839 | -2.399 | 66.175 |
| ATOM | 3487 OE1 | GLN 1051 | 33.586 | -2.013 | 67.081 |
| ATOM | 3488 NE2 | GLN 1051 | 33.144 | -3.413 | 65.381 |
| ATOM | 3489 C | GLN 1051 | 30.428 | -4.594 | 67.468 |
| ATOM | 3490 O | GLN 1051 | 30.946 | -5.646 | 67.116 |
| ATOM | 3491 N | LYS 1052 | 30.102 | -4.296 | 68.727 |
| ATOM | 3492 CA | LYS 1052 | 30.514 | -5.085 | 69.889 |
| ATOM | 3493 CB | LYS 1052 | 30.470 | -4.214 | 71.143 |
| ATOM | 3494 CG | LYS 1052 | 31.187 | -2.869 | 71.052 |
| ATOM | 3495 CD | LYS 1052 | 32.667 | -3.058 | 70.865 |
| ATOM | 3496 CE | LYS 1052 | 33.428 | -1.754 | 71.023 |
| ATOM | 3497 NZ | LYS 1052 | 34.874 | -1.806 | 70.568 |
| ATOM | 3498 C | LYS 1052 | 29.755 | -6.382 | 70.145 |
| ATOM | 3499 O | LYS 1052 | 30.364 | -7.407 | 70.418 |
| ATOM | 3500 N | PHE 1053 | 28.436 | -6.344 | 70.055 |
| ATOM | 3501 CA | PHE 1053 | 27.632 | -7.536 | 70.286 |
| ATOM | 3502 CB | PHE 1053 | 26.182 | -7.153 | 70.521 |

FIGURE 1VVV

| Atom | | Residue AA No. | X | Y | Z |
|---|---|---|---|---|---|
| ATOM | 3503 CG | PHE 1053 | 25.843 | -6.979 | 71.961 |
| ATOM | 3504 CD1 | PHE 1053 | 25.881 | -5.730 | 72.543 |
| ATOM | 3505 CD2 | PHE 1053 | 25.517 | -8.073 | 72.756 |
| ATOM | 3506 CE1 | PHE 1053 | 25.599 | -5.570 | 73.910 |
| ATOM | 3507 CE2 | PHE 1053 | 25.237 | -7.916 | 74.116 |
| ATOM | 3508 CZ | PHE 1053 | 25.278 | -6.669 | 74.690 |
| ATOM | 3509 C | PHE 1053 | 27.667 | -8.672 | 69.269 |
| ATOM | 3510 O | PHE 1053 | 27.268 | -9.787 | 69.578 |
| ATOM | 3511 N | ILE 1054 | 28.119 | -8.396 | 68.053 |
| ATOM | 3512 CA | ILE 1054 | 28.158 | -9.416 | 66.995 |
| ATOM | 3513 CB | ILE 1054 | 27.085 | -9.142 | 65.942 |
| ATOM | 3514 CG2 | ILE 1054 | 26.901 | -10.351 | 65.075 |
| ATOM | 3515 CG1 | ILE 1054 | 25.773 | -8.725 | 66.592 |
| ATOM | 3516 CD1 | ILE 1054 | 25.062 | -9.805 | 67.306 |
| ATOM | 3517 C | ILE 1054 | 29.467 | -9.495 | 66.211 |
| ATOM | 3518 O | ILE 1054 | 30.024 | -10.584 | 65.965 |
| ATOM | 3519 N | THR 1055 | 29.911 | -8.328 | 65.762 |
| ATOM | 3520 CA | THR 1055 | 31.115 | -8.273 | 64.969 |
| ATOM | 3521 CB | THR 1055 | 31.374 | -6.848 | 64.368 |
| ATOM | 3522 OG1 | THR 1055 | 30.339 | -6.527 | 63.420 |
| ATOM | 3523 CG2 | THR 1055 | 32.724 | -6.809 | 63.637 |
| ATOM | 3524 C | THR 1055 | 32.315 | -8.820 | 65.721 |
| ATOM | 3525 O | THR 1055 | 32.998 | -9.715 | 65.231 |
| ATOM | 3526 N | GLN 1056 | 32.530 | -8.337 | 66.935 |
| ATOM | 3527 CA | GLN 1056 | 33.663 | -8.784 | 67.720 |
| ATOM | 3528 CB | GLN 1056 | 34.167 | -7.646 | 68.600 |
| ATOM | 3529 CG | GLN 1056 | 34.785 | -6.526 | 67.791 |
| ATOM | 3530 CD | GLN 1056 | 34.650 | -5.175 | 68.454 |
| ATOM | 3531 OE1 | GLN 1056 | 33.572 | -4.605 | 68.502 |
| ATOM | 3532 NE2 | GLN 1056 | 35.746 | -4.655 | 68.969 |
| ATOM | 3533 C | GLN 1056 | 33.470 | -10.067 | 68.520 |
| ATOM | 3534 O | GLN 1056 | 34.394 | -10.853 | 68.621 |
| ATOM | 3535 N | SER 1057 | 32.277 | -10.316 | 69.047 |
| ATOM | 3536 CA | SER 1057 | 32.034 | -11.515 | 69.844 |
| ATOM | 3537 CB | SER 1057 | 30.842 | -11.284 | 70.757 |
| ATOM | 3538 OG | SER 1057 | 29.737 | -10.882 | 69.977 |
| ATOM | 3539 C | SER 1057 | 31.773 | -12.722 | 68.984 |
| ATOM | 3540 O | SER 1057 | 30.644 | -12.970 | 68.622 |
| ATOM | 3541 N | PRO 1058 | 32.782 | -13.575 | 68.793 |
| ATOM | 3542 CD | PRO 1058 | 34.055 | -13.526 | 69.510 |
| ATOM | 3543 CA | PRO 1058 | 32.729 | -14.796 | 67.989 |
| ATOM | 3544 CB | PRO 1058 | 34.023 | -15.494 | 68.359 |
| ATOM | 3545 CG | PRO 1058 | 34.906 | -14.388 | 68.639 |
| ATOM | 3546 C | PRO 1058 | 31.543 | -15.689 | 68.303 |
| ATOM | 3547 O | PRO 1058 | 31.174 | -16.556 | 67.532 |
| ATOM | 3548 N | PHE 1059 | 30.956 | -15.493 | 69.462 |
| ATOM | 3549 CA | PHE 1059 | 29.812 | -16.288 | 69.846 |
| ATOM | 3550 CB | PHE 1059 | 29.321 | -15.873 | 71.242 |

FIGURE 1WWW

| Atom | | Residue AA | No. | X | Y | Z |
|---|---|---|---|---|---|---|
| ATOM | 3551 | CG | PHE | 1059 | 30.318 | -16.081 | 72.317 |
| ATOM | 3552 | CD1 | PHE | 1059 | 30.733 | -17.367 | 72.656 |
| ATOM | 3553 | CD2 | PHE | 1059 | 30.827 | -14.986 | 73.016 |
| ATOM | 3554 | CE1 | PHE | 1059 | 31.652 | -17.578 | 73.696 |
| ATOM | 3555 | CE2 | PHE | 1059 | 31.752 | -15.163 | 74.065 |
| ATOM | 3556 | CZ | PHE | 1059 | 32.168 | -16.470 | 74.412 |
| ATOM | 3557 | C | PHE | 1059 | 28.640 | -16.112 | 68.897 |
| ATOM | 3558 | O | PHE | 1059 | 28.062 | -17.073 | 68.418 |
| ATOM | 3559 | N | ASN | 1060 | 28.321 | -14.870 | 68.604 |
| ATOM | 3560 | CA | ASN | 1060 | 27.143 | -14.595 | 67.826 |
| ATOM | 3561 | CB | ASN | 1060 | 26.298 | -13.595 | 68.593 |
| ATOM | 3562 | CG | ASN | 1060 | 26.832 | -13.324 | 69.961 |
| ATOM | 3563 | OD1 | ASN | 1060 | 26.202 | -13.659 | 70.944 |
| ATOM | 3564 | ND2 | ASN | 1060 | 28.018 | -12.750 | 70.036 |
| ATOM | 3565 | C | ASN | 1060 | 27.233 | -14.173 | 66.364 |
| ATOM | 3566 | O | ASN | 1060 | 28.276 | -13.706 | 65.873 |
| ATOM | 3567 | N | VAL | 1061 | 26.083 | -14.305 | 65.701 |
| ATOM | 3568 | CA | VAL | 1061 | 25.896 | -13.971 | 64.306 |
| ATOM | 3569 | CB | VAL | 1061 | 25.641 | -15.228 | 63.468 |
| ATOM | 3570 | CG1 | VAL | 1061 | 26.875 | -16.099 | 63.424 |
| ATOM | 3571 | CG2 | VAL | 1061 | 24.468 | -16.001 | 64.024 |
| ATOM | 3572 | C | VAL | 1061 | 24.648 | -13.140 | 64.265 |
| ATOM | 3573 | O | VAL | 1061 | 23.841 | -13.223 | 65.168 |
| ATOM | 3574 | N | GLY | 1062 | 24.483 | -12.338 | 63.230 |
| ATOM | 3575 | CA | GLY | 1062 | 23.291 | -11.533 | 63.160 |
| ATOM | 3576 | C | GLY | 1062 | 22.385 | -12.065 | 62.095 |
| ATOM | 3577 | O | GLY | 1062 | 22.748 | -13.010 | 61.414 |
| ATOM | 3578 | N | ILE | 1063 | 21.153 | -11.575 | 62.077 |
| ATOM | 3579 | CA | ILE | 1063 | 20.173 | -11.915 | 61.054 |
| ATOM | 3580 | CB | ILE | 1063 | 19.431 | -13.277 | 61.289 |
| ATOM | 3581 | CG2 | ILE | 1063 | 20.326 | -14.290 | 61.870 |
| ATOM | 3582 | CG1 | ILE | 1063 | 18.250 | -13.128 | 62.209 |
| ATOM | 3583 | CD1 | ILE | 1063 | 17.295 | -14.279 | 62.064 |
| ATOM | 3584 | C | ILE | 1063 | 19.190 | -10.719 | 60.845 |
| ATOM | 3585 | O | ILE | 1063 | 19.408 | -9.602 | 61.339 |
| ATOM | 3586 | N | ASP | 1064 | 18.210 | -10.907 | 59.976 |
| ATOM | 3587 | CA | ASP | 1064 | 17.207 | -9.890 | 59.702 |
| ATOM | 3588 | CB | ASP | 1064 | 17.657 | -8.958 | 58.567 |
| ATOM | 3589 | CG | ASP | 1064 | 16.753 | -7.731 | 58.400 |
| ATOM | 3590 | OD1 | ASP | 1064 | 15.524 | -7.882 | 58.274 |
| ATOM | 3591 | OD2 | ASP | 1064 | 17.276 | -6.599 | 58.374 |
| ATOM | 3592 | C | ASP | 1064 | 15.975 | -10.677 | 59.276 |
| ATOM | 3593 | O | ASP | 1064 | 15.893 | -11.125 | 58.135 |
| ATOM | 3594 | N | ALA | 1065 | 15.071 | -10.924 | 60.223 |
| ATOM | 3595 | CA | ALA | 1065 | 13.849 | -11.655 | 59.949 |
| ATOM | 3596 | CB | ALA | 1065 | 13.348 | -12.314 | 61.179 |
| ATOM | 3597 | C | ALA | 1065 | 12.795 | -10.723 | 59.390 |
| ATOM | 3598 | O | ALA | 1065 | 12.952 | -9.500 | 59.399 |

FIGURE 1XXX

| Atom | | Residue AA | No. | X | Y | Z |
|---|---|---|---|---|---|---|
| ATOM | 3599 | N | ALA | 1066 | 11.683 | -11.310 | 58.981 |
| ATOM | 3600 | CA | ALA | 1066 | 10.593 | -10.568 | 58.373 |
| ATOM | 3601 | CB | ALA | 1066 | 9.923 | -11.466 | 57.329 |
| ATOM | 3602 | C | ALA | 1066 | 9.546 | -10.040 | 59.363 |
| ATOM | 3603 | O | ALA | 1066 | 9.060 | -10.784 | 60.194 |
| ATOM | 3604 | N | ILE | 1067 | 9.173 | -8.772 | 59.266 |
| ATOM | 3605 | CA | ILE | 1067 | 8.163 | -8.265 | 60.158 |
| ATOM | 3606 | CB | ILE | 1067 | 7.889 | -6.832 | 59.885 |
| ATOM | 3607 | CG2 | ILE | 1067 | 6.698 | -6.378 | 60.633 |
| ATOM | 3608 | CG1 | ILE | 1067 | 9.080 | -6.005 | 60.300 |
| ATOM | 3609 | CD1 | ILE | 1067 | 8.840 | -4.563 | 60.098 |
| ATOM | 3610 | C | ILE | 1067 | 6.896 | -9.076 | 59.950 |
| ATOM | 3611 | O | ILE | 1067 | 6.111 | -9.251 | 60.853 |
| ATOM | 3612 | N | LEU | 1068 | 6.705 | -9.599 | 58.757 |
| ATOM | 3613 | CA | LEU | 1068 | 5.525 | -10.408 | 58.469 |
| ATOM | 3614 | CB | LEU | 1068 | 4.983 | -10.089 | 57.062 |
| ATOM | 3615 | CG | LEU | 1068 | 4.171 | -8.836 | 56.686 |
| ATOM | 3616 | CD1 | LEU | 1068 | 2.824 | -8.875 | 57.365 |
| ATOM | 3617 | CD2 | LEU | 1068 | 4.915 | -7.564 | 57.024 |
| ATOM | 3618 | C | LEU | 1068 | 5.846 | -11.904 | 58.550 |
| ATOM | 3619 | O | LEU | 1068 | 6.740 | -12.409 | 57.852 |
| ATOM | 3620 | N | MET | 1069 | 5.118 | -12.622 | 59.393 |
| ATOM | 3621 | CA | MET | 1069 | 5.337 | -14.058 | 59.504 |
| ATOM | 3622 | CB | MET | 1069 | 6.527 | -14.410 | 60.429 |
| ATOM | 3623 | CG | MET | 1069 | 6.660 | -13.695 | 61.790 |
| ATOM | 3624 | SD | MET | 1069 | 8.204 | -14.269 | 62.657 |
| ATOM | 3625 | CE | MET | 1069 | 9.378 | -12.878 | 62.538 |
| ATOM | 3626 | C | MET | 1069 | 4.115 | -14.915 | 59.811 |
| ATOM | 3627 | O | MET | 1069 | 3.081 | -14.428 | 60.277 |
| ATOM | 3628 | N | ASN | 1070 | 4.231 | -16.171 | 59.395 |
| ATOM | 3629 | CA | ASN | 1070 | 3.232 | -17.214 | 59.565 |
| ATOM | 3630 | CB | ASN | 1070 | 3.883 | -18.581 | 59.295 |
| ATOM | 3631 | CG | ASN | 1070 | 2.879 | -19.721 | 59.268 |
| ATOM | 3632 | OD1 | ASN | 1070 | 3.036 | -20.727 | 59.959 |
| ATOM | 3633 | ND2 | ASN | 1070 | 1.848 | -19.573 | 58.461 |
| ATOM | 3634 | C | ASN | 1070 | 2.609 | -17.200 | 60.958 |
| ATOM | 3635 | O | ASN | 1070 | 3.222 | -17.627 | 61.934 |
| ATOM | 3636 | N | PRO | 1071 | 1.333 | -16.820 | 61.046 |
| ATOM | 3637 | CD | PRO | 1071 | 0.430 | -16.583 | 59.913 |
| ATOM | 3638 | CA | PRO | 1071 | 0.607 | -16.748 | 62.316 |
| ATOM | 3639 | CB | PRO | 1071 | -0.843 | -16.599 | 61.888 |
| ATOM | 3640 | CG | PRO | 1071 | -0.737 | -15.885 | 60.591 |
| ATOM | 3641 | C | PRO | 1071 | 0.783 | -17.960 | 63.189 |
| ATOM | 3642 | O | PRO | 1071 | 0.831 | -17.796 | 64.400 |
| ATOM | 3643 | N | ALA | 1072 | 0.909 | -19.155 | 62.596 |
| ATOM | 3644 | CA | ALA | 1072 | 1.078 | -20.390 | 63.377 |
| ATOM | 3645 | CB | ALA | 1072 | 1.395 | -21.592 | 62.475 |
| ATOM | 3646 | C | ALA | 1072 | 2.148 | -20.202 | 64.459 |

FIGURE 1YYY

| Atom | | Residue AA No. | X | Y | Z |
|---|---|---|---|---|---|
| ATOM | 3647 O | ALA 1072 | 2.017 | -20.728 | 65.572 |
| ATOM | 3648 N | VAL 1073 | 3.159 | -19.390 | 64.161 |
| ATOM | 3649 CA | VAL 1073 | 4.202 | -19.105 | 65.131 |
| ATOM | 3650 CB | VAL 1073 | 5.247 | -18.146 | 64.572 |
| ATOM | 3651 CG1 | VAL 1073 | 5.878 | -17.312 | 65.670 |
| ATOM | 3652 CG2 | VAL 1073 | 6.298 | -18.941 | 63.866 |
| ATOM | 3653 C | VAL 1073 | 3.583 | -18.478 | 66.360 |
| ATOM | 3654 O | VAL 1073 | 3.705 | -18.996 | 67.466 |
| ATOM | 3655 N | TRP 1074 | 2.839 | -17.407 | 66.150 |
| ATOM | 3656 CA | TRP 1074 | 2.208 | -16.681 | 67.244 |
| ATOM | 3657 CB | TRP 1074 | 1.464 | -15.468 | 66.702 |
| ATOM | 3658 CG | TRP 1074 | 2.434 | -14.506 | 66.057 |
| ATOM | 3659 CD2 | TRP 1074 | 3.554 | -13.868 | 66.690 |
| ATOM | 3660 CE2 | TRP 1074 | 4.214 | -13.102 | 65.700 |
| ATOM | 3661 CE3 | TRP 1074 | 4.063 | -13.874 | 67.997 |
| ATOM | 3662 CD1 | TRP 1074 | 2.459 | -14.108 | 64.747 |
| ATOM | 3663 NE1 | TRP 1074 | 3.528 | -13.267 | 64.526 |
| ATOM | 3664 CZ2 | TRP 1074 | 5.362 | -12.346 | 65.976 |
| ATOM | 3665 CZ3 | TRP 1074 | 5.207 | -13.124 | 68.276 |
| ATOM | 3666 CH2 | TRP 1074 | 5.844 | -12.369 | 67.268 |
| ATOM | 3667 C | TRP 1074 | 1.371 | -17.510 | 68.200 |
| ATOM | 3668 O | TRP 1074 | 0.939 | -17.014 | 69.240 |
| ATOM | 3669 N | GLU 1075 | 1.206 | -18.786 | 67.875 |
| ATOM | 3670 CA | GLU 1075 | 0.482 | -19.700 | 68.733 |
| ATOM | 3671 CB | GLU 1075 | -0.276 | -20.713 | 67.917 |
| ATOM | 3672 CG | GLU 1075 | -1.314 | -20.100 | 67.030 |
| ATOM | 3673 CD | GLU 1075 | -1.974 | -21.142 | 66.138 |
| ATOM | 3674 OE1 | GLU 1075 | -1.229 | -21.854 | 65.403 |
| ATOM | 3675 OE2 | GLU 1075 | -3.230 | -21.254 | 66.193 |
| ATOM | 3676 C | GLU 1075 | 1.496 | -20.437 | 69.579 |
| ATOM | 3677 O | GLU 1075 | 1.320 | -20.621 | 70.794 |
| ATOM | 3678 N | ALA 1076 | 2.564 | -20.883 | 68.933 |
| ATOM | 3679 CA | ALA 1076 | 3.614 | -21.581 | 69.663 |
| ATOM | 3680 CB | ALA 1076 | 4.616 | -22.185 | 68.720 |
| ATOM | 3681 C | ALA 1076 | 4.296 | -20.589 | 70.576 |
| ATOM | 3682 O | ALA 1076 | 5.158 | -20.962 | 71.365 |
| ATOM | 3683 N | SER 1077 | 3.988 | -19.312 | 70.362 |
| ATOM | 3684 CA | SER 1077 | 4.530 | -18.234 | 71.177 |
| ATOM | 3685 CB | SER 1077 | 4.853 | -16.980 | 70.312 |
| ATOM | 3686 OG | SER 1077 | 3.700 | -16.209 | 69.986 |
| ATOM | 3687 C | SER 1077 | 3.519 | -17.915 | 72.313 |
| ATOM | 3688 O | SER 1077 | 3.899 | -17.362 | 73.370 |
| ATOM | 3689 N | GLY 1078 | 2.250 | -18.292 | 72.100 |
| ATOM | 3690 CA | GLY 1078 | 1.195 | -18.026 | 73.069 |
| ATOM | 3691 C | GLY 1078 | 0.729 | -16.578 | 73.030 |
| ATOM | 3692 O | GLY 1078 | -0.236 | -16.226 | 73.691 |
| ATOM | 3693 N | HIS 1079 | 1.394 | -15.748 | 72.225 |
| ATOM | 3694 CA | HIS 1079 | 1.063 | -14.336 | 72.111 |

FIGURE 1ZZZ

| Atom | | Residue AA No. | X | Y | Z |
|---|---|---|---|---|---|
| ATOM | 3695 CB | HIS 1079 | 1.971 | -13.634 | 71.103 |
| ATOM | 3696 CG | HIS 1079 | 3.228 | -13.075 | 71.695 |
| ATOM | 3697 CD2 | HIS 1079 | 3.977 | -12.002 | 71.346 |
| ATOM | 3698 ND1 | HIS 1079 | 3.878 | -13.664 | 72.760 |
| ATOM | 3699 CE1 | HIS 1079 | 4.977 | -12.981 | 73.037 |
| ATOM | 3700 NE2 | HIS 1079 | 5.061 | -11.968 | 72.193 |
| ATOM | 3701 C | HIS 1079 | -0.352 | -14.205 | 71.650 |
| ATOM | 3702 O | HIS 1079 | -0.989 | -13.196 | 71.887 |
| ATOM | 3703 N | LEU 1080 | -0.827 | -15.234 | 70.967 |
| ATOM | 3704 CA | LEU 1080 | -2.185 | -15.259 | 70.457 |
| ATOM | 3705 CB | LEU 1080 | -2.520 | -16.675 | 69.975 |
| ATOM | 3706 CG | LEU 1080 | -3.005 | -16.863 | 68.525 |
| ATOM | 3707 CD1 | LEU 1080 | -4.457 | -16.329 | 68.400 |
| ATOM | 3708 CD2 | LEU 1080 | -2.037 | -16.206 | 67.498 |
| ATOM | 3709 C | LEU 1080 | -3.130 | -14.848 | 71.567 |
| ATOM | 3710 O | LEU 1080 | -4.083 | -14.102 | 71.332 |
| ATOM | 3711 N | ASN 1081 | -2.810 | -15.298 | 72.788 |
| ATOM | 3712 CA | ASN 1081 | -3.612 | -15.026 | 74.016 |
| ATOM | 3713 CB | ASN 1081 | -4.473 | -16.252 | 74.416 |
| ATOM | 3714 CG | ASN 1081 | -3.829 | -17.599 | 74.031 |
| ATOM | 3715 OD1 | ASN 1081 | -2.727 | -17.947 | 74.508 |
| ATOM | 3716 ND2 | ASN 1081 | -4.513 | -18.354 | 73.146 |
| ATOM | 3717 C | ASN 1081 | -2.837 | -14.545 | 75.250 |
| ATOM | 3718 O | ASN 1081 | -3.168 | -13.510 | 75.841 |
| ATOM | 3719 N | ASN 1082 | -1.832 | -15.316 | 75.650 |
| ATOM | 3720 CA | ASN 1082 | -1.010 | -14.948 | 76.802 |
| ATOM | 3721 CB | ASN 1082 | 0.126 | -15.964 | 77.017 |
| ATOM | 3722 CG | ASN 1082 | -0.380 | -17.403 | 77.172 |
| ATOM | 3723 OD1 | ASN 1082 | 0.340 | -18.359 | 76.822 |
| ATOM | 3724 ND2 | ASN 1082 | -1.608 | -17.568 | 77.714 |
| ATOM | 3725 C | ASN 1082 | -0.431 | -13.524 | 76.664 |
| ATOM | 3726 O | ASN 1082 | -0.189 | -12.860 | 77.674 |
| ATOM | 3727 N | PHE 1083 | -0.160 | -13.079 | 75.429 |
| ATOM | 3728 CA | PHE 1083 | 0.351 | -11.724 | 75.217 |
| ATOM | 3729 CB | PHE 1083 | 0.812 | -11.454 | 73.782 |
| ATOM | 3730 CG | PHE 1083 | 1.110 | -9.995 | 73.528 |
| ATOM | 3731 CD1 | PHE 1083 | 0.083 | -9.116 | 73.158 |
| ATOM | 3732 CD2 | PHE 1083 | 2.397 | -9.480 | 73.758 |
| ATOM | 3733 CE1 | PHE 1083 | 0.322 | -7.762 | 73.030 |
| ATOM | 3734 CE2 | PHE 1083 | 2.653 | -8.114 | 73.632 |
| ATOM | 3735 CZ | PHE 1083 | 1.602 | -7.247 | 73.266 |
| ATOM | 3736 C | PHE 1083 | -0.828 | -10.839 | 75.511 |
| ATOM | 3737 O | PHE 1083 | -1.793 | -10.787 | 74.743 |
| ATOM | 3738 N | ASN 1084 | -0.695 | -10.054 | 76.561 |
| ATOM | 3739 CA | ASN 1084 | -1.807 | -9.229 | 76.956 |
| ATOM | 3740 CB | ASN 1084 | -2.836 | -10.139 | 77.675 |
| ATOM | 3741 CG | ASN 1084 | -4.109 | -10.374 | 76.874 |
| ATOM | 3742 OD1 | ASN 1084 | -5.185 | -9.930 | 77.286 |

FIGURE 1AAAA

|  |  | Residue |  |  |  |
|---|---|---|---|---|---|
| Atom |  | AA No. | X | Y | Z |
| ATOM | 3743 ND2 | ASN 1084 | -4.016 | -11.140 | 75.785 |
| ATOM | 3744 C | ASN 1084 | -1.457 | -8.052 | 77.876 |
| ATOM | 3745 O | ASN 1084 | -0.299 | -7.841 | 78.302 |
| ATOM | 3746 N | ALA 1085 | -2.510 | -7.278 | 78.110 |
| ATOM | 3747 CA | ALA 1085 | -2.544 | -6.138 | 78.996 |
| ATOM | 3748 CB | ALA 1085 | -2.436 | -4.809 | 78.213 |
| ATOM | 3749 C | ALA 1085 | -3.969 | -6.334 | 79.546 |
| ATOM | 3750 O | ALA 1085 | -4.954 | -6.136 | 78.792 |
| ATOM | 3751 N | PRO 1086 | -4.080 | -6.992 | 80.742 |
| ATOM | 3752 CD | PRO 1086 | -3.006 | -7.791 | 81.385 |
| ATOM | 3753 CA | PRO 1086 | -5.372 | -7.251 | 81.419 |
| ATOM | 3754 CB | PRO 1086 | -4.962 | -8.071 | 82.659 |
| ATOM | 3755 CG | PRO 1086 | -3.797 | -8.869 | 82.148 |
| ATOM | 3756 C | PRO 1086 | -6.124 | -5.951 | 81.828 |
| ATOM | 3757 O | PRO 1086 | -5.455 | -4.940 | 82.204 |
| ATOM | 3758 OT | PRO 1086 | -7.383 | -5.965 | 81.731 |
| ATOM | 3759 CB | ALA 1150 | -7.496 | -10.159 | 79.486 |
| ATOM | 3760 C | ALA 1150 | -7.626 | -8.262 | 77.737 |
| ATOM | 3761 O | ALA 1150 | -8.642 | -8.564 | 77.046 |
| ATOM | 3762 N | ALA 1150 | -8.693 | -8.028 | 80.045 |
| ATOM | 3763 CA | ALA 1150 | -7.556 | -8.618 | 79.258 |
| ATOM | 3764 N | ALA 1151 | -6.547 | -7.636 | 77.232 |
| ATOM | 3765 CA | ALA 1151 | -6.446 | -7.204 | 75.816 |
| ATOM | 3766 CB | ALA 1151 | -6.531 | -5.645 | 75.746 |
| ATOM | 3767 C | ALA 1151 | -5.186 | -7.700 | 75.045 |
| ATOM | 3768 O | ALA 1151 | -4.045 | -7.487 | 75.513 |
| ATOM | 3769 N | ASN 1152 | -5.390 | -8.349 | 73.882 |
| ATOM | 3770 CA | ASN 1152 | -4.263 | -8.833 | 73.046 |
| ATOM | 3771 CB | ASN 1152 | -4.567 | -10.186 | 72.388 |
| ATOM | 3772 CG | ASN 1152 | -3.404 | -10.706 | 71.584 |
| ATOM | 3773 OD1 | ASN 1152 | -3.569 | -11.137 | 70.441 |
| ATOM | 3774 ND2 | ASN 1152 | -2.211 | -10.638 | 72.163 |
| ATOM | 3775 C | ASN 1152 | -3.854 | -7.767 | 72.003 |
| ATOM | 3776 O | ASN 1152 | -4.387 | -7.657 | 70.887 |
| ATOM | 3777 N | LEU 1153 | -2.850 | -7.011 | 72.409 |
| ATOM | 3778 CA | LEU 1153 | -2.304 | -5.871 | 71.681 |
| ATOM | 3779 CB | LEU 1153 | -1.532 | -5.003 | 72.717 |
| ATOM | 3780 CG | LEU 1153 | -1.585 | -5.320 | 74.245 |
| ATOM | 3781 CD1 | LEU 1153 | -0.292 | -4.869 | 74.968 |
| ATOM | 3782 CD2 | LEU 1153 | -2.836 | -4.693 | 74.876 |
| ATOM | 3783 C | LEU 1153 | -1.421 | -6.107 | 70.424 |
| ATOM | 3784 O | LEU 1153 | -0.600 | -5.243 | 70.068 |
| ATOM | 3785 N | MET 1154 | -1.529 | -7.262 | 69.779 |
| ATOM | 3786 CA | MET 1154 | -0.709 | -7.492 | 68.582 |
| ATOM | 3787 CB | MET 1154 | -0.651 | -8.980 | 68.247 |
| ATOM | 3788 CG | MET 1154 | -0.048 | -9.879 | 69.319 |
| ATOM | 3789 SD | MET 1154 | -0.115 | -11.612 | 68.764 |
| ATOM | 3790 CE | MET 1154 | 1.037 | -11.544 | 67.377 |

FIGURE 1BBBB

| Atom | | Residue AA | No. | X | Y | Z |
|---|---|---|---|---|---|---|
| ATOM | 3791 C   | MET | 1154 | -1.392  | -6.732  | 67.434 |
| ATOM | 3792 O   | MET | 1154 | -2.637  | -6.677  | 67.400 |
| ATOM | 3793 N   | PHE | 1155 | -0.622  | -6.153  | 66.503 |
| ATOM | 3794 CA  | PHE | 1155 | -1.253  | -5.399  | 65.409 |
| ATOM | 3795 CB  | PHE | 1155 | -0.313  | -4.334  | 64.894 |
| ATOM | 3796 CG  | PHE | 1155 | -0.770  | -2.946  | 65.208 |
| ATOM | 3797 CD1 | PHE | 1155 | -2.093  | -2.574  | 64.989 |
| ATOM | 3798 CD2 | PHE | 1155 | 0.121   | -1.998  | 65.706 |
| ATOM | 3799 CE1 | PHE | 1155 | -2.517  | -1.270  | 65.260 |
| ATOM | 3800 CE2 | PHE | 1155 | -0.297  | -0.692  | 65.980 |
| ATOM | 3801 CZ  | PHE | 1155 | -1.617  | -0.330  | 65.755 |
| ATOM | 3802 C   | PHE | 1155 | -1.882  | -6.209  | 64.271 |
| ATOM | 3803 O   | PHE | 1155 | -1.199  | -6.874  | 63.495 |
| ATOM | 3804 N   | ALA | 1156 | -3.193  | -6.082  | 64.135 |
| ATOM | 3805 CA  | ALA | 1156 | -3.969  | -6.855  | 63.150 |
| ATOM | 3806 CB  | ALA | 1156 | -5.418  | -6.972  | 63.632 |
| ATOM | 3807 C   | ALA | 1156 | -3.973  | -6.479  | 61.672 |
| ATOM | 3808 O   | ALA | 1156 | -4.372  | -5.363  | 61.308 |
| ATOM | 3809 N   | THR | 1157 | -3.616  | -7.442  | 60.817 |
| ATOM | 3810 CA  | THR | 1157 | -3.624  | -7.216  | 59.353 |
| ATOM | 3811 CB  | THR | 1157 | -2.207  | -6.894  | 58.726 |
| ATOM | 3812 OG1 | THR | 1157 | -2.386  | -6.093  | 57.551 |
| ATOM | 3813 CG2 | THR | 1157 | -1.479  | -8.155  | 58.294 |
| ATOM | 3814 C   | THR | 1157 | -4.268  | -8.345  | 58.538 |
| ATOM | 3815 O   | THR | 1157 | -4.480  | -9.472  | 59.020 |
| ATOM | 3816 N   | ALA | 1158 | -4.605  | -8.012  | 57.302 |
| ATOM | 3817 CA  | ALA | 1158 | -5.209  | -8.970  | 56.403 |
| ATOM | 3818 CB  | ALA | 1158 | -6.675  | -8.634  | 56.177 |
| ATOM | 3819 C   | ALA | 1158 | -4.422  | -8.933  | 55.095 |
| ATOM | 3820 O   | ALA | 1158 | -4.085  | -7.860  | 54.586 |
| ATOM | 3821 N   | GLN | 1159 | -4.105  | -10.116 | 54.586 |
| ATOM | 3822 CA  | GLN | 1159 | -3.342  | -10.266 | 53.361 |
| ATOM | 3823 CB  | GLN | 1159 | -2.073  | -11.035 | 53.675 |
| ATOM | 3824 CG  | GLN | 1159 | -1.192  | -11.291 | 52.478 |
| ATOM | 3825 CD  | GLN | 1159 | -0.055  | -12.221 | 52.819 |
| ATOM | 3826 OE1 | GLN | 1159 | 1.115   | -11.902 | 52.582 |
| ATOM | 3827 NE2 | GLN | 1159 | -0.389  | -13.378 | 53.411 |
| ATOM | 3828 C   | GLN | 1159 | -4.119  | -10.987 | 52.247 |
| ATOM | 3829 O   | GLN | 1159 | -4.077  | -12.226 | 52.159 |
| ATOM | 3830 N   | GLY | 1160 | -4.785  | -10.200 | 51.389 |
| ATOM | 3831 CA  | GLY | 1160 | -5.601  | -10.720 | 50.286 |
| ATOM | 3832 C   | GLY | 1160 | -6.997  | -10.073 | 50.202 |
| ATOM | 3833 O   | GLY | 1160 | -7.168  | -9.080  | 49.451 |
| ATOM | 3834 N   | ALA | 1161 | -7.981  | -10.660 | 50.922 |
| ATOM | 3835 CA  | ALA | 1161 | -9.381  | -10.161 | 51.013 |
| ATOM | 3836 CB  | ALA | 1161 | -10.017 | -9.969  | 49.596 |
| ATOM | 3837 C   | ALA | 1161 | -10.318 | -10.999 | 51.937 |
| ATOM | 3838 O   | ALA | 1161 | -10.878 | -10.382 | 52.894 |

FIGURE 1CCCC

| Atom | | Residue AA | No. | X | Y | Z |
|---|---|---|---|---|---|---|
| ATOM | 3839 | OT | ALA | 1161 | -10.455 | -12.249 | 51.736 |
| ATOM | 3840 | CB | ALA | 1164 | -13.078 | -13.598 | 55.906 |
| ATOM | 3841 | C | ALA | 1164 | -10.884 | -12.981 | 57.076 |
| ATOM | 3842 | O | ALA | 1164 | -9.875 | -12.267 | 57.330 |
| ATOM | 3843 | N | ALA | 1164 | -11.377 | -12.265 | 54.682 |
| ATOM | 3844 | CA | ALA | 1164 | -11.968 | -12.530 | 56.042 |
| ATOM | 3845 | N | ALA | 1165 | -11.131 | -14.135 | 57.707 |
| ATOM | 3846 | CA | ALA | 1165 | -10.184 | -14.728 | 58.658 |
| ATOM | 3847 | CB | ALA | 1165 | -10.942 | -15.364 | 59.852 |
| ATOM | 3848 | C | ALA | 1165 | -9.409 | -15.806 | 57.853 |
| ATOM | 3849 | O | ALA | 1165 | -10.044 | -16.632 | 57.160 |
| ATOM | 3850 | N | THR | 1166 | -8.068 | -15.708 | 57.894 |
| ATOM | 3851 | CA | THR | 1166 | -7.058 | -16.576 | 57.223 |
| ATOM | 3852 | CB | THR | 1166 | -7.595 | -17.461 | 56.059 |
| ATOM | 3853 | OG1 | THR | 1166 | -8.464 | -16.694 | 55.197 |
| ATOM | 3854 | CG2 | THR | 1166 | -8.270 | -18.765 | 56.620 |
| ATOM | 3855 | C | THR | 1166 | -6.002 | -15.645 | 56.638 |
| ATOM | 3856 | O | THR | 1166 | -4.797 | -15.953 | 56.579 |
| ATOM | 3857 | N | ASN | 1167 | -6.512 | -14.528 | 56.127 |
| ATOM | 3858 | CA | ASN | 1167 | -5.694 | -13.442 | 55.587 |
| ATOM | 3859 | CB | ASN | 1167 | -6.612 | -12.361 | 54.935 |
| ATOM | 3860 | CG | ASN | 1167 | -7.782 | -12.960 | 54.119 |
| ATOM | 3861 | OD1 | ASN | 1167 | -8.823 | -13.327 | 54.685 |
| ATOM | 3862 | ND2 | ASN | 1167 | -7.616 | -13.045 | 52.785 |
| ATOM | 3863 | C | ASN | 1167 | -5.047 | -12.874 | 56.889 |
| ATOM | 3864 | O | ASN | 1167 | -3.919 | -12.344 | 56.899 |
| ATOM | 3865 | N | ALA | 1168 | -5.825 | -13.016 | 57.972 |
| ATOM | 3866 | CA | ALA | 1168 | -5.501 | -12.595 | 59.330 |
| ATOM | 3867 | CB | ALA | 1168 | -6.592 | -13.138 | 60.310 |
| ATOM | 3868 | C | ALA | 1168 | -4.091 | -13.014 | 59.784 |
| ATOM | 3869 | O | ALA | 1168 | -3.874 | -14.119 | 60.285 |
| ATOM | 3870 | N | ILE | 1169 | -3.130 | -12.133 | 59.557 |
| ATOM | 3871 | CA | ILE | 1169 | -1.744 | -12.365 | 59.954 |
| ATOM | 3872 | CB | ILE | 1169 | -0.857 | -12.597 | 58.719 |
| ATOM | 3873 | CG2 | ILE | 1169 | -1.516 | -13.635 | 57.798 |
| ATOM | 3874 | CG1 | ILE | 1169 | -0.685 | -11.302 | 57.928 |
| ATOM | 3875 | CD1 | ILE | 1169 | 0.437 | -11.346 | 56.903 |
| ATOM | 3876 | C | ILE | 1169 | -1.365 | -11.072 | 60.682 |
| ATOM | 3877 | O | ILE | 1169 | -2.078 | -10.067 | 60.529 |
| ATOM | 3878 | N | PHE | 1170 | -0.307 | -11.052 | 61.487 |
| ATOM | 3879 | CA | PHE | 1170 | -0.022 | -9.795 | 62.183 |
| ATOM | 3880 | CB | PHE | 1170 | -0.381 | -9.878 | 63.663 |
| ATOM | 3881 | CG | PHE | 1170 | -1.596 | -10.647 | 63.924 |
| ATOM | 3882 | CD1 | PHE | 1170 | -2.838 | -10.169 | 63.492 |
| ATOM | 3883 | CD2 | PHE | 1170 | -1.506 | -11.892 | 64.514 |
| ATOM | 3884 | CE1 | PHE | 1170 | -3.983 | -10.939 | 63.639 |
| ATOM | 3885 | CE2 | PHE | 1170 | -2.631 | -12.675 | 64.672 |
| ATOM | 3886 | CZ | PHE | 1170 | -3.882 | -12.206 | 64.233 |

FIGURE 1DDDD

|  | Residue | | | | |
|---|---|---|---|---|---|
| Atom | AA | No. | X | Y | Z |
| ATOM 3887 C | PHE | 1170 | 1.398 | -9.399 | 62.119 |
| ATOM 3888 O | PHE | 1170 | 2.226 | -10.147 | 61.599 |
| ATOM 3889 N | LEU | 1171 | 1.668 | -8.252 | 62.739 |
| ATOM 3890 CA | LEU | 1171 | 2.999 | -7.700 | 62.836 |
| ATOM 3891 CB | LEU | 1171 | 2.954 | -6.178 | 62.815 |
| ATOM 3892 CG | LEU | 1171 | 1.848 | -5.444 | 62.037 |
| ATOM 3893 CD1 | LEU | 1171 | 2.344 | -4.010 | 61.724 |
| ATOM 3894 CD2 | LEU | 1171 | 1.443 | -6.170 | 60.749 |
| ATOM 3895 C | LEU | 1171 | 3.596 | -8.175 | 64.148 |
| ATOM 3896 O | LEU | 1171 | 2.901 | -8.265 | 65.164 |
| ATOM 3897 N | ARG | 1172 | 4.884 | -8.493 | 64.106 |
| ATOM 3898 CA | ARG | 1172 | 5.618 | -8.983 | 65.264 |
| ATOM 3899 CB | ARG | 1172 | 7.047 | -9.406 | 64.854 |
| ATOM 3900 CG | ARG | 1172 | 8.017 | -8.255 | 64.463 |
| ATOM 3901 CD | ARG | 1172 | 9.386 | -8.816 | 64.107 |
| ATOM 3902 NE | ARG | 1172 | 10.273 | -7.860 | 63.454 |
| ATOM 3903 CZ | ARG | 1172 | 11.495 | -8.158 | 63.014 |
| ATOM 3904 NH1 | ARG | 1172 | 11.973 | -9.387 | 63.148 |
| ATOM 3905 NH2 | ARG | 1172 | 12.251 | -7.226 | 62.443 |
| ATOM 3906 C | ARG | 1172 | 5.717 | -7.978 | 66.418 |
| ATOM 3907 O | ARG | 1172 | 6.117 | -6.824 | 66.204 |
| ATOM 3908 N | PRO | 1173 | 5.278 | -8.373 | 67.634 |
| ATOM 3909 CD | PRO | 1173 | 4.355 | -9.486 | 67.899 |
| ATOM 3910 CA | PRO | 1173 | 5.354 | -7.484 | 68.808 |
| ATOM 3911 CB | PRO | 1173 | 4.210 | -7.985 | 69.701 |
| ATOM 3912 CG | PRO | 1173 | 3.345 | -8.819 | 68.777 |
| ATOM 3913 C | PRO | 1173 | 6.714 | -7.750 | 69.483 |
| ATOM 3914 O | PRO | 1173 | 7.199 | -6.976 | 70.319 |
| ATOM 3915 N | GLU | 1174 | 7.331 | -8.851 | 69.061 |
| ATOM 3916 CA | GLU | 1174 | 8.602 | -9.286 | 69.592 |
| ATOM 3917 CB | GLU | 1174 | 8.339 | -10.296 | 70.694 |
| ATOM 3918 CG | GLU | 1174 | 9.583 | -10.955 | 71.222 |
| ATOM 3919 CD | GLU | 1174 | 9.300 | -11.838 | 72.410 |
| ATOM 3920 OE1 | GLU | 1174 | 10.191 | -11.884 | 73.309 |
| ATOM 3921 OE2 | GLU | 1174 | 8.194 | -12.457 | 72.436 |
| ATOM 3922 C | GLU | 1174 | 9.526 | -9.881 | 68.517 |
| ATOM 3923 O | GLU | 1174 | 9.227 | -10.902 | 67.865 |
| ATOM 3924 N | THR | 1175 | 10.688 | -9.257 | 68.419 |
| ATOM 3925 CA | THR | 1175 | 11.731 | -9.597 | 67.465 |
| ATOM 3926 CB | THR | 1175 | 12.804 | -8.509 | 67.560 |
| ATOM 3927 OG1 | THR | 1175 | 12.182 | -7.224 | 67.388 |
| ATOM 3928 CG2 | THR | 1175 | 13.884 | -8.710 | 66.538 |
| ATOM 3929 C | THR | 1175 | 12.376 | -10.976 | 67.597 |
| ATOM 3930 O | THR | 1175 | 12.994 | -11.480 | 66.658 |
| ATOM 3931 N | ALA | 1176 | 12.175 | -11.608 | 68.744 |
| ATOM 3932 CA | ALA | 1176 | 12.783 | -12.904 | 69.032 |
| ATOM 3933 CB | ALA | 1176 | 12.656 | -13.228 | 70.510 |
| ATOM 3934 C | ALA | 1176 | 12.269 | -14.062 | 68.221 |

FIGURE 1EEEE

|  | Atom | Residue AA | No. | X | Y | Z |
|---|---|---|---|---|---|---|
| ATOM | 3935 O | ALA | 1176 | 13.030 | -14.914 | 67.769 |
| ATOM | 3936 N | GLN | 1177 | 10.964 | -14.129 | 68.076 |
| ATOM | 3937 CA | GLN | 1177 | 10.406 | -15.219 | 67.339 |
| ATOM | 3938 CB | GLN | 1177 | 8.928 | -14.975 | 67.154 |
| ATOM | 3939 CG | GLN | 1177 | 8.195 | -15.045 | 68.463 |
| ATOM | 3940 CD | GLN | 1177 | 8.703 | -16.182 | 69.310 |
| ATOM | 3941 OE1 | GLN | 1177 | 8.703 | -17.336 | 68.882 |
| ATOM | 3942 NE2 | GLN | 1177 | 9.208 | -15.859 | 70.491 |
| ATOM | 3943 C | GLN | 1177 | 11.137 | -15.401 | 66.027 |
| ATOM | 3944 O | GLN | 1177 | 11.512 | -16.523 | 65.679 |
| ATOM | 3945 N | GLY | 1178 | 11.456 | -14.274 | 65.389 |
| ATOM | 3946 CA | GLY | 1178 | 12.161 | -14.289 | 64.129 |
| ATOM | 3947 C | GLY | 1178 | 13.474 | -15.019 | 64.261 |
| ATOM | 3948 O | GLY | 1178 | 13.958 | -15.632 | 63.316 |
| ATOM | 3949 N | ILE | 1179 | 14.073 | -14.943 | 65.433 |
| ATOM | 3950 CA | ILE | 1179 | 15.319 | -15.644 | 65.640 |
| ATOM | 3951 CB | ILE | 1179 | 16.132 | -15.073 | 66.792 |
| ATOM | 3952 CG2 | ILE | 1179 | 17.541 | -15.597 | 66.711 |
| ATOM | 3953 CG1 | ILE | 1179 | 16.130 | -13.545 | 66.750 |
| ATOM | 3954 CD1 | ILE | 1179 | 16.937 | -12.886 | 67.857 |
| ATOM | 3955 C | ILE | 1179 | 15.053 | -17.112 | 65.927 |
| ATOM | 3956 O | ILE | 1179 | 15.607 | -17.980 | 65.275 |
| ATOM | 3957 N | PHE | 1180 | 14.154 | -17.400 | 66.853 |
| ATOM | 3958 CA | PHE | 1180 | 13.873 | -18.782 | 67.201 |
| ATOM | 3959 CB | PHE | 1180 | 12.770 | -18.861 | 68.229 |
| ATOM | 3960 CG | PHE | 1180 | 13.181 | -18.337 | 69.534 |
| ATOM | 3961 CD1 | PHE | 1180 | 12.331 | -17.551 | 70.285 |
| ATOM | 3962 CD2 | PHE | 1180 | 14.467 | -18.555 | 69.982 |
| ATOM | 3963 CE1 | PHE | 1180 | 12.763 | -16.974 | 71.474 |
| ATOM | 3964 CE2 | PHE | 1180 | 14.911 | -17.992 | 71.159 |
| ATOM | 3965 CZ | PHE | 1180 | 14.061 | -17.197 | 71.910 |
| ATOM | 3966 C | PHE | 1180 | 13.547 | -19.670 | 66.042 |
| ATOM | 3967 O | PHE | 1180 | 14.037 | -20.791 | 65.944 |
| ATOM | 3968 N | VAL | 1181 | 12.696 | -19.181 | 65.170 |
| ATOM | 3969 CA | VAL | 1181 | 12.319 | -19.953 | 64.022 |
| ATOM | 3970 CB | VAL | 1181 | 11.224 | -19.239 | 63.282 |
| ATOM | 3971 CG1 | VAL | 1181 | 9.951 | -19.318 | 64.065 |
| ATOM | 3972 CG2 | VAL | 1181 | 11.600 | -17.774 | 63.077 |
| ATOM | 3973 C | VAL | 1181 | 13.517 | -20.175 | 63.099 |
| ATOM | 3974 O | VAL | 1181 | 13.543 | -21.133 | 62.307 |
| ATOM | 3975 N | ASN | 1182 | 14.503 | -19.287 | 63.201 |
| ATOM | 3976 CA | ASN | 1182 | 15.704 | -19.372 | 62.376 |
| ATOM | 3977 CB | ASN | 1182 | 16.078 | -17.994 | 61.772 |
| ATOM | 3978 CG | ASN | 1182 | 15.217 | -17.604 | 60.562 |
| ATOM | 3979 OD1 | ASN | 1182 | 15.674 | -17.597 | 59.420 |
| ATOM | 3980 ND2 | ASN | 1182 | 13.986 | -17.238 | 60.825 |
| ATOM | 3981 C | ASN | 1182 | 16.882 | -19.921 | 63.166 |
| ATOM | 3982 O | ASN | 1182 | 18.025 | -19.608 | 62.869 |

FIGURE 1FFFF

| Atom | | Residue AA | No. | X | Y | Z |
|---|---|---|---|---|---|---|
| ATOM | 3983 N | TYR | 1183 | 16.616 | -20.743 | 64.169 |
| ATOM | 3984 CA | TYR | 1183 | 17.706 | -21.301 | 64.961 |
| ATOM | 3985 CB | TYR | 1183 | 17.205 | -21.910 | 66.271 |
| ATOM | 3986 CG | TYR | 1183 | 18.199 | -22.845 | 66.941 |
| ATOM | 3987 CD1 | TYR | 1183 | 17.882 | -24.193 | 67.165 |
| ATOM | 3988 CE1 | TYR | 1183 | 18.797 | -25.077 | 67.776 |
| ATOM | 3989 CD2 | TYR | 1183 | 19.453 | -22.395 | 67.346 |
| ATOM | 3990 CE2 | TYR | 1183 | 20.377 | -23.271 | 67.962 |
| ATOM | 3991 CZ | TYR | 1183 | 20.038 | -24.609 | 68.166 |
| ATOM | 3992 OH | TYR | 1183 | 20.945 | -25.491 | 68.707 |
| ATOM | 3993 C | TYR | 1183 | 18.432 | -22.363 | 64.184 |
| ATOM | 3994 O | TYR | 1183 | 19.611 | -22.226 | 63.894 |
| ATOM | 3995 N | ALA | 1184 | 17.713 | -23.423 | 63.836 |
| ATOM | 3996 CA | ALA | 1184 | 18.306 | -24.530 | 63.126 |
| ATOM | 3997 CB | ALA | 1184 | 17.245 | -25.534 | 62.768 |
| ATOM | 3998 C | ALA | 1184 | 19.079 | -24.057 | 61.895 |
| ATOM | 3999 O | ALA | 1184 | 20.212 | -24.485 | 61.683 |
| ATOM | 4000 N | ASN | 1185 | 18.518 | -23.098 | 61.157 |
| ATOM | 4001 CA | ASN | 1185 | 19.145 | -22.567 | 59.939 |
| ATOM | 4002 CB | ASN | 1185 | 18.297 | -21.446 | 59.301 |
| ATOM | 4003 CG | ASN | 1185 | 16.901 | -21.914 | 58.813 |
| ATOM | 4004 OD1 | ASN | 1185 | 16.639 | -23.109 | 58.649 |
| ATOM | 4005 ND2 | ASN | 1185 | 16.011 | -20.949 | 58.567 |
| ATOM | 4006 C | ASN | 1185 | 20.538 | -22.029 | 60.207 |
| ATOM | 4007 O | ASN | 1185 | 21.501 | -22.569 | 59.700 |
| ATOM | 4008 N | VAL | 1186 | 20.644 | -20.974 | 61.007 |
| ATOM | 4009 CA | VAL | 1186 | 21.932 | -20.354 | 61.320 |
| ATOM | 4010 CB | VAL | 1186 | 21.816 | -19.310 | 62.422 |
| ATOM | 4011 CG1 | VAL | 1186 | 23.187 | -18.763 | 62.765 |
| ATOM | 4012 CG2 | VAL | 1186 | 20.872 | -18.211 | 62.012 |
| ATOM | 4013 C | VAL | 1186 | 22.884 | -21.401 | 61.815 |
| ATOM | 4014 O | VAL | 1186 | 24.085 | -21.338 | 61.574 |
| ATOM | 4015 N | GLN | 1187 | 22.325 | -22.352 | 62.548 |
| ATOM | 4016 CA | GLN | 1187 | 23.084 | -23.451 | 63.102 |
| ATOM | 4017 CB | GLN | 1187 | 22.122 | -24.456 | 63.750 |
| ATOM | 4018 CG | GLN | 1187 | 22.556 | -25.900 | 63.755 |
| ATOM | 4019 CD | GLN | 1187 | 23.909 | -26.099 | 64.387 |
| ATOM | 4020 OE1 | GLN | 1187 | 24.434 | -25.199 | 65.023 |
| ATOM | 4021 NE2 | GLN | 1187 | 24.496 | -27.273 | 64.191 |
| ATOM | 4022 C | GLN | 1187 | 23.894 | -24.061 | 61.975 |
| ATOM | 4023 O | GLN | 1187 | 25.101 | -23.865 | 61.896 |
| ATOM | 4024 N | ALA | 1188 | 23.194 | -24.679 | 61.034 |
| ATOM | 4025 CA | ALA | 1188 | 23.802 | -25.341 | 59.870 |
| ATOM | 4026 CB | ALA | 1188 | 22.730 | -26.114 | 59.087 |
| ATOM | 4027 C | ALA | 1188 | 24.585 | -24.423 | 58.919 |
| ATOM | 4028 O | ALA | 1188 | 25.802 | -24.565 | 58.789 |
| ATOM | 4029 N | SER | 1189 | 23.886 | -23.495 | 58.260 |
| ATOM | 4030 CA | SER | 1189 | 24.493 | -22.550 | 57.330 |

FIGURE 1GGGG

| Atom | | Residue | | X | Y | Z |
|---|---|---|---|---|---|---|
| | | AA | No. | | | |
| ATOM | 4031 CB | SER | 1189 | 23.458 | -21.520 | 56.913 |
| ATOM | 4032 OG | SER | 1189 | 23.027 | -20.781 | 58.032 |
| ATOM | 4033 C | SER | 1189 | 25.737 | -21.842 | 57.900 |
| ATOM | 4034 O | SER | 1189 | 26.569 | -21.320 | 57.150 |
| ATOM | 4035 N | MET | 1190 | 25.860 | -21.832 | 59.225 |
| ATOM | 4036 CA | MET | 1190 | 27.008 | -21.223 | 59.896 |
| ATOM | 4037 CB | MET | 1190 | 26.535 | -20.155 | 60.865 |
| ATOM | 4038 CG | MET | 1190 | 25.803 | -19.044 | 60.174 |
| ATOM | 4039 SD | MET | 1190 | 26.726 | -18.377 | 58.805 |
| ATOM | 4040 CE | MET | 1190 | 28.426 | -18.033 | 59.554 |
| ATOM | 4041 C | MET | 1190 | 27.937 | -22.220 | 60.610 |
| ATOM | 4042 O | MET | 1190 | 29.073 | -21.868 | 60.992 |
| ATOM | 4043 N | ALA | 1191 | 27.443 | -23.452 | 60.769 |
| ATOM | 4044 CA | ALA | 1191 | 28.164 | -24.563 | 61.410 |
| ATOM | 4045 CB | ALA | 1191 | 29.403 | -24.925 | 60.593 |
| ATOM | 4046 C | ALA | 1191 | 28.545 | -24.284 | 62.865 |
| ATOM | 4047 O | ALA | 1191 | 29.715 | -24.426 | 63.252 |
| ATOM | 4048 N | LYS | 1192 | 27.539 | -23.992 | 63.688 |
| ATOM | 4049 CA | LYS | 1192 | 27.763 | -23.623 | 65.083 |
| ATOM | 4050 CB | LYS | 1192 | 26.681 | -22.628 | 65.537 |
| ATOM | 4051 CG | LYS | 1192 | 26.612 | -21.323 | 64.733 |
| ATOM | 4052 CD | LYS | 1192 | 27.584 | -20.250 | 65.216 |
| ATOM | 4053 CE | LYS | 1192 | 29.035 | -20.688 | 65.158 |
| ATOM | 4054 NZ | LYS | 1192 | 29.984 | -19.582 | 65.414 |
| ATOM | 4055 C | LYS | 1192 | 27.890 | -24.721 | 66.120 |
| ATOM | 4056 O | LYS | 1192 | 27.266 | -25.774 | 66.016 |
| ATOM | 4057 N | LYS | 1193 | 28.749 | -24.473 | 67.101 |
| ATOM | 4058 CA | LYS | 1193 | 28.936 | -25.380 | 68.215 |
| ATOM | 4059 CB | LYS | 1193 | 30.409 | -25.480 | 68.588 |
| ATOM | 4060 CG | LYS | 1193 | 31.285 | -26.175 | 67.531 |
| ATOM | 4061 CD | LYS | 1193 | 30.673 | -27.520 | 67.091 |
| ATOM | 4062 CE | LYS | 1193 | 31.131 | -27.933 | 65.645 |
| ATOM | 4063 NZ | LYS | 1193 | 30.128 | -28.782 | 64.836 |
| ATOM | 4064 C | LYS | 1193 | 28.152 | -24.609 | 69.254 |
| ATOM | 4065 O | LYS | 1193 | 28.229 | -23.375 | 69.265 |
| ATOM | 4066 N | LEU | 1194 | 27.489 | -25.314 | 70.174 |
| ATOM | 4067 CA | LEU | 1194 | 26.588 | -24.665 | 71.140 |
| ATOM | 4068 CB | LEU | 1194 | 26.037 | -25.600 | 72.202 |
| ATOM | 4069 CG | LEU | 1194 | 24.515 | -25.706 | 71.969 |
| ATOM | 4070 CD1 | LEU | 1194 | 23.899 | -26.628 | 72.981 |
| ATOM | 4071 CD2 | LEU | 1194 | 23.811 | -24.363 | 72.009 |
| ATOM | 4072 C | LEU | 1194 | 26.812 | -23.277 | 71.691 |
| ATOM | 4073 O | LEU | 1194 | 25.844 | -22.508 | 71.815 |
| ATOM | 4074 N | PRO | 1195 | 28.022 | -22.964 | 72.152 |
| ATOM | 4075 CD | PRO | 1195 | 29.222 | -23.770 | 72.404 |
| ATOM | 4076 CA | PRO | 1195 | 28.160 | -21.584 | 72.643 |
| ATOM | 4077 CB | PRO | 1195 | 29.536 | -21.602 | 73.279 |
| ATOM | 4078 CG | PRO | 1195 | 30.261 | -22.708 | 72.483 |

FIGURE 1HHHH

| Atom | | Residue AA | No. | X | Y | Z |
|---|---|---|---|---|---|---|
| ATOM | 4079 C | PRO | 1195 | 28.089 | -20.626 | 71.408 |
| ATOM | 4080 O | PRO | 1195 | 29.071 | -20.459 | 70.673 |
| ATOM | 4081 N | PHE | 1196 | 26.903 | -20.086 | 71.129 |
| ATOM | 4082 CA | PHE | 1196 | 26.725 | -19.200 | 69.993 |
| ATOM | 4083 CB | PHE | 1196 | 26.767 | -20.006 | 68.693 |
| ATOM | 4084 CG | PHE | 1196 | 25.436 | -20.596 | 68.280 |
| ATOM | 4085 CD1 | PHE | 1196 | 24.463 | -19.806 | 67.648 |
| ATOM | 4086 CD2 | PHE | 1196 | 25.157 | -21.936 | 68.489 |
| ATOM | 4087 CE1 | PHE | 1196 | 23.249 | -20.344 | 67.239 |
| ATOM | 4088 CE2 | PHE | 1196 | 23.940 | -22.480 | 68.082 |
| ATOM | 4089 CZ | PHE | 1196 | 22.992 | -21.679 | 67.457 |
| ATOM | 4090 C | PHE | 1196 | 25.423 | -18.417 | 70.116 |
| ATOM | 4091 O | PHE | 1196 | 24.423 | -18.956 | 70.537 |
| ATOM | 4092 N | GLY | 1197 | 25.428 | -17.157 | 69.707 |
| ATOM | 4093 CA | GLY | 1197 | 24.235 | -16.342 | 69.811 |
| ATOM | 4094 C | GLY | 1197 | 23.731 | -15.921 | 68.461 |
| ATOM | 4095 O | GLY | 1197 | 24.375 | -16.231 | 67.484 |
| ATOM | 4096 N | ILE | 1198 | 22.622 | -15.188 | 68.390 |
| ATOM | 4097 CA | ILE | 1198 | 22.058 | -14.756 | 67.102 |
| ATOM | 4098 CB | ILE | 1198 | 20.995 | -15.759 | 66.586 |
| ATOM | 4099 CG2 | ILE | 1198 | 20.519 | -15.367 | 65.262 |
| ATOM | 4100 CG1 | ILE | 1198 | 21.565 | -17.153 | 66.440 |
| ATOM | 4101 CD1 | ILE | 1198 | 20.552 | -18.129 | 65.957 |
| ATOM | 4102 C | ILE | 1198 | 21.367 | -13.399 | 67.211 |
| ATOM | 4103 O | ILE | 1198 | 20.154 | -13.343 | 67.332 |
| ATOM | 4104 N | GLY | 1199 | 22.110 | -12.307 | 67.103 |
| ATOM | 4105 CA | GLY | 1199 | 21.501 | -10.992 | 67.226 |
| ATOM | 4106 C | GLY | 1199 | 20.701 | -10.518 | 66.035 |
| ATOM | 4107 O | GLY | 1199 | 20.740 | -11.157 | 65.012 |
| ATOM | 4108 N | GLN | 1200 | 19.949 | -9.431 | 66.184 |
| ATOM | 4109 CA | GLN | 1200 | 19.189 | -8.876 | 65.088 |
| ATOM | 4110 CB | GLN | 1200 | 18.276 | -9.933 | 64.478 |
| ATOM | 4111 CG | GLN | 1200 | 17.126 | -10.369 | 65.314 |
| ATOM | 4112 CD | GLN | 1200 | 15.802 | -10.407 | 64.538 |
| ATOM | 4113 OE1 | GLN | 1200 | 14.986 | -11.311 | 64.747 |
| ATOM | 4114 NE2 | GLN | 1200 | 15.563 | -9.405 | 63.678 |
| ATOM | 4115 C | GLN | 1200 | 18.384 | -7.633 | 65.422 |
| ATOM | 4116 O | GLN | 1200 | 17.424 | -7.735 | 66.137 |
| ATOM | 4117 N | ILE | 1201 | 18.735 | -6.470 | 64.872 |
| ATOM | 4118 CA | ILE | 1201 | 17.985 | -5.237 | 65.144 |
| ATOM | 4119 CB | ILE | 1201 | 18.726 | -4.058 | 64.682 |
| ATOM | 4120 CG2 | ILE | 1201 | 17.903 | -2.825 | 64.848 |
| ATOM | 4121 CG1 | ILE | 1201 | 20.003 | -3.975 | 65.473 |
| ATOM | 4122 CD1 | ILE | 1201 | 20.883 | -2.895 | 65.035 |
| ATOM | 4123 C | ILE | 1201 | 16.701 | -5.258 | 64.393 |
| ATOM | 4124 O | ILE | 1201 | 16.646 | -5.855 | 63.342 |
| ATOM | 4125 N | GLY | 1202 | 15.671 | -4.584 | 64.874 |
| ATOM | 4126 CA | GLY | 1202 | 14.442 | -4.656 | 64.122 |

FIGURE IIIII

| Atom | | Residue AA No. | X | Y | Z |
|---|---|---|---|---|---|
| ATOM | 4127 C | GLY 1202 | 13.217 | -3.901 | 64.558 |
| ATOM | 4128 O | GLY 1202 | 13.220 | -3.207 | 65.561 |
| ATOM | 4129 N | LYS 1203 | 12.164 | -4.039 | 63.764 |
| ATOM | 4130 CA | LYS 1203 | 10.918 | -3.369 | 64.036 |
| ATOM | 4131 CB | LYS 1203 | 10.307 | -2.842 | 62.727 |
| ATOM | 4132 CG | LYS 1203 | 9.913 | -1.349 | 62.736 |
| ATOM | 4133 CD | LYS 1203 | 11.136 | -0.448 | 62.588 |
| ATOM | 4134 CE | LYS 1203 | 10.899 | 0.968 | 63.099 |
| ATOM | 4135 NZ | LYS 1203 | 9.769 | 1.672 | 62.496 |
| ATOM | 4136 C | LYS 1203 | 9.967 | -4.339 | 64.718 |
| ATOM | 4137 O | LYS 1203 | 9.875 | -5.497 | 64.332 |
| ATOM | 4138 N | SER 1204 | 9.349 | -3.876 | 65.796 |
| ATOM | 4139 CA | SER 1204 | 8.371 | -4.644 | 66.556 |
| ATOM | 4140 CB | SER 1204 | 8.928 | -5.085 | 67.931 |
| ATOM | 4141 OG | SER 1204 | 9.731 | -6.261 | 67.875 |
| ATOM | 4142 C | SER 1204 | 7.243 | -3.629 | 66.718 |
| ATOM | 4143 O | SER 1204 | 7.507 | -2.432 | 66.707 |
| ATOM | 4144 N | PHE 1205 | 5.996 | -4.087 | 66.811 |
| ATOM | 4145 CA | PHE 1205 | 4.837 | -3.183 | 66.944 |
| ATOM | 4146 CB | PHE 1205 | 4.065 | -3.055 | 65.616 |
| ATOM | 4147 CG | PHE 1205 | 4.918 | -2.709 | 64.424 |
| ATOM | 4148 CD1 | PHE 1205 | 5.640 | -3.688 | 63.765 |
| ATOM | 4149 CD2 | PHE 1205 | 4.959 | -1.416 | 63.939 |
| ATOM | 4150 CE1 | PHE 1205 | 6.384 | -3.378 | 62.644 |
| ATOM | 4151 CE2 | PHE 1205 | 5.703 | -1.105 | 62.818 |
| ATOM | 4152 CZ | PHE 1205 | 6.418 | -2.085 | 62.167 |
| ATOM | 4153 C | PHE 1205 | 3.835 | -3.634 | 68.008 |
| ATOM | 4154 O | PHE 1205 | 3.332 | -4.767 | 67.962 |
| ATOM | 4155 N | ARG 1206 | 3.448 | -2.699 | 68.871 |
| ATOM | 4156 CA | ARG 1206 | 2.517 | -2.980 | 69.957 |
| ATOM | 4157 CB | ARG 1206 | 3.209 | -2.757 | 71.302 |
| ATOM | 4158 CG | ARG 1206 | 3.507 | -4.022 | 72.094 |
| ATOM | 4159 CD | ARG 1206 | 4.737 | -4.811 | 71.605 |
| ATOM | 4160 NE | ARG 1206 | 5.814 | -4.900 | 72.597 |
| ATOM | 4161 CZ | ARG 1206 | 5.668 | -5.215 | 73.893 |
| ATOM | 4162 NH1 | ARG 1206 | 4.470 | -5.479 | 74.415 |
| ATOM | 4163 NH2 | ARG 1206 | 6.744 | -5.301 | 74.683 |
| ATOM | 4164 C | ARG 1206 | 1.299 | -2.083 | 69.895 |
| ATOM | 4165 O | ARG 1206 | 1.428 | -0.858 | 69.903 |
| ATOM | 4166 N | ASN 1207 | 0.117 | -2.689 | 69.851 |
| ATOM | 4167 CA | ASN 1207 | -1.134 | -1.935 | 69.817 |
| ATOM | 4168 CB | ASN 1207 | -2.274 | -2.827 | 69.309 |
| ATOM | 4169 CG | ASN 1207 | -3.524 | -2.030 | 68.889 |
| ATOM | 4170 OD1 | ASN 1207 | -3.574 | -0.792 | 69.000 |
| ATOM | 4171 ND2 | ASN 1207 | -4.533 | -2.746 | 68.378 |
| ATOM | 4172 C | ASN 1207 | -1.383 | -1.524 | 71.265 |
| ATOM | 4173 O | ASN 1207 | -2.094 | -2.203 | 71.999 |
| ATOM | 4174 N | GLU 1208 | -0.759 | -0.420 | 71.668 |

FIGURE 1JJJJ

|  | Residue | | | | |
|---|---|---|---|---|---|
| Atom | AA | No. | X | Y | Z |
| ATOM 4175 CA | GLU | 1208 | -0.827 | 0.108 | 73.043 |
| ATOM 4176 CB | GLU | 1208 | 0.235 | 1.203 | 73.232 |
| ATOM 4177 CG | GLU | 1208 | 1.028 | 1.022 | 74.489 |
| ATOM 4178 CD | GLU | 1208 | 1.462 | -0.422 | 74.712 |
| ATOM 4179 OE1 | GLU | 1208 | 2.668 | -0.695 | 74.521 |
| ATOM 4180 OE2 | GLU | 1208 | 0.615 | -1.278 | 75.081 |
| ATOM 4181 C | GLU | 1208 | -2.179 | 0.577 | 73.606 |
| ATOM 4182 O | GLU | 1208 | -3.248 | 0.181 | 73.100 |
| ATOM 4183 N | ILE | 1209 | -2.127 | 1.365 | 74.694 |
| ATOM 4184 CA | ILE | 1209 | -3.344 | 1.905 | 75.353 |
| ATOM 4185 CB | ILE | 1209 | -3.654 | 1.246 | 76.766 |
| ATOM 4186 CG2 | ILE | 1209 | -4.326 | -0.143 | 76.583 |
| ATOM 4187 CG1 | ILE | 1209 | -2.407 | 1.220 | 77.681 |
| ATOM 4188 CD1 | ILE | 1209 | -1.350 | 0.154 | 77.344 |
| ATOM 4189 C | ILE | 1209 | -3.264 | 3.421 | 75.519 |
| ATOM 4190 O | ILE | 1209 | -3.901 | 4.185 | 74.792 |
| ATOM 4191 N | THR | 1210 | -2.421 | 3.848 | 76.442 |
| ATOM 4192 CA | THR | 1210 | -2.231 | 5.257 | 76.707 |
| ATOM 4193 CB | THR | 1210 | -2.756 | 5.581 | 78.148 |
| ATOM 4194 OG1 | THR | 1210 | -2.551 | 6.973 | 78.449 |
| ATOM 4195 CG2 | THR | 1210 | -2.098 | 4.642 | 79.224 |
| ATOM 4196 C | THR | 1210 | -0.732 | 5.560 | 76.528 |
| ATOM 4197 O | THR | 1210 | -0.041 | 5.960 | 77.478 |
| ATOM 4198 N | PRO | 1211 | -0.202 | 5.327 | 75.302 |
| ATOM 4199 CD | PRO | 1211 | -0.867 | 4.892 | 74.046 |
| ATOM 4200 CA | PRO | 1211 | 1.225 | 5.586 | 75.064 |
| ATOM 4201 CB | PRO | 1211 | 1.280 | 5.777 | 73.547 |
| ATOM 4202 CG | PRO | 1211 | 0.315 | 4.686 | 73.085 |
| ATOM 4203 C | PRO | 1211 | 1.887 | 6.704 | 75.899 |
| ATOM 4204 O | PRO | 1211 | 1.574 | 7.913 | 75.790 |
| ATOM 4205 N | GLY | 1212 | 2.686 | 6.210 | 76.848 |
| ATOM 4206 CA | GLY | 1212 | 3.433 | 7.036 | 77.770 |
| ATOM 4207 C | GLY | 1212 | 4.434 | 7.918 | 77.067 |
| ATOM 4208 O | GLY | 1212 | 5.434 | 7.434 | 76.502 |
| ATOM 4209 N | ASN | 1213 | 4.100 | 9.210 | 77.086 |
| ATOM 4210 CA | ASN | 1213 | 4.877 | 10.302 | 76.486 |
| ATOM 4211 CB | ASN | 1213 | 4.906 | 11.527 | 77.430 |
| ATOM 4212 CG | ASN | 1213 | 5.157 | 11.143 | 78.900 |
| ATOM 4213 OD1 | ASN | 1213 | 4.521 | 10.211 | 79.430 |
| ATOM 4214 ND2 | ASN | 1213 | 6.090 | 11.857 | 79.564 |
| ATOM 4215 C | ASN | 1213 | 6.285 | 9.989 | 75.947 |
| ATOM 4216 O | ASN | 1213 | 7.017 | 9.170 | 76.475 |
| ATOM 4217 N | PHE | 1214 | 6.617 | 10.640 | 74.846 |
| ATOM 4218 CA | PHE | 1214 | 7.895 | 10.468 | 74.175 |
| ATOM 4219 CB | PHE | 1214 | 9.014 | 11.227 | 74.885 |
| ATOM 4220 CG | PHE | 1214 | 9.923 | 11.970 | 73.950 |
| ATOM 4221 CD1 | PHE | 1214 | 11.224 | 12.238 | 74.309 |
| ATOM 4222 CD2 | `PHE | 1214 | 9.456 | 12.447 | 72.744 |

FIGURE 1KKKK

| Atom | | Residue AA | No. | X | Y | Z |
|---|---|---|---|---|---|---|
| ATOM | 4223 CE1 | PHE | 1214 | 12.044 | 12.981 | 73.481 |
| ATOM | 4224 CE2 | PHE | 1214 | 10.258 | 13.179 | 71.920 |
| ATOM | 4225 CZ | PHE | 1214 | 11.558 | 13.453 | 72.286 |
| ATOM | 4226 C | PHE | 1214 | 8.324 | 9.032 | 73.902 |
| ATOM | 4227 O | PHE | 1214 | 7.605 | 8.066 | 74.213 |
| ATOM | 4228 N | ILE | 1215 | 9.541 | 8.930 | 73.367 |
| ATOM | 4229 CA | ILE | 1215 | 10.153 | 7.679 | 72.973 |
| ATOM | 4230 CB | ILE | 1215 | 11.641 | 7.875 | 72.650 |
| ATOM | 4231 CG2 | ILE | 1215 | 12.090 | 6.837 | 71.672 |
| ATOM | 4232 CG1 | ILE | 1215 | 11.892 | 9.206 | 71.960 |
| ATOM | 4233 CD1 | ILE | 1215 | 13.368 | 9.401 | 71.583 |
| ATOM | 4234 C | ILE | 1215 | 10.011 | 6.518 | 73.960 |
| ATOM | 4235 O | ILE | 1215 | 10.216 | 5.356 | 73.575 |
| ATOM | 4236 N | PHE | 1216 | 9.681 | 6.792 | 75.223 |
| ATOM | 4237 CA | PHE | 1216 | 9.542 | 5.670 | 76.152 |
| ATOM | 4238 CB | PHE | 1216 | 9.565 | 6.047 | 77.670 |
| ATOM | 4239 CG | PHE | 1216 | 8.908 | 7.404 | 78.037 |
| ATOM | 4240 CD1 | PHE | 1216 | 7.656 | 7.452 | 78.704 |
| ATOM | 4241 CD2 | PHE | 1216 | 9.619 | 8.629 | 77.873 |
| ATOM | 4242 CE1 | PHE | 1216 | 7.146 | 8.678 | 79.210 |
| ATOM | 4243 CE2 | PHE | 1216 | 9.103 | 9.874 | 78.385 |
| ATOM | 4244 CZ | PHE | 1216 | 7.883 | 9.888 | 79.048 |
| ATOM | 4245 C | PHE | 1216 | 8.396 | 4.726 | 75.774 |
| ATOM | 4246 O | PHE | 1216 | 8.603 | 3.505 | 75.729 |
| ATOM | 4247 N | ARG | 1217 | 7.218 | 5.258 | 75.450 |
| ATOM | 4248 CA | ARG | 1217 | 6.148 | 4.360 | 75.066 |
| ATOM | 4249 CB | ARG | 1217 | 5.091 | 4.224 | 76.162 |
| ATOM | 4250 CG | ARG | 1217 | 4.708 | 2.745 | 76.487 |
| ATOM | 4251 CD | ARG | 1217 | 3.482 | 2.610 | 77.429 |
| ATOM | 4252 NE | ARG | 1217 | 2.210 | 2.715 | 76.704 |
| ATOM | 4253 CZ | ARG | 1217 | 0.998 | 2.658 | 77.261 |
| ATOM | 4254 NH1 | ARG | 1217 | 0.842 | 2.502 | 78.567 |
| ATOM | 4255 NH2 | ARG | 1217 | -0.074 | 2.727 | 76.491 |
| ATOM | 4256 C | ARG | 1217 | 5.527 | 4.776 | 73.756 |
| ATOM | 4257 O | ARG | 1217 | 4.594 | 5.577 | 73.731 |
| ATOM | 4258 N | THR | 1218 | 6.050 | 4.187 | 72.675 |
| ATOM | 4259 CA | THR | 1218 | 5.632 | 4.427 | 71.281 |
| ATOM | 4260 CB | THR | 1218 | 6.864 | 4.725 | 70.364 |
| ATOM | 4261 OG1 | THR | 1218 | 7.969 | 3.894 | 70.756 |
| ATOM | 4262 CG2 | THR | 1218 | 7.280 | 6.204 | 70.428 |
| ATOM | 4263 C | THR | 1218 | 4.930 | 3.187 | 70.744 |
| ATOM | 4264 O | THR | 1218 | 5.350 | 2.063 | 71.026 |
| ATOM | 4265 N | ARG | 1219 | 3.886 | 3.398 | 69.382 |
| ATOM | 4267 CB | ARG | 1219 | 1.920 | 2.842 | 68.594 |
| ATOM | 4268 CG | ARG | 1219 | 1.315 | 4.067 | 69.213 |
| ATOM | 4269 CD | ARG | 1219 | -0.160 | 4.181 | 68.931 |
| ATOM | 4270 NE | ARG | 1219 | -0.941 | 3.021 | 69.388 |

FIGURE 1LLLL

| Atom | | Residue AA No. | X | Y | Z |
|---|---|---|---|---|---|
| ATOM | 4271 CZ | ARG 1219 | -1.764 | 2.979 | 70.450 |
| ATOM | 4272 NH1 | ARG 1219 | -1.959 | 4.030 | 71.255 |
| ATOM | 4273 NH2 | ARG 1219 | -2.471 | 1.873 | 70.661 |
| ATOM | 4274 C | ARG 1219 | 3.981 | 1.458 | 68.459 |
| ATOM | 4275 O | ARG 1219 | 3.657 | 0.305 | 68.160 |
| ATOM | 4276 N | GLU 1220 | 5.112 | 2.023 | 68.051 |
| ATOM | 4277 CA | GLU 1220 | 6.021 | 1.359 | 67.131 |
| ATOM | 4278 CB | GLU 1220 | 5.799 | 1.965 | 65.744 |
| ATOM | 4279 CG | GLU 1220 | 6.755 | 1.516 | 64.672 |
| ATOM | 4280 CD | GLU 1220 | 6.724 | 2.425 | 63.482 |
| ATOM | 4281 OE1 | GLU 1220 | 7.798 | 2.952 | 63.118 |
| ATOM | 4282 OE2 | GLU 1220 | 5.622 | 2.622 | 62.936 |
| ATOM | 4283 C | GLU 1220 | 7.433 | 1.627 | 67.614 |
| ATOM | 4284 O | GLU 1220 | 7.725 | 2.747 | 68.008 |
| ATOM | 4285 N | PHE 1221 | 8.321 | 0.638 | 67.532 |
| ATOM | 4286 CA | PHE 1221 | 9.693 | 0.800 | 68.026 |
| ATOM | 4287 CB | PHE 1221 | 9.702 | 0.622 | 69.548 |
| ATOM | 4288 CG | PHE 1221 | 9.070 | -0.683 | 70.007 |
| ATOM | 4289 CD1 | PHE 1221 | 9.829 | -1.845 | 70.112 |
| ATOM | 4290 CD2 | PHE 1221 | 7.697 | -0.754 | 70.269 |
| ATOM | 4291 CE1 | PHE 1221 | 9.235 | -3.048 | 70.459 |
| ATOM | 4292 CE2 | PHE 1221 | 7.099 | -1.955 | 70.618 |
| ATOM | 4293 CZ | PHE 1221 | 7.870 | -3.106 | 70.710 |
| ATOM | 4294 C | PHE 1221 | 10.665 | -0.223 | 67.471 |
| ATOM | 4295 O | PHE 1221 | 10.264 | -1.255 | 66.949 |
| ATOM | 4296 N | GLU 1222 | 11.943 | 0.008 | 67.735 |
| ATOM | 4297 CA | GLU 1222 | 13.005 | -0.883 | 67.305 |
| ATOM | 4298 CB | GLU 1222 | 14.028 | -0.101 | 66.526 |
| ATOM | 4299 CG | GLU 1222 | 13.741 | 0.045 | 65.087 |
| ATOM | 4300 CD | GLU 1222 | 14.925 | 0.635 | 64.362 |
| ATOM | 4301 OE1 | GLU 1222 | 15.828 | -0.116 | 63.924 |
| ATOM | 4302 OE2 | GLU 1222 | 14.966 | 1.861 | 64.248 |
| ATOM | 4303 C | GLU 1222 | 13.691 | -1.533 | 68.513 |
| ATOM | 4304 O | GLU 1222 | 14.141 | -0.830 | 69.412 |
| ATOM | 4305 N | GLN 1223 | 13.795 | -2.862 | 68.502 |
| ATOM | 4306 CA | GLN 1223 | 14.407 | -3.647 | 69.567 |
| ATOM | 4307 CB | GLN 1223 | 13.912 | -5.070 | 69.502 |
| ATOM | 4308 CG | GLN 1223 | 12.436 | -5.166 | 69.348 |
| ATOM | 4309 CD | GLN 1223 | 11.742 | -5.556 | 70.621 |
| ATOM | 4310 OE1 | GLN 1223 | 12.170 | -5.170 | 71.700 |
| ATOM | 4311 NE2 | GLN 1223 | 10.646 | -6.320 | 70.504 |
| ATOM | 4312 C | GLN 1223 | 15.905 | -3.638 | 69.412 |
| ATOM | 4313 O | GLN 1223 | 16.478 | -2.600 | 69.158 |
| ATOM | 4314 N | MET 1224 | 16.539 | -4.786 | 69.595 |
| ATOM | 4315 CA | MET 1224 | 17.984 | -4.903 | 69.471 |
| ATOM | 4316 CB | MET 1224 | 18.671 | -3.718 | 70.101 |
| ATOM | 4317 CG | MET 1224 | 19.667 | -3.108 | 69.226 |
| ATOM | 4318 SD | MET 1224 | 19.537 | -1.389 | 69.461 |

FIGURE 1MMMM

| Atom | | Residue AA No. | X | Y | Z |
|---|---|---|---|---|---|
| ATOM | 4319 CE | MET 1224 | 21.150 | -1.001 | 69.569 |
| ATOM | 4320 C | MET 1224 | 18.396 | -6.122 | 70.239 |
| ATOM | 4321 O | MET 1224 | 19.353 | -6.076 | 70.972 |
| ATOM | 4322 N | GLU 1225 | 17.708 | -7.227 | 70.011 |
| ATOM | 4323 CA | GLU 1225 | 17.916 | -8.479 | 70.724 |
| ATOM | 4324 CB | GLU 1225 | 16.618 | -9.243 | 70.637 |
| ATOM | 4325 CG | GLU 1225 | 15.432 | -8.304 | 70.735 |
| ATOM | 4326 CD | GLU 1225 | 14.132 | -9.016 | 70.913 |
| ATOM | 4327 OE1 | GLU 1225 | 13.980 | -10.092 | 70.310 |
| ATOM | 4328 OE2 | GLU 1225 | 13.262 | -8.508 | 71.648 |
| ATOM | 4329 C | GLU 1225 | 19.058 | -9.379 | 70.322 |
| ATOM | 4330 O | GLU 1225 | 19.657 | -9.185 | 69.293 |
| ATOM | 4331 N | LEU 1226 | 19.360 | -10.365 | 71.148 |
| ATOM | 4332 CA | LEU 1226 | 20.414 | -11.317 | 70.855 |
| ATOM | 4333 CB | LEU 1226 | 21.767 | -10.809 | 71.329 |
| ATOM | 4334 CG | LEU 1226 | 22.959 | -11.780 | 71.360 |
| ATOM | 4335 CD1 | LEU 1226 | 24.240 | -10.999 | 71.262 |
| ATOM | 4336 CD2 | LEU 1226 | 22.991 | -12.622 | 72.597 |
| ATOM | 4337 C | LEU 1226 | 20.065 | -12.505 | 71.659 |
| ATOM | 4338 O | LEU 1226 | 19.815 | -12.359 | 72.818 |
| ATOM | 4339 N | GLU 1227 | 19.993 | -13.673 | 71.057 |
| ATOM | 4340 CA | GLU 1227 | 19.687 | -14.863 | 71.814 |
| ATOM | 4341 CB | GLU 1227 | 18.570 | -15.659 | 71.171 |
| ATOM | 4342 CG | GLU 1227 | 17.357 | -15.790 | 72.050 |
| ATOM | 4343 CD | GLU 1227 | 16.566 | -14.504 | 72.143 |
| ATOM | 4344 OE1 | GLU 1227 | 15.321 | -14.547 | 72.052 |
| ATOM | 4345 OE2 | GLU 1227 | 17.188 | -13.441 | 72.297 |
| ATOM | 4346 C | GLU 1227 | 20.921 | -15.716 | 71.886 |
| ATOM | 4347 O | GLU 1227 | 21.388 | -16.195 | 70.862 |
| ATOM | 4348 N | PHE 1228 | 21.453 | -15.879 | 73.093 |
| ATOM | 4349 CA | PHE 1228 | 22.641 | -16.680 | 73.342 |
| ATOM | 4350 CB | PHE 1228 | 23.432 | -16.084 | 74.501 |
| ATOM | 4351 CG | PHE 1228 | 24.833 | -16.611 | 74.620 |
| ATOM | 4352 CD1 | PHE 1228 | 25.090 | -17.807 | 75.265 |
| ATOM | 4353 CD2 | PHE 1228 | 25.905 | -15.900 | 74.081 |
| ATOM | 4354 CE1 | PHE 1228 | 26.397 | -18.290 | 75.375 |
| ATOM | 4355 CE2 | PHE 1228 | 27.211 | -16.370 | 74.185 |
| ATOM | 4356 CZ | PHE 1228 | 27.455 | -17.567 | 74.834 |
| ATOM | 4357 C | PHE 1228 | 22.228 | -18.099 | 73.680 |
| ATOM | 4358 O | PHE 1228 | 21.475 | -18.308 | 74.599 |
| ATOM | 4359 N | PHE 1229 | 22.672 | -19.062 | 72.890 |
| ATOM | 4360 CA | PHE 1229 | 22.346 | -20.461 | 73.118 |
| ATOM | 4361 CB | PHE 1229 | 22.065 | -21.182 | 71.796 |
| ATOM | 4362 CG | PHE 1229 | 20.811 | -20.696 | 71.148 |
| ATOM | 4363 CD1 | PHE 1229 | 20.776 | -19.443 | 70.554 |
| ATOM | 4364 CD2 | PHE 1229 | 19.630 | -21.377 | 71.324 |
| ATOM | 4365 CE1 | PHE 1229 | 19.599 | -18.877 | 70.177 |
| ATOM | 4366 CE2 | PHE 1229 | 18.450 | -20.809 | 70.943 |

FIGURE 1NNNN

| Atom | | Residue AA | No. | X | Y | Z |
|---|---|---|---|---|---|---|
| ATOM | 4367 CZ | PHE | 1229 | 18.434 | -19.554 | 70.373 |
| ATOM | 4368 C | PHE | 1229 | 23.456 | -21.047 | 73.938 |
| ATOM | 4369 O | PHE | 1229 | 24.637 | -20.906 | 73.625 |
| ATOM | 4370 N | CYS | 1230 | 23.047 | -21.714 | 75.005 |
| ATOM | 4371 CA | CYS | 1230 | 23.953 | -22.243 | 76.014 |
| ATOM | 4372 CB | CYS | 1230 | 23.668 | -21.474 | 77.284 |
| ATOM | 4373 SG | CYS | 1230 | 25.007 | -21.474 | 78.344 |
| ATOM | 4374 C | CYS | 1230 | 23.767 | -23.696 | 76.328 |
| ATOM | 4375 O | CYS | 1230 | 22.632 | -24.171 | 76.410 |
| ATOM | 4376 N | LYS | 1231 | 24.868 | -24.400 | 76.546 |
| ATOM | 4377 CA | LYS | 1231 | 24.762 | -25.807 | 76.893 |
| ATOM | 4378 CB | LYS | 1231 | 26.164 | -26.408 | 77.028 |
| ATOM | 4379 CG | LYS | 1231 | 26.210 | -27.896 | 77.444 |
| ATOM | 4380 CD | LYS | 1231 | 26.078 | -28.111 | 78.978 |
| ATOM | 4381 CE | LYS | 1231 | 27.348 | -27.676 | 79.784 |
| ATOM | 4382 NZ | LYS | 1231 | 27.194 | -27.627 | 81.299 |
| ATOM | 4383 C | LYS | 1231 | 24.015 | -25.790 | 78.236 |
| ATOM | 4384 O | LYS | 1231 | 24.452 | -25.108 | 79.153 |
| ATOM | 4385 N | PRO | 1232 | 22.911 | -26.559 | 78.381 |
| ATOM | 4386 CD | PRO | 1232 | 22.552 | -27.573 | 77.373 |
| ATOM | 4387 CA | PRO | 1232 | 22.025 | -26.704 | 79.546 |
| ATOM | 4388 CB | PRO | 1232 | 21.381 | -28.074 | 79.312 |
| ATOM | 4389 CG | PRO | 1232 | 21.202 | -28.095 | 77.869 |
| ATOM | 4390 C | PRO | 1232 | 22.518 | -26.560 | 81.003 |
| ATOM | 4391 O | PRO | 1232 | 21.707 | -26.682 | 81.926 |
| ATOM | 4392 N | GLY | 1233 | 23.803 | -26.316 | 81.244 |
| ATOM | 4393 CA | GLY | 1233 | 24.254 | -26.173 | 82.616 |
| ATOM | 4394 C | GLY | 1233 | 24.700 | -24.773 | 82.946 |
| ATOM | 4395 O | GLY | 1233 | 24.422 | -24.254 | 84.019 |
| ATOM | 4396 N | GLU | 1234 | 25.247 | -24.099 | 81.959 |
| ATOM | 4397 CA | GLU | 1234 | 25.768 | -22.770 | 82.181 |
| ATOM | 4398 CB | GLU | 1234 | 26.896 | -22.542 | 81.191 |
| ATOM | 4399 CG | GLU | 1234 | 27.840 | -23.721 | 81.151 |
| ATOM | 4400 CD | GLU | 1234 | 28.260 | -24.119 | 79.745 |
| ATOM | 4401 OE1 | GLU | 1234 | 27.681 | -23.601 | 78.754 |
| ATOM | 4402 OE2 | GLU | 1234 | 29.179 | -24.967 | 79.627 |
| ATOM | 4403 C | GLU | 1234 | 24.785 | -21.606 | 82.179 |
| ATOM | 4404 O | GLU | 1234 | 25.184 | -20.450 | 82.291 |
| ATOM | 4405 N | GLU | 1235 | 23.501 | -21.907 | 82.147 |
| ATOM | 4406 CA | GLU | 1235 | 22.492 | -20.859 | 82.099 |
| ATOM | 4407 CB | GLU | 1235 | 21.090 | -21.384 | 82.457 |
| ATOM | 4408 CG | GLU | 1235 | 20.920 | -22.049 | 83.832 |
| ATOM | 4409 CD | GLU | 1235 | 21.558 | -23.455 | 83.958 |
| ATOM | 4410 OE1 | GLU | 1235 | 21.476 | -24.088 | 85.048 |
| ATOM | 4411 OE2 | GLU | 1235 | 22.130 | -23.941 | 82.971 |
| ATOM | 4412 C | GLU | 1235 | 22.835 | -19.637 | 82.905 |
| ATOM | 4413 O | GLU | 1235 | 22.743 | -18.524 | 82.426 |
| ATOM | 4414 N | ILE | 1236 | 23.372 | -19.854 | 84.083 |

FIGURE 10000

| Atom | | Residue | | X | Y | Z |
|---|---|---|---|---|---|---|
| | | AA | No. | | | |
| ATOM | 4415 CA | ILE | 1236 | 23.713 | -18.737 | 84.932 |
| ATOM | 4416 CB | ILE | 1236 | 23.659 | -19.067 | 86.439 |
| ATOM | 4417 CG2 | ILE | 1236 | 22.236 | -19.199 | 86.878 |
| ATOM | 4418 CG1 | ILE | 1236 | 24.526 | -20.288 | 86.786 |
| ATOM | 4419 CD1 | ILE | 1236 | 23.944 | -21.685 | 86.490 |
| ATOM | 4420 C | ILE | 1236 | 25.040 | -18.112 | 84.611 |
| ATOM | 4421 O | ILE | 1236 | 25.187 | -16.909 | 84.742 |
| ATOM | 4422 N | GLU | 1237 | 26.006 | -18.907 | 84.175 |
| ATOM | 4423 CA | GLU | 1237 | 27.324 | -18.349 | 83.855 |
| ATOM | 4424 CB | GLU | 1237 | 28.256 | -19.399 | 83.220 |
| ATOM | 4425 CG | GLU | 1237 | 28.892 | -20.353 | 84.186 |
| ATOM | 4426 CD | GLU | 1237 | 27.918 | -20.756 | 85.277 |
| ATOM | 4427 OE1 | GLU | 1237 | 27.033 | -21.601 | 84.998 |
| ATOM | 4428 OE2 | GLU | 1237 | 28.015 | -20.193 | 86.403 |
| ATOM | 4429 C | GLU | 1237 | 27.089 | -17.265 | 82.843 |
| ATOM | 4430 O | GLU | 1237 | 27.528 | -16.124 | 82.977 |
| ATOM | 4431 N | TRP | 1238 | 26.313 | -17.627 | 81.849 |
| ATOM | 4432 CA | TRP | 1238 | 26.041 | -16.704 | 80.807 |
| ATOM | 4433 CB | TRP | 1238 | 25.593 | -17.475 | 79.575 |
| ATOM | 4434 CG | TRP | 1238 | 26.763 | -18.286 | 79.050 |
| ATOM | 4435 CD2 | TRP | 1238 | 27.960 | -17.769 | 78.472 |
| ATOM | 4436 CE2 | TRP | 1238 | 28.791 | -18.857 | 78.198 |
| ATOM | 4437 CE3 | TRP | 1238 | 28.408 | -16.483 | 78.157 |
| ATOM | 4438 CD1 | TRP | 1238 | 26.915 | -19.630 | 79.097 |
| ATOM | 4439 NE1 | TRP | 1238 | 28.125 | -19.985 | 78.589 |
| ATOM | 4440 CZ2 | TRP | 1238 | 30.051 | -18.705 | 77.625 |
| ATOM | 4441 CZ3 | TRP | 1238 | 29.657 | -16.331 | 77.588 |
| ATOM | 4442 CH2 | TRP | 1238 | 30.464 | -17.433 | 77.329 |
| ATOM | 4443 C | TRP | 1238 | 25.087 | -15.667 | 81.317 |
| ATOM | 4444 O | TRP | 1238 | 25.420 | -14.495 | 81.302 |
| ATOM | 4445 N | GLN | 1239 | 24.022 | -16.099 | 81.969 |
| ATOM | 4446 CA | GLN | 1239 | 23.043 | -15.169 | 82.492 |
| ATOM | 4447 CB | GLN | 1239 | 22.122 | -15.867 | 83.470 |
| ATOM | 4448 CG | GLN | 1239 | 21.479 | -14.971 | 84.466 |
| ATOM | 4449 CD | GLN | 1239 | 20.657 | -13.892 | 83.842 |
| ATOM | 4450 OE1 | GLN | 1239 | 20.792 | -12.733 | 84.194 |
| ATOM | 4451 NE2 | GLN | 1239 | 19.778 | -14.260 | 82.929 |
| ATOM | 4452 C | GLN | 1239 | 23.675 | -13.973 | 83.128 |
| ATOM | 4453 O | GLN | 1239 | 23.081 | -12.935 | 83.227 |
| ATOM | 4454 N | ASN | 1240 | 24.907 | -14.110 | 83.547 |
| ATOM | 4455 CA | ASN | 1240 | 25.562 | -12.982 | 84.151 |
| ATOM | 4456 CB | ASN | 1240 | 26.206 | -13.354 | 85.485 |
| ATOM | 4457 CG | ASN | 1240 | 25.166 | -13.567 | 86.614 |
| ATOM | 4458 OD1 | ASN | 1240 | 25.334 | -14.486 | 87.453 |
| ATOM | 4459 ND2 | ASN | 1240 | 24.084 | -12.727 | 86.641 |
| ATOM | 4460 C | ASN | 1240 | 26.593 | -12.386 | 83.255 |
| ATOM | 4461 O | ASN | 1240 | 26.842 | -11.193 | 83.311 |
| ATOM | 4462 N | TYR | 1241 | 27.221 | -13.208 | 82.435 |

FIGURE 1PPPP

| Atom | | Residue AA No. | X | Y | Z |
|---|---|---|---|---|---|
| ATOM | 4463 CA | TYR 1241 | 28.247 | -12.708 | 81.535 |
| ATOM | 4464 CB | TYR 1241 | 28.673 | -13.797 | 80.563 |
| ATOM | 4465 CG | TYR 1241 | 29.562 | -13.275 | 79.469 |
| ATOM | 4466 CD1 | TYR 1241 | 29.098 | -13.166 | 78.154 |
| ATOM | 4467 CE1 | TYR 1241 | 29.887 | -12.641 | 77.162 |
| ATOM | 4468 CD2 | TYR 1241 | 30.846 | -12.848 | 79.753 |
| ATOM | 4469 CE2 | TYR 1241 | 31.645 | -12.323 | 78.770 |
| ATOM | 4470 CZ | TYR 1241 | 31.161 | -12.216 | 77.471 |
| ATOM | 4471 OH | TYR 1241 | 31.947 | -11.645 | 76.493 |
| ATOM | 4472 C | TYR 1241 | 27.700 | -11.543 | 80.753 |
| ATOM | 4473 O | TYR 1241 | 28.330 | -10.506 | 80.618 |
| ATOM | 4474 N | TRP 1242 | 26.484 | -11.717 | 80.276 |
| ATOM | 4475 CA | TRP 1242 | 25.857 | -10.689 | 79.492 |
| ATOM | 4476 CB | TRP 1242 | 24.723 | -11.284 | 78.622 |
| ATOM | 4477 CG | TRP 1242 | 25.268 | -12.246 | 77.579 |
| ATOM | 4478 CD2 | TRP 1242 | 26.030 | -11.905 | 76.419 |
| ATOM | 4479 CE2 | TRP 1242 | 26.502 | -13.092 | 75.872 |
| ATOM | 4480 CE3 | TRP 1242 | 26.368 | -10.700 | 75.799 |
| ATOM | 4481 CD1 | TRP 1242 | 25.287 | -13.593 | 77.658 |
| ATOM | 4482 NE1 | TRP 1242 | 26.035 | -14.112 | 76.650 |
| ATOM | 4483 CZ2 | TRP 1242 | 27.299 | -13.122 | 74.732 |
| ATOM | 4484 CZ3 | TRP 1242 | 27.162 | -10.726 | 74.664 |
| ATOM | 4485 CH2 | TRP 1242 | 27.618 | -11.926 | 74.144 |
| ATOM | 4486 C | TRP 1242 | 25.415 | -9.496 | 80.325 |
| ATOM | 4487 O | TRP 1242 | 25.512 | -8.364 | 79.853 |
| ATOM | 4488 N | ALA 1243 | 24.953 | -9.737 | 81.557 |
| ATOM | 4489 CA | ALA 1243 | 24.531 | -8.648 | 82.455 |
| ATOM | 4490 CB | ALA 1243 | 24.031 | -9.207 | 83.806 |
| ATOM | 4491 C | ALA 1243 | 25.737 | -7.716 | 82.666 |
| ATOM | 4492 O | ALA 1243 | 25.631 | -6.502 | 82.507 |
| ATOM | 4493 N | THR 1244 | 26.895 | -8.306 | 82.951 |
| ATOM | 4494 CA | THR 1244 | 28.130 | -7.558 | 83.158 |
| ATOM | 4495 CB | THR 1244 | 29.301 | -8.498 | 83.566 |
| ATOM | 4496 OG1 | THR 1244 | 28.942 | -9.270 | 84.724 |
| ATOM | 4497 CG2 | THR 1244 | 30.564 | -7.691 | 83.870 |
| ATOM | 4498 C | THR 1244 | 28.496 | -6.846 | 81.854 |
| ATOM | 4499 O | THR 1244 | 28.781 | -5.647 | 81.853 |
| ATOM | 4500 N | PHE 1245 | 28.418 | -7.582 | 80.746 |
| ATOM | 4501 CA | PHE 1245 | 28.732 | -7.083 | 79.404 |
| ATOM | 4502 CB | PHE 1245 | 28.603 | -8.225 | 78.422 |
| ATOM | 4503 CG | PHE 1245 | 29.045 | -7.878 | 77.057 |
| ATOM | 4504 CD1 | PHE 1245 | 30.292 | -7.331 | 76.857 |
| ATOM | 4505 CD2 | PHE 1245 | 28.214 | -8.090 | 75.975 |
| ATOM | 4506 CE1 | PHE 1245 | 30.702 | -7.000 | 75.606 |
| ATOM | 4507 CE2 | PHE 1245 | 28.612 | -7.767 | 74.717 |
| ATOM | 4508 CZ | PHE 1245 | 29.860 | -7.217 | 74.526 |
| ATOM | 4509 C | PHE 1245 | 27.863 | -5.936 | 78.909 |
| ATOM | 4510 O | PHE 1245 | 28.359 | -4.929 | 78.422 |

FIGURE 1QQQQ

| Atom | | Residue | | X | Y | Z |
|---|---|---|---|---|---|---|
| | | AA | No. | | | |
| ATOM | 4511 | N | ALA | 1246 | 26.564 | -6.182 | 78.933 |
| ATOM | 4512 | CA | ALA | 1246 | 25.545 | -5.231 | 78.547 |
| ATOM | 4513 | CB | ALA | 1246 | 24.176 | -5.852 | 78.746 |
| ATOM | 4514 | C | ALA | 1246 | 25.666 | -3.965 | 79.389 |
| ATOM | 4515 | O | ALA | 1246 | 25.579 | -2.853 | 78.874 |
| ATOM | 4516 | N | SER | 1247 | 25.878 | -4.137 | 80.690 |
| ATOM | 4517 | CA | SER | 1247 | 26.014 | -3.015 | 81.609 |
| ATOM | 4518 | CB | SER | 1247 | 25.881 | -3.502 | 83.029 |
| ATOM | 4519 | OG | SER | 1247 | 24.616 | -4.119 | 83.172 |
| ATOM | 4520 | C | SER | 1247 | 27.325 | -2.317 | 81.407 |
| ATOM | 4521 | O | SER | 1247 | 27.387 | -1.113 | 81.394 |
| ATOM | 4522 | N | ASP | 1248 | 28.378 | -3.083 | 81.230 |
| ATOM | 4523 | CA | ASP | 1248 | 29.654 | -2.489 | 80.960 |
| ATOM | 4524 | CB | ASP | 1248 | 30.711 | -3.557 | 80.738 |
| ATOM | 4525 | CG | ASP | 1248 | 31.627 | -3.736 | 81.937 |
| ATOM | 4526 | OD1 | ASP | 1248 | 32.027 | -2.729 | 82.565 |
| ATOM | 4527 | OD2 | ASP | 1248 | 31.972 | -4.895 | 82.246 |
| ATOM | 4528 | C | ASP | 1248 | 29.473 | -1.695 | 79.671 |
| ATOM | 4529 | O | ASP | 1248 | 29.948 | -0.574 | 79.554 |
| ATOM | 4530 | N | TRP | 1249 | 28.743 | -2.246 | 78.715 |
| ATOM | 4531 | CA | TRP | 1249 | 28.529 | -1.548 | 77.460 |
| ATOM | 4532 | CB | TRP | 1249 | 27.568 | -2.337 | 76.578 |
| ATOM | 4533 | CG | TRP | 1249 | 27.523 | -1.887 | 75.143 |
| ATOM | 4534 | CD2 | TRP | 1249 | 26.480 | -1.139 | 74.505 |
| ATOM | 4535 | CE2 | TRP | 1249 | 26.885 | -0.898 | 73.198 |
| ATOM | 4536 | CE3 | TRP | 1249 | 25.244 | -0.639 | 74.926 |
| ATOM | 4537 | CD1 | TRP | 1249 | 28.481 | -2.073 | 74.209 |
| ATOM | 4538 | NE1 | TRP | 1249 | 28.110 | -1.483 | 73.042 |
| ATOM | 4539 | CZ2 | TRP | 1249 | 26.108 | -0.174 | 72.297 |
| ATOM | 4540 | CZ3 | TRP | 1249 | 24.469 | 0.085 | 74.022 |
| ATOM | 4541 | CH2 | TRP | 1249 | 24.908 | 0.308 | 72.729 |
| ATOM | 4542 | C | TRP | 1249 | 27.967 | -0.166 | 77.713 |
| ATOM | 4543 | O | TRP | 1249 | 28.571 | 0.824 | 77.349 |
| ATOM | 4544 | N | LEU | 1250 | 26.856 | -0.093 | 78.418 |
| ATOM | 4545 | CA | LEU | 1250 | 26.242 | 1.186 | 78.660 |
| ATOM | 4546 | CB | LEU | 1250 | 25.112 | 1.036 | 79.636 |
| ATOM | 4547 | CG | LEU | 1250 | 23.892 | 0.564 | 78.889 |
| ATOM | 4548 | CD1 | LEU | 1250 | 23.021 | -0.280 | 79.772 |
| ATOM | 4549 | CD2 | LEU | 1250 | 23.159 | 1.762 | 78.371 |
| ATOM | 4550 | C | LEU | 1250 | 27.185 | 2.284 | 79.087 |
| ATOM | 4551 | O | LEU | 1250 | 27.371 | 3.263 | 78.369 |
| ATOM | 4552 | N | THR | 1251 | 27.853 | 2.109 | 80.215 |
| ATOM | 4553 | CA | THR | 1251 | 28.754 | 3.153 | 80.670 |
| ATOM | 4554 | CB | THR | 1251 | 29.245 | 2.965 | 82.168 |
| ATOM | 4555 | OG1 | THR | 1251 | 30.067 | 1.800 | 82.290 |
| ATOM | 4556 | CG2 | THR | 1251 | 28.063 | 2.839 | 83.141 |
| ATOM | 4557 | C | THR | 1251 | 29.915 | 3.397 | 79.692 |
| ATOM | 4558 | O | THR | 1251 | 30.352 | 4.533 | 79.570 |

FIGURE 1RRRR

| Atom | | Residue AA | No. | X | Y | Z |
|---|---|---|---|---|---|---|
| ATOM | 4559 N | SER | 1252 | 30.336 | 2.382 | 78.927 |
| ATOM | 4560 CA | SER | 1252 | 31.447 | 2.530 | 77.954 |
| ATOM | 4561 CB | SER | 1252 | 31.921 | 1.167 | 77.420 |
| ATOM | 4562 OG | SER | 1252 | 30.897 | 0.461 | 76.729 |
| ATOM | 4563 C | SER | 1252 | 31.127 | 3.486 | 76.783 |
| ATOM | 4564 O | SER | 1252 | 32.026 | 4.115 | 76.203 |
| ATOM | 4565 N | ALA | 1253 | 29.846 | 3.555 | 76.424 |
| ATOM | 4566 CA | ALA | 1253 | 29.378 | 4.470 | 75.395 |
| ATOM | 4567 CB | ALA | 1253 | 28.115 | 3.923 | 74.717 |
| ATOM | 4568 C | ALA | 1253 | 29.105 | 5.808 | 76.129 |
| ATOM | 4569 O | ALA | 1253 | 28.651 | 6.784 | 75.515 |
| ATOM | 4570 N | ASN | 1254 | 29.384 | 5.808 | 77.447 |
| ATOM | 4571 CA | ASN | 1254 | 29.295 | 6.947 | 78.388 |
| ATOM | 4572 CB | ASN | 1254 | 29.566 | 8.255 | 77.677 |
| ATOM | 4573 CG | ASN | 1254 | 30.828 | 8.907 | 78.154 |
| ATOM | 4574 OD1 | ASN | 1254 | 30.893 | 10.130 | 78.266 |
| ATOM | 4575 ND2 | ASN | 1254 | 31.863 | 8.106 | 78.408 |
| ATOM | 4576 C | ASN | 1254 | 28.113 | 7.156 | 79.321 |
| ATOM | 4577 O | ASN | 1254 | 27.873 | 8.277 | 79.767 |
| ATOM | 4578 N | MET | 1255 | 27.425 | 6.101 | 79.724 |
| ATOM | 4579 CA | MET | 1255 | 26.255 | 6.330 | 80.562 |
| ATOM | 4580 CB | MET | 1255 | 25.092 | 5.491 | 80.094 |
| ATOM | 4581 CG | MET | 1255 | 23.808 | 6.135 | 80.448 |
| ATOM | 4582 SD | MET | 1255 | 22.593 | 4.998 | 80.090 |
| ATOM | 4583 CE | MET | 1255 | 22.834 | 3.961 | 81.447 |
| ATOM | 4584 C | MET | 1255 | 26.386 | 6.209 | 82.067 |
| ATOM | 4585 O | MET | 1255 | 25.968 | 5.186 | 82.659 |
| ATOM | 4586 N | SER | 1256 | 26.845 | 7.307 | 82.678 |
| ATOM | 4587 CA | SER | 1256 | 27.068 | 7.424 | 84.132 |
| ATOM | 4588 CB | SER | 1256 | 26.746 | 8.834 | 84.599 |
| ATOM | 4589 OG | SER | 1256 | 25.424 | 9.177 | 84.230 |
| ATOM | 4590 C | SER | 1256 | 26.341 | 6.415 | 85.020 |
| ATOM | 4591 O | SER | 1256 | 25.102 | 6.369 | 85.086 |
| ATOM | 4592 N | SER | 1257 | 27.149 | 5.624 | 85.713 |
| ATOM | 4593 CA | SER | 1257 | 26.654 | 4.593 | 86.592 |
| ATOM | 4594 CB | SER | 1257 | 27.838 | 3.944 | 87.317 |
| ATOM | 4595 OG | SER | 1257 | 28.784 | 4.919 | 87.756 |
| ATOM | 4596 C | SER | 1257 | 25.654 | 5.158 | 87.587 |
| ATOM | 4597 O | SER | 1257 | 24.549 | 4.621 | 87.758 |
| ATOM | 4598 N | GLU | 1258 | 26.011 | 6.304 | 88.154 |
| ATOM | 4599 CA | GLU | 1258 | 25.185 | 6.976 | 89.144 |
| ATOM | 4600 CB | GLU | 1258 | 25.959 | 8.182 | 89.715 |
| ATOM | 4601 CG | GLU | 1258 | 27.006 | 7.797 | 90.834 |
| ATOM | 4602 CD | GLU | 1258 | 28.522 | 8.041 | 90.479 |
| ATOM | 4603 OE1 | GLU | 1258 | 28.844 | 8.792 | 89.509 |
| ATOM | 4604 OE2 | GLU | 1258 | 29.394 | 7.486 | 91.216 |
| ATOM | 4605 C | GLU | 1258 | 23.756 | 7.346 | 88.690 |
| ATOM | 4606 O | GLU | 1258 | 23.043 | 8.095 | 89.383 |

FIGURE 1SSSS

| Atom | Residue AA | No. | X | Y | Z |
|---|---|---|---|---|---|
| ATOM 4607 N | ASN | 1259 | 23.333 | 6.775 | 87.555 |
| ATOM 4608 CA | ASN | 1259 | 22.008 | 7.012 | 87.001 |
| ATOM 4609 CB | ASN | 1259 | 22.114 | 7.956 | 85.825 |
| ATOM 4610 CG | ASN | 1259 | 21.360 | 9.211 | 86.054 |
| ATOM 4611 OD1 | ASN | 1259 | 20.260 | 9.174 | 86.598 |
| ATOM 4612 ND2 | ASN | 1259 | 21.939 | 10.344 | 85.667 |
| ATOM 4613 C | ASN | 1259 | 21.243 | 5.755 | 86.599 |
| ATOM 4614 O | ASN | 1259 | 20.069 | 5.826 | 86.250 |
| ATOM 4615 N | MET | 1260 | 21.871 | 4.604 | 86.799 |
| ATOM 4616 CA | MET | 1260 | 21.298 | 3.314 | 86.440 |
| ATOM 4617 CB | MET | 1260 | 21.913 | 2.872 | 85.106 |
| ATOM 4618 CG | MET | 1260 | 23.429 | 3.262 | 84.963 |
| ATOM 4619 SD | MET | 1260 | 24.505 | 2.346 | 84.068 |
| ATOM 4621 C | MET | 1260 | 21.625 | 2.257 | 87.489 |
| ATOM 4622 O | MET | 1260 | 22.704 | 2.306 | 88.080 |
| ATOM 4623 N | ARG | 1261 | 20.748 | 1.260 | 87.652 |
| ATOM 4624 CA | ARG | 1261 | 20.944 | 0.165 | 88.628 |
| ATOM 4625 CB | ARG | 1261 | 20.067 | 0.407 | 89.861 |
| ATOM 4626 CG | ARG | 1261 | 18.540 | 0.165 | 89.658 |
| ATOM 4627 CD | ARG | 1261 | 17.754 | 0.490 | 90.927 |
| ATOM 4628 NE | ARG | 1261 | 16.332 | 0.158 | 90.873 |
| ATOM 4629 CZ | ARG | 1261 | 15.355 | 1.012 | 91.183 |
| ATOM 4630 NH1 | ARG | 1261 | 14.080 | 0.650 | 91.148 |
| ATOM 4631 NH2 | ARG | 1261 | 15.637 | 2.259 | 91.476 |
| ATOM 4632 C | ARG | 1261 | 20.461 | -1.110 | 87.977 |
| ATOM 4633 O | ARG | 1261 | 19.993 | -1.058 | 86.867 |
| ATOM 4634 N | LEU | 1262 | 20.583 | -2.259 | 88.626 |
| ATOM 4635 CA | LEU | 1262 | 20.023 | -3.484 | 88.032 |
| ATOM 4636 CB | LEU | 1262 | 21.083 | -4.518 | 87.676 |
| ATOM 4637 CG | LEU | 1262 | 22.518 | -4.169 | 87.328 |
| ATOM 4638 CD1 | LEU | 1262 | 23.105 | -5.411 | 86.684 |
| ATOM 4639 CD2 | LEU | 1262 | 22.622 | -2.971 | 86.411 |
| ATOM 4640 C | LEU | 1262 | 19.018 | -4.141 | 88.992 |
| ATOM 4641 O | LEU | 1262 | 19.389 | -4.954 | 89.839 |
| ATOM 4642 N | ARG | 1263 | 17.747 | -3.777 | 88.865 |
| ATOM 4643 CA | ARG | 1263 | 16.683 | -4.313 | 89.712 |
| ATOM 4644 CB | ARG | 1263 | 15.432 | -3.423 | 89.581 |
| ATOM 4645 CG | ARG | 1263 | 14.186 | -3.921 | 90.285 |
| ATOM 4646 CD | ARG | 1263 | 13.137 | -4.390 | 89.292 |
| ATOM 4647 NE | ARG | 1263 | 12.335 | -5.466 | 89.863 |
| ATOM 4648 CZ | ARG | 1263 | 11.191 | -5.921 | 89.352 |
| ATOM 4649 NH1 | ARG | 1263 | 10.544 | -6.900 | 89.970 |
| ATOM 4650 NH2 | ARG | 1263 | 10.715 | -5.446 | 88.203 |
| ATOM 4651 C | ARG | 1263 | 16.375 | -5.787 | 89.388 |
| ATOM 4652 O | ARG | 1263 | 15.236 | -6.149 | 89.066 |
| ATOM 4653 N | ASP | 1264 | 17.411 | -6.622 | 89.438 |
| ATOM 4654 CA | ASP | 1264 | 17.321 | -8.066 | 89.184 |

FIGURE 1TTTT

| Atom | | Residue AA | No. | X | Y | Z |
|---|---|---|---|---|---|---|
| ATOM | 4655 | CB | ASP | 1264 | 18.516 | -8.717 | 89.898 |
| ATOM | 4656 | CG | ASP | 1264 | 18.681 | -10.203 | 89.594 |
| ATOM | 4657 | OD1 | ASP | 1264 | 17.931 | -10.815 | 88.776 |
| ATOM | 4658 | OD2 | ASP | 1264 | 19.620 | -10.755 | 90.199 |
| ATOM | 4659 | C | ASP | 1264 | 15.986 | -8.544 | 89.782 |
| ATOM | 4660 | O | ASP | 1264 | 15.833 | -8.542 | 91.009 |
| ATOM | 4661 | N | HIS | 1265 | 15.034 | -8.987 | 88.958 |
| ATOM | 4662 | CA | HIS | 1265 | 13.753 | -9.320 | 89.559 |
| ATOM | 4663 | CB | HIS | 1265 | 12.617 | -8.503 | 88.949 |
| ATOM | 4664 | CG | HIS | 1265 | 12.242 | -8.877 | 87.558 |
| ATOM | 4665 | CD2 | HIS | 1265 | 11.577 | -9.953 | 87.075 |
| ATOM | 4666 | ND1 | HIS | 1265 | 12.422 | -8.024 | 86.491 |
| ATOM | 4667 | CE1 | HIS | 1265 | 11.875 | -8.551 | 85.412 |
| ATOM | 4668 | NE2 | HIS | 1265 | 11.356 | -9.722 | 85.740 |
| ATOM | 4669 | C | HIS | 1265 | 13.239 | -10.654 | 90.078 |
| ATOM | 4670 | O | HIS | 1265 | 13.770 | -11.743 | 89.808 |
| ATOM | 4671 | N | ASP | 1266 | 12.199 | -10.464 | 90.897 |
| ATOM | 4672 | CA | ASP | 1266 | 11.459 | -11.459 | 91.674 |
| ATOM | 4673 | CB | ASP | 1266 | 10.719 | -10.741 | 92.833 |
| ATOM | 4674 | CG | ASP | 1266 | 9.616 | -9.745 | 92.341 |
| ATOM | 4675 | OD1 | ASP | 1266 | 9.955 | -8.778 | 91.607 |
| ATOM | 4676 | OD2 | ASP | 1266 | 8.427 | -9.917 | 92.730 |
| ATOM | 4677 | C | ASP | 1266 | 10.480 | -12.404 | 91.024 |
| ATOM | 4678 | O | ASP | 1266 | 10.009 | -12.168 | 89.912 |
| ATOM | 4679 | N | ALA | 1267 | 10.051 | -13.365 | 91.846 |
| ATOM | 4680 | CA | ALA | 1267 | 9.101 | -14.397 | 91.464 |
| ATOM | 4681 | CB | ALA | 1267 | 9.218 | -15.600 | 92.390 |
| ATOM | 4682 | C | ALA | 1267 | 7.663 | -13.902 | 91.394 |
| ATOM | 4683 | O | ALA | 1267 | 6.721 | -14.677 | 91.594 |
| ATOM | 4684 | N | ASP | 1268 | 7.499 | -12.592 | 91.222 |
| ATOM | 4685 | CA | ASP | 1268 | 6.165 | -12.031 | 91.031 |
| ATOM | 4686 | CB | ASP | 1268 | 6.131 | -10.511 | 91.323 |
| ATOM | 4687 | CG | ASP | 1268 | 4.928 | -9.776 | 90.656 |
| ATOM | 4688 | OD1 | ASP | 1268 | 5.144 | -8.630 | 90.174 |
| ATOM | 4689 | OD2 | ASP | 1268 | 3.777 | -10.322 | 90.628 |
| ATOM | 4690 | C | ASP | 1268 | 5.995 | -12.261 | 89.534 |
| ATOM | 4691 | O | ASP | 1268 | 5.299 | -13.203 | 89.085 |
| ATOM | 4692 | N | GLU | 1269 | 6.771 | -11.461 | 88.798 |
| ATOM | 4693 | CA | GLU | 1269 | 6.790 | -11.454 | 87.346 |
| ATOM | 4694 | CB | GLU | 1269 | 6.855 | -9.996 | 86.835 |
| ATOM | 4695 | CG | GLU | 1269 | 8.220 | -9.262 | 87.017 |
| ATOM | 4696 | CD | GLU | 1269 | 8.517 | -8.821 | 88.452 |
| ATOM | 4697 | OE1 | GLU | 1269 | 9.195 | -9.574 | 89.184 |
| ATOM | 4698 | OE2 | GLU | 1269 | 8.100 | -7.706 | 88.827 |
| ATOM | 4699 | C | GLU | 1269 | 7.910 | -12.315 | 86.732 |
| ATOM | 4700 | O | GLU | 1269 | 8.167 | -12.218 | 85.519 |
| ATOM | 4701 | N | LEU | 1270 | 8.633 | -13.079 | 87.561 |
| ATOM | 4702 | CA | LEU | 1270 | 9.668 | -13.965 | 87.029 |

FIGURE 1UUUU

| Atom | | Residue AA | No. | X | Y | Z |
|---|---|---|---|---|---|---|
| ATOM | 4703 | CB | LEU 1270 | 10.541 | -14.615 | 88.103 |
| ATOM | 4704 | CG | LEU 1270 | 11.569 | -15.559 | 87.474 |
| ATOM | 4705 | CD1 | LEU 1270 | 12.922 | -15.470 | 88.126 |
| ATOM | 4706 | CD2 | LEU 1270 | 11.051 | -16.963 | 87.515 |
| ATOM | 4707 | C | LEU 1270 | 8.832 | -15.020 | 86.320 |
| ATOM | 4708 | O | LEU 1270 | 7.763 | -15.439 | 86.811 |
| ATOM | 4709 | N | SER 1271 | 9.281 | -15.414 | 85.138 |
| ATOM | 4710 | CA | SER 1271 | 8.490 | -16.348 | 84.423 |
| ATOM | 4711 | CB | SER 1271 | 8.643 | -16.169 | 82.922 |
| ATOM | 4712 | OG | SER 1271 | 7.344 | -15.952 | 82.367 |
| ATOM | 4713 | C | SER 1271 | 8.634 | -17.773 | 84.858 |
| ATOM | 4714 | O | SER 1271 | 9.644 | -18.173 | 85.418 |
| ATOM | 4715 | N | ALA 1272 | 7.518 | -18.477 | 84.689 |
| ATOM | 4716 | CA | ALA 1272 | 7.367 | -19.897 | 84.968 |
| ATOM | 4717 | CB | ALA 1272 | 6.043 | -20.380 | 84.363 |
| ATOM | 4718 | C | ALA 1272 | 8.548 | -20.645 | 84.327 |
| ATOM | 4719 | O | ALA 1272 | 9.114 | -21.569 | 84.928 |
| ATOM | 4720 | N | TYR 1273 | 8.901 | -20.226 | 83.103 |
| ATOM | 4721 | CA | TYR 1273 | 10.027 | -20.789 | 82.328 |
| ATOM | 4722 | CB | TYR 1273 | 9.818 | -20.541 | 80.822 |
| ATOM | 4723 | CG | TYR 1273 | 9.634 | -19.091 | 80.367 |
| ATOM | 4724 | CD1 | TYR 1273 | 8.349 | -18.547 | 80.240 |
| ATOM | 4725 | CE1 | TYR 1273 | 8.148 | -17.266 | 79.693 |
| ATOM | 4726 | CD2 | TYR 1273 | 10.732 | -18.310 | 79.948 |
| ATOM | 4727 | CE2 | TYR 1273 | 10.545 | -17.023 | 79.405 |
| ATOM | 4728 | CZ | TYR 1273 | 9.246 | -16.504 | 79.277 |
| ATOM | 4729 | OH | TYR 1273 | 9.031 | -15.236 | 78.749 |
| ATOM | 4730 | C | TYR 1273 | 11.376 | -20.200 | 82.734 |
| ATOM | 4731 | O | TYR 1273 | 12.409 | -20.877 | 82.724 |
| ATOM | 4732 | N | SER 1274 | 11.335 | -18.898 | 82.984 |
| ATOM | 4733 | CA | SER 1274 | 12.485 | -18.148 | 83.392 |
| ATOM | 4734 | CB | SER 1274 | 12.119 | -16.652 | 83.444 |
| ATOM | 4735 | OG | SER 1274 | 13.200 | -15.842 | 83.897 |
| ATOM | 4736 | C | SER 1274 | 12.931 | -18.643 | 84.763 |
| ATOM | 4737 | O | SER 1274 | 12.332 | -19.532 | 85.366 |
| ATOM | 4738 | N | ASN 1275 | 13.993 | -18.027 | 85.245 |
| ATOM | 4739 | CA | ASN 1275 | 14.576 | -18.321 | 86.534 |
| ATOM | 4740 | CB | ASN 1275 | 14.951 | -19.790 | 86.625 |
| ATOM | 4741 | CG | ASN 1275 | 15.622 | -20.263 | 85.403 |
| ATOM | 4742 | OD1 | ASN 1275 | 14.948 | -20.650 | 84.467 |
| ATOM | 4743 | ND2 | ASN 1275 | 16.951 | -20.160 | 85.353 |
| ATOM | 4744 | C | ASN 1275 | 15.819 | -17.448 | 86.540 |
| ATOM | 4745 | O | ASN 1275 | 16.946 | -17.909 | 86.781 |
| ATOM | 4746 | N | ALA 1276 | 15.591 | -16.194 | 86.167 |
| ATOM | 4747 | CA | ALA 1276 | 16.612 | -15.163 | 86.092 |
| ATOM | 4748 | CB | ALA 1276 | 17.909 | -15.705 | 85.528 |
| ATOM | 4749 | C | ALA 1276 | 16.033 | -14.154 | 85.146 |
| ATOM | 4750 | O | ALA 1276 | 15.466 | -14.516 | 84.124 |

FIGURE 1VVVV

| Atom | | Residue AA | No. | X | Y | Z |
|---|---|---|---|---|---|---|
| ATOM | 4751 N | THR | 1277 | 16.129 | -12.894 | 85.514 |
| ATOM | 4752 CA | THR | 1277 | 15.604 | -11.834 | 84.698 |
| ATOM | 4753 CB | THR | 1277 | 14.087 | -11.994 | 84.422 |
| ATOM | 4754 OG1 | THR | 1277 | 13.552 | -10.748 | 83.973 |
| ATOM | 4755 CG2 | THR | 1277 | 13.328 | -12.484 | 85.635 |
| ATOM | 4756 C | THR | 1277 | 15.928 | -10.537 | 85.388 |
| ATOM | 4757 O | THR | 1277 | 15.094 | -9.938 | 86.076 |
| ATOM | 4758 N | THR | 1278 | 17.193 | -10.168 | 85.264 |
| ATOM | 4759 CA | THR | 1278 | 17.705 | -8.954 | 85.840 |
| ATOM | 4760 CB | THR | 1278 | 19.199 | -9.121 | 86.193 |
| ATOM | 4761 OG1 | THR | 1278 | 19.875 | -7.865 | 86.113 |
| ATOM | 4762 CG2 | THR | 1278 | 19.870 | -10.101 | 85.294 |
| ATOM | 4763 C | THR | 1278 | 17.518 | -7.806 | 84.864 |
| ATOM | 4764 O | THR | 1278 | 18.108 | -7.824 | 83.803 |
| ATOM | 4765 N | ASP | 1279 | 16.621 | -6.870 | 85.150 |
| ATOM | 4766 CA | ASP | 1279 | 16.461 | -5.710 | 84.276 |
| ATOM | 4767 CB | ASP | 1279 | 15.134 | -5.001 | 84.545 |
| ATOM | 4768 CG | ASP | 1279 | 13.949 | -5.765 | 84.063 |
| ATOM | 4769 OD1 | ASP | 1279 | 14.149 | -6.827 | 83.460 |
| ATOM | 4770 OD2 | ASP | 1279 | 12.812 | -5.292 | 84.287 |
| ATOM | 4771 C | ASP | 1279 | 17.581 | -4.726 | 84.660 |
| ATOM | 4772 O | ASP | 1279 | 18.201 | -4.869 | 85.713 |
| ATOM | 4773 N | ILE | 1280 | 17.880 | -3.768 | 83.791 |
| ATOM | 4774 CA | ILE | 1280 | 18.855 | -2.719 | 84.090 |
| ATOM | 4775 CB | ILE | 1280 | 19.989 | -2.653 | 83.071 |
| ATOM | 4776 CG2 | ILE | 1280 | 20.973 | -1.557 | 83.460 |
| ATOM | 4777 CG1 | ILE | 1280 | 20.689 | -4.002 | 82.985 |
| ATOM | 4778 CD1 | ILE | 1280 | 21.921 | -3.987 | 82.139 |
| ATOM | 4779 C | ILE | 1280 | 17.934 | -1.502 | 83.942 |
| ATOM | 4780 O | ILE | 1280 | 17.115 | -1.467 | 83.041 |
| ATOM | 4781 N | GLU | 1281 | 18.010 | -0.518 | 84.816 |
| ATOM | 4782 CA | GLU | 1281 | 17.079 | 0.576 | 84.702 |
| ATOM | 4783 CB | GLU | 1281 | 16.136 | 0.588 | 85.910 |
| ATOM | 4784 CG | GLU | 1281 | 15.509 | -0.769 | 86.333 |
| ATOM | 4785 CD | GLU | 1281 | 14.451 | -0.658 | 87.463 |
| ATOM | 4786 OE1 | GLU | 1281 | 13.677 | -1.616 | 87.664 |
| ATOM | 4787 OE2 | GLU | 1281 | 14.366 | 0.386 | 88.142 |
| ATOM | 4788 C | GLU | 1281 | 17.767 | 1.896 | 84.599 |
| ATOM | 4789 O | GLU | 1281 | 18.945 | 2.015 | 84.895 |
| ATOM | 4790 N | TYR | 1282 | 17.013 | 2.899 | 84.197 |
| ATOM | 4791 CA | TYR | 1282 | 17.551 | 4.217 | 84.080 |
| ATOM | 4792 CB | TYR | 1282 | 17.635 | 4.698 | 82.622 |
| ATOM | 4793 CG | TYR | 1282 | 18.405 | 6.013 | 82.436 |
| ATOM | 4794 CD1 | TYR | 1282 | 17.752 | 7.248 | 82.448 |
| ATOM | 4796 CD2 | TYR | 1282 | 19.793 | 6.025 | 82.262 |
| ATOM | 4797 CE2 | TYR | 1282 | 20.505 | 7.229 | 82.190 |
| ATOM | 4798 CZ | TYR | 1282 | 19.829 | 8.430 | 82.291 |

FIGURE 1WWWW

|  | Atom | Residue AA | No. | X | Y | Z |
|---|---|---|---|---|---|---|
| ATOM | 4799 OH | TYR | 1282 | 20.521 | 9.604 | 82.300 |
| ATOM | 4800 C | TYR | 1282 | 16.684 | 5.145 | 84.861 |
| ATOM | 4801 O | TYR | 1282 | 15.479 | 4.963 | 84.966 |
| ATOM | 4802 N | ALA | 1283 | 17.358 | 6.124 | 85.439 |
| ATOM | 4803 CA | ALA | 1283 | 16.757 | 7.178 | 86.218 |
| ATOM | 4804 CB | ALA | 1283 | 17.766 | 7.683 | 87.241 |
| ATOM | 4805 C | ALA | 1283 | 16.331 | 8.313 | 85.271 |
| ATOM | 4806 O | ALA | 1283 | 16.953 | 9.385 | 85.223 |
| ATOM | 4807 N | PHE | 1284 | 15.306 | 8.041 | 84.470 |
| ATOM | 4808 CA | PHE | 1284 | 14.784 | 9.040 | 83.531 |
| ATOM | 4809 CB | PHE | 1284 | 13.733 | 8.412 | 82.602 |
| ATOM | 4810 CG | PHE | 1284 | 14.275 | 7.383 | 81.673 |
| ATOM | 4811 CD1 | PHE | 1284 | 15.347 | 7.671 | 80.851 |
| ATOM | 4812 CD2 | PHE | 1284 | 13.699 | 6.118 | 81.614 |
| ATOM | 4813 CE1 | PHE | 1284 | 15.844 | 6.710 | 79.983 |
| ATOM | 4814 CE2 | PHE | 1284 | 14.190 | 5.145 | 80.742 |
| ATOM | 4815 CZ | PHE | 1284 | 15.266 | 5.445 | 79.928 |
| ATOM | 4816 C | PHE | 1284 | 14.126 | 10.201 | 84.305 |
| ATOM | 4817 O | PHE | 1284 | 13.709 | 10.045 | 85.452 |
| ATOM | 4818 N | PRO | 1285 | 13.966 | 11.361 | 83.656 |
| ATOM | 4819 CD | PRO | 1285 | 14.279 | 11.749 | 82.268 |
| ATOM | 4820 CA | PRO | 1285 | 13.342 | 12.464 | 84.375 |
| ATOM | 4821 CB | PRO | 1285 | 13.184 | 13.519 | 83.271 |
| ATOM | 4822 CG | PRO | 1285 | 14.339 | 13.240 | 82.375 |
| ATOM | 4823 C | PRO | 1285 | 11.975 | 12.030 | 84.947 |
| ATOM | 4824 O | PRO | 1285 | 11.596 | 12.392 | 86.064 |
| ATOM | 4825 N | PHE | 1286 | 11.255 | 11.217 | 84.193 |
| ATOM | 4826 CA | PHE | 1286 | 9.944 | 10.773 | 84.631 |
| ATOM | 4827 CB | PHE | 1286 | 9.060 | 10.468 | 83.403 |
| ATOM | 4828 CG | PHE | 1286 | 9.675 | 9.469 | 82.456 |
| ATOM | 4829 CD1 | PHE | 1286 | 9.407 | 8.102 | 82.595 |
| ATOM | 4830 CD2 | PHE | 1286 | 10.616 | 9.880 | 81.507 |
| ATOM | 4831 CE1 | PHE | 1286 | 10.075 | 7.167 | 81.823 |
| ATOM | 4832 CE2 | PHE | 1286 | 11.285 | 8.954 | 80.891 |
| ATOM | 4834 C | PHE | 1286 | 9.995 | 9.564 | 85.583 |
| ATOM | 4835 O | PHE | 1286 | 8.953 | 8.982 | 85.909 |
| ATOM | 4836 N | GLY | 1287 | 11.183 | 9.141 | 85.993 |
| ATOM | 4837 CA | GLY | 1287 | 11.238 | 8.009 | 86.900 |
| ATOM | 4838 C | GLY | 1287 | 12.203 | 6.902 | 86.564 |
| ATOM | 4839 O | GLY | 1287 | 13.154 | 7.093 | 85.818 |
| ATOM | 4840 N | TRP | 1288 | 12.011 | 5.756 | 87.197 |
| ATOM | 4841 CA | TRP | 1288 | 12.868 | 4.621 | 86.922 |
| ATOM | 4842 CB | TRP | 1288 | 12.972 | 3.689 | 88.125 |
| ATOM | 4843 CG | TRP | 1288 | 13.905 | 4.213 | 89.150 |
| ATOM | 4844 CD2 | TRP | 1288 | 15.303 | 3.925 | 89.280 |
| ATOM | 4845 CE2 | TRP | 1288 | 15.809 | 4.758 | 90.293 |
| ATOM | 4846 CE3 | TRP | 1288 | 16.178 | 3.051 | 88.633 |

FIGURE 1XXXX

| Atom | | AA | Residue No. | X | Y | Z |
|---|---|---|---|---|---|---|
| ATOM | 4847 | CD1 | TRP | 1288 | 13.628 | 5.159 | 90.079 |
| ATOM | 4848 | NE1 | TRP | 1288 | 14.765 | 5.500 | 90.767 |
| ATOM | 4849 | CZ2 | TRP | 1288 | 17.153 | 4.748 | 90.673 |
| ATOM | 4850 | CZ3 | TRP | 1288 | 17.518 | 3.041 | 89.014 |
| ATOM | 4851 | CH2 | TRP | 1288 | 17.989 | 3.883 | 90.022 |
| ATOM | 4852 | C | TRP | 1288 | 12.225 | 3.895 | 85.768 |
| ATOM | 4853 | O | TRP | 1288 | 10.992 | 3.928 | 85.629 |
| ATOM | 4854 | N | GLY | 1289 | 13.052 | 3.283 | 84.920 |
| ATOM | 4855 | CA | GLY | 1289 | 12.540 | 2.546 | 83.775 |
| ATOM | 4856 | C | GLY | 1289 | 13.591 | 1.583 | 83.292 |
| ATOM | 4857 | O | GLY | 1289 | 14.767 | 1.751 | 83.628 |
| ATOM | 4858 | N | GLU | 1290 | 13.192 | 0.586 | 82.512 |
| ATOM | 4859 | CA | GLU | 1290 | 14.158 | -0.382 | 82.030 |
| ATOM | 4860 | CB | GLU | 1290 | 13.525 | -1.764 | 81.915 |
| ATOM | 4861 | CG | GLU | 1290 | 12.445 | -1.909 | 80.851 |
| ATOM | 4862 | CD | GLU | 1290 | 11.737 | -3.283 | 80.901 |
| ATOM | 4863 | OE1 | GLU | 1290 | 10.747 | -3.420 | 81.666 |
| ATOM | 4864 | OE2 | GLU | 1290 | 12.169 | -4.224 | 80.184 |
| ATOM | 4865 | C | GLU | 1290 | 14.825 | 0.002 | 80.727 |
| ATOM | 4866 | O | GLU | 1290 | 14.314 | 0.817 | 79.978 |
| ATOM | 4867 | N | LEU | 1291 | 16.055 | -0.456 | 80.574 |
| ATOM | 4868 | CA | LEU | 1291 | 16.828 | -0.263 | 79.367 |
| ATOM | 4869 | CB | LEU | 1291 | 18.280 | 0.100 | 79.655 |
| ATOM | 4870 | CG | LEU | 1291 | 18.580 | 1.523 | 80.011 |
| ATOM | 4871 | CD1 | LEU | 1291 | 19.880 | 1.923 | 79.370 |
| ATOM | 4872 | CD2 | LEU | 1291 | 17.459 | 2.390 | 79.522 |
| ATOM | 4873 | C | LEU | 1291 | 16.798 | -1.665 | 78.785 |
| ATOM | 4874 | O | LEU | 1291 | 15.839 | -2.032 | 78.093 |
| ATOM | 4875 | N | TRP | 1292 | 17.813 | -2.460 | 79.142 |
| ATOM | 4876 | CA | TRP | 1292 | 17.962 | -3.833 | 78.714 |
| ATOM | 4877 | CB | TRP | 1292 | 19.366 | -4.264 | 79.020 |
| ATOM | 4878 | CG | TRP | 1292 | 20.165 | -4.612 | 77.853 |
| ATOM | 4879 | CD2 | TRP | 1292 | 21.281 | -3.892 | 77.341 |
| ATOM | 4880 | CE2 | TRP | 1292 | 21.810 | -4.645 | 76.274 |
| ATOM | 4881 | CE3 | TRP | 1292 | 21.898 | -2.683 | 77.686 |
| ATOM | 4882 | CD1 | TRP | 1292 | 20.059 | -5.723 | 77.103 |
| ATOM | 4883 | NE1 | TRP | 1292 | 21.035 | -5.761 | 76.145 |
| ATOM | 4884 | CZ2 | TRP | 1292 | 22.923 | -4.238 | 75.553 |
| ATOM | 4885 | CZ3 | TRP | 1292 | 23.010 | -2.278 | 76.965 |
| ATOM | 4886 | CH2 | TRP | 1292 | 23.509 | -3.055 | 75.914 |
| ATOM | 4887 | C | TRP | 1292 | 17.006 | -4.757 | 79.456 |
| ATOM | 4888 | O | TRP | 1292 | 16.148 | -4.335 | 80.200 |
| ATOM | 4889 | N | GLY | 1293 | 17.187 | -6.044 | 79.269 |
| ATOM | 4890 | CA | GLY | 1293 | 16.347 | -7.019 | 79.928 |
| ATOM | 4891 | C | GLY | 1293 | 16.998 | -8.386 | 79.773 |
| ATOM | 4892 | O | GLY | 1293 | 16.509 | -9.212 | 79.010 |
| ATOM | 4893 | N | ILE | 1294 | 18.126 | -8.609 | 80.445 |
| ATOM | 4894 | CA | ILE | 1294 | 18.825 | -9.880 | 80.368 |

FIGURE 1YYYY

|  |  | Residue |  |  |  |
|---|---|---|---|---|---|
| Atom | AA | No. | X | Y | Z |
| ATOM 4895 CB | ILE | 1294 | 20.216 | -9.796 | 81.025 |
| ATOM 4896 CG2 | ILE | 1294 | 21.006 | -11.040 | 80.734 |
| ATOM 4897 CG1 | ILE | 1294 | 21.028 | -8.631 | 80.466 |
| ATOM 4898 CD1 | ILE | 1294 | 20.774 | -7.320 | 81.136 |
| ATOM 4899 C | ILE | 1294 | 17.984 | -10.892 | 81.129 |
| ATOM 4900 O | ILE | 1294 | 17.516 | -10.598 | 82.212 |
| ATOM 4901 N | ALA | 1295 | 17.810 | -12.091 | 80.593 |
| ATOM 4902 CA | ALA | 1295 | 16.983 | -13.083 | 81.265 |
| ATOM 4903 CB | ALA | 1295 | 15.514 | -12.746 | 81.055 |
| ATOM 4904 C | ALA | 1295 | 17.234 | -14.511 | 80.810 |
| ATOM 4905 O | ALA | 1295 | 17.409 | -14.761 | 79.625 |
| ATOM 4906 N | SER | 1296 | 17.188 | -15.450 | 81.753 |
| ATOM 4907 CA | SER | 1296 | 17.395 | -16.874 | 81.469 |
| ATOM 4908 CB | SER | 1296 | 18.155 | -17.548 | 82.637 |
| ATOM 4909 OG | SER | 1296 | 18.658 | -18.844 | 82.315 |
| ATOM 4910 C | SER | 1296 | 16.026 | -17.531 | 81.257 |
| ATOM 4911 O | SER | 1296 | 15.239 | -17.639 | 82.211 |
| ATOM 4912 N | ARG | 1297 | 15.732 | -17.925 | 80.015 |
| ATOM 4913 CA | ARG | 1297 | 14.453 | -18.562 | 79.689 |
| ATOM 4914 CB | ARG | 1297 | 13.869 | -17.935 | 78.429 |
| ATOM 4915 CG | ARG | 1297 | 14.052 | -16.449 | 78.328 |
| ATOM 4916 CD | ARG | 1297 | 13.754 | -16.023 | 76.908 |
| ATOM 4917 NE | ARG | 1297 | 12.398 | -16.366 | 76.498 |
| ATOM 4918 CZ | ARG | 1297 | 11.424 | -15.477 | 76.322 |
| ATOM 4919 NH1 | ARG | 1297 | 11.633 | -14.179 | 76.520 |
| ATOM 4920 NH2 | ARG | 1297 | 10.230 | -15.885 | 75.932 |
| ATOM 4921 C | ARG | 1297 | 14.593 | -20.073 | 79.469 |
| ATOM 4922 O | ARG | 1297 | 13.641 | -20.726 | 78.998 |
| ATOM 4923 N | THR | 1298 | 15.770 | -20.608 | 79.821 |
| ATOM 4924 CA | THR | 1298 | 16.118 | -22.027 | 79.666 |
| ATOM 4925 CB | THR | 1298 | 15.272 | -22.966 | 80.583 |
| ATOM 4926 OG1 | THR | 1298 | 13.875 | -22.886 | 80.254 |
| ATOM 4927 CG2 | THR | 1298 | 15.478 | -22.622 | 82.023 |
| ATOM 4928 C | THR | 1298 | 15.989 | -22.458 | 78.207 |
| ATOM 4929 O | THR | 1298 | 16.727 | -21.997 | 77.347 |
| ATOM 4930 N | ASP | 1299 | 15.070 | -23.357 | 77.921 |
| ATOM 4931 CA | ASP | 1299 | 14.899 | -23.747 | 76.554 |
| ATOM 4932 CB | ASP | 1299 | 15.163 | -25.247 | 76.330 |
| ATOM 4933 CG | ASP | 1299 | 14.591 | -26.138 | 77.422 |
| ATOM 4934 OD1 | ASP | 1299 | 15.390 | -26.905 | 78.015 |
| ATOM 4935 OD2 | ASP | 1299 | 13.350 | -26.109 | 77.646 |
| ATOM 4936 C | ASP | 1299 | 13.551 | -23.279 | 76.017 |
| ATOM 4937 O | ASP | 1299 | 13.511 | -22.664 | 74.939 |
| ATOM 4938 N | PHE | 1300 | 12.474 | -23.525 | 76.772 |
| ATOM 4939 CA | PHE | 1300 | 11.090 | -23.121 | 76.418 |
| ATOM 4940 CB | PHE | 1300 | 10.675 | -21.917 | 77.274 |
| ATOM 4941 CG | PHE | 1300 | 9.249 | -21.435 | 77.029 |
| ATOM 4942 CD1 | PHE | 1300 | 8.162 | -22.293 | 77.174 |

FIGURE 1ZZZZ

|  |  | Residue |  |  |  |
|---|---|---|---|---|---|
| Atom |  | AA No. | X | Y | Z |
| ATOM | 4943 CD2 | PHE 1300 | 9.002 | -20.098 | 76.735 |
| ATOM | 4944 CE1 | PHE 1300 | 6.872 | -21.830 | 77.041 |
| ATOM | 4945 CE2 | PHE 1300 | 7.701 | -19.628 | 76.601 |
| ATOM | 4946 CZ | PHE 1300 | 6.639 | -20.500 | 76.758 |
| ATOM | 4947 C | PHE 1300 | 10.696 | -22.826 | 74.947 |
| ATOM | 4948 O | PHE 1300 | 9.836 | -23.504 | 74.371 |
| ATOM | 4949 N | ASP 1301 | 11.275 | -21.758 | 74.391 |
| ATOM | 4950 CA | ASP 1301 | 11.012 | -21.304 | 73.031 |
| ATOM | 4951 CB | ASP 1301 | 11.687 | -19.975 | 72.812 |
| ATOM | 4952 CG | ASP 1301 | 11.315 | -18.986 | 73.872 |
| ATOM | 4953 OD1 | ASP 1301 | 12.118 | -18.824 | 74.831 |
| ATOM | 4954 OD2 | ASP 1301 | 10.199 | -18.414 | 73.757 |
| ATOM | 4955 C | ASP 1301 | 11.396 | -22.279 | 71.951 |
| ATOM | 4956 O | ASP 1301 | 10.527 | -22.701 | 71.183 |
| ATOM | 4957 N | LEU 1302 | 12.675 | -22.635 | 71.862 |
| ATOM | 4958 CA | LEU 1302 | 13.062 | -23.588 | 70.840 |
| ATOM | 4959 CB | LEU 1302 | 14.480 | -24.103 | 71.014 |
| ATOM | 4960 CG | LEU 1302 | 15.638 | -23.149 | 70.876 |
| ATOM | 4961 CD1 | LEU 1302 | 15.361 | -22.163 | 69.749 |
| ATOM | 4962 CD2 | LEU 1302 | 15.798 | -22.450 | 72.193 |
| ATOM | 4963 C | LEU 1302 | 12.121 | -24.743 | 71.031 |
| ATOM | 4964 O | LEU 1302 | 11.408 | -25.119 | 70.107 |
| ATOM | 4965 N | ALA 1303 | 12.001 | -25.169 | 72.285 |
| ATOM | 4966 CA | ALA 1303 | 11.153 | -26.296 | 72.664 |
| ATOM | 4967 CB | ALA 1303 | 11.473 | -26.743 | 74.087 |
| ATOM | 4968 C | ALA 1303 | 9.647 | -26.112 | 72.489 |
| ATOM | 4969 O | ALA 1303 | 8.896 | -27.087 | 72.588 |
| ATOM | 4970 N | ALA 1304 | 9.197 | -24.877 | 72.282 |
| ATOM | 4971 CA | ALA 1304 | 7.770 | -24.618 | 72.062 |
| ATOM | 4972 CB | ALA 1304 | 7.410 | -23.197 | 72.487 |
| ATOM | 4973 C | ALA 1304 | 7.500 | -24.813 | 70.566 |
| ATOM | 4974 O | ALA 1304 | 6.427 | -25.282 | 70.165 |
| ATOM | 4975 N | HIS 1305 | 8.516 | -24.484 | 69.764 |
| ATOM | 4976 CA | HIS 1305 | 8.496 | -24.591 | 68.319 |
| ATOM | 4977 CB | HIS 1305 | 9.583 | -23.706 | 67.766 |
| ATOM | 4978 CG | HIS 1305 | 9.313 | -22.248 | 67.947 |
| ATOM | 4979 CD2 | HIS 1305 | 10.153 | -21.197 | 68.101 |
| ATOM | 4980 ND1 | HIS 1305 | 8.040 | -21.723 | 67.923 |
| ATOM | 4981 CE1 | HIS 1305 | 8.108 | -20.411 | 68.048 |
| ATOM | 4982 NE2 | HIS 1305 | 9.378 | -20.068 | 68.158 |
| ATOM | 4983 C | HIS 1305 | 8.765 | -26.015 | 67.951 |
| ATOM | 4984 O | HIS 1305 | 7.979 | -26.631 | 67.272 |
| ATOM | 4985 N | ALA 1306 | 9.880 | -26.528 | 68.442 |
| ATOM | 4986 CA | ALA 1306 | 10.302 | -27.904 | 68.233 |
| ATOM | 4987 CB | ALA 1306 | 11.466 | -28.238 | 69.148 |
| ATOM | 4988 C | ALA 1306 | 9.173 | -28.871 | 68.520 |
| ATOM | 4989 O | ALA 1306 | 9.158 | -29.996 | 68.025 |
| ATOM | 4990 N | GLU 1307 | 8.267 | -28.467 | 69.393 |

FIGURE 1AAAAA

| Atom | | AA | Residue No. | X | Y | Z |
|---|---|---|---|---|---|---|
| ATOM | 4991 | CA | GLU 1307 | 7.153 | -29.333 | 69.737 |
| ATOM | 4992 | CB | GLU 1307 | 6.851 | -29.304 | 71.247 |
| ATOM | 4993 | CG | GLU 1307 | 5.717 | -30.260 | 71.698 |
| ATOM | 4994 | CD | GLU 1307 | 4.365 | -29.550 | 71.929 |
| ATOM | 4995 | OE1 | GLU 1307 | 4.116 | -29.111 | 73.081 |
| ATOM | 4996 | OE2 | GLU 1307 | 3.541 | -29.457 | 70.976 |
| ATOM | 4997 | C | GLU 1307 | 5.930 | -28.923 | 68.995 |
| ATOM | 4998 | O | GLU 1307 | 5.440 | -29.672 | 68.154 |
| ATOM | 4999 | N | HIS 1308 | 5.433 | -27.735 | 69.333 |
| ATOM | 5000 | CA | HIS 1308 | 4.231 | -27.201 | 68.723 |
| ATOM | 5001 | CB | HIS 1308 | 3.920 | -25.824 | 69.291 |
| ATOM | 5002 | CG | HIS 1308 | 2.674 | -25.204 | 68.738 |
| ATOM | 5003 | CD2 | HIS 1308 | 1.379 | -25.300 | 69.135 |
| ATOM | 5004 | ND1 | HIS 1308 | 2.687 | -24.305 | 67.691 |
| ATOM | 5005 | CE1 | HIS 1308 | 1.458 | -23.865 | 67.475 |
| ATOM | 5006 | NE2 | HIS 1308 | 0.644 | -24.453 | 68.337 |
| ATOM | 5007 | C | HIS 1308 | 4.256 | -27.166 | 67.197 |
| ATOM | 5008 | O | HIS 1308 | 3.197 | -27.073 | 66.588 |
| ATOM | 5009 | N | SER 1309 | 5.443 | -27.240 | 66.584 |
| ATOM | 5010 | CA | SER 1309 | 5.548 | -27.254 | 65.119 |
| ATOM | 5011 | CB | SER 1309 | 5.542 | -25.839 | 64.573 |
| ATOM | 5012 | OG | SER 1309 | 4.281 | -25.238 | 64.836 |
| ATOM | 5013 | C | SER 1309 | 6.642 | -28.114 | 64.452 |
| ATOM | 5014 | O | SER 1309 | 7.695 | -27.624 | 64.027 |
| ATOM | 5015 | N | GLY 1310 | 6.350 | -29.414 | 64.420 |
| ATOM | 5016 | CA | GLY 1310 | 7.169 | -30.451 | 63.816 |
| ATOM | 5017 | C | GLY 1310 | 8.672 | -30.652 | 63.940 |
| ATOM | 5018 | O | GLY 1310 | 9.149 | -31.753 | 64.234 |
| ATOM | 5019 | N | GLU 1311 | 9.412 | -29.596 | 63.659 |
| ATOM | 5020 | CA | GLU 1311 | 10.860 | -29.612 | 63.629 |
| ATOM | 5021 | CB | GLU 1311 | 11.364 | -28.163 | 63.561 |
| ATOM | 5022 | CG | GLU 1311 | 12.587 | -27.959 | 62.640 |
| ATOM | 5023 | CD | GLU 1311 | 12.298 | -28.201 | 61.141 |
| ATOM | 5024 | OE1 | GLU 1311 | 13.157 | -27.806 | 60.301 |
| ATOM | 5025 | OE2 | GLU 1311 | 11.236 | -28.783 | 60.795 |
| ATOM | 5026 | C | GLU 1311 | 11.729 | -30.464 | 64.564 |
| ATOM | 5027 | O | GLU 1311 | 12.165 | -31.542 | 64.177 |
| ATOM | 5028 | N | ASP 1312 | 12.018 | -29.922 | 65.747 |
| ATOM | 5029 | CA | ASP 1312 | 12.884 | -30.490 | 66.807 |
| ATOM | 5030 | CB | ASP 1312 | 13.185 | -32.015 | 66.634 |
| ATOM | 5031 | CG | ASP 1312 | 14.573 | -32.314 | 66.040 |
| ATOM | 5032 | OD1 | ASP 1312 | 14.679 | -32.501 | 64.816 |
| ATOM | 5033 | OD2 | ASP 1312 | 15.555 | -32.410 | 66.799 |
| ATOM | 5034 | C | ASP 1312 | 14.151 | -29.608 | 66.779 |
| ATOM | 5035 | O | ASP 1312 | 14.589 | -29.191 | 65.699 |
| ATOM | 5036 | N | PHE 1313 | 14.708 | -29.261 | 67.938 |
| ATOM | 5037 | CA | PHE 1313 | 15.883 | -28.394 | 67.929 |
| ATOM | 5038 | CB | PHE 1313 | 15.442 | -26.948 | 68.238 |

FIGURE 1BBBBB

| Atom | | Residue AA | No. | X | Y | Z |
|---|---|---|---|---|---|---|
| ATOM | 5039 CG | PHE | 1313 | 14.483 | -26.335 | 67.217 |
| ATOM | 5040 CD1 | PHE | 1313 | 13.111 | -26.433 | 67.396 |
| ATOM | 5041 CD2 | PHE | 1313 | 14.957 | -25.569 | 66.142 |
| ATOM | 5042 CE1 | PHE | 1313 | 12.221 | -25.780 | 66.542 |
| ATOM | 5043 CE2 | PHE | 1313 | 14.073 | -24.909 | 65.281 |
| ATOM | 5044 CZ | PHE | 1313 | 12.707 | -25.014 | 65.484 |
| ATOM | 5045 C | PHE | 1313 | 17.072 | -28.797 | 68.840 |
| ATOM | 5046 O | PHE | 1313 | 17.964 | -27.990 | 69.109 |
| ATOM | 5047 N | ALA | 1314 | 17.122 | -30.050 | 69.259 |
| ATOM | 5048 CA | ALA | 1314 | 18.176 | -30.504 | 70.149 |
| ATOM | 5049 CB | ALA | 1314 | 17.845 | -31.863 | 70.684 |
| ATOM | 5050 C | ALA | 1314 | 19.543 | -30.534 | 69.516 |
| ATOM | 5051 O | ALA | 1314 | 19.698 | -30.995 | 68.409 |
| ATOM | 5052 N | TYR | 1315 | 20.536 | -30.034 | 70.237 |
| ATOM | 5053 CA | TYR | 1315 | 21.922 | -30.033 | 69.776 |
| ATOM | 5054 CB | TYR | 1315 | 22.742 | -29.055 | 70.607 |
| ATOM | 5055 CG | TYR | 1315 | 24.197 | -28.994 | 70.269 |
| ATOM | 5056 CD1 | TYR | 1315 | 25.103 | -29.796 | 70.918 |
| ATOM | 5057 CE1 | TYR | 1315 | 26.455 | -29.707 | 70.655 |
| ATOM | 5058 CD2 | TYR | 1315 | 24.669 | -28.096 | 69.337 |
| ATOM | 5059 CE2 | TYR | 1315 | 26.018 | -27.992 | 69.058 |
| ATOM | 5060 CZ | TYR | 1315 | 26.919 | -28.799 | 69.721 |
| ATOM | 5061 OH | TYR | 1315 | 28.280 | -28.679 | 69.461 |
| ATOM | 5062 C | TYR | 1315 | 22.398 | -31.445 | 70.030 |
| ATOM | 5063 O | TYR | 1315 | 21.736 | -32.194 | 70.740 |
| ATOM | 5064 N | ALA | 1316 | 23.532 | -31.829 | 69.470 |
| ATOM | 5065 CA | ALA | 1316 | 24.002 | -33.179 | 69.697 |
| ATOM | 5066 CB | ALA | 1316 | 23.523 | -34.086 | 68.593 |
| ATOM | 5067 C | ALA | 1316 | 25.507 | -33.252 | 69.832 |
| ATOM | 5068 O | ALA | 1316 | 26.208 | -33.142 | 68.823 |
| ATOM | 5069 N | ASP | 1317 | 25.982 | -33.431 | 71.077 |
| ATOM | 5070 CA | ASP | 1317 | 27.407 | -33.526 | 71.376 |
| ATOM | 5071 CB | ASP | 1317 | 28.173 | -32.703 | 70.337 |
| ATOM | 5072 CG | ASP | 1317 | 29.636 | -32.832 | 70.459 |
| ATOM | 5073 OD1 | ASP | 1317 | 30.238 | -32.060 | 71.243 |
| ATOM | 5074 OD2 | ASP | 1317 | 30.186 | -33.682 | 69.747 |
| ATOM | 5075 C | ASP | 1317 | 27.883 | -33.097 | 72.798 |
| ATOM | 5076 O | ASP | 1317 | 28.071 | -31.896 | 73.055 |
| ATOM | 5077 N | PRO | 1318 | 28.062 | -34.055 | 73.752 |
| ATOM | 5078 CD | PRO | 1318 | 27.798 | -35.506 | 73.702 |
| ATOM | 5079 CA | PRO | 1318 | 28.542 | -33.702 | 75.102 |
| ATOM | 5080 CB | PRO | 1318 | 27.800 | -34.711 | 75.993 |
| ATOM | 5081 CG | PRO | 1318 | 27.947 | -35.987 | 75.183 |
| ATOM | 5082 C | PRO | 1318 | 30.022 | -34.107 | 74.929 |
| ATOM | 5083 O | PRO | 1318 | 30.507 | -35.048 | 75.583 |
| ATOM | 5084 N | ALA | 1319 | 30.646 | -33.485 | 73.914 |
| ATOM | 5085 CA | ALA | 1319 | 32.032 | -33.732 | 73.448 |
| ATOM | 5086 CB | ALA | 1319 | 32.965 | -34.207 | 74.600 |

FIGURE 1CCCCC

| Atom | | AA | Residue No. | X | Y | Z |
|---|---|---|---|---|---|---|
| ATOM | 5087 C | ALA | 1319 | 31.971 | -34.801 | 72.338 |
| ATOM | 5088 O | ALA | 1319 | 32.704 | -34.747 | 71.334 |
| ATOM | 5089 N | THR | 1320 | 31.052 | -35.744 | 72.538 |
| ATOM | 5090 CA | THR | 1320 | 30.811 | -36.868 | 71.645 |
| ATOM | 5091 CB | THR | 1320 | 30.750 | -38.161 | 72.507 |
| ATOM | 5092 OG1 | THR | 1320 | 29.859 | -37.944 | 73.630 |
| ATOM | 5093 CG2 | THR | 1320 | 32.191 | -38.565 | 72.987 |
| ATOM | 5094 C | THR | 1320 | 29.459 | -36.642 | 70.954 |
| ATOM | 5095 O | THR | 1320 | 29.368 | -35.963 | 69.910 |
| ATOM | 5096 N | ASN | 1321 | 28.427 | -37.260 | 71.542 |
| ATOM | 5097 CA | ASN | 1321 | 27.042 | -37.123 | 71.106 |
| ATOM | 5098 CB | ASN | 1321 | 26.688 | -37.955 | 69.849 |
| ATOM | 5099 CG | ASN | 1321 | 25.936 | -37.097 | 68.757 |
| ATOM | 5100 OD1 | ASN | 1321 | 24.691 | -37.158 | 68.597 |
| ATOM | 5101 ND2 | ASN | 1321 | 26.705 | -36.277 | 68.037 |
| ATOM | 5102 C | ASN | 1321 | 26.125 | -37.455 | 72.290 |
| ATOM | 5103 O | ASN | 1321 | 26.423 | -38.394 | 73.068 |
| ATOM | 5104 N | ALA | 1322 | 25.258 | -36.455 | 72.559 |
| ATOM | 5105 CA | ALA | 1322 | 24.187 | -36.407 | 73.584 |
| ATOM | 5106 CB | ALA | 1322 | 24.692 | -35.920 | 74.977 |
| ATOM | 5107 C | ALA | 1322 | 23.262 | -35.356 | 72.990 |
| ATOM | 5108 O | ALA | 1322 | 23.738 | -34.316 | 72.524 |
| ATOM | 5109 N | ALA | 1323 | 21.973 | -35.671 | 72.923 |
| ATOM | 5110 CA | ALA | 1323 | 20.968 | -34.762 | 72.386 |
| ATOM | 5111 CB | ALA | 1323 | 20.000 | -35.549 | 71.500 |
| ATOM | 5112 C | ALA | 1323 | 20.230 | -34.031 | 73.558 |
| ATOM | 5113 O | ALA | 1323 | 19.769 | -34.680 | 74.527 |
| ATOM | 5114 N | TYR | 1324 | 20.180 | -32.691 | 73.490 |
| ATOM | 5115 CA | TYR | 1324 | 19.554 | -31.841 | 74.510 |
| ATOM | 5116 CB | TYR | 1324 | 20.496 | -31.636 | 75.704 |
| ATOM | 5117 CG | TYR | 1324 | 21.925 | -31.260 | 75.341 |
| ATOM | 5118 CD1 | TYR | 1324 | 22.839 | -32.242 | 74.998 |
| ATOM | 5119 CE1 | TYR | 1324 | 24.155 | -31.937 | 74.748 |
| ATOM | 5120 CD2 | TYR | 1324 | 22.373 | -29.949 | 75.411 |
| ATOM | 5121 CE2 | TYR | 1324 | 23.687 | -29.629 | 75.166 |
| ATOM | 5122 CZ | TYR | 1324 | 24.576 | -30.629 | 74.843 |
| ATOM | 5123 OH | TYR | 1324 | 25.916 | -30.362 | 74.688 |
| ATOM | 5124 C | TYR | 1324 | 19.305 | -30.484 | 73.912 |
| ATOM | 5125 O | TYR | 1324 | 20.255 | -29.818 | 73.509 |
| ATOM | 5126 N | ILE | 1325 | 18.051 | -30.058 | 73.854 |
| ATOM | 5127 CA | ILE | 1325 | 17.736 | -28.740 | 73.303 |
| ATOM | 5128 CB | ILE | 1325 | 16.252 | -28.496 | 73.329 |
| ATOM | 5129 CG2 | ILE | 1325 | 15.724 | -28.711 | 74.729 |
| ATOM | 5130 CG1 | ILE | 1325 | 15.953 | -27.089 | 72.867 |
| ATOM | 5131 CD1 | ILE | 1325 | 14.533 | -26.909 | 72.555 |
| ATOM | 5132 C | ILE | 1325 | 18.465 | -27.685 | 74.136 |
| ATOM | 5133 O | ILE | 1325 | 18.545 | -27.801 | 75.360 |
| ATOM | 5134 N | PRO | 1326 | 19.038 | -26.670 | 73.483 |

FIGURE 1DDDDD

|      |      |     | Residue |        |         |        |
|------|------|-----|-----|-----|--------|---------|--------|
|      | Atom |     | AA  | No. | X      | Y       | Z      |
| ATOM | 5135 | CD  | PRO | 1326 | 19.185 | -26.519 | 72.034 |
| ATOM | 5136 | CA  | PRO | 1326 | 19.774 | -25.614 | 74.185 |
| ATOM | 5137 | CB  | PRO | 1326 | 20.433 | -24.860 | 73.043 |
| ATOM | 5138 | CG  | PRO | 1326 | 20.505 | -25.888 | 71.958 |
| ATOM | 5139 | C   | PRO | 1326 | 19.008 | -24.666 | 75.111 |
| ATOM | 5140 | O   | PRO | 1326 | 17.783 | -24.560 | 75.069 |
| ATOM | 5141 | N   | TYR | 1327 | 19.759 | -23.956 | 75.936 |
| ATOM | 5142 | CA  | TYR | 1327 | 19.191 | -23.011 | 76.867 |
| ATOM | 5143 | CB  | TYR | 1327 | 19.848 | -23.174 | 78.227 |
| ATOM | 5144 | CG  | TYR | 1327 | 19.118 | -24.029 | 79.234 |
| ATOM | 5145 | CD1 | TYR | 1327 | 19.138 | -23.700 | 80.596 |
| ATOM | 5146 | CE1 | TYR | 1327 | 18.547 | -24.521 | 81.552 |
| ATOM | 5147 | CD2 | TYR | 1327 | 18.477 | -25.196 | 78.854 |
| ATOM | 5148 | CE2 | TYR | 1327 | 17.883 | -26.028 | 79.806 |
| ATOM | 5149 | CZ  | TYR | 1327 | 17.926 | -25.686 | 81.150 |
| ATOM | 5150 | OH  | TYR | 1327 | 17.365 | -26.522 | 82.085 |
| ATOM | 5151 | C   | TYR | 1327 | 19.599 | -21.662 | 76.365 |
| ATOM | 5152 | O   | TYR | 1327 | 20.744 | -21.501 | 75.999 |
| ATOM | 5153 | N   | CYS | 1328 | 18.703 | -20.684 | 76.339 |
| ATOM | 5154 | CA  | CYS | 1328 | 19.112 | -19.356 | 75.897 |
| ATOM | 5155 | CB  | CYS | 1328 | 18.372 | -18.902 | 74.629 |
| ATOM | 5156 | SG  | CYS | 1328 | 16.696 | -18.266 | 74.798 |
| ATOM | 5157 | C   | CYS | 1328 | 19.019 | -18.307 | 76.995 |
| ATOM | 5158 | O   | CYS | 1328 | 18.500 | -18.570 | 78.079 |
| ATOM | 5159 | N   | ILE | 1329 | 19.574 | -17.135 | 76.709 |
| ATOM | 5160 | CA  | ILE | 1329 | 19.609 | -15.991 | 77.613 |
| ATOM | 5161 | CB  | ILE | 1329 | 21.031 | -15.795 | 78.181 |
| ATOM | 5162 | CG2 | ILE | 1329 | 21.168 | -14.438 | 78.753 |
| ATOM | 5163 | CG1 | ILE | 1329 | 21.367 | -16.853 | 79.228 |
| ATOM | 5164 | CD1 | ILE | 1329 | 21.987 | -18.107 | 78.705 |
| ATOM | 5165 | C   | ILE | 1329 | 19.284 | -14.799 | 76.718 |
| ATOM | 5166 | O   | ILE | 1329 | 20.034 | -14.514 | 75.824 |
| ATOM | 5167 | N   | GLU | 1330 | 18.206 | -14.079 | 76.941 |
| ATOM | 5168 | CA  | GLU | 1330 | 17.954 | -13.020 | 76.028 |
| ATOM | 5169 | CB  | GLU | 1330 | 16.576 | -13.172 | 75.387 |
| ATOM | 5170 | CG  | GLU | 1330 | 15.379 | -12.642 | 76.157 |
| ATOM | 5171 | CD  | GLU | 1330 | 14.124 | -12.570 | 75.294 |
| ATOM | 5172 | OE1 | GLU | 1330 | 13.620 | -11.466 | 75.044 |
| ATOM | 5173 | OE2 | GLU | 1330 | 13.631 | -13.619 | 74.845 |
| ATOM | 5174 | C   | GLU | 1330 | 18.191 | -11.621 | 76.469 |
| ATOM | 5175 | O   | GLU | 1330 | 17.347 | -11.006 | 77.065 |
| ATOM | 5176 | N   | PRO | 1331 | 19.390 | -11.113 | 76.251 |
| ATOM | 5177 | CD  | PRO | 1331 | 20.674 | -11.792 | 76.078 |
| ATOM | 5178 | CA  | PRO | 1331 | 19.614 | -9.740  | 76.658 |
| ATOM | 5179 | CB  | PRO | 1331 | 21.152 | -9.632  | 76.652 |
| ATOM | 5180 | CG  | PRO | 1331 | 21.594 | -10.652 | 75.765 |
| ATOM | 5181 | C   | PRO | 1331 | 18.944 | -8.724  | 75.709 |
| ATOM | 5182 | O   | PRO | 1331 | 19.624 | -8.009  | 74.983 |

FIGURE 1EEEEE

| Atom | Residue AA | No. | X | Y | Z |
|---|---|---|---|---|---|
| ATOM 5183 N | SER | 1332 | 17.614 | -8.659 | 75.732 |
| ATOM 5184 CA | SER | 1332 | 16.823 | -7.734 | 74.893 |
| ATOM 5185 CB | SER | 1332 | 15.325 | -7.979 | 75.115 |
| ATOM 5186 OG | SER | 1332 | 14.540 | -6.824 | 74.874 |
| ATOM 5187 C | SER | 1332 | 17.140 | -6.257 | 75.138 |
| ATOM 5188 O | SER | 1332 | 17.741 | -5.927 | 76.124 |
| ATOM 5189 N | LEU | 1333 | 16.672 | -5.356 | 74.290 |
| ATOM 5190 CA | LEU | 1333 | 16.968 | -3.948 | 74.479 |
| ATOM 5191 CB | LEU | 1333 | 18.310 | -3.603 | 73.831 |
| ATOM 5192 CG | LEU | 1333 | 18.994 | -2.329 | 74.347 |
| ATOM 5193 CD1 | LEU | 1333 | 18.905 | -2.277 | 75.854 |
| ATOM 5194 CD2 | LEU | 1333 | 20.454 | -2.215 | 73.894 |
| ATOM 5195 C | LEU | 1333 | 15.846 | -3.069 | 73.949 |
| ATOM 5196 O | LEU | 1333 | 14.689 | -3.451 | 74.001 |
| ATOM 5197 N | GLY | 1334 | 16.169 | -1.868 | 73.500 |
| ATOM 5198 CA | GLY | 1334 | 15.162 | -0.970 | 72.967 |
| ATOM 5199 C | GLY | 1334 | 16.001 | 0.111 | 72.335 |
| ATOM 5200 O | GLY | 1334 | 16.610 | 0.894 | 73.056 |
| ATOM 5201 N | ALA | 1335 | 16.138 | 0.094 | 71.009 |
| ATOM 5202 CA | ALA | 1335 | 16.960 | 1.082 | 70.330 |
| ATOM 5203 CB | ALA | 1335 | 17.022 | 0.786 | 68.865 |
| ATOM 5204 C | ALA | 1335 | 16.353 | 2.440 | 70.588 |
| ATOM 5205 O | ALA | 1335 | 17.055 | 3.390 | 70.978 |
| ATOM 5206 N | ASP | 1336 | 15.035 | 2.507 | 70.433 |
| ATOM 5207 CA | ASP | 1336 | 14.352 | 3.748 | 70.676 |
| ATOM 5208 CB | ASP | 1336 | 12.833 | 3.594 | 70.454 |
| ATOM 5209 CG | ASP | 1336 | 12.407 | 3.743 | 68.973 |
| ATOM 5210 OD1 | ASP | 1336 | 11.835 | 4.793 | 68.584 |
| ATOM 5211 OD2 | ASP | 1336 | 12.582 | 2.779 | 68.212 |
| ATOM 5212 C | ASP | 1336 | 14.724 | 4.222 | 72.111 |
| ATOM 5213 O | ASP | 1336 | 15.316 | 5.290 | 72.244 |
| ATOM 5214 N | ARG | 1337 | 14.514 | 3.392 | 73.148 |
| ATOM 5215 CA | ARG | 1337 | 14.842 | 3.749 | 74.556 |
| ATOM 5216 CB | ARG | 1337 | 14.397 | 2.667 | 75.546 |
| ATOM 5217 CG | ARG | 1337 | 12.918 | 2.579 | 75.815 |
| ATOM 5218 CD | ARG | 1337 | 12.645 | 2.204 | 77.286 |
| ATOM 5219 NE | ARG | 1337 | 11.473 | 1.342 | 77.438 |
| ATOM 5220 CZ | ARG | 1337 | 11.517 | 0.012 | 77.360 |
| ATOM 5221 NH1 | ARG | 1337 | 12.680 | -0.613 | 77.154 |
| ATOM 5222 NH2 | ARG | 1337 | 10.389 | -0.693 | 77.385 |
| ATOM 5223 C | ARG | 1337 | 16.316 | 4.045 | 74.842 |
| ATOM 5224 O | ARG | 1337 | 16.654 | 5.114 | 75.327 |
| ATOM 5225 N | VAL | 1338 | 17.190 | 3.084 | 74.580 |
| ATOM 5226 CA | VAL | 1338 | 18.606 | 3.270 | 74.818 |
| ATOM 5227 CB | VAL | 1338 | 19.453 | 2.188 | 74.118 |
| ATOM 5228 CG1 | VAL | 1338 | 20.911 | 2.395 | 74.399 |
| ATOM 5229 CG2 | VAL | 1338 | 19.084 | 0.869 | 74.622 |
| ATOM 5230 C | VAL | 1338 | 19.044 | 4.651 | 74.356 |

FIGURE 1FFFFF

|  | Residue | | | | |
|---|---|---|---|---|---|
| Atom | AA | No. | X | Y | Z |
| ATOM 5231 O | VAL | 1338 | 19.937 | 5.245 | 74.953 |
| ATOM 5232 N | THR | 1339 | 18.402 | 5.185 | 73.317 |
| ATOM 5233 CA | THR | 1339 | 18.789 | 6.514 | 72.836 |
| ATOM 5234 CB | THR | 1339 | 18.508 | 6.749 | 71.281 |
| ATOM 5235 OG1 | THR | 1339 | 17.125 | 6.977 | 71.014 |
| ATOM 5236 CG2 | THR | 1339 | 18.918 | 5.556 | 70.513 |
| ATOM 5237 C | THR | 1339 | 18.246 | 7.635 | 73.751 |
| ATOM 5238 O | THR | 1339 | 18.965 | 8.601 | 74.052 |
| ATOM 5239 N | LEU | 1340 | 17.037 | 7.456 | 74.287 |
| ATOM 5240 CA | LEU | 1340 | 16.442 | 8.466 | 75.154 |
| ATOM 5241 CB | LEU | 1340 | 15.052 | 8.049 | 75.588 |
| ATOM 5242 CG | LEU | 1340 | 14.254 | 9.105 | 76.336 |
| ATOM 5243 CD1 | LEU | 1340 | 14.454 | 10.426 | 75.668 |
| ATOM 5244 CD2 | LEU | 1340 | 12.763 | 8.737 | 76.371 |
| ATOM 5245 C | LEU | 1340 | 17.336 | 8.628 | 76.346 |
| ATOM 5246 O | LEU | 1340 | 17.590 | 9.743 | 76.787 |
| ATOM 5247 N | ALA | 1341 | 17.866 | 7.496 | 76.803 |
| ATOM 5248 CA | ALA | 1341 | 18.771 | 7.454 | 77.934 |
| ATOM 5249 CB | ALA | 1341 | 19.303 | 6.054 | 78.140 |
| ATOM 5250 C | ALA | 1341 | 19.887 | 8.382 | 77.574 |
| ATOM 5251 O | ALA | 1341 | 19.893 | 9.536 | 77.980 |
| ATOM 5252 N | PHE | 1342 | 20.743 | 7.896 | 76.688 |
| ATOM 5253 CA | PHE | 1342 | 21.887 | 8.636 | 76.199 |
| ATOM 5254 CB | PHE | 1342 | 22.430 | 7.960 | 74.949 |
| ATOM 5255 CG | PHE | 1342 | 23.215 | 6.701 | 75.214 |
| ATOM 5256 CD1 | PHE | 1342 | 22.661 | 5.455 | 74.943 |
| ATOM 5257 CD2 | PHE | 1342 | 24.546 | 6.772 | 75.646 |
| ATOM 5258 CE1 | PHE | 1342 | 23.406 | 4.307 | 75.086 |
| ATOM 5259 CE2 | PHE | 1342 | 25.310 | 5.621 | 75.793 |
| ATOM 5260 CZ | PHE | 1342 | 24.737 | 4.384 | 75.510 |
| ATOM 5261 C | PHE | 1342 | 21.588 | 10.112 | 75.912 |
| ATOM 5262 O | PHE | 1342 | 22.479 | 10.954 | 76.082 |
| ATOM 5263 N | LEU | 1343 | 20.357 | 10.434 | 75.493 |
| ATOM 5264 CA | LEU | 1343 | 19.991 | 11.837 | 75.236 |
| ATOM 5265 CB | LEU | 1343 | 18.655 | 11.943 | 74.474 |
| ATOM 5266 CG | LEU | 1343 | 18.415 | 13.071 | 73.444 |
| ATOM 5267 CD1 | LEU | 1343 | 16.935 | 13.188 | 73.180 |
| ATOM 5268 CD2 | LEU | 1343 | 18.950 | 14.414 | 73.910 |
| ATOM 5269 C | LEU | 1343 | 19.875 | 12.563 | 76.601 |
| ATOM 5270 O | LEU | 1343 | 20.593 | 13.545 | 76.882 |
| ATOM 5271 N | CYS | 1344 | 19.007 | 12.039 | 77.463 |
| ATOM 5272 CA | CYS | 1344 | 18.796 | 12.607 | 78.781 |
| ATOM 5273 CB | CYS | 1344 | 17.807 | 11.754 | 79.541 |
| ATOM 5274 SG | CYS | 1344 | 16.138 | 11.957 | 78.978 |
| ATOM 5275 C | CYS | 1344 | 20.070 | 12.687 | 79.583 |
| ATOM 5276 O | CYS | 1344 | 20.470 | 13.745 | 79.762 |
| ATOM 5278 CA | ASP | 1345 | 21.910 | 11.380 | 80.511 |

FIGURE 1GGGGG

| Atom | | Residue AA | No. | X | Y | Z |
|---|---|---|---|---|---|---|
| ATOM | 5279 | CB | ASP 1345 | 22.456 | 9.983 | 80.256 |
| ATOM | 5280 | CG | ASP 1345 | 23.471 | 9.567 | 81.266 |
| ATOM | 5281 | OD1 | ASP 1345 | 24.693 | 9.734 | 81.010 |
| ATOM | 5282 | OD2 | ASP 1345 | 23.021 | 9.061 | 82.310 |
| ATOM | 5283 | C | ASP 1345 | 22.955 | 12.387 | 80.078 |
| ATOM | 5284 | O | ASP 1345 | 23.842 | 12.760 | 80.853 |
| ATOM | 5285 | N | ALA 1346 | 22.854 | 12.807 | 78.827 |
| ATOM | 5286 | CA | ALA 1346 | 23.804 | 13.749 | 78.270 |
| ATOM | 5287 | CB | ALA 1346 | 24.129 | 13.365 | 76.858 |
| ATOM | 5288 | C | ALA 1346 | 23.350 | 15.194 | 78.339 |
| ATOM | 5289 | O | ALA 1346 | 24.184 | 16.114 | 78.255 |
| ATOM | 5290 | N | TYR 1347 | 22.038 | 15.398 | 78.462 |
| ATOM | 5291 | CA | TYR 1347 | 21.516 | 16.743 | 78.570 |
| ATOM | 5292 | CB | TYR 1347 | 20.035 | 16.740 | 78.849 |
| ATOM | 5293 | CG | TYR 1347 | 19.546 | 18.131 | 78.839 |
| ATOM | 5294 | CD1 | TYR 1347 | 19.228 | 18.798 | 80.006 |
| ATOM | 5295 | CE1 | TYR 1347 | 18.840 | 20.150 | 79.979 |
| ATOM | 5296 | CD2 | TYR 1347 | 19.471 | 18.819 | 77.650 |
| ATOM | 5297 | CE2 | TYR 1347 | 19.093 | 20.153 | 77.586 |
| ATOM | 5298 | CZ | TYR 1347 | 18.775 | 20.827 | 78.742 |
| ATOM | 5299 | OH | TYR 1347 | 18.387 | 22.160 | 78.617 |
| ATOM | 5300 | C | TYR 1347 | 22.213 | 17.394 | 79.744 |
| ATOM | 5301 | O | TYR 1347 | 22.738 | 16.700 | 80.623 |
| ATOM | 5302 | N | ASP 1348 | 22.198 | 18.715 | 79.794 |
| ATOM | 5303 | CA | ASP 1348 | 22.837 | 19.442 | 80.892 |
| ATOM | 5304 | CB | ASP 1348 | 24.368 | 19.200 | 80.875 |
| ATOM | 5305 | CG | ASP 1348 | 25.113 | 19.932 | 82.018 |
| ATOM | 5306 | OD1 | ASP 1348 | 25.080 | 19.447 | 83.186 |
| ATOM | 5307 | OD2 | ASP 1348 | 25.736 | 20.990 | 81.738 |
| ATOM | 5308 | C | ASP 1348 | 22.536 | 20.924 | 80.690 |
| ATOM | 5309 | O | ASP 1348 | 21.994 | 21.304 | 79.659 |
| ATOM | 5310 | N | GLU 1349 | 22.819 | 21.745 | 81.694 |
| ATOM | 5311 | CA | GLU 1349 | 22.634 | 23.188 | 81.610 |
| ATOM | 5312 | CB | GLU 1349 | 21.337 | 23.616 | 82.303 |
| ATOM | 5313 | CG | GLU 1349 | 20.089 | 23.055 | 81.585 |
| ATOM | 5314 | CD | GLU 1349 | 18.739 | 23.367 | 82.250 |
| ATOM | 5315 | OE1 | GLU 1349 | 17.858 | 24.011 | 81.609 |
| ATOM | 5316 | OE2 | GLU 1349 | 18.546 | 22.923 | 83.404 |
| ATOM | 5317 | C | GLU 1349 | 23.872 | 23.646 | 82.345 |
| ATOM | 5318 | O | GLU 1349 | 24.161 | 23.172 | 83.435 |
| ATOM | 5319 | N | GLU 1350 | 24.687 | 24.433 | 81.673 |
| ATOM | 5320 | CA | GLU 1350 | 25.929 | 24.880 | 82.255 |
| ATOM | 5321 | CB | GLU 1350 | 27.093 | 24.568 | 81.320 |
| ATOM | 5322 | CG | GLU 1350 | 27.948 | 23.395 | 81.797 |
| ATOM | 5323 | CD | GLU 1350 | 29.432 | 23.525 | 81.424 |
| ATOM | 5324 | OE1 | GLU 1350 | 30.057 | 22.486 | 81.081 |
| ATOM | 5325 | OE2 | GLU 1350 | 29.974 | 24.659 | 81.499 |
| ATOM | 5326 | C | GLU 1350 | 26.044 | 26.319 | 82.685 |

FIGURE 1HHHHH

| Atom | | AA | Residue No. | X | Y | Z |
|---|---|---|---|---|---|---|
| ATOM | 5327 | O | GLU | 1350 | 25.035 | 27.036 | 82.836 |
| ATOM | 5328 | N | GLY | 1351 | 27.317 | 26.656 | 82.954 |
| ATOM | 5329 | CA | GLY | 1351 | 27.797 | 27.970 | 83.371 |
| ATOM | 5330 | C | GLY | 1351 | 26.944 | 28.883 | 84.239 |
| ATOM | 5331 | O | GLY | 1351 | 27.299 | 29.131 | 85.406 |
| ATOM | 5332 | N | VAL | 1352 | 25.860 | 29.386 | 83.630 |
| ATOM | 5333 | CA | VAL | 1352 | 24.867 | 30.315 | 84.201 |
| ATOM | 5334 | CB | VAL | 1352 | 24.265 | 29.785 | 85.575 |
| ATOM | 5335 | CG1 | VAL | 1352 | 23.280 | 30.844 | 86.245 |
| ATOM | 5336 | CG2 | VAL | 1352 | 23.560 | 28.416 | 85.319 |
| ATOM | 5337 | C | VAL | 1352 | 25.311 | 31.817 | 84.229 |
| ATOM | 5338 | O | VAL | 1352 | 26.451 | 32.133 | 84.703 |
| ATOM | 5339 | OT | VAL | 1352 | 24.514 | 32.656 | 83.680 |
| ATOM | 5340 | CB | ALA | 1356 | 26.519 | 35.797 | 83.628 |
| ATOM | 5341 | C | ALA | 1356 | 26.395 | 34.681 | 81.284 |
| ATOM | 5342 | O | ALA | 1356 | 26.040 | 34.653 | 80.073 |
| ATOM | 5343 | N | ALA | 1356 | 24.298 | 35.160 | 82.580 |
| ATOM | 5344 | CA | ALA | 1356 | 25.692 | 35.645 | 82.288 |
| ATOM | 5345 | N | ALA | 1357 | 27.304 | 33.846 | 81.825 |
| ATOM | 5346 | CA | ALA | 1357 | 28.098 | 32.840 | 81.084 |
| ATOM | 5347 | CB | ALA | 1357 | 29.530 | 32.729 | 81.727 |
| ATOM | 5348 | C | ALA | 1357 | 27.414 | 31.429 | 80.990 |
| ATOM | 5349 | O | ALA | 1357 | 28.072 | 30.381 | 81.175 |
| ATOM | 5350 | N | ALA | 1358 | 26.122 | 31.421 | 80.636 |
| ATOM | 5351 | CA | ALA | 1358 | 25.349 | 30.184 | 80.512 |
| ATOM | 5352 | CB | ALA | 1358 | 23.862 | 30.496 | 80.388 |
| ATOM | 5353 | C | ALA | 1358 | 25.803 | 29.285 | 79.355 |
| ATOM | 5354 | O | ALA | 1358 | 26.817 | 29.568 | 78.704 |
| ATOM | 5355 | N | ARG | 1359 | 25.034 | 28.220 | 79.097 |
| ATOM | 5356 | CA | ARG | 1359 | 25.337 | 27.251 | 78.039 |
| ATOM | 5357 | CB | ARG | 1359 | 26.823 | 26.832 | 78.127 |
| ATOM | 5358 | CG | ARG | 1359 | 27.215 | 25.595 | 77.302 |
| ATOM | 5359 | CD | ARG | 1359 | 28.726 | 25.450 | 77.140 |
| ATOM | 5360 | NE | ARG | 1359 | 29.148 | 24.078 | 77.400 |
| ATOM | 5361 | CZ | ARG | 1359 | 30.188 | 23.473 | 76.838 |
| ATOM | 5362 | NH1 | ARG | 1359 | 30.940 | 24.134 | 75.974 |
| ATOM | 5363 | NH2 | ARG | 1359 | 30.462 | 22.198 | 77.130 |
| ATOM | 5364 | C | ARG | 1359 | 24.483 | 25.996 | 78.204 |
| ATOM | 5365 | O | ARG | 1359 | 24.199 | 25.610 | 79.336 |
| ATOM | 5366 | N | THR | 1360 | 24.003 | 25.418 | 77.096 |
| ATOM | 5367 | CA | THR | 1360 | 23.254 | 24.137 | 77.127 |
| ATOM | 5368 | CB | THR | 1360 | 21.906 | 24.102 | 76.305 |
| ATOM | 5369 | OG1 | THR | 1360 | 20.864 | 24.793 | 77.006 |
| ATOM | 5370 | CG2 | THR | 1360 | 21.452 | 22.650 | 76.105 |
| ATOM | 5371 | C | THR | 1360 | 24.215 | 23.223 | 76.391 |
| ATOM | 5372 | O | THR | 1360 | 24.685 | 23.580 | 75.309 |
| ATOM | 5373 | N | VAL | 1361 | 24.558 | 22.087 | 76.984 |
| ATOM | 5374 | CA | VAL | 1361 | 25.472 | 21.167 | 76.332 |

FIGURE 1IIIII

| Atom | | Residue AA | No. | X | Y | Z |
|---|---|---|---|---|---|---|
| ATOM | 5375 CB | VAL | 1361 | 26.789 | 20.990 | 77.107 |
| ATOM | 5376 CG1 | VAL | 1361 | 27.929 | 20.662 | 76.167 |
| ATOM | 5377 CG2 | VAL | 1361 | 27.085 | 22.193 | 77.882 |
| ATOM | 5378 C | VAL | 1361 | 24.795 | 19.826 | 76.333 |
| ATOM | 5379 O | VAL | 1361 | 23.749 | 19.651 | 76.960 |
| ATOM | 5380 N | LEU | 1362 | 25.329 | 18.933 | 75.516 |
| ATOM | 5381 CA | LEU | 1362 | 24.878 | 17.570 | 75.442 |
| ATOM | 5382 CB | LEU | 1362 | 24.070 | 17.267 | 74.176 |
| ATOM | 5383 CG | LEU | 1362 | 22.608 | 17.734 | 74.078 |
| ATOM | 5384 CD1 | LEU | 1362 | 21.766 | 16.777 | 73.257 |
| ATOM | 5385 CD2 | LEU | 1362 | 22.009 | 17.813 | 75.426 |
| ATOM | 5386 C | LEU | 1362 | 26.257 | 16.996 | 75.363 |
| ATOM | 5387 O | LEU | 1362 | 27.112 | 17.519 | 74.660 |
| ATOM | 5388 N | HIS | 1363 | 26.535 | 16.059 | 76.244 |
| ATOM | 5389 CA | HIS | 1363 | 27.843 | 15.448 | 76.248 |
| ATOM | 5390 CB | HIS | 1363 | 28.445 | 15.489 | 77.668 |
| ATOM | 5391 CG | HIS | 1363 | 28.754 | 16.871 | 78.176 |
| ATOM | 5392 CD2 | HIS | 1363 | 29.909 | 17.580 | 78.186 |
| ATOM | 5393 ND1 | HIS | 1363 | 27.821 | 17.663 | 78.818 |
| ATOM | 5394 CE1 | HIS | 1363 | 28.391 | 18.793 | 79.203 |
| ATOM | 5395 NE2 | HIS | 1363 | 29.659 | 18.767 | 78.829 |
| ATOM | 5396 C | HIS | 1363 | 27.739 | 14.000 | 75.723 |
| ATOM | 5397 O | HIS | 1363 | 27.637 | 13.050 | 76.527 |
| ATOM | 5398 N | PHE | 1364 | 27.703 | 13.841 | 74.386 |
| ATOM | 5399 CA | PHE | 1364 | 27.610 | 12.517 | 73.731 |
| ATOM | 5400 CB | PHE | 1364 | 27.058 | 12.639 | 72.308 |
| ATOM | 5401 CG | PHE | 1364 | 25.629 | 13.025 | 72.223 |
| ATOM | 5402 CD1 | PHE | 1364 | 25.259 | 14.219 | 71.625 |
| ATOM | 5403 CD2 | PHE | 1364 | 24.641 | 12.171 | 72.664 |
| ATOM | 5404 CE1 | PHE | 1364 | 23.922 | 14.556 | 71.457 |
| ATOM | 5405 CE2 | PHE | 1364 | 23.290 | 12.497 | 72.502 |
| ATOM | 5406 CZ | PHE | 1364 | 22.934 | 13.691 | 71.896 |
| ATOM | 5407 C | PHE | 1364 | 29.011 | 11.931 | 73.600 |
| ATOM | 5408 O | PHE | 1364 | 29.954 | 12.667 | 73.337 |
| ATOM | 5409 N | HIS | 1365 | 29.178 | 10.636 | 73.837 |
| ATOM | 5410 CA | HIS | 1365 | 30.489 | 10.038 | 73.631 |
| ATOM | 5411 CB | HIS | 1365 | 30.410 | 8.550 | 73.957 |
| ATOM | 5412 CG | HIS | 1365 | 31.624 | 7.782 | 73.544 |
| ATOM | 5413 CD2 | HIS | 1365 | 32.929 | 7.919 | 73.882 |
| ATOM | 5414 ND1 | HIS | 1365 | 31.576 | 6.765 | 72.618 |
| ATOM | 5415 CE1 | HIS | 1365 | 32.801 | 6.312 | 72.395 |
| ATOM | 5416 NE2 | HIS | 1365 | 33.640 | 6.996 | 73.151 |
| ATOM | 5417 C | HIS | 1365 | 30.703 | 10.247 | 72.116 |
| ATOM | 5418 O | HIS | 1365 | 29.766 | 10.050 | 71.358 |
| ATOM | 5419 N | PRO | 1366 | 31.912 | 10.633 | 71.641 |
| ATOM | 5420 CD | PRO | 1366 | 33.200 | 10.780 | 72.331 |
| ATOM | 5421 CA | PRO | 1366 | 32.112 | 10.837 | 70.197 |
| ATOM | 5422 CB | PRO | 1366 | 33.630 | 10.763 | 70.060 |

FIGURE 1JJJJJ

| Atom | | Residue AA | No. | X | Y | Z |
|---|---|---|---|---|---|---|
| ATOM | 5423 | CG | PRO | 1366 | 34.078 | 11.410 | 71.252 |
| ATOM | 5424 | C | PRO | 1366 | 31.419 | 9.797 | 69.306 |
| ATOM | 5425 | O | PRO | 1366 | 30.535 | 10.130 | 68.521 |
| ATOM | 5426 | N | ALA | 1367 | 31.758 | 8.529 | 69.511 |
| ATOM | 5427 | CA | ALA | 1367 | 31.190 | 7.424 | 68.755 |
| ATOM | 5428 | CB | ALA | 1367 | 31.938 | 6.145 | 69.100 |
| ATOM | 5429 | C | ALA | 1367 | 29.683 | 7.234 | 68.957 |
| ATOM | 5430 | O | ALA | 1367 | 29.164 | 6.138 | 68.795 |
| ATOM | 5431 | N | LEU | 1368 | 28.985 | 8.297 | 69.310 |
| ATOM | 5432 | CA | LEU | 1368 | 27.559 | 8.241 | 69.519 |
| ATOM | 5433 | CB | LEU | 1368 | 27.269 | 7.901 | 70.973 |
| ATOM | 5434 | CG | LEU | 1368 | 26.421 | 6.712 | 71.399 |
| ATOM | 5435 | CD1 | LEU | 1368 | 25.029 | 6.903 | 70.971 |
| ATOM | 5436 | CD2 | LEU | 1368 | 26.973 | 5.445 | 70.858 |
| ATOM | 5437 | C | LEU | 1368 | 27.011 | 9.624 | 69.195 |
| ATOM | 5438 | O | LEU | 1368 | 25.807 | 9.795 | 69.060 |
| ATOM | 5439 | N | ALA | 1369 | 27.897 | 10.611 | 69.089 |
| ATOM | 5440 | CA | ALA | 1369 | 27.509 | 11.980 | 68.785 |
| ATOM | 5441 | CB | ALA | 1369 | 28.678 | 12.888 | 68.961 |
| ATOM | 5442 | C | ALA | 1369 | 27.046 | 12.023 | 67.347 |
| ATOM | 5443 | O | ALA | 1369 | 27.663 | 11.399 | 66.488 |
| ATOM | 5444 | N | PRO | 1370 | 25.969 | 12.782 | 67.049 |
| ATOM | 5445 | CD | PRO | 1370 | 25.209 | 13.732 | 67.888 |
| ATOM | 5446 | CA | PRO | 1370 | 25.494 | 12.839 | 65.659 |
| ATOM | 5447 | CB | PRO | 1370 | 24.329 | 13.841 | 65.739 |
| ATOM | 5448 | CG | PRO | 1370 | 24.729 | 14.742 | 66.858 |
| ATOM | 5449 | C | PRO | 1370 | 26.596 | 13.261 | 64.663 |
| ATOM | 5450 | O | PRO | 1370 | 26.801 | 12.592 | 63.639 |
| ATOM | 5451 | N | TYR | 1371 | 27.278 | 14.373 | 64.959 |
| ATOM | 5452 | CA | TYR | 1371 | 28.368 | 14.869 | 64.115 |
| ATOM | 5453 | CB | TYR | 1371 | 28.232 | 16.367 | 63.834 |
| ATOM | 5454 | CG | TYR | 1371 | 27.079 | 16.743 | 62.936 |
| ATOM | 5455 | CD1 | TYR | 1371 | 27.197 | 16.696 | 61.545 |
| ATOM | 5456 | CE1 | TYR | 1371 | 26.143 | 17.065 | 60.713 |
| ATOM | 5457 | CD2 | TYR | 1371 | 25.884 | 17.165 | 63.472 |
| ATOM | 5458 | CE2 | TYR | 1371 | 24.828 | 17.533 | 62.658 |
| ATOM | 5459 | CZ | TYR | 1371 | 24.953 | 17.487 | 61.282 |
| ATOM | 5460 | OH | TYR | 1371 | 23.879 | 17.887 | 60.497 |
| ATOM | 5461 | C | TYR | 1371 | 29.659 | 14.618 | 64.861 |
| ATOM | 5462 | O | TYR | 1371 | 29.667 | 14.637 | 66.077 |
| ATOM | 5463 | N | LYS | 1372 | 30.752 | 14.408 | 64.149 |
| ATOM | 5464 | CA | LYS | 1372 | 32.000 | 14.134 | 64.820 |
| ATOM | 5465 | CB | LYS | 1372 | 32.751 | 13.018 | 64.127 |
| ATOM | 5466 | CG | LYS | 1372 | 31.986 | 11.734 | 64.116 |
| ATOM | 5467 | CD | LYS | 1372 | 31.736 | 11.246 | 65.509 |
| ATOM | 5468 | CE | LYS | 1372 | 30.296 | 10.763 | 65.660 |
| ATOM | 5469 | NZ | LYS | 1372 | 29.878 | 9.639 | 64.781 |
| ATOM | 5470 | C | LYS | 1372 | 32.873 | 15.349 | 64.924 |

FIGURE 1KKKKK

| Atom | | Residue AA | No. | X | Y | Z |
|---|---|---|---|---|---|---|
| ATOM | 5471 | O | LYS 1372 | 33.830 | 15.386 | 65.696 |
| ATOM | 5472 | N | ALA 1373 | 32.586 | 16.351 | 64.130 |
| ATOM | 5473 | CA | ALA 1373 | 33.368 | 17.560 | 64.204 |
| ATOM | 5474 | CB | ALA 1373 | 34.710 | 17.385 | 63.526 |
| ATOM | 5475 | C | ALA 1373 | 32.513 | 18.516 | 63.448 |
| ATOM | 5476 | O | ALA 1373 | 31.374 | 18.200 | 63.108 |
| ATOM | 5477 | N | ALA 1374 | 33.040 | 19.702 | 63.214 |
| ATOM | 5478 | CA | ALA 1374 | 32.324 | 20.723 | 62.466 |
| ATOM | 5479 | CB | ALA 1374 | 31.260 | 21.404 | 63.336 |
| ATOM | 5480 | C | ALA 1374 | 33.347 | 21.737 | 61.977 |
| ATOM | 5481 | O | ALA 1374 | 34.245 | 22.152 | 62.725 |
| ATOM | 5482 | N | ILE 1375 | 33.274 | 22.042 | 60.687 |
| ATOM | 5483 | CA | ILE 1375 | 34.174 | 23.016 | 60.108 |
| ATOM | 5484 | CB | ILE 1375 | 34.696 | 22.583 | 58.744 |
| ATOM | 5485 | CG2 | ILE 1375 | 36.129 | 23.033 | 58.614 |
| ATOM | 5486 | CG1 | ILE 1375 | 34.664 | 21.068 | 58.626 |
| ATOM | 5487 | CD1 | ILE 1375 | 35.715 | 20.423 | 59.437 |
| ATOM | 5488 | C | ILE 1375 | 33.404 | 24.336 | 59.989 |
| ATOM | 5489 | O | ILE 1375 | 32.396 | 24.445 | 59.264 |
| ATOM | 5490 | N | LEU 1376 | 33.790 | 25.278 | 60.835 |
| ATOM | 5491 | CA | LEU 1376 | 33.187 | 26.590 | 60.837 |
| ATOM | 5492 | CB | LEU 1376 | 33.070 | 27.136 | 62.258 |
| ATOM | 5493 | CG | LEU 1376 | 32.195 | 26.449 | 63.301 |
| ATOM | 5494 | CD1 | LEU 1376 | 30.727 | 26.660 | 62.988 |
| ATOM | 5495 | CD2 | LEU 1376 | 32.547 | 24.966 | 63.403 |
| ATOM | 5496 | C | LEU 1376 | 34.268 | 27.355 | 60.149 |
| ATOM | 5497 | O | LEU 1376 | 35.449 | 27.131 | 60.429 |
| ATOM | 5498 | N | PRO 1377 | 33.918 | 28.159 | 59.145 |
| ATOM | 5499 | CD | PRO 1377 | 32.664 | 28.421 | 58.426 |
| ATOM | 5500 | CA | PRO 1377 | 35.029 | 28.885 | 58.533 |
| ATOM | 5501 | CB | PRO 1377 | 34.352 | 29.600 | 57.352 |
| ATOM | 5502 | CG | PRO 1377 | 32.931 | 29.782 | 57.830 |
| ATOM | 5503 | C | PRO 1377 | 35.479 | 29.872 | 59.602 |
| ATOM | 5504 | O | PRO 1377 | 36.018 | 29.485 | 60.645 |
| ATOM | 5505 | N | LEU 1378 | 35.220 | 31.144 | 59.338 |
| ATOM | 5506 | CA | LEU 1378 | 35.522 | 32.245 | 60.244 |
| ATOM | 5507 | CB | LEU 1378 | 36.997 | 32.704 | 60.135 |
| ATOM | 5508 | CG | LEU 1378 | 37.538 | 33.689 | 61.193 |
| ATOM | 5509 | CD1 | LEU 1378 | 36.559 | 34.841 | 61.473 |
| ATOM | 5510 | CD2 | LEU 1378 | 37.793 | 32.944 | 62.504 |
| ATOM | 5511 | C | LEU 1378 | 34.627 | 33.305 | 59.636 |
| ATOM | 5512 | O | LEU 1378 | 33.741 | 33.872 | 60.295 |
| ATOM | 5513 | N | SER 1379 | 34.845 | 33.490 | 58.334 |
| ATOM | 5514 | CA | SER 1379 | 34.130 | 34.463 | 57.539 |
| ATOM | 5515 | CB | SER 1379 | 35.053 | 35.658 | 57.244 |
| ATOM | 5516 | OG | SER 1379 | 34.323 | 36.800 | 56.819 |
| ATOM | 5517 | C | SER 1379 | 33.791 | 33.763 | 56.241 |
| ATOM | 5518 | O | SER 1379 | 34.574 | 32.894 | 55.776 |

FIGURE 1LLLLL

| Atom | | Residue AA | No. | X | Y | Z |
|---|---|---|---|---|---|---|
| ATOM | 5519 | N | ALA 1380 | 32.647 | 34.166 | 55.663 |
| ATOM | 5520 | CA | ALA 1380 | 32.165 | 33.637 | 54.378 |
| ATOM | 5521 | CB | ALA 1380 | 30.981 | 34.479 | 53.828 |
| ATOM | 5522 | C | ALA 1380 | 33.330 | 33.616 | 53.371 |
| ATOM | 5523 | O | ALA 1380 | 33.348 | 32.799 | 52.451 |
| ATOM | 5524 | N | ALA 1381 | 34.311 | 34.499 | 53.579 |
| ATOM | 5525 | CA | ALA 1381 | 35.505 | 34.572 | 52.737 |
| ATOM | 5526 | CB | ALA 1381 | 36.476 | 35.635 | 53.267 |
| ATOM | 5527 | C | ALA 1381 | 36.193 | 33.212 | 52.724 |
| ATOM | 5528 | O | ALA 1381 | 36.327 | 32.572 | 51.653 |
| ATOM | 5529 | N | LEU 1382 | 36.584 | 32.739 | 53.906 |
| ATOM | 5530 | CA | LEU 1382 | 37.247 | 31.445 | 53.941 |
| ATOM | 5531 | CB | LEU 1382 | 38.090 | 31.263 | 55.214 |
| ATOM | 5532 | CG | LEU 1382 | 39.101 | 32.307 | 55.693 |
| ATOM | 5533 | CD1 | LEU 1382 | 39.878 | 32.903 | 54.535 |
| ATOM | 5534 | CD2 | LEU 1382 | 38.339 | 33.367 | 56.469 |
| ATOM | 5535 | C | LEU 1382 | 36.279 | 30.252 | 53.752 |
| ATOM | 5536 | O | LEU 1382 | 36.625 | 29.127 | 54.141 |
| ATOM | 5537 | N | SER 1383 | 35.083 | 30.482 | 53.184 |
| ATOM | 5538 | CA | SER 1383 | 34.138 | 29.388 | 52.942 |
| ATOM | 5539 | CB | SER 1383 | 32.900 | 29.873 | 52.215 |
| ATOM | 5540 | OG | SER 1383 | 32.065 | 30.534 | 53.130 |
| ATOM | 5541 | C | SER 1383 | 34.860 | 28.366 | 52.090 |
| ATOM | 5542 | O | SER 1383 | 34.927 | 27.183 | 52.445 |
| ATOM | 5543 | N | GLY 1384 | 35.385 | 28.806 | 50.952 |
| ATOM | 5544 | CA | GLY 1384 | 36.160 | 27.888 | 50.140 |
| ATOM | 5545 | C | GLY 1384 | 37.421 | 27.721 | 50.986 |
| ATOM | 5546 | O | GLY 1384 | 37.860 | 28.695 | 51.649 |
| ATOM | 5547 | N | ALA 1385 | 37.993 | 26.510 | 50.962 |
| ATOM | 5548 | CA | ALA 1385 | 39.202 | 26.101 | 51.741 |
| ATOM | 5549 | CB | ALA 1385 | 40.119 | 27.313 | 52.173 |
| ATOM | 5550 | C | ALA 1385 | 38.692 | 25.338 | 52.968 |
| ATOM | 5551 | O | ALA 1385 | 39.183 | 24.256 | 53.298 |
| ATOM | 5552 | N | ALA 1386 | 37.665 | 25.891 | 53.609 |
| ATOM | 5553 | CA | ALA 1386 | 37.050 | 25.249 | 54.757 |
| ATOM | 5554 | CB | ALA 1386 | 36.114 | 26.217 | 55.492 |
| ATOM | 5555 | C | ALA 1386 | 36.279 | 24.063 | 54.186 |
| ATOM | 5556 | O | ALA 1386 | 36.350 | 22.968 | 54.733 |
| ATOM | 5557 | N | ILE 1387 | 35.608 | 24.258 | 53.048 |
| ATOM | 5558 | CA | ILE 1387 | 34.864 | 23.169 | 52.416 |
| ATOM | 5559 | CB | ILE 1387 | 34.167 | 23.620 | 51.149 |
| ATOM | 5560 | CG2 | ILE 1387 | 33.291 | 22.513 | 50.635 |
| ATOM | 5561 | CG1 | ILE 1387 | 33.295 | 24.828 | 51.449 |
| ATOM | 5562 | CD1 | ILE 1387 | 32.855 | 25.600 | 50.219 |
| ATOM | 5563 | C | ILE 1387 | 35.824 | 22.044 | 52.051 |
| ATOM | 5564 | O | ILE 1387 | 35.420 | 20.882 | 51.943 |
| ATOM | 5565 | N | ALA 1388 | 37.106 | 22.397 | 51.904 |
| ATOM | 5566 | CA | ALA 1388 | 38.169 | 21.436 | 51.565 |

FIGURE 1MMMMM

| Atom | Residue AA | No. | X | Y | Z |
|---|---|---|---|---|---|
| ATOM 5567 CB | ALA | 1388 | 39.442 | 22.171 | 51.151 |
| ATOM 5568 C | ALA | 1388 | 38.463 | 20.424 | 52.698 |
| ATOM 5569 O | ALA | 1388 | 38.522 | 19.204 | 52.473 |
| ATOM 5570 N | ILE | 1389 | 38.704 | 20.920 | 53.906 |
| ATOM 5571 CA | ILE | 1389 | 38.916 | 20.005 | 55.017 |
| ATOM 5572 CB | ILE | 1389 | 39.296 | 20.686 | 56.324 |
| ATOM 5573 CG2 | ILE | 1389 | 40.717 | 20.344 | 56.657 |
| ATOM 5574 CG1 | ILE | 1389 | 38.982 | 22.175 | 56.267 |
| ATOM 5575 CD1 | ILE | 1389 | 39.882 | 23.023 | 57.131 |
| ATOM 5576 C | ILE | 1389 | 37.605 | 19.288 | 55.255 |
| ATOM 5577 O | ILE | 1389 | 37.599 | 18.121 | 55.637 |
| ATOM 5578 N | PHE | 1390 | 36.493 | 19.976 | 55.023 |
| ATOM 5579 CA | PHE | 1390 | 35.206 | 19.354 | 55.207 |
| ATOM 5580 CB | PHE | 1390 | 34.091 | 20.212 | 54.635 |
| ATOM 5581 CG | PHE | 1390 | 32.824 | 19.460 | 54.464 |
| ATOM 5582 CD1 | PHE | 1390 | 32.625 | 18.637 | 53.355 |
| ATOM 5583 CD2 | PHE | 1390 | 31.883 | 19.465 | 55.459 |
| ATOM 5584 CE1 | PHE | 1390 | 31.524 | 17.833 | 53.255 |
| ATOM 5585 CE2 | PHE | 1390 | 30.769 | 18.661 | 55.370 |
| ATOM 5586 CZ | PHE | 1390 | 30.592 | 17.841 | 54.267 |
| ATOM 5587 C | PHE | 1390 | 35.209 | 18.000 | 54.511 |
| ATOM 5588 O | PHE | 1390 | 35.038 | 16.965 | 55.161 |
| ATOM 5589 N | GLU | 1391 | 35.446 | 18.009 | 53.199 |
| ATOM 5590 CA | GLU | 1391 | 35.456 | 16.779 | 52.398 |
| ATOM 5591 CB | GLU | 1391 | 35.676 | 17.108 | 50.939 |
| ATOM 5592 CG | GLU | 1391 | 34.535 | 17.835 | 50.312 |
| ATOM 5593 CD | GLU | 1391 | 34.901 | 18.397 | 48.937 |
| ATOM 5594 OE1 | GLU | 1391 | 36.133 | 18.491 | 48.620 |
| ATOM 5595 OE2 | GLU | 1391 | 33.937 | 18.745 | 48.189 |
| ATOM 5596 C | GLU | 1391 | 36.478 | 15.720 | 52.800 |
| ATOM 5597 O | GLU | 1391 | 36.141 | 14.532 | 52.930 |
| ATOM 5598 N | GLN | 1392 | 37.731 | 16.143 | 52.943 |
| ATOM 5599 CA | GLN | 1392 | 38.804 | 15.244 | 53.324 |
| ATOM 5600 CB | GLN | 1392 | 40.002 | 16.062 | 53.823 |
| ATOM 5601 CG | GLN | 1392 | 41.203 | 15.214 | 54.335 |
| ATOM 5602 CD | GLN | 1392 | 42.069 | 15.937 | 55.399 |
| ATOM 5603 OE1 | GLN | 1392 | 42.470 | 15.337 | 56.423 |
| ATOM 5604 NE2 | GLN | 1392 | 42.359 | 17.224 | 55.156 |
| ATOM 5605 C | GLN | 1392 | 38.332 | 14.300 | 54.433 |
| ATOM 5606 O | GLN | 1392 | 38.689 | 13.121 | 54.461 |
| ATOM 5607 N | LEU | 1393 | 37.495 | 14.826 | 55.318 |
| ATOM 5608 CA | LEU | 1393 | 37.007 | 14.071 | 56.443 |
| ATOM 5609 CB | LEU | 1393 | 36.937 | 14.971 | 57.674 |
| ATOM 5610 CG | LEU | 1393 | 38.295 | 15.633 | 57.962 |
| ATOM 5611 CD1 | LEU | 1393 | 38.117 | 16.725 | 58.956 |
| ATOM 5612 CD2 | LEU | 1393 | 39.352 | 14.646 | 58.432 |
| ATOM 5613 C | LEU | 1393 | 35.693 | 13.387 | 56.199 |
| ATOM 5614 O | LEU | 1393 | 35.477 | 12.293 | 56.727 |

FIGURE 1NNNNN

| Atom | | Residue | | X | Y | Z |
|---|---|---|---|---|---|---|
| | | AA | No. | | | |
| ATOM | 5615 N | SER | 1394 | 34.832 | 13.997 | 55.384 |
| ATOM | 5616 CA | SER | 1394 | 33.506 | 13.431 | 55.097 |
| ATOM | 5617 CB | SER | 1394 | 32.797 | 14.200 | 53.979 |
| ATOM | 5618 OG | SER | 1394 | 32.866 | 15.583 | 54.174 |
| ATOM | 5619 C | SER | 1394 | 33.635 | 11.968 | 54.686 |
| ATOM | 5620 O | SER | 1394 | 32.754 | 11.134 | 54.941 |
| ATOM | 5621 N | SER | 1395 | 34.762 | 11.664 | 54.061 |
| ATOM | 5622 CA | SER | 1395 | 35.084 | 10.322 | 53.590 |
| ATOM | 5623 CB | SER | 1395 | 36.556 | 10.334 | 53.183 |
| ATOM | 5624 OG | SER | 1395 | 37.284 | 11.169 | 54.090 |
| ATOM | 5625 C | SER | 1395 | 34.881 | 9.255 | 54.673 |
| ATOM | 5626 O | SER | 1395 | 34.810 | 8.052 | 54.382 |
| ATOM | 5627 N | LYS | 1396 | 34.871 | 9.706 | 55.926 |
| ATOM | 5628 CA | LYS | 1396 | 34.730 | 8.813 | 57.045 |
| ATOM | 5629 CB | LYS | 1396 | 36.117 | 8.493 | 57.595 |
| ATOM | 5630 CG | LYS | 1396 | 36.826 | 7.348 | 56.858 |
| ATOM | 5631 CD | LYS | 1396 | 37.576 | 7.769 | 55.608 |
| ATOM | 5632 CE | LYS | 1396 | 38.941 | 8.379 | 55.947 |
| ATOM | 5633 NZ | LYS | 1396 | 38.812 | 9.631 | 56.743 |
| ATOM | 5634 C | LYS | 1396 | 33.797 | 9.238 | 58.183 |
| ATOM | 5635 O | LYS | 1396 | 33.016 | 8.399 | 58.678 |
| ATOM | 5636 N | PHE | 1397 | 33.856 | 10.515 | 58.589 |
| ATOM | 5637 CA | PHE | 1397 | 33.040 | 11.011 | 59.720 |
| ATOM | 5638 CB | PHE | 1397 | 33.932 | 11.772 | 60.705 |
| ATOM | 5639 CG | PHE | 1397 | 35.223 | 11.087 | 60.995 |
| ATOM | 5640 CD1 | PHE | 1397 | 35.249 | 9.734 | 61.326 |
| ATOM | 5641 CD2 | PHE | 1397 | 36.415 | 11.772 | 60.891 |
| ATOM | 5642 CE1 | PHE | 1397 | 36.460 | 9.071 | 61.543 |
| ATOM | 5643 CE2 | PHE | 1397 | 37.629 | 11.123 | 61.106 |
| ATOM | 5644 CZ | PHE | 1397 | 37.655 | 9.769 | 61.432 |
| ATOM | 5645 C | PHE | 1397 | 31.836 | 11.888 | 59.399 |
| ATOM | 5646 O | PHE | 1397 | 31.912 | 12.772 | 58.553 |
| ATOM | 5647 N | SER | 1398 | 30.759 | 11.709 | 60.149 |
| ATOM | 5648 CA | SER | 1398 | 29.556 | 12.505 | 59.938 |
| ATOM | 5649 CB | SER | 1398 | 28.376 | 11.912 | 60.732 |
| ATOM | 5650 OG | SER | 1398 | 28.586 | 10.532 | 61.059 |
| ATOM | 5651 C | SER | 1398 | 29.796 | 13.934 | 60.409 |
| ATOM | 5652 O | SER | 1398 | 29.296 | 14.309 | 61.457 |
| ATOM | 5653 N | ILE | 1399 | 30.546 | 14.736 | 59.658 |
| ATOM | 5654 CA | ILE | 1399 | 30.801 | 16.115 | 60.083 |
| ATOM | 5655 CB | ILE | 1399 | 32.287 | 16.474 | 59.931 |
| ATOM | 5656 CG2 | ILE | 1399 | 33.137 | 15.271 | 60.277 |
| ATOM | 5657 CG1 | ILE | 1399 | 32.595 | 16.925 | 58.520 |
| ATOM | 5658 CD1 | ILE | 1399 | 34.028 | 17.276 | 58.330 |
| ATOM | 5659 C | ILE | 1399 | 29.885 | 17.222 | 59.494 |
| ATOM | 5660 O | ILE | 1399 | 29.275 | 17.062 | 58.441 |
| ATOM | 5661 N | ASP | 1400 | 29.730 | 18.310 | 60.238 |
| ATOM | 5662 CA | ASP | 1400 | 28.895 | 19.440 | 59.831 |

FIGURE 100000

| Atom | | Residue | | X | Y | Z |
|---|---|---|---|---|---|---|
| | | AA | No. | | | |
| ATOM | 5663 CB | ASP | 1400 | 28.145 | 19.992 | 61.077 |
| ATOM | 5664 CG | ASP | 1400 | 26.953 | 20.937 | 60.746 |
| ATOM | 5665 OD1 | ASP | 1400 | 27.023 | 21.748 | 59.806 |
| ATOM | 5666 OD2 | ASP | 1400 | 25.939 | 20.907 | 61.490 |
| ATOM | 5667 C | ASP | 1400 | 29.877 | 20.491 | 59.315 |
| ATOM | 5668 O | ASP | 1400 | 31.113 | 20.340 | 59.438 |
| ATOM | 5669 N | PHE | 1401 | 29.318 | 21.510 | 58.671 |
| ATOM | 5670 CA | PHE | 1401 | 30.064 | 22.653 | 58.159 |
| ATOM | 5671 CB | PHE | 1401 | 30.312 | 22.515 | 56.656 |
| ATOM | 5672 CG | PHE | 1401 | 31.106 | 23.654 | 56.061 |
| ATOM | 5673 CD1 | PHE | 1401 | 32.500 | 23.596 | 56.003 |
| ATOM | 5674 CD2 | PHE | 1401 | 30.460 | 24.796 | 55.569 |
| ATOM | 5675 CE1 | PHE | 1401 | 33.238 | 24.666 | 55.463 |
| ATOM | 5676 CE2 | PHE | 1401 | 31.189 | 25.872 | 55.028 |
| ATOM | 5677 CZ | PHE | 1401 | 32.579 | 25.810 | 54.975 |
| ATOM | 5678 C | PHE | 1401 | 29.124 | 23.827 | 58.419 |
| ATOM | 5679 O | PHE | 1401 | 27.910 | 23.742 | 58.108 |
| ATOM | 5680 N | ASP | 1402 | 29.636 | 24.885 | 59.049 |
| ATOM | 5681 CA | ASP | 1402 | 28.783 | 26.039 | 59.317 |
| ATOM | 5682 CB | ASP | 1402 | 28.076 | 25.947 | 60.681 |
| ATOM | 5683 CG | ASP | 1402 | 26.811 | 26.833 | 60.764 |
| ATOM | 5684 OD1 | ASP | 1402 | 26.045 | 26.699 | 61.748 |
| ATOM | 5685 OD2 | ASP | 1402 | 26.570 | 27.657 | 59.849 |
| ATOM | 5686 C | ASP | 1402 | 29.543 | 27.321 | 59.231 |
| ATOM | 5687 O | ASP | 1402 | 30.560 | 27.517 | 59.899 |
| ATOM | 5688 N | GLU | 1403 | 29.020 | 28.185 | 58.381 |
| ATOM | 5689 CA | GLU | 1403 | 29.591 | 29.490 | 58.161 |
| ATOM | 5690 CB | GLU | 1403 | 29.914 | 29.660 | 56.678 |
| ATOM | 5691 CG | GLU | 1403 | 28.782 | 29.203 | 55.765 |
| ATOM | 5692 CD | GLU | 1403 | 29.073 | 29.456 | 54.279 |
| ATOM | 5693 OE1 | GLU | 1403 | 28.233 | 30.151 | 53.625 |
| ATOM | 5694 OE2 | GLU | 1403 | 30.128 | 28.953 | 53.773 |
| ATOM | 5695 C | GLU | 1403 | 28.601 | 30.560 | 58.624 |
| ATOM | 5696 O | GLU | 1403 | 28.988 | 31.527 | 59.281 |
| ATOM | 5697 N | SER | 1404 | 27.320 | 30.363 | 58.300 |
| ATOM | 5698 CA | SER | 1404 | 26.271 | 31.319 | 58.661 |
| ATOM | 5699 CB | SER | 1404 | 24.885 | 30.747 | 58.304 |
| ATOM | 5700 OG | SER | 1404 | 23.889 | 31.760 | 58.190 |
| ATOM | 5701 C | SER | 1404 | 26.348 | 31.675 | 60.153 |
| ATOM | 5702 O | SER | 1404 | 26.531 | 30.788 | 61.002 |
| ATOM | 5703 N | GLN | 1405 | 26.206 | 32.972 | 60.442 |
| ATOM | 5704 CA | GLN | 1405 | 26.243 | 33.534 | 61.798 |
| ATOM | 5705 CB | GLN | 1405 | 25.683 | 32.554 | 62.850 |
| ATOM | 5706 CG | GLN | 1405 | 24.287 | 32.025 | 62.557 |
| ATOM | 5707 CD | GLN | 1405 | 23.436 | 33.070 | 61.871 |
| ATOM | 5708 OE1 | GLN | 1405 | 22.746 | 32.771 | 60.893 |
| ATOM | 5709 NE2 | GLN | 1405 | 23.512 | 34.320 | 62.349 |
| ATOM | 5710 C | GLN | 1405 | 27.630 | 34.035 | 62.231 |

FIGURE 1PPPPP

| Atom | | Residue AA No. | X | Y | Z |
|---|---|---|---|---|---|
| ATOM | 5711 O | GLN 1405 | 28.522 | 34.245 | 61.397 |
| ATOM | 5712 N | SER 1406 | 27.795 | 34.277 | 63.533 |
| ATOM | 5713 CA | SER 1406 | 29.064 | 34.775 | 64.056 |
| ATOM | 5714 CB | SER 1406 | 28.848 | 35.382 | 65.449 |
| ATOM | 5715 OG | SER 1406 | 28.293 | 34.427 | 66.346 |
| ATOM | 5716 C | SER 1406 | 30.116 | 33.673 | 64.099 |
| ATOM | 5717 O | SER 1406 | 30.685 | 33.310 | 63.074 |
| ATOM | 5718 N | ILE 1407 | 30.375 | 33.180 | 65.307 |
| ATOM | 5719 CA | ILE 1407 | 31.329 | 32.107 | 65.586 |
| ATOM | 5720 CB | ILE 1407 | 32.842 | 32.570 | 65.507 |
| ATOM | 5721 CG2 | ILE 1407 | 33.467 | 32.778 | 66.904 |
| ATOM | 5722 CG1 | ILE 1407 | 33.672 | 31.516 | 64.762 |
| ATOM | 5723 CD1 | ILE 1407 | 33.500 | 30.118 | 65.304 |
| ATOM | 5724 C | ILE 1407 | 30.964 | 31.656 | 66.998 |
| ATOM | 5725 O | ILE 1407 | 30.803 | 30.460 | 67.252 |
| ATOM | 5726 N | GLY 1408 | 30.771 | 32.632 | 67.890 |
| ATOM | 5727 CA | GLY 1408 | 30.387 | 32.335 | 69.256 |
| ATOM | 5728 C | GLY 1408 | 28.977 | 31.773 | 69.238 |
| ATOM | 5729 O | GLY 1408 | 28.703 | 30.753 | 69.886 |
| ATOM | 5730 N | LYS 1409 | 28.097 | 32.418 | 68.461 |
| ATOM | 5731 CA | LYS 1409 | 26.698 | 31.988 | 68.319 |
| ATOM | 5732 CB | LYS 1409 | 25.886 | 33.035 | 67.548 |
| ATOM | 5733 CG | LYS 1409 | 24.788 | 33.723 | 68.364 |
| ATOM | 5734 CD | LYS 1409 | 23.586 | 32.789 | 68.629 |
| ATOM | 5735 CE | LYS 1409 | 22.443 | 33.533 | 69.367 |
| ATOM | 5736 NZ | LYS 1409 | 21.202 | 32.712 | 69.624 |
| ATOM | 5737 C | LYS 1409 | 26.661 | 30.644 | 67.587 |
| ATOM | 5738 O | LYS 1409 | 25.744 | 29.817 | 67.800 |
| ATOM | 5739 N | ARG 1410 | 27.681 | 30.451 | 66.739 |
| ATOM | 5740 CA | ARG 1410 | 27.877 | 29.223 | 65.958 |
| ATOM | 5741 CB | ARG 1410 | 28.991 | 29.407 | 64.889 |
| ATOM | 5742 CG | ARG 1410 | 28.464 | 29.389 | 63.421 |
| ATOM | 5743 CD | ARG 1410 | 29.213 | 30.311 | 62.424 |
| ATOM | 5744 NE | ARG 1410 | 30.488 | 29.760 | 61.961 |
| ATOM | 5745 CZ | ARG 1410 | 31.351 | 30.413 | 61.180 |
| ATOM | 5746 NH1 | ARG 1410 | 32.489 | 29.834 | 60.821 |
| ATOM | 5747 NH2 | ARG 1410 | 31.081 | 31.646 | 60.756 |
| ATOM | 5748 C | ARG 1410 | 28.240 | 28.116 | 66.956 |
| ATOM | 5749 O | ARG 1410 | 27.581 | 27.063 | 66.998 |
| ATOM | 5750 N | TYR 1411 | 29.225 | 28.401 | 67.807 |
| ATOM | 5751 CA | TYR 1411 | 29.652 | 27.465 | 68.815 |
| ATOM | 5752 CB | TYR 1411 | 30.679 | 28.108 | 69.718 |
| ATOM | 5753 CG | TYR 1411 | 32.063 | 28.164 | 69.134 |
| ATOM | 5754 CD1 | TYR 1411 | 32.883 | 29.265 | 69.366 |
| ATOM | 5755 CE1 | TYR 1411 | 34.216 | 29.302 | 68.905 |
| ATOM | 5756 CD2 | TYR 1411 | 32.593 | 27.094 | 68.418 |
| ATOM | 5757 CE2 | TYR 1411 | 33.928 | 27.116 | 67.956 |
| ATOM | 5758 CZ | TYR 1411 | 34.736 | 28.224 | 68.207 |

FIGURE 1QQQQQ

| Atom | | Residue AA | No. | X | Y | Z |
|---|---|---|---|---|---|---|
| ATOM | 5759 | OH | TYR | 1411 | 36.066 | 28.239 | 67.810 |
| ATOM | 5760 | C | TYR | 1411 | 28.454 | 27.039 | 69.640 |
| ATOM | 5761 | O | TYR | 1411 | 28.177 | 25.852 | 69.751 |
| ATOM | 5762 | N | ARG | 1412 | 27.715 | 28.004 | 70.183 |
| ATOM | 5763 | CA | ARG | 1412 | 26.533 | 27.684 | 70.998 |
| ATOM | 5764 | CB | ARG | 1412 | 25.639 | 28.922 | 71.267 |
| ATOM | 5765 | CG | ARG | 1412 | 24.282 | 28.597 | 72.016 |
| ATOM | 5766 | CD | ARG | 1412 | 22.997 | 29.418 | 71.543 |
| ATOM | 5767 | NE | ARG | 1412 | 22.447 | 29.065 | 70.204 |
| ATOM | 5768 | CZ | ARG | 1412 | 21.138 | 28.888 | 69.912 |
| ATOM | 5769 | NH1 | ARG | 1412 | 20.768 | 28.575 | 68.653 |
| ATOM | 5770 | NH2 | ARG | 1412 | 20.193 | 28.987 | 70.868 |
| ATOM | 5771 | C | ARG | 1412 | 25.666 | 26.596 | 70.366 |
| ATOM | 5772 | O | ARG | 1412 | 25.497 | 25.520 | 70.971 |
| ATOM | 5773 | N | ARG | 1413 | 25.152 | 26.863 | 69.152 |
| ATOM | 5774 | CA | ARG | 1413 | 24.264 | 25.912 | 68.458 |
| ATOM | 5775 | CB | ARG | 1413 | 23.886 | 26.402 | 67.057 |
| ATOM | 5776 | CG | ARG | 1413 | 22.892 | 25.475 | 66.360 |
| ATOM | 5777 | CD | ARG | 1413 | 23.167 | 25.336 | 64.862 |
| ATOM | 5778 | NE | ARG | 1413 | 22.619 | 24.090 | 64.302 |
| ATOM | 5779 | CZ | ARG | 1413 | 21.315 | 23.805 | 64.189 |
| ATOM | 5780 | NH1 | ARG | 1413 | 20.386 | 24.681 | 64.594 |
| ATOM | 5781 | NH2 | ARG | 1413 | 20.935 | 22.630 | 63.684 |
| ATOM | 5782 | C | ARG | 1413 | 24.797 | 24.480 | 68.363 |
| ATOM | 5783 | O | ARG | 1413 | 24.012 | 23.518 | 68.415 |
| ATOM | 5784 | N | ALA | 1414 | 26.125 | 24.356 | 68.226 |
| ATOM | 5785 | CA | ALA | 1414 | 26.814 | 23.054 | 68.130 |
| ATOM | 5786 | CB | ALA | 1414 | 28.296 | 23.261 | 67.694 |
| ATOM | 5787 | C | ALA | 1414 | 26.744 | 22.226 | 69.442 |
| ATOM | 5788 | O | ALA | 1414 | 26.478 | 21.012 | 69.436 |
| ATOM | 5789 | N | ASP | 1415 | 26.950 | 22.892 | 70.568 |
| ATOM | 5790 | CA | ASP | 1415 | 26.908 | 22.219 | 71.839 |
| ATOM | 5791 | CB | ASP | 1415 | 27.367 | 23.171 | 72.925 |
| ATOM | 5792 | CG | ASP | 1415 | 28.797 | 23.622 | 72.701 |
| ATOM | 5793 | OD1 | ASP | 1415 | 29.623 | 22.754 | 72.311 |
| ATOM | 5794 | OD2 | ASP | 1415 | 29.091 | 24.829 | 72.860 |
| ATOM | 5795 | C | ASP | 1415 | 25.529 | 21.692 | 72.090 |
| ATOM | 5796 | O | ASP | 1415 | 25.360 | 20.509 | 72.314 |
| ATOM | 5797 | N | GLU | 1416 | 24.524 | 22.528 | 71.921 |
| ATOM | 5798 | CA | GLU | 1416 | 23.173 | 22.059 | 72.164 |
| ATOM | 5799 | CB | GLU | 1416 | 22.176 | 23.201 | 72.104 |
| ATOM | 5800 | CG | GLU | 1416 | 22.410 | 24.091 | 70.933 |
| ATOM | 5801 | CD | GLU | 1416 | 21.265 | 25.027 | 70.672 |
| ATOM | 5802 | OE1 | GLU | 1416 | 20.163 | 24.849 | 71.263 |
| ATOM | 5803 | OE2 | GLU | 1416 | 21.474 | 25.930 | 69.837 |
| ATOM | 5804 | C | GLU | 1416 | 22.714 | 20.900 | 71.285 |
| ATOM | 5805 | O | GLU | 1416 | 21.651 | 20.332 | 71.543 |
| ATOM | 5806 | N | ILE | 1417 | 23.444 | 20.594 | 70.206 |

FIGURE 1RRRRR

| Atom | | Residue AA | No. | X | Y | Z |
|---|---|---|---|---|---|---|
| ATOM | 5807 | CA | ILE | 1417 | 23.070 | 19.442 | 69.359 |
| ATOM | 5808 | CB | ILE | 1417 | 23.187 | 19.684 | 67.812 |
| ATOM | 5809 | CG2 | ILE | 1417 | 22.704 | 21.067 | 67.425 |
| ATOM | 5810 | CG1 | ILE | 1417 | 24.612 | 19.466 | 67.338 |
| ATOM | 5811 | CD1 | ILE | 1417 | 24.771 | 19.596 | 65.847 |
| ATOM | 5812 | C | ILE | 1417 | 24.002 | 18.311 | 69.799 |
| ATOM | 5813 | O | ILE | 1417 | 23.741 | 17.129 | 69.560 |
| ATOM | 5814 | N | GLY | 1418 | 25.119 | 18.705 | 70.401 |
| ATOM | 5815 | CA | GLY | 1418 | 26.044 | 17.744 | 70.940 |
| ATOM | 5816 | C | GLY | 1418 | 27.193 | 17.263 | 70.117 |
| ATOM | 5817 | O | GLY | 1418 | 27.389 | 16.065 | 70.021 |
| ATOM | 5818 | N | THR | 1419 | 28.008 | 18.160 | 69.590 |
| ATOM | 5819 | CA | THR | 1419 | 29.135 | 17.679 | 68.815 |
| ATOM | 5820 | CB | THR | 1419 | 29.019 | 18.064 | 67.319 |
| ATOM | 5821 | OG1 | THR | 1419 | 29.062 | 19.491 | 66.750 |
| ATOM | 5823 | C | THR | 1419 | 30.507 | 17.975 | 69.417 |
| ATOM | 5824 | O | THR | 1419 | 30.811 | 19.104 | 69.793 |
| ATOM | 5825 | N | PRO | 1420 | 31.325 | 16.925 | 69.561 |
| ATOM | 5826 | CD | PRO | 1420 | 30.837 | 15.584 | 69.185 |
| ATOM | 5827 | CA | PRO | 1420 | 32.682 | 16.827 | 70.096 |
| ATOM | 5828 | CB | PRO | 1420 | 33.098 | 15.419 | 69.673 |
| ATOM | 5829 | CG | PRO | 1420 | 31.845 | 14.662 | 69.810 |
| ATOM | 5830 | C | PRO | 1420 | 33.761 | 17.864 | 69.741 |
| ATOM | 5831 | O | PRO | 1420 | 34.659 | 18.123 | 70.562 |
| ATOM | 5832 | N | TYR | 1421 | 33.738 | 18.402 | 68.522 |
| ATOM | 5833 | CA | TYR | 1421 | 34.762 | 19.379 | 68.114 |
| ATOM | 5834 | CB | TYR | 1421 | 35.999 | 18.669 | 67.585 |
| ATOM | 5835 | CG | TYR | 1421 | 36.568 | 17.693 | 68.556 |
| ATOM | 5836 | CD1 | TYR | 1421 | 36.223 | 16.345 | 68.473 |
| ATOM | 5837 | CE1 | TYR | 1421 | 36.703 | 15.446 | 69.367 |
| ATOM | 5838 | CD2 | TYR | 1421 | 37.420 | 18.109 | 69.569 |
| ATOM | 5839 | CE2 | TYR | 1421 | 37.908 | 17.216 | 70.466 |
| ATOM | 5840 | CZ | TYR | 1421 | 37.544 | 15.883 | 70.362 |
| ATOM | 5841 | OH | TYR | 1421 | 38.002 | 14.961 | 71.259 |
| ATOM | 5842 | C | TYR | 1421 | 34.376 | 20.422 | 67.075 |
| ATOM | 5843 | O | TYR | 1421 | 33.687 | 20.112 | 66.098 |
| ATOM | 5844 | N | CYS | 1422 | 34.936 | 21.622 | 67.239 |
| ATOM | 5845 | CA | CYS | 1422 | 34.700 | 22.734 | 66.331 |
| ATOM | 5846 | CB | CYS | 1422 | 34.048 | 23.872 | 67.076 |
| ATOM | 5847 | SG | CYS | 1422 | 32.378 | 23.466 | 67.547 |
| ATOM | 5848 | C | CYS | 1422 | 35.989 | 23.215 | 65.698 |
| ATOM | 5849 | O | CYS | 1422 | 36.753 | 23.939 | 66.333 |
| ATOM | 5850 | N | VAL | 1423 | 36.236 | 22.775 | 64.463 |
| ATOM | 5851 | CA | VAL | 1423 | 37.439 | 23.149 | 63.718 |
| ATOM | 5852 | CB | VAL | 1423 | 37.876 | 22.066 | 62.693 |
| ATOM | 5853 | CG1 | VAL | 1423 | 39.181 | 22.469 | 62.036 |
| ATOM | 5854 | CG2 | VAL | 1423 | 38.019 | 20.712 | 63.373 |

FIGURE 1SSSSS

|  |  | Residue |  |  |  |  |
|---|---|---|---|---|---|---|
| Atom |  | AA | No. | X | Y | Z |
| ATOM | 5855 C | VAL | 1423 | 37.156 | 24.440 | 62.968 |
| ATOM | 5856 O | VAL | 1423 | 36.412 | 24.470 | 61.959 |
| ATOM | 5857 N | THR | 1424 | 37.741 | 25.511 | 63.494 |
| ATOM | 5858 CA | THR | 1424 | 37.577 | 26.835 | 62.907 |
| ATOM | 5859 CB | THR | 1424 | 37.392 | 27.919 | 64.005 |
| ATOM | 5860 OG1 | THR | 1424 | 38.439 | 27.830 | 64.987 |
| ATOM | 5861 CG2 | THR | 1424 | 36.037 | 27.714 | 64.686 |
| ATOM | 5862 C | THR | 1424 | 38.720 | 27.183 | 61.956 |
| ATOM | 5863 O | THR | 1424 | 39.919 | 26.988 | 62.284 |
| ATOM | 5864 N | PHE | 1425 | 38.326 | 27.577 | 60.745 |
| ATOM | 5865 CA | PHE | 1425 | 39.281 | 27.956 | 59.723 |
| ATOM | 5866 CB | PHE | 1425 | 38.917 | 27.380 | 58.332 |
| ATOM | 5867 CG | PHE | 1425 | 40.011 | 27.543 | 57.302 |
| ATOM | 5868 CD1 | PHE | 1425 | 40.816 | 26.468 | 56.960 |
| ATOM | 5869 CD2 | PHE | 1425 | 40.285 | 28.796 | 56.748 |
| ATOM | 5870 CE1 | PHE | 1425 | 41.872 | 26.638 | 56.098 |
| ATOM | 5871 CE2 | PHE | 1425 | 41.334 | 28.980 | 55.891 |
| ATOM | 5872 CZ | PHE | 1425 | 42.135 | 27.903 | 55.562 |
| ATOM | 5873 C | PHE | 1425 | 39.210 | 29.461 | 59.682 |
| ATOM | 5874 O | PHE | 1425 | 38.156 | 30.051 | 59.427 |
| ATOM | 5875 N | ASP | 1426 | 40.331 | 30.089 | 59.968 |
| ATOM | 5876 CA | ASP | 1426 | 40.367 | 31.525 | 59.932 |
| ATOM | 5877 CB | ASP | 1426 | 40.748 | 32.070 | 61.306 |
| ATOM | 5878 CG | ASP | 1426 | 42.229 | 31.931 | 61.583 |
| ATOM | 5879 OD1 | ASP | 1426 | 42.909 | 32.971 | 61.526 |
| ATOM | 5880 OD2 | ASP | 1426 | 42.710 | 30.797 | 61.795 |
| ATOM | 5881 C | ASP | 1426 | 41.437 | 31.905 | 58.923 |
| ATOM | 5882 O | ASP | 1426 | 41.982 | 31.056 | 58.184 |
| ATOM | 5883 N | PHE | 1427 | 41.807 | 33.177 | 58.995 |
| ATOM | 5884 CA | PHE | 1427 | 42.810 | 33.746 | 58.126 |
| ATOM | 5885 CB | PHE | 1427 | 42.824 | 35.266 | 58.306 |
| ATOM | 5886 CG | PHE | 1427 | 41.501 | 35.911 | 57.936 |
| ATOM | 5887 CD1 | PHE | 1427 | 41.400 | 36.765 | 56.831 |
| ATOM | 5888 CD2 | PHE | 1427 | 40.341 | 35.633 | 58.680 |
| ATOM | 5889 CE1 | PHE | 1427 | 40.155 | 37.341 | 56.469 |
| ATOM | 5890 CE2 | PHE | 1427 | 39.101 | 36.197 | 58.330 |
| ATOM | 5891 CZ | PHE | 1427 | 39.006 | 37.056 | 57.220 |
| ATOM | 5892 C | PHE | 1427 | 44.160 | 33.089 | 58.359 |
| ATOM | 5893 O | PHE | 1427 | 44.777 | 32.573 | 57.426 |
| ATOM | 5894 N | ASP | 1428 | 44.610 | 33.046 | 59.598 |
| ATOM | 5895 CA | ASP | 1428 | 45.881 | 32.389 | 59.837 |
| ATOM | 5896 CB | ASP | 1428 | 46.346 | 32.584 | 61.276 |
| ATOM | 5897 CG | ASP | 1428 | 46.573 | 34.051 | 61.614 |
| ATOM | 5898 OD1 | ASP | 1428 | 45.673 | 34.879 | 61.264 |
| ATOM | 5899 OD2 | ASP | 1428 | 47.649 | 34.368 | 62.202 |
| ATOM | 5900 C | ASP | 1428 | 45.783 | 30.918 | 59.512 |
| ATOM | 5901 O | ASP | 1428 | 46.783 | 30.313 | 59.165 |
| ATOM | 5902 N | SER | 1429 | 44.577 | 30.354 | 59.590 |

FIGURE 1TTTTT

| Atom | | Residue AA | No. | X | Y | Z |
|---|---|---|---|---|---|---|
| ATOM | 5903 | CA | SER | 1429 | 44.398 | 28.935 | 59.281 |
| ATOM | 5904 | CB | SER | 1429 | 42.916 | 28.529 | 59.313 |
| ATOM | 5905 | OG | SER | 1429 | 42.423 | 28.446 | 60.640 |
| ATOM | 5906 | C | SER | 1429 | 45.014 | 28.634 | 57.919 |
| ATOM | 5907 | O | SER | 1429 | 45.747 | 27.650 | 57.759 |
| ATOM | 5908 | N | LEU | 1430 | 44.716 | 29.477 | 56.935 |
| ATOM | 5909 | CA | LEU | 1430 | 45.326 | 29.256 | 55.640 |
| ATOM | 5910 | CB | LEU | 1430 | 44.641 | 30.026 | 54.484 |
| ATOM | 5911 | CG | LEU | 1430 | 44.289 | 31.512 | 54.304 |
| ATOM | 5912 | CD1 | LEU | 1430 | 43.056 | 31.881 | 55.109 |
| ATOM | 5913 | CD2 | LEU | 1430 | 45.456 | 32.424 | 54.590 |
| ATOM | 5914 | C | LEU | 1430 | 46.817 | 29.586 | 55.758 |
| ATOM | 5915 | O | LEU | 1430 | 47.666 | 28.712 | 55.554 |
| ATOM | 5916 | N | ALA | 1431 | 47.114 | 30.785 | 56.252 |
| ATOM | 5917 | CA | ALA | 1431 | 48.487 | 31.245 | 56.403 |
| ATOM | 5918 | CB | ALA | 1431 | 48.527 | 32.487 | 57.312 |
| ATOM | 5919 | C | ALA | 1431 | 49.437 | 30.162 | 56.935 |
| ATOM | 5920 | O | ALA | 1431 | 50.385 | 29.753 | 56.230 |
| ATOM | 5921 | N | ASP | 1432 | 49.178 | 29.707 | 58.169 |
| ATOM | 5922 | CA | ASP | 1432 | 50.010 | 28.688 | 58.827 |
| ATOM | 5923 | CB | ASP | 1432 | 50.000 | 28.869 | 60.354 |
| ATOM | 5924 | CG | ASP | 1432 | 48.695 | 28.402 | 61.025 |
| ATOM | 5925 | OD1 | ASP | 1432 | 47.613 | 28.404 | 60.414 |
| ATOM | 5926 | OD2 | ASP | 1432 | 48.763 | 28.031 | 62.209 |
| ATOM | 5927 | C | ASP | 1432 | 49.615 | 27.277 | 58.448 |
| ATOM | 5928 | O | ASP | 1432 | 50.356 | 26.324 | 58.711 |
| ATOM | 5929 | N | ASN | 1433 | 48.432 | 27.159 | 57.847 |
| ATOM | 5930 | CA | ASN | 1433 | 47.915 | 25.868 | 57.408 |
| ATOM | 5931 | CB | ASN | 1433 | 48.870 | 25.250 | 56.361 |
| ATOM | 5932 | CG | ASN | 1433 | 48.140 | 24.794 | 55.065 |
| ATOM | 5933 | OD1 | ASN | 1433 | 48.596 | 23.855 | 54.398 |
| ATOM | 5934 | ND2 | ASN | 1433 | 47.025 | 25.465 | 54.706 |
| ATOM | 5935 | C | ASN | 1433 | 47.617 | 24.887 | 58.576 |
| ATOM | 5936 | O | ASN | 1433 | 47.848 | 23.655 | 58.488 |
| ATOM | 5937 | N | GLN | 1434 | 47.058 | 25.449 | 59.650 |
| ATOM | 5938 | CA | GLN | 1434 | 46.661 | 24.701 | 60.846 |
| ATOM | 5939 | CB | GLN | 1434 | 47.713 | 24.805 | 61.940 |
| ATOM | 5940 | CG | GLN | 1434 | 49.042 | 24.150 | 61.569 |
| ATOM | 5941 | CD | GLN | 1434 | 50.035 | 24.079 | 62.742 |
| ATOM | 5942 | OE1 | GLN | 1434 | 51.248 | 24.257 | 62.562 |
| ATOM | 5943 | NE2 | GLN | 1434 | 49.521 | 23.808 | 63.947 |
| ATOM | 5944 | C | GLN | 1434 | 45.356 | 25.311 | 61.318 |
| ATOM | 5945 | O | GLN | 1434 | 45.022 | 26.441 | 60.958 |
| ATOM | 5946 | N | VAL | 1435 | 44.614 | 24.585 | 62.130 |
| ATOM | 5947 | CA | VAL | 1435 | 43.335 | 25.105 | 62.586 |
| ATOM | 5948 | CB | VAL | 1435 | 42.202 | 24.471 | 61.784 |
| ATOM | 5949 | CG1 | VAL | 1435 | 42.142 | 25.102 | 60.383 |
| ATOM | 5950 | CG2 | VAL | 1435 | 42.451 | 22.961 | 61.666 |

FIGURE 1UUUUU

| Atom | Residue AA | No. | X | Y | Z |
|---|---|---|---|---|---|
| ATOM 5951 C | VAL | 1435 | 43.079 | 24.951 | 64.082 |
| ATOM 5952 O | VAL | 1435 | 43.751 | 24.175 | 64.768 |
| ATOM 5953 N | THR | 1436 | 42.109 | 25.700 | 64.590 |
| ATOM 5954 CA | THR | 1436 | 41.786 | 25.658 | 66.020 |
| ATOM 5955 CB | THR | 1436 | 41.288 | 27.046 | 66.503 |
| ATOM 5956 OG1 | THR | 1436 | 40.778 | 27.796 | 65.377 |
| ATOM 5957 CG2 | THR | 1436 | 42.426 | 27.808 | 67.176 |
| ATOM 5958 C | THR | 1436 | 40.728 | 24.594 | 66.355 |
| ATOM 5959 O | THR | 1436 | 39.567 | 24.698 | 65.905 |
| ATOM 5960 N | VAL | 1437 | 41.156 | 23.537 | 67.060 |
| ATOM 5961 CA | VAL | 1437 | 40.266 | 22.430 | 67.488 |
| ATOM 5962 CB | VAL | 1437 | 40.969 | 21.036 | 67.421 |
| ATOM 5963 CG1 | VAL | 1437 | 39.999 | 19.960 | 67.849 |
| ATOM 5964 CG2 | VAL | 1437 | 41.472 | 20.746 | 66.015 |
| ATOM 5965 C | VAL | 1437 | 39.831 | 22.651 | 68.945 |
| ATOM 5966 O | VAL | 1437 | 40.614 | 22.405 | 69.887 |
| ATOM 5967 N | ARG | 1438 | 38.610 | 23.149 | 69.128 |
| ATOM 5968 CA | ARG | 1438 | 38.097 | 23.403 | 70.461 |
| ATOM 5969 CB | ARG | 1438 | 37.193 | 24.634 | 70.442 |
| ATOM 5970 CG | ARG | 1438 | 35.732 | 24.390 | 70.786 |
| ATOM 5971 CD | ARG | 1438 | 35.185 | 25.635 | 71.436 |
| ATOM 5972 NE | ARG | 1438 | 33.768 | 25.522 | 71.741 |
| ATOM 5973 CZ | ARG | 1438 | 33.119 | 26.338 | 72.571 |
| ATOM 5974 NH1 | ARG | 1438 | 33.770 | 27.328 | 73.188 |
| ATOM 5975 NH2 | ARG | 1438 | 31.809 | 26.186 | 72.761 |
| ATOM 5976 C | ARG | 1438 | 37.346 | 22.177 | 70.942 |
| ATOM 5977 O | ARG | 1438 | 36.713 | 21.480 | 70.143 |
| ATOM 5978 N | ASP | 1439 | 37.470 | 21.876 | 72.226 |
| ATOM 5979 CA | ASP | 1439 | 36.780 | 20.731 | 72.800 |
| ATOM 5980 CB | ASP | 1439 | 37.560 | 20.211 | 74.014 |
| ATOM 5981 CG | ASP | 1439 | 36.836 | 19.056 | 74.747 |
| ATOM 5982 OD1 | ASP | 1439 | 35.690 | 19.241 | 75.226 |
| ATOM 5983 OD2 | ASP | 1439 | 37.427 | 17.953 | 74.870 |
| ATOM 5984 C | ASP | 1439 | 35.397 | 21.212 | 73.235 |
| ATOM 5985 O | ASP | 1439 | 35.250 | 22.388 | 73.546 |
| ATOM 5986 N | ARG | 1440 | 34.399 | 20.321 | 73.266 |
| ATOM 5987 CA | ARG | 1440 | 33.042 | 20.702 | 73.716 |
| ATOM 5988 CB | ARG | 1440 | 32.000 | 19.609 | 73.411 |
| ATOM 5989 CG | ARG | 1440 | 30.582 | 19.909 | 73.993 |
| ATOM 5990 CD | ARG | 1440 | 29.766 | 18.638 | 74.127 |
| ATOM 5991 NE | ARG | 1440 | 30.639 | 17.493 | 74.404 |
| ATOM 5992 CZ | ARG | 1440 | 30.356 | 16.230 | 74.099 |
| ATOM 5993 NH1 | ARG | 1440 | 29.208 | 15.915 | 73.522 |
| ATOM 5994 NH2 | ARG | 1440 | 31.270 | 15.294 | 74.281 |
| ATOM 5995 C | ARG | 1440 | 32.968 | 21.038 | 75.228 |
| ATOM 5996 O | ARG | 1440 | 32.914 | 22.215 | 75.627 |
| ATOM 5997 N | ASP | 1441 | 32.923 | 20.003 | 76.070 |
| ATOM 5998 CA | ASP | 1441 | 32.855 | 20.216 | 77.514 |

FIGURE 1VVVVV

| Atom | | Residue AA | No. | X | Y | Z |
|---|---|---|---|---|---|---|
| ATOM | 5999 | CB | ASP | 1441 | 32.984 | 18.878 | 78.309 |
| ATOM | 6000 | CG | ASP | 1441 | 33.191 | 17.610 | 77.407 |
| ATOM | 6001 | OD1 | ASP | 1441 | 34.344 | 17.122 | 77.295 |
| ATOM | 6002 | OD2 | ASP | 1441 | 32.201 | 17.053 | 76.878 |
| ATOM | 6003 | C | ASP | 1441 | 33.963 | 21.218 | 77.897 |
| ATOM | 6004 | O | ASP | 1441 | 33.673 | 22.356 | 78.249 |
| ATOM | 6005 | N | SER | 1442 | 35.209 | 20.820 | 77.624 |
| ATOM | 6006 | CA | SER | 1442 | 36.428 | 21.586 | 77.914 |
| ATOM | 6007 | CB | SER | 1442 | 37.667 | 20.867 | 77.336 |
| ATOM | 6008 | OG | SER | 1442 | 38.679 | 21.765 | 76.889 |
| ATOM | 6009 | C | SER | 1442 | 36.478 | 23.055 | 77.526 |
| ATOM | 6010 | O | SER | 1442 | 37.151 | 23.846 | 78.190 |
| ATOM | 6011 | N | MET | 1443 | 35.878 | 23.407 | 76.400 |
| ATOM | 6012 | CA | MET | 1443 | 35.883 | 24.794 | 75.933 |
| ATOM | 6013 | CB | MET | 1443 | 35.266 | 25.698 | 76.984 |
| ATOM | 6014 | CG | MET | 1443 | 33.864 | 25.328 | 77.288 |
| ATOM | 6015 | SD | MET | 1443 | 32.966 | 26.822 | 77.067 |
| ATOM | 6016 | CE | MET | 1443 | 31.494 | 26.481 | 78.064 |
| ATOM | 6017 | C | MET | 1443 | 37.263 | 25.315 | 75.557 |
| ATOM | 6018 | O | MET | 1443 | 37.394 | 26.417 | 75.029 |
| ATOM | 6019 | N | GLU | 1444 | 38.296 | 24.542 | 75.855 |
| ATOM | 6020 | CA | GLU | 1444 | 39.627 | 24.964 | 75.508 |
| ATOM | 6021 | CB | GLU | 1444 | 40.653 | 24.343 | 76.443 |
| ATOM | 6022 | CG | GLU | 1444 | 41.547 | 25.408 | 77.066 |
| ATOM | 6023 | CD | GLU | 1444 | 40.772 | 26.689 | 77.535 |
| ATOM | 6024 | OE1 | GLU | 1444 | 40.006 | 26.635 | 78.552 |
| ATOM | 6025 | OE2 | GLU | 1444 | 40.952 | 27.763 | 76.887 |
| ATOM | 6026 | C | GLU | 1444 | 39.857 | 24.562 | 74.059 |
| ATOM | 6027 | O | GLU | 1444 | 39.189 | 23.640 | 73.551 |
| ATOM | 6028 | N | GLN | 1445 | 40.747 | 25.282 | 73.373 |
| ATOM | 6029 | CA | GLN | 1445 | 41.039 | 25.006 | 71.967 |
| ATOM | 6030 | CB | GLN | 1445 | 40.197 | 25.917 | 71.059 |
| ATOM | 6031 | CG | GLN | 1445 | 40.206 | 27.404 | 71.438 |
| ATOM | 6032 | CD | GLN | 1445 | 39.254 | 28.258 | 70.567 |
| ATOM | 6033 | OE1 | GLN | 1445 | 39.671 | 29.273 | 69.979 |
| ATOM | 6034 | NE2 | GLN | 1445 | 37.976 | 27.863 | 70.501 |
| ATOM | 6035 | C | GLN | 1445 | 42.515 | 25.112 | 71.584 |
| ATOM | 6036 | O | GLN | 1445 | 43.201 | 26.068 | 71.941 |
| ATOM | 6037 | N | VAL | 1446 | 42.970 | 24.148 | 70.793 |
| ATOM | 6038 | CA | VAL | 1446 | 44.345 | 24.100 | 70.320 |
| ATOM | 6039 | CB | VAL | 1446 | 44.995 | 22.759 | 70.717 |
| ATOM | 6040 | CG1 | VAL | 1446 | 44.000 | 21.605 | 70.393 |
| ATOM | 6041 | CG2 | VAL | 1446 | 46.371 | 22.550 | 69.986 |
| ATOM | 6042 | C | VAL | 1446 | 44.397 | 24.212 | 68.793 |
| ATOM | 6043 | O | VAL | 1446 | 43.495 | 23.770 | 68.086 |
| ATOM | 6044 | N | ARG | 1447 | 45.452 | 24.839 | 68.293 |
| ATOM | 6045 | CA | ARG | 1447 | 45.632 | 24.950 | 66.853 |
| ATOM | 6046 | CB | ARG | 1447 | 46.233 | 26.312 | 66.459 |

FIGURE 1WWWWW

| Atom | | Residue AA | No. | X | Y | Z |
|---|---|---|---|---|---|---|
| ATOM | 6047 | CG | ARG 1447 | 46.396 | 26.467 | 64.943 |
| ATOM | 6048 | CD | ARG 1447 | 46.868 | 27.862 | 64.506 |
| ATOM | 6049 | NE | ARG 1447 | 45.827 | 28.900 | 64.592 |
| ATOM | 6050 | CZ | ARG 1447 | 45.295 | 29.547 | 63.553 |
| ATOM | 6051 | NH1 | ARG 1447 | 45.685 | 29.283 | 62.310 |
| ATOM | 6052 | NH2 | ARG 1447 | 44.370 | 30.468 | 63.774 |
| ATOM | 6053 | C | ARG 1447 | 46.544 | 23.776 | 66.406 |
| ATOM | 6054 | O | ARG 1447 | 47.697 | 23.625 | 66.873 |
| ATOM | 6055 | N | MET 1448 | 45.996 | 22.917 | 65.550 |
| ATOM | 6056 | CA | MET 1448 | 46.728 | 21.767 | 65.047 |
| ATOM | 6057 | CB | MET 1448 | 46.081 | 20.464 | 65.533 |
| ATOM | 6058 | CG | MET 1448 | 44.606 | 20.288 | 65.180 |
| ATOM | 6059 | SD | MET 1448 | 43.876 | 18.775 | 65.962 |
| ATOM | 6060 | CE | MET 1448 | 45.192 | 17.493 | 65.463 |
| ATOM | 6061 | C | MET 1448 | 46.897 | 21.753 | 63.534 |
| ATOM | 6062 | O | MET 1448 | 46.162 | 22.427 | 62.794 |
| ATOM | 6063 | N | PRO 1449 | 47.932 | 21.040 | 63.063 |
| ATOM | 6064 | CD | PRO 1449 | 48.924 | 20.314 | 63.879 |
| ATOM | 6065 | CA | PRO 1449 | 48.246 | 20.913 | 61.635 |
| ATOM | 6066 | CB | PRO 1449 | 49.453 | 19.970 | 61.642 |
| ATOM | 6067 | CG | PRO 1449 | 50.116 | 20.271 | 62.969 |
| ATOM | 6068 | C | PRO 1449 | 47.056 | 20.289 | 60.915 |
| ATOM | 6069 | O | PRO 1449 | 46.791 | 19.087 | 61.070 |
| ATOM | 6070 | N | ILE 1450 | 46.376 | 21.098 | 60.106 |
| ATOM | 6071 | CA | ILE 1450 | 45.180 | 20.659 | 59.387 |
| ATOM | 6072 | CB | ILE 1450 | 44.895 | 21.550 | 58.148 |
| ATOM | 6073 | CG2 | ILE 1450 | 43.635 | 21.048 | 57.449 |
| ATOM | 6074 | CG1 | ILE 1450 | 44.688 | 23.023 | 58.585 |
| ATOM | 6075 | CD1 | ILE 1450 | 44.264 | 24.020 | 57.471 |
| ATOM | 6076 | C | ILE 1450 | 45.208 | 19.188 | 58.982 |
| ATOM | 6077 | O | ILE 1450 | 44.194 | 18.487 | 59.035 |
| ATOM | 6078 | N | SER 1451 | 46.401 | 18.728 | 58.638 |
| ATOM | 6079 | CA | SER 1451 | 46.606 | 17.356 | 58.240 |
| ATOM | 6080 | CB | SER 1451 | 48.103 | 17.139 | 57.965 |
| ATOM | 6081 | OG | SER 1451 | 48.591 | 15.890 | 58.478 |
| ATOM | 6082 | C | SER 1451 | 46.120 | 16.375 | 59.297 |
| ATOM | 6083 | O | SER 1451 | 45.236 | 15.555 | 59.049 |
| ATOM | 6084 | N | GLU 1452 | 46.694 | 16.503 | 60.485 |
| ATOM | 6085 | CA | GLU 1452 | 46.405 | 15.612 | 61.597 |
| ATOM | 6086 | CB | GLU 1452 | 47.295 | 16.000 | 62.787 |
| ATOM | 6087 | CG | GLU 1452 | 48.782 | 16.047 | 62.390 |
| ATOM | 6088 | CD | GLU 1452 | 49.771 | 16.039 | 63.583 |
| ATOM | 6089 | OE1 | GLU 1452 | 49.709 | 16.984 | 64.446 |
| ATOM | 6090 | OE2 | GLU 1452 | 50.628 | 15.092 | 63.617 |
| ATOM | 6091 | C | GLU 1452 | 44.926 | 15.424 | 62.007 |
| ATOM | 6092 | O | GLU 1452 | 44.570 | 14.427 | 62.662 |
| ATOM | 6093 | N | LEU 1453 | 44.064 | 16.337 | 61.574 |
| ATOM | 6094 | CA | LEU 1453 | 42.646 | 16.261 | 61.892 |

FIGURE 1XXXXX

| Atom | | AA | Residue No. | X | Y | Z |
|---|---|---|---|---|---|---|
| ATOM | 6095 | CB | LEU 1453 | 41.869 | 17.247 | 61.007 |
| ATOM | 6096 | CG | LEU 1453 | 41.838 | 18.749 | 61.325 |
| ATOM | 6097 | CD1 | LEU 1453 | 40.829 | 19.054 | 62.430 |
| ATOM | 6098 | CD2 | LEU 1453 | 43.221 | 19.238 | 61.718 |
| ATOM | 6099 | C | LEU 1453 | 42.101 | 14.828 | 62.430 |
| ATOM | 6101 | N | GLU 1454 | 42.675 | 14.115 | 60.716 |
| ATOM | 6102 | CA | GLU 1454 | 42.275 | 12.747 | 60.378 |
| ATOM | 6103 | CB | GLU 1454 | 43.030 | 12.239 | 59.142 |
| ATOM | 6104 | CG | GLU 1454 | 42.280 | 12.426 | 57.796 |
| ATOM | 6105 | CD | GLU 1454 | 41.782 | 11.100 | 57.169 |
| ATOM | 6106 | OE1 | GLU 1454 | 41.474 | 11.091 | 55.938 |
| ATOM | 6107 | OE2 | GLU 1454 | 41.697 | 10.071 | 57.903 |
| ATOM | 6108 | C | GLU 1454 | 42.544 | 11.832 | 61.524 |
| ATOM | 6109 | O | GLU 1454 | 41.626 | 11.265 | 62.093 |
| ATOM | 6110 | N | ALA 1455 | 43.815 | 11.731 | 61.880 |
| ATOM | 6111 | CA | ALA 1455 | 44.249 | 10.875 | 62.985 |
| ATOM | 6112 | CB | ALA 1455 | 45.751 | 11.000 | 63.181 |
| ATOM | 6113 | C | ALA 1455 | 43.526 | 11.205 | 64.296 |
| ATOM | 6114 | O | ALA 1455 | 43.064 | 10.305 | 65.017 |
| ATOM | 6115 | N | PHE 1456 | 43.444 | 12.500 | 64.595 |
| ATOM | 6116 | CA | PHE 1456 | 42.784 | 12.983 | 65.795 |
| ATOM | 6117 | CB | PHE 1456 | 42.739 | 14.525 | 65.791 |
| ATOM | 6118 | CG | PHE 1456 | 42.128 | 15.134 | 67.045 |
| ATOM | 6119 | CD1 | PHE 1456 | 42.835 | 16.064 | 67.783 |
| ATOM | 6120 | CD2 | PHE 1456 | 40.846 | 14.772 | 67.490 |
| ATOM | 6121 | CE1 | PHE 1456 | 42.274 | 16.619 | 68.940 |
| ATOM | 6122 | CE2 | PHE 1456 | 40.281 | 15.321 | 68.637 |
| ATOM | 6123 | CZ | PHE 1456 | 40.986 | 16.238 | 69.362 |
| ATOM | 6124 | C | PHE 1456 | 41.373 | 12.411 | 65.900 |
| ATOM | 6125 | O | PHE 1456 | 41.124 | 11.549 | 66.735 |
| ATOM | 6126 | N | LEU 1457 | 40.469 | 12.886 | 65.043 |
| ATOM | 6127 | CA | LEU 1457 | 39.080 | 12.464 | 65.071 |
| ATOM | 6128 | CB | LEU 1457 | 38.307 | 13.128 | 63.950 |
| ATOM | 6129 | CG | LEU 1457 | 38.107 | 14.624 | 64.106 |
| ATOM | 6130 | CD1 | LEU 1457 | 37.332 | 15.138 | 62.925 |
| ATOM | 6131 | CD2 | LEU 1457 | 37.338 | 14.881 | 65.373 |
| ATOM | 6132 | C | LEU 1457 | 38.856 | 10.968 | 65.031 |
| ATOM | 6133 | O | LEU 1457 | 37.786 | 10.489 | 65.380 |
| ATOM | 6134 | N | THR 1458 | 39.861 | 10.235 | 64.584 |
| ATOM | 6135 | CA | THR 1458 | 39.774 | 8.786 | 64.509 |
| ATOM | 6136 | CB | THR 1458 | 40.864 | 8.243 | 63.636 |
| ATOM | 6137 | OG1 | THR 1458 | 40.777 | 8.863 | 62.352 |
| ATOM | 6138 | CG2 | THR 1458 | 40.725 | 6.752 | 63.503 |
| ATOM | 6139 | C | THR 1458 | 39.944 | 8.145 | 65.873 |
| ATOM | 6140 | O | THR 1458 | 39.142 | 7.281 | 66.248 |
| ATOM | 6141 | N | ALA 1459 | 41.013 | 8.541 | 66.580 |
| ATOM | 6142 | CA | ALA 1459 | 41.347 | 8.030 | 67.920 |

FIGURE 1YYYYY

|      | Atom     | Residue AA | No.  | X      | Y      | Z      |
|------|----------|------------|------|--------|--------|--------|
| ATOM | 6143 CB  | ALA        | 1459 | 42.732 | 8.524  | 68.347 |
| ATOM | 6144 C   | ALA        | 1459 | 40.317 | 8.444  | 68.962 |
| ATOM | 6145 O   | ALA        | 1459 | 39.791 | 7.600  | 69.699 |
| ATOM | 6146 N   | LYS        | 1460 | 39.997 | 9.739  | 68.977 |
| ATOM | 6147 CA  | LYS        | 1460 | 39.041 | 10.310 | 69.924 |
| ATOM | 6148 CB  | LYS        | 1460 | 39.098 | 11.839 | 69.909 |
| ATOM | 6149 CG  | LYS        | 1460 | 39.123 | 12.447 | 71.298 |
| ATOM | 6150 CD  | LYS        | 1460 | 40.561 | 12.592 | 71.811 |
| ATOM | 6151 CE  | LYS        | 1460 | 40.707 | 12.559 | 73.366 |
| ATOM | 6152 NZ  | LYS        | 1460 | 40.124 | 13.711 | 74.175 |
| ATOM | 6153 C   | LYS        | 1460 | 37.629 | 9.880  | 69.620 |
| ATOM | 6154 O   | LYS        | 1460 | 36.677 | 10.618 | 69.895 |
| ATOM | 6155 N   | THR        | 1461 | 37.501 | 8.655  | 69.123 |
| ATOM | 6156 CA  | THR        | 1461 | 36.221 | 8.087  | 68.732 |
| ATOM | 6157 CB  | THR        | 1461 | 36.066 | 8.102  | 67.210 |
| ATOM | 6158 OG1 | THR        | 1461 | 36.151 | 9.448  | 66.722 |
| ATOM | 6159 CG2 | THR        | 1461 | 34.738 | 7.501  | 66.836 |
| ATOM | 6160 C   | THR        | 1461 | 36.076 | 6.641  | 69.136 |
| ATOM | 6161 O   | THR        | 1461 | 35.024 | 6.245  | 69.628 |
| ATOM | 6162 N   | ALA        | 1462 | 37.109 | 5.873  | 68.795 |
| ATOM | 6163 CA  | ALA        | 1462 | 37.258 | 4.446  | 69.038 |
| ATOM | 6164 CB  | ALA        | 1462 | 38.566 | 4.179  | 69.742 |
| ATOM | 6165 C   | ALA        | 1462 | 36.119 | 3.661  | 69.699 |
| ATOM | 6166 O   | ALA        | 1462 | 35.898 | 2.494  | 69.338 |
| ATOM | 6167 N   | PHE        | 1463 | 35.436 | 4.259  | 70.682 |
| ATOM | 6168 CA  | PHE        | 1463 | 34.306 | 3.623  | 71.373 |
| ATOM | 6169 CB  | PHE        | 1463 | 33.286 | 3.090  | 70.373 |
| ATOM | 6170 CG  | PHE        | 1463 | 32.034 | 2.638  | 71.003 |
| ATOM | 6171 CD1 | PHE        | 1463 | 31.195 | 3.565  | 71.623 |
| ATOM | 6172 CD2 | PHE        | 1463 | 31.696 | 1.288  | 71.016 |
| ATOM | 6173 CE1 | PHE        | 1463 | 30.012 | 3.167  | 72.271 |
| ATOM | 6174 CE2 | PHE        | 1463 | 30.536 | 0.855  | 71.646 |
| ATOM | 6175 CZ  | PHE        | 1463 | 29.677 | 1.811  | 72.288 |
| ATOM | 6176 C   | PHE        | 1463 | 34.778 | 2.506  | 72.289 |
| ATOM | 6177 O   | PHE        | 1463 | 35.824 | 2.745  | 72.915 |
| ATOM | 6178 OT  | PHE        | 1463 | 34.142 | 1.434  | 72.379 |

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 463 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:1:

```
Met Ala Lys Asp Met Asp Thr Ile Val Ser Leu Ala Lys His Arg Gly
1               5                   10                  15

Phe Val Phe Pro Gly Ser Asp Ile Tyr Gly Gly Leu Ser Asn Thr Trp
                20                  25                  30

Asp Tyr Gly Pro Leu Gly Val Glu Leu Lys Asn Asn Val Lys Lys Ala
            35                  40                  45

Trp Trp Gln Lys Phe Ile Thr Gln Ser Pro Phe Asn Val Gly Ile Asp
        50                  55                  60

Ala Ala Ile Leu Met Asn Pro Lys Val Trp Glu Ala Ser Gly His Leu
```

-continued

```
 65                     70                      75                      80
Asn Asn Phe Asn Asp Pro Met Ile Asp Asn Lys Asp Ser Lys Ile Arg
                    85                      90                      95
Tyr Arg Ala Asp Lys Leu Ile Glu Asp Tyr Met Gln Asp Val Lys Gly
                100                     105                     110
Asp Glu Asn Phe Ile Ala Asp Gly Leu Ser Phe Glu Gln Met Lys Lys
                115                     120                     125
Ile Ile Asp Asp Glu Gly Ile Val Cys Pro Val Ser Lys Thr Ala Asn
            130                     135                     140
Trp Thr Glu Ile Arg Gln Phe Asn Leu Met Phe Lys Thr Phe Gln Gly
145                     150                     155                     160
Val Thr Glu Asp Ser Thr Asn Glu Ile Phe Leu Arg Pro Glu Thr Ala
                    165                     170                     175
Gln Gly Ile Phe Val Asn Tyr Lys Asn Val Gln Arg Ser Met Arg Lys
                180                     185                     190
Lys Leu Pro Phe Gly Ile Gly Gln Ile Gly Lys Ser Phe Arg Asn Glu
                195                     200                     205
Ile Thr Pro Gly Asn Phe Ile Phe Arg Thr Arg Glu Phe Glu Gln Met
            210                     215                     220
Glu Leu Glu Phe Phe Cys Lys Pro Gly Glu Glu Ile Glu Trp Gln Asn
225                     230                     235                     240
Tyr Trp Lys Thr Phe Ala Ser Asp Trp Leu Thr Ser Leu Asn Met Ser
                    245                     250                     255
Ser Glu Asn Met Arg Leu Arg Asp His Asp Glu Asp Glu Leu Ser His
                260                     265                     270
Tyr Ser Asn Ala Thr Thr Asp Ile Glu Tyr Lys Phe Pro Phe Gly Trp
                275                     280                     285
Gly Glu Leu Trp Gly Ile Ala Ser Arg Thr Asp Phe Asp Leu Arg Lys
            290                     295                     300
His Ala Glu His Ser Gly Glu Asp Phe Arg Tyr His Asp Pro Glu Thr
305                     310                     315                     320
Asn Glu Lys Tyr Ile Pro Tyr Cys Ile Glu Pro Ser Leu Gly Ala Asp
                    325                     330                     335
Arg Val Thr Leu Ala Phe Leu Cys Asp Ala Tyr Asp Glu Glu Gly Val
                340                     345                     350
Glu Gly Ser Lys Asp Ala Arg Thr Val Leu His Phe His Pro Ala Leu
                355                     360                     365
Ala Pro Tyr Lys Ala Ala Ile Leu Pro Leu Ser Lys Lys Leu Ser Gly
            370                     375                     380
Glu Ala Ile Lys Ile Phe Glu Gln Leu Ser Ser Lys Phe Ser Ile Asp
385                     390                     395                     400
Phe Asp Glu Ser Gln Ser Ile Gly Lys Arg Tyr Arg Arg Gln Asp Glu
                    405                     410                     415
Ile Gly Thr Pro Tyr Cys Val Thr Phe Asp Phe Asp Ser Leu Glu Asp
                420                     425                     430
Asn Gln Val Thr Val Arg Asp Arg Asp Ser Met Glu Gln Val Arg Met
                435                     440                     445
Pro Ile Ser Glu Leu Glu Ala Phe Leu Thr Glu Lys Thr Lys Phe
            450                     455                     460
```

(2) INFORMATION FOR SEQ ID NO:2:

(i) SEQUENCE CHARACTERISTICS:
        (A) LENGTH: 42 base pairs

```
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "primer GRS1"

(xi) SEQUENCE DESCRIPTION: SEQ ID NO:2:

GGGGTACCGC TAGCAGGAGA GGTAATTATG GCAAAAGATA TG                      42

(2) INFORMATION FOR SEQ ID NO:3:

(i) SEQUENCE CHARACTERISTICS:
            (A) LENGTH: 45 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "primer GRS2"

(xi) SEQUENCE DESCRIPTION: SEQ ID NO:3:

GCTCTAGATT AGTCATTTAA TTAGAATTTT GTTTTTTCAG TTAAG                   45
```

METHODS USING THE *STAPHYLOCOCCUS AUREUS* GLYCYL TRNA SYNTHETASE CRYSTALLINE STRUCTURE

TECHNICAL FIELD OF THE INVENTION

The invention relates to the identification of a novel enzyme active site and methods enabling the design and selection of inhibitors of that active site.

BACKGROUND OF THE INVENTION

Transfer RNA (tRNA) synthetase enzymes are of interest as potential targets for antibacterial agents. Mupirocin, a selective inhibitor of bacterial isoleucyl tRNA synthetase, is marketed for the treatment of skin infections and the eradication of nasal carriage of MRSA (methicillin-resistant *Staphylococcus aureus*) in hospital staff and patients.

Glycyl tRNA synthetase, a class I enzyme, is unusual in that its oligomeric structure varies depending on the organism from which it was isolated. Nucleic acid and amino acid sequences for glycyl tRNA synthetases are publicly available, including those of *Thermus thermophilus, Mycoplasma genitalium, Homo sapiens,* yeast, *Bombyx mori* and *Caenorhabditis elegans*, which are all characterized by a2 dimers, and *Coxiella burnetti, Escherichia coli, Chlamydia trachomatous, Neisseria gonorrheae,* Synechocystis sp., and *Haemophilus influenzae*, which are all characterized by being a2b2 tetramers.

There is a need in the art for novel tRNA synthetase enzyme active sites and catalytic sequences to enable identification and structure-based design of synthetase inhibitors, which are useful in the treatment or prophylaxis of diseases, particularly bacterial diseases caused by bacteria of the genus Staphylococcus, as well as other bacteria which may share catalytic domains with those of the genus Staphylococcus.

SUMMARY OF THE INVENTION

In one aspect, the present invention provides a novel *Staphylococcus aureus* tRNA synthetase enzyme active site crystalline form.

In still another aspect, the present invention provides a novel tRNA synthetase composition characterized by a catalytic site of 16 amino acid residues.

In yet another aspect, the invention provides a method for identifying inhibitors of the compositions described above which methods involve the steps of: providing the coordinates of the tRNA synthetase structure of the invention to a computerized modeling system; identifying compounds which will bind to the structure; and screening the compounds identified for tRNA synthetase inhibitory bioactivity.

In a further aspect, the present invention provides an inhibitor of the catalytic activity of any composition bearing the catalytic domain described above.

Another aspect of this invention includes machine readable media encoded with data representing the coordinates of the three-dimensional structure of the tRNA synthetase crystal.

Other aspects and advantages of the present invention are described further in the following detailed description of the preferred embodiments thereof.

BRIEF DESCRIPTION OF THE DRAWINGS

FIGS. 1A through 1YYYYY provides the atomic coordinates of the *Staph aureus* glycyl tRNA synthetase. The occupancy factor is 1.0 and the B factor is 19.60 for each coordinate.

DETAILED DESCRIPTION OF THE INVENTION

Figure 2:
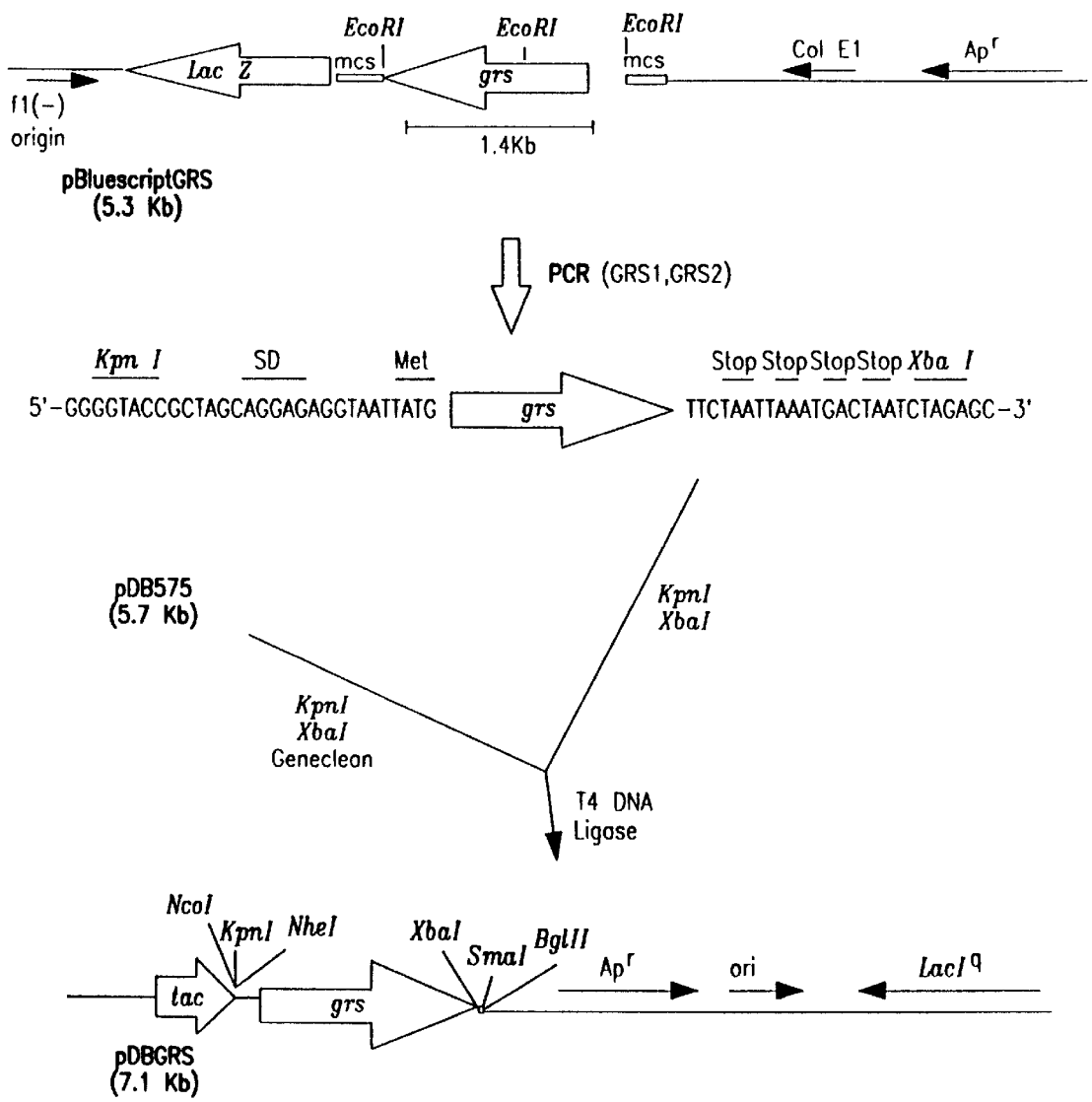
FIG. 2 illustrates the cloning of the grs gene in pDB575. Briefly, the grs gene was PCR amplified out of the pBluescript GRS vector using a GRS1 primer which provided the KpnI restriction site and the Shine-Dalgarno consensus sequence. The GRS2 primer contains the XbaI site and stop codons in the three possible reading frames.

The present invention provides a novel glycyl tRNA synthetase crystalline structure, a novel *Staph aureus* tRNA synthetase active site, and methods of use of the crystalline form and active site to identify synthetase inhibitor compounds (peptide, peptidomimetic or synthetic compositions) characterized by the ability to competitively inhibit binding to the active site of a glycyl tRNA synthetase. Also provided herein is a novel human glycyl tRNA synthetase crystalline structure. This structure can be used as described below for the Staph tRNA synthetase crystal structure.

I. The Novel Synthetase Crystalline Three-Dimensional Structure The present invention provides a novel glycyl tRNA synthetase crystalline structure based on the *Staph aureus* tRNA synthetase. The amino acid sequences of the synthetase are provided in SEQ ID NO:1. As illustrated herein, the crystal structure is a tightly associated *S. aureus* GRS dimer. Each monomer has three structural domains: the N-terminal domain (residues 1–86 of SEQ ID NO: 1), the active site domain (residues 150–340 of SEQ ID NO: 1) and the C-terminal domain (residues 341–463 of SEQ ID NO: 1). The N-terminal domain, having three a-helices and three b-strands, wraps around the active site domain with its second a-helix lying in the core of the dimer interface and its third b-strand adding to the central b-sheet of the active site domain to form the 7-stranded anti-parallel b sheet where the enzyme active site locates. The C-terminal domain contains mainly a 5-stranded mixed b-sheet with three flanking helices and is believed to be important to anticodon recognition. While the overall architecture of the *S. aureus* GRS is similar to that of the *T. thermophilus* GRS, differences exit in the conformation of a number of surface loops, as well as the relative orientation of between the active site and C-terminal domains. With only 44% sequence identity, many amino acid side chains are also different, including several residues near the active site.

As described above, the *Staph aureus* synthetase is a dimer. The present invention provides both a crystalline monomer and dimer structure of *Staph aureus* synthetase. Inhibitors that perturb or interact with this dimer interface are another target for the design and selection of antibacterial agents.

According to the present invention, the crystal structure of *Staph aureus* tRNA synthetase has been resolved at 3.5A. The structure was determined using the method of molecular replacement, and refined to an R-factor of 23.4% with goal geometry.

For example, further refinement of the atomic coordinates will change the numbers in FIG. 1 and Tables I–III, refinement of the crystal structure from another crystal form will result in a new set of coordinates. However, distances and angles in FIG. 1 and Tables I–III will remain the same within experimental errors, and relative conformation of residues in the active site will remain the same within experimental error.

FIG. 1 provides the atomic coordinates of the *Staph aureus* glycyl tRNA synthetase dimer, which contains 790 amino acids; with 130 residues disordered in the crystal. The occupancy factor is 1.0 and the B factor is 19.60.

The tRNA synthetase is characterized by an active site which preferably contains a binding site for glycyl-adenylate and the receptor stem of tRNA (glycines). The crystal structure described herein was solved in the absence of glycine, ATP or tRNA. However, the region of the active site can be inferred from that of the homologous aspartyl tRNA synthetase. Particularly, the crystalline active site consists of 16 amino acid residues. These residues include Glu174, Arg206, Glu208, Phe216, Arg217, Thr218, Phe221, Gln223, Glu225, Asp279, Glu290, Leu291, Arg297, Glu330, Ser332 and Arg337 [SEQ ID NO:1]. The atomic coordinates of the active site residues are provided in Table I.

TABLE I

| NO. | ATOM | X | Y | Z |
|---|---|---|---|---|
| 1 | 174N | 4.941000 | 3.175000 | 50.397999 |
| 2 | 174CA | 5.955000 | 4.038000 | 49.859001 |
| 3 | 174CB | 5.335000 | 4.880000 | 48.750000 |
| 4 | 174CG | 6.198000 | 6.021000 | 48.222000 |
| 5 | 174CD | 5.581000 | 6.686000 | 46.986000 |
| 6 | 174OE1 | 6.341000 | 7.002000 | 46.035999 |
| 7 | 174OE2 | 4.332000 | 6.862000 | 46.949001 |
| 8 | 174C | 6.562000 | 4.919000 | 50.930000 |
| 9 | 174O | 5.886000 | 5.710000 | 51.594002 |
| 10 | 206N | 3.716000 | -3.980000 | 50.544998 |
| 11 | 206CA | 2.750000 | -4.082000 | 49.455002 |
| 12 | 206CB | 3.479000 | -4.007000 | 48.122002 |
| 13 | 206CG | 3.246000 | -2.730000 | 47.368999 |
| 14 | 206CD | 4.122000 | -1.569000 | 47.855999 |
| 15 | 206NE | 5.071000 | -1.073000 | 46.834000 |
| 16 | 206CZ | 4.798000 | -0.830000 | 45.534000 |
| 17 | 206NH1 | 3.575000 | -1.030000 | 45.014999 |
| 18 | 206NH2 | 5.765000 | -0.360000 | 44.730999 |
| 19 | 206C | 1.978000 | -5.398000 | 49.502998 |
| 20 | 206O | 2.574000 | -6.489000 | 49.485001 |
| 21 | 208N | 0.743000 | -7.731000 | 47.730999 |
| 22 | 208CA | 0.888000 | -8.258000 | 46.355999 |
| 23 | 208CB | 2.298000 | -8.843000 | 46.164001 |
| 24 | 208CG | 2.966000 | -8.376000 | 44.889000 |
| 25 | 208CD | 2.847000 | -6.871000 | 44.637001 |
| 26 | 208OE1 | 3.887000 | -6.191000 | 44.762001 |
| 27 | 208OE2 | 1.741000 | -6.362000 | 44.299000 |
| 28 | 208C | -0.174000 | -9.223000 | 45.783001 |
| 29 | 208O | -1.329000 | -9.263000 | 46.256001 |
| 30 | 216N | 13.129000 | -10.373000 | 44.237999 |
| 31 | 216CA | 12.590000 | -9.384000 | 43.311001 |
| 32 | 216CB | 12.766000 | -9.728000 | 41.810001 |
| 33 | 216CG | 12.693000 | -11.233000 | 41.452000 |

TABLE I-continued

| NO. | ATOM | X | Y | Z |
|---|---|---|---|---|
| 34 | 216CD1 | 11.571000 | -11.762000 | 40.764999 |
| 35 | 216CD2 | 13.816000 | -12.076000 | 41.622002 |
| 36 | 216CE1 | 11.579000 | -13.076000 | 40.243999 |
| 37 | 216CE2 | 13.827000 | -13.408000 | 41.095001 |
| 38 | 216CZ | 12.713000 | -13.890000 | 40.409000 |
| 39 | 216C | 11.174000 | -8.954000 | 43.654999 |
| 40 | 216O | 10.867000 | -7.753000 | 43.624001 |
| 41 | 217N | 10.311000 | -9.898000 | 44.009998 |
| 42 | 217CA | 8.961000 | -9.483000 | 44.380001 |
| 43 | 217CB | 7.932000 | -9.752000 | 43.272999 |
| 44 | 217CG | 7.030000 | -8.552000 | 42.960999 |
| 45 | 217CD | 5.864000 | -8.929000 | 42.049999 |
| 46 | 217NE | 4.737000 | -9.519000 | 42.785000 |
| 47 | 217CZ | 3.574000 | -9.900000 | 42.235001 |
| 48 | 217NH1 | 3.363000 | -9.770000 | 40.926998 |
| 49 | 217NH2 | 2.591000 | -10.372000 | 42.997002 |
| 50 | 217C | 8.523000 | -10.098000 | 45.709999 |
| 51 | 217O | 7.943000 | -11.195000 | 45.757999 |
| 52 | 218N | 8.772000 | -9.337000 | 46.778000 |
| 53 | 218CA | 8.472000 | -9.725000 | 48.148998 |
| 54 | 218CB | 9.711000 | -9.500000 | 49.070999 |
| 55 | 218OG1 | 10.388000 | -8.300000 | 48.671001 |
| 56 | 218CG2 | 10.689000 | -10.687000 | 49.019001 |
| 57 | 218C | 7.346000 | -8.848000 | 48.647999 |
| 58 | 218O | 7.290000 | -7.657000 | 48.326000 |
| 59 | 221N | 9.504000 | -5.218000 | 51.894001 |
| 60 | 221CA | 10.836000 | -4.815000 | 51.400002 |
| 61 | 221CB | 10.783000 | -4.649000 | 49.875000 |
| 62 | 221CG | 9.708000 | -3.696000 | 49.418999 |
| 63 | 221CD1 | 9.956000 | -2.330000 | 49.346001 |
| 64 | 221CD2 | 8.407000 | -4.164000 | 49.141998 |
| 65 | 221CE1 | 8.92600 | -1.445000 | 49.012001 |
| 66 | 221CE2 | 7.360000 | -3.282000 | 48.805000 |
| 67 | 221CZ | 7.619000 | -1.928000 | 48.743000 |
| 68 | 221C | 11.326000 | -3.494000 | 51.951000 |
| 69 | 221O | 10.551000 | -2.673000 | 52.439999 |
| 70 | 223N | 13.206000 | 0.141000 | 50.983002 |
| 71 | 223CA | 13.480000 | 1.112000 | 49.938000 |
| 72 | 223CB | 12.461000 | 2.215000 | 50.000000 |
| 73 | 223CG | 11.053000 | 1.686000 | 50.096001 |
| 74 | 223CD | 10.275000 | 1.809000 | 48.803001 |
| 75 | 223OE1 | 10.824000 | 1.639000 | 47.716000 |
| 76 | 223NE2 | 8.980000 | 2.098000 | 48.918999 |
| 77 | 223C | 14.863000 | 1.698000 | 50.092999 |
| 78 | 223O | 15.811000 | 0.967000 | 50.327999 |
| 79 | 225N | 15.128000 | 5.689000 | 49.512001 |
| 80 | 225CA | 14.827000 | 6.937000 | 48.806000 |
| 81 | 225CB | 13.335000 | 7.143000 | 48.845001 |
| 82 | 225CG | 12.636000 | 5.820000 | 48.712002 |
| 83 | 225CD | 11.176000 | 5.961000 | 48.533001 |
| 84 | 225OE1 | 10.626000 | 6.903000 | 49.126999 |
| 85 | 225OE2 | 10.582000 | 5.139000 | 47.798000 |
| 86 | 225C | 15.517000 | 8.213000 | 49.247002 |
| 87 | 225O | 16.087000 | 8.285000 | 50.326000 |
| 88 | 279N | 14.349000 | 4.904000 | 34.318001 |
| 89 | 279CA | 14.639000 | 3.772000 | 35.201000 |
| 90 | 279CB | 13.700000 | 2.601000 | 34.933998 |
| 91 | 279CG | 12.310000 | 2.839000 | 35.416000 |
| 92 | 279OD1 | 12.056000 | 3.903000 | 36.011002 |
| 93 | 279OD2 | 11.468000 | 1.941000 | 35.206001 |
| 94 | 279C | 16.046000 | 3.310000 | 34.823002 |
| 95 | 279O | 16.563000 | 3.722000 | 33.782001 |
| 96 | 290N | 14.061000 | -3.246000 | 36.935001 |
| 97 | 290CA | 14.561000 | -1.978000 | 37.402000 |
| 98 | 290CB | 13.425000 | -0.977000 | 37.536999 |
| 99 | 290CG | 12.391000 | -1.284000 | 38.611000 |
| 100 | 290CD | 11.205000 | -0.284000 | 38.606998 |
| 101 | 290OE1 | 10.212000 | -0.542000 | 37.867001 |
| 102 | 290OE2 | 11.260000 | 0.749000 | 39.338001 |
| 103 | 290C | 15.324000 | -2.075000 | 38.700001 |
| 104 | 290O | 15.162000 | -3.026000 | 39.450001 |
| 105 | 291N | 16.257999 | -1.155000 | 38.882000 |
| 106 | 291CA | 17.030001 | -1.073000 | 40.099998 |
| 107 | 291CB | 18.528000 | -0.882000 | 39.824001 |
| 108 | 291CG | 19.368999 | -2.096000 | 39.455002 |
| 109 | 291CD1 | 20.739000 | -1.973000 | 40.076000 |
| 110 | 291CD2 | 18.683001 | -3.342000 | 39.924999 |

TABLE I-continued

| NO. | ATOM | X | Y | Z |
|---|---|---|---|---|
| 111 | 291C | 16.466000 | 0.189000 | 40.699001 |
| 112 | 291O | 15.445000 | 0.171000 | 41.387001 |
| 113 | 297N | 9.206000 | 14.779000 | 39.366001 |
| 114 | 297CA | 7.788000 | 14.867000 | 39.709000 |
| 115 | 297CB | 7.520000 | 14.064000 | 40.992001 |
| 116 | 297CG | 8.285000 | 12.757000 | 41.123001 |
| 117 | 297CD | 8.166000 | 12.209000 | 42.539001 |
| 118 | 297NE | 6.771000 | 12.005000 | 42.935001 |
| 119 | 297CZ | 6.197000 | 10.821000 | 43.125999 |
| 120 | 297NH1 | 6.901000 | 9.720000 | 42.958000 |
| 121 | 297NH2 | 4.913000 | 10.735000 | 43.479000 |
| 122 | 297C | 7.342000 | 16.333000 | 39.926998 |
| 123 | 297O | 6.193000 | 16.584999 | 40.372002 |
| 124 | 330N | 12.945000 | 12.193000 | 42.535999 |
| 125 | 330CA | 13.135000 | 11.123000 | 43.480999 |
| 126 | 330CB | 11.811000 | 10.733000 | 44.127998 |
| 127 | 330CG | 10.940000 | 9.803000 | 43.354000 |
| 128 | 330CD | 9.806000 | 9.249000 | 44.179001 |
| 129 | 330OE1 | 9.784000 | 8.026000 | 44.432999 |
| 130 | 330OE2 | 8.930000 | 10.041000 | 44.563000 |
| 131 | 330C | 13.907000 | 9.910000 | 43.026001 |
| 132 | 330O | 13.355000 | 9.017000 | 42.432999 |
| 133 | 332N | 14.529000 | 6.954000 | 43.724998 |
| 134 | 332CA | 14.141000 | 5.801000 | 44.557999 |
| 135 | 332CB | 12.663000 | 5.457000 | 44.334999 |
| 136 | 332OG | 12.375000 | 4.105000 | 44.611000 |
| 137 | 332C | 15.000000 | 4.581000 | 44.297001 |
| 138 | 332O | 15.668000 | 4.512000 | 43.289001 |
| 139 | 337N | 16.296000 | −5.378000 | 46.342999 |
| 140 | 337CA | 16.743999 | −5.561000 | 44.936001 |
| 141 | 337CB | 15.916000 | −4.737000 | 43.957001 |
| 142 | 337CG | 14.513000 | −5.233000 | 43.710999 |
| 143 | 337CD | 14.111000 | −5.006000 | 42.230000 |
| 144 | 337NE | 12.699000 | −4.631000 | 42.080002 |
| 145 | 337CZ | 12.236000 | −3.377000 | 42.169998 |
| 146 | 337NH1 | 13.073000 | −2.349000 | 42.389000 |
| 147 | 337NH2 | 10.919000 | −3.156000 | 42.146999 |
| 148 | 337C | 18.207001 | −5.259000 | 44.654999 |
| 149 | 337O | 18.920000 | −6.130000 | 44.188000 |

Table II provides the distances between (D) atoms of the active site residues that are within 5.0 angstroms of one another.

TABLE II

| Atom 1 | Atom 2 | Distance Between |
|---|---|---|
| 174N | 174CA | D = 1.436 |
| 174N | 174CB | D = 2.404 |
| 174N | 174C | D = 2.440 |
| 174N | 174O | D = 2.958 |
| 174N | 174CG | D = 3.797 |
| 174N | 223NE2 | D = 4.434 |
| 174N | 174CD | D = 4.937 |
| 174CA | 174N | D = 1.436 |
| 174CA | 174C | D = 1.514 |
| 174CA | 174CB | D = 1.524 |
| 174CA | 174O | D = 2.411 |
| 174CA | 174CG | D = 2.583 |
| 174CA | 223NE2 | D = 3.715 |
| 174CA | 174CD | D = 3.925 |
| 174CA | 174OE2 | D = 4.368 |
| 174CA | 174OE1 | D = 4.853 |
| 174CA | 223CD | D = 4.975 |
| 174CB | 174CA | D = 1.524 |
| 174CB | 174CG | D = 1.525 |
| 174CB | 174N | D = 2.404 |
| 174CB | 174C | D = 2.502 |
| 174CB | 174CD | D = 2.537 |
| 174CB | 174OE2 | D = 2.860 |
| 174CB | 174O | D = 3.013 |
| 174CB | 174OE1 | D = 3.589 |
| 174CB | 223NE2 | D = 4.588 |

TABLE II-continued

| Atom 1 | Atom 2 | Distance Between |
|---|---|---|
| 174CG | 174CB | D = 1.525 |
| 174CG | 174CD | D = 1.533 |
| 174CG | 174OE1 | D = 2.400 |
| 174CG | 174OE2 | D = 2.410 |
| 174CG | 174CA | D = 2.583 |
| 174CG | 174C | D = 2.946 |
| 174CG | 174O | D = 3.401 |
| 174CG | 174N | D = 3.797 |
| 174CG | 225OE2 | D = 4.492 |
| 174CG | 225OE1 | D = 4.605 |
| 174CG | 223NE2 | D = 4.860 |
| 174CG | 225CD | D = 4.988 |
| 174CD | 174OE1 | D = 1.257 |
| 174CD | 174OE2 | D = 1.262 |
| 174CD | 174CG | D = 1.533 |
| 174CD | 174CB | D = 2.537 |
| 174CD | 174CA | D = 3.925 |
| 174CD | 174C | D = 4.432 |
| 174CD | 174O | D = 4.720 |
| 174CD | 174N | D = 4.937 |
| 174OE1 | 174CD | D = 1.257 |
| 174OE1 | 174OE2 | D = 2.211 |
| 174OE1 | 174CG | D = 2.400 |
| 174OE1 | 174CB | D = 3.589 |
| 174OE1 | 330OE1 | D = 3.934 |
| 174OE1 | 297NH1 | D = 4.144 |
| 174OE1 | 330OE2 | D = 4.255 |
| 174OE1 | 330CD | D = 4.528 |
| 174OE1 | 297NH2 | D = 4.745 |
| 174OE1 | 297CZ | D = 4.803 |
| 174OE1 | 174CA | D = 4.853 |
| 174OE1 | 225OE2 | D = 4.956 |
| 174OE2 | 174CD | D = 1.262 |
| 174OE2 | 174OE1 | D = 2.211 |
| 174OE2 | 174CG | D = 2.410 |
| 174OE2 | 174CB | D = 2.860 |
| 174OE2 | 174CA | D = 4.368 |
| 174OE2 | 174C | D = 4.959 |
| 174C | 174O | D = 1.234 |
| 174C | 174CA | D = 1.514 |
| 174C | 174N | D = 2.440 |
| 174C | 174CB | D = 2.502 |
| 174C | 174CG | D = 2.946 |
| 174C | 223NE2 | D = 4.225 |
| 174C | 174CD | D = 4.432 |
| 174C | 225OE1 | D = 4.869 |
| 174C | 174OE2 | D = 4.959 |
| 174O | 174C | D = 1.234 |
| 174O | 174CA | D = 2.411 |
| 174O | 174N | D = 2.958 |
| 174O | 174CB | D = 3.013 |
| 174O | 174CG | D = 3.401 |
| 174O | 174CD | D = 4.720 |
| 206N | 206CA | D = 1.460 |
| 206N | 206CB | D = 2.435 |
| 206N | 206C | D = 2.473 |
| 206N | 206O | D = 2.953 |
| 206N | 206CG | D = 3.445 |
| 206N | 206CD | D = 3.634 |
| 206N | 221CE2 | D = 4.098 |
| 206N | 221CZ | D = 4.764 |
| 206N | 221CD2 | D = 4.900 |
| 206N | 206NE | D = 4.905 |
| 206CA | 206N | D = 1.460 |
| 206CA | 206CB | D = 1.521 |
| 206CA | 206C | D = 1.526 |
| 206CA | 206O | D = 2.414 |
| 206CA | 206CG | D = 2.535 |
| 206CA | 206CD | D = 3.279 |
| 206CA | 208N | D = 4.507 |
| 206CA | 206NE | D = 4.616 |
| 206CA | 221CE2 | D = 4.724 |
| 206CB | 206CG | D = 1.501 |
| 206CB | 206CA | D = 1.521 |
| 206CB | 206N | D = 2.435 |
| 206CB | 206C | D = 2.469 |

TABLE II-continued

| Atom 1 | Atom 2 | Distance Between |
|---|---|---|
| 206CB | 206CD | D = 2.535 |
| 206CB | 206O | D = 2.973 |
| 206CB | 206NE | D = 3.578 |
| 206CB | 221CE2 | D = 4.007 |
| 206CB | 208OE1 | D = 4.028 |
| 206CB | 206NH1 | D = 4.304 |
| 206CB | 206CZ | D = 4.305 |
| 206CB | 208CD | D = 4.555 |
| 206CB | 208N | D = 4.638 |
| 206CB | 221CZ | D = 4.674 |
| 206CB | 208OE2 | D = 4.815 |
| 206CG | 206CB | D = 1.501 |
| 206CG | 206CD | D = 1.534 |
| 206CG | 206NE | D = 2.522 |
| 206CG | 206CA | D = 2.535 |
| 206CG | 206NH1 | D = 2.922 |
| 206CG | 206CZ | D = 3.064 |
| 206CG | 206N | D = 3.445 |
| 206CG | 206C | D = 3.644 |
| 206CG | 206NH2 | D = 4.350 |
| 206CG | 206O | D = 4.366 |
| 206CG | 208OE1 | D = 4.380 |
| 206CG | 221CE2 | D = 4.392 |
| 206CG | 221CZ | D = 4.653 |
| 206CG | 208CD | D = 4.977 |
| 206CG | 208OE2 | D = 4.988 |
| 206CD | 206NE | D = 1.480 |
| 206CD | 206CG | D = 1.534 |
| 206CD | 206CZ | D = 2.529 |
| 206CD | 206CB | D = 2.535 |
| 206CD | 206NH1 | D = 2.943 |
| 206CD | 206CA | D = 3.279 |
| 206CD | 221CZ | D = 3.626 |
| 206CD | 206N | D = 3.634 |
| 206CD | 206NH2 | D = 3.732 |
| 206CD | 221CE2 | D = 3.784 |
| 206CD | 206C | D = 4.687 |
| 206CD | 221CE1 | D = 4.943 |
| 206NE | 206CZ | D = 1.350 |
| 206NE | 206CD | D = 1.480 |
| 206NE | 206NH2 | D = 2.327 |
| 206NE | 206NH1 | D = 2.356 |
| 206NE | 206CG | D = 2.522 |
| 206NE | 221CZ | D = 3.297 |
| 206NE | 206CB | D = 3.578 |
| 206NE | 221CE2 | D = 3.742 |
| 206NE | 221CB1 | D = 4.443 |
| 206NE | 206CA | D = 4.616 |
| 206NE | 206N | D = 4.905 |
| 206CZ | 206NH2 | D = 1.342 |
| 206CZ | 206NH1 | D = 1.344 |
| 206CZ | 206NE | D = 1.350 |
| 206CZ | 206CD | D = 2.529 |
| 206CZ | 206CG | D = 3.064 |
| 206CZ | 206CB | D = 4.305 |
| 206CZ | 221CZ | D = 4.411 |
| 206CZ | 221CE2 | D = 4.824 |
| 206NH1 | 206CZ | D = 1.344 |
| 206NH1 | 206NH2 | D = 2.308 |
| 206NH1 | 206NE | D = 2.356 |
| 206NH1 | 206CG | D = 2.922 |
| 206NH1 | 206CD | D = 2.943 |
| 206NH1 | 206CB | D = 4.304 |
| 206NH2 | 206CZ | D = 1.342 |
| 206NH2 | 206NH1 | D = 2.308 |
| 206NH2 | 206NE | D = 2.327 |
| 206NH2 | 206CD | D = 3.732 |
| 206NH2 | 206CG | D = 4.350 |
| 206NH2 | 221CZ | D = 4.690 |
| 206C | 206O | D = 1.243 |
| 206C | 206CA | D = 1.526 |
| 206C | 206CB | D = 2.469 |
| 206C | 206N | D = 2.473 |
| 206C | 208N | D = 3.179 |
| 206C | 206CG | D = 3.644 |
| 206C | 208CA | D = 4.390 |

TABLE II-continued

| Atom 1 | Atom 2 | Distance Between |
|---|---|---|
| 206C | 206CD | D = 4.687 |
| 206C | 208CB | D = 4.808 |
| 206O | 206C | D = 1.243 |
| 206O | 206CA | D = 2.414 |
| 206O | 208N | D = 2.823 |
| 206O | 206N | D = 2.953 |
| 206O | 206CB | D = 2.973 |
| 206O | 208CA | D = 3.970 |
| 206O | 208CB | D = 4.080 |
| 206O | 206CG | D = 4.366 |
| 206O | 208CD | D = 4.871 |
| 206O | 208OE1 | D = 4.911 |
| 206O | 208CG | D = 4.984 |
| 206O | 218O | D = 4.995 |
| 208N | 208CA | D = 1.480 |
| 208N | 208CB | D = 2.472 |
| 208N | 208C | D = 2.619 |
| 208N | 206O | D = 2.823 |
| 208N | 208O | D = 2.969 |
| 208N | 206C | D = 3.179 |
| 208N | 208CG | D = 3.665 |
| 208N | 208OE2 | D = 3.827 |
| 208N | 208CD | D = 3.839 |
| 208N | 206CA | D = 4.507 |
| 208N | 208OE1 | D = 4.590 |
| 208N | 206CB | D = 4.638 |
| 208CA | 208N | D = 1.480 |
| 208CA | 208CB | D = 1.539 |
| 208CA | 208C | D = 1.545 |
| 208CA | 208O | D = 2.436 |
| 208CA | 208CG | D = 2.546 |
| 208CA | 208OE2 | D = 2.925 |
| 208CA | 208CD | D = 2.952 |
| 208CA | 206O | D = 3.970 |
| 208CA | 208OE1 | D = 3.976 |
| 208CA | 217NH2 | D = 4.319 |
| 208CA | 206C | D = 4.390 |
| 208CB | 208CG | D = 1.513 |
| 208CB | 208CA | D = 1.539 |
| 208CB | 208N | D = 2.472 |
| 208CB | 208C | D = 2.530 |
| 208CB | 208CD | D = 2.554 |
| 208CB | 208OE2 | D = 3.153 |
| 208CB | 208OE1 | D = 3.395 |

Table III provides the angles (A) between active site atoms at are within 4.0 angstrom of each other. For simplicity, intra-residue angles are omitted.

TABLE III

| | Middle | | |
|---|---|---|---|
| Atom 1 | Atom 2 | Atom 3 | Angle° |
| 174N | 174CA | 223NE2 | A = 110.86 |
| 174C | 174CA | 223NE2 | A = 99.00 |
| l74CB | 174CA | 223NE2 | A = 115.83 |
| 174O | 174CA | 223NE2 | A = 124.59 |
| 174CG | 174CA | 223NE2 | A = 99.44 |
| 223NE2 | 174CA | 174CD | A = 104.16 |
| 174CD | 174OE1 | 330OE1 | A = 154.51 |
| 174OE2 | 174OE1 | 330OE1 | A = 168.53 |
| 174CG | 174OE1 | 330OE1 | A = 121.98 |
| 174CB | 174OE1 | 330OE1 | A = 135.03 |
| 206NE | 206CD | 221CZ | A = 65.40 |
| 206NE | 206CD | 221CE2 | A = 77.07 |
| 206CG | 206CD | 221CZ | A = 123.62 |
| 206CG | 206CD | 221CE2 | A = 103.04 |
| 206CZ | 206CD | 221CZ | A = 89.76 |
| 206CZ | 206CD | 221CE2 | A = 97.69 |
| 206CB | 206CD | 221CZ | A = 97.11 |
| 206CB | 206CD | 221CE2 | A = 75.84 |
| 206NH1 | 206CD | 221CZ | A = 115.70 |

TABLE III-continued

Middle

| Atom 1 | Atom 2 | Atom 3 | Angle° |
|---|---|---|---|
| 206NH1 | 206CD | 221CE2 | A = 118.95 |
| 206CA | 206CD | 221CZ | A = 102.03 |
| 206CA | 206CD | 221CE2 | A = 83.62 |
| 221CZ | 206CD | 206N | A = 82.01 |
| 221CZ | 206CD | 206NH2 | A = 79.18 |
| 221CZ | 206CD | 221CE2 | A = 21.33 |
| 206N | 206CD | 221CE2 | A = 67.03 |
| 206NH2 | 206CD | 221CE2 | A = 88.85 |
| 206CZ | 206NE | 221CZ | A = 139.50 |
| 206CZ | 206NE | 221CE2 | A = 137.47 |
| 206CD | 206NE | 221CZ | A = 90.50 |
| 206CD | 206NE | 221CE2 | A = 80.25 |
| 206NH2 | 206NE | 221CZ | A = 111.86 |
| 206NH2 | 206NE | 221CE2 | A = 118.33 |
| 206NH1 | 206NE | 221CZ | A = 160.52 |
| 206NH1 | 206NE | 221CE2 | A = 143.70 |
| 206CG | 206NE | 221CZ | A = 105.43 |
| 206CG | 206NE | 221CE2 | A = 86.74 |
| 221CZ | 206NE | 206CB | A = 85.57 |
| 221CZ | 206NE | 221CE2 | A = 21.43 |
| 206CB | 206NE | 221CE2 | A = 66.33 |
| 206O | 206C | 208N | A = 62.24 |
| 206CB | 206C | 208N | A = 109.75 |
| 206N | 206C | 208N | A = 158.20 |
| 208N | 206C | 206CG | A = 110.24 |
| 206C | 206O | 208N | A = 94.83 |
| 206C | 206O | 208CA | A = 101.47 |
| 206CA | 206O | 208N | A = 118.57 |
| 206CA | 206O | 208CA | A = 117.74 |
| 208N | 206O | 206N | A = 147.93 |
| 208N | 206O | 206CB | A = 106.25 |
| 208N | 206O | 208CA | A = 16.05 |
| 206N | 206O | 208CA | A = 145.65 |
| 206CB | 206O | 208CA | A = 98.04 |
| 208CG | 208CB | 217NH2 | A = 48.77 |
| 208CA | 208CB | 217NH2 | A = 110.66 |
| 208N | 208CB | 217NH2 | A = 144.69 |
| 208C | 208CB | 217NH2 | A = 83.16 |
| 208CD | 208CB | 217NH2 | A = 77.30 |
| 208OE2 | 208CB | 217NH2 | A = 79.91 |
| 208OE1 | 208CB | 217NH2 | A = 85.93 |
| 208CB | 208CG | 217NH2 | A = 107.02 |
| 208CB | 208CG | 217NE | A = 137.67 |
| 208CB | 208CG | 217CZ | A = 130.69 |
| 208CD | 208CG | 217NH2 | A = 125.76 |
| 208CD | 208CG | 217NE | A = 107.90 |
| 208CD | 208CG | 217CZ | A = 110.82 |
| 208OE1 | 208CG | 217NH2 | A = 132.66 |
| 208OE1 | 208CG | 217NE | A = 94.86 |
| 208OE1 | 208CG | 217CZ | A = 109.17 |
| 208OE2 | 208CG | 217NH2 | A = 111.25 |
| 208OE2 | 208CG | 217NE | A = 116.51 |
| 208OE2 | 208CG | 217CZ | A = 107.25 |
| 208CA | 208CG | 217NH2 | A = 108.41 |
| 208CA | 208CG | 217NE | A = 155.51 |
| 208CA | 208CG | 217CZ | A = 132.20 |
| 217NE | 208CG | 217NE | A = 47.37 |
| 217NH2 | 208CG | 217CZ | A = 25.22 |
| 217NH2 | 208CG | 208C | A = 82.78 |
| 217NH2 | 208CG | 208N | A = 124.97 |
| 217CZ | 208CG | 217CZ | A = 25.28 |
| 217NE | 208CG | 208C | A = 130.13 |
| 217NE | 208CG | 208N | A = 167.41 |
| 217CZ | 208CG | 208C | A = 106.51 |
| 217CZ | 208CG | 208N | A = 149.73 |
| 208OE1 | 208CD | 217NE | A = 90.82 |
| 208OE1 | 208CD | 217NH2 | A = 126.11 |
| 208OE1 | 208CD | 217CZ | A = 109.06 |
| 298OE2 | 208CD | 217NE | A = 126.48 |
| 208OE2 | 208CD | 217NH2 | A = 101.12 |
| 208OE2 | 208CD | 217CZ | A = 107.98 |
| 208CG | 208CD | 217NE | A = 49.21 |
| 208CG | 208CD | 217NH2 | A = 35.55 |
| 208CG | 208CD | 217CZ | A = 47.86 |
| 208CB | 208CD | 217NE | A = 81.84 |

TABLE III-continued

Middle

| Atom 1 | Atom 2 | Atom 3 | Angle° |
|---|---|---|---|
| 208CB | 208CD | 217NH2 | A = 62.69 |
| 208CB | 208CD | 217CZ | A = 79.06 |
| 208CA | 208CD | 217NE | A = 106.90 |
| 208CA | 208CD | 217NH2 | A = 77.18 |
| 208CA | 208CD | 217CZ | A = 96.69 |
| 217NE | 208CD | 208N | A = 121.13 |
| 217NE | 208CD | 217NH2 | A = 35.39 |
| 217NE | 208CD | 217CZ | A = 19.93 |
| 217NE | 208CD | 208C | A = 96.15 |
| 208N | 208CD | 217NH2 | A = 95.88 |
| 208N | 208CD | 217CZ | A = 114.89 |
| 217NH2 | 208CD | 217CZ | A = 19.60 |
| 217NH2 | 208CD | 208C | A = 62.59 |
| 217CZ | 208CD | 208C | A = 82.05 |
| 208CD | 208OE1 | 217NE | A = 70.82 |
| 208OE2 | 208OE1 | 217NE | A = 92.23 |
| 208CG | 208OE1 | 217NE | A = 48.48 |
| 208CB | 208OE1 | 217NE | A = 69.54 |
| 216CA | 216N | 217N | A = 58.26 |
| 216C | 216N | 217N | A = 27.55 |
| 216CB | 216N | 217N | A = 75.00 |
| 217N | 216N | 216CG | A = 80.08 |
| 217N | 216N | 216CD2 | A = 103.56 |
| 217N | 216N | 216O | A = 39.66 |
| 216N | 216CA | 217N | A = 91.16 |
| 216N | 216CA | 217CA | A = 99.04 |
| 216C | 216CA | 217N | A = 28.81 |
| 216C | 216CA | 217CA | A = 18.15 |
| 216CB | 216CA | 217N | A = 109.69 |
| 216CB | 216CA | 217CA | A = 112.13 |
| 216O | 216CA | 217N | A = 55.48 |
| 216O | 216CA | 217CA | A = 44.80 |
| 217N | 216CA | 216CG | A = 95.23 |
| 217N | 216CA | 216CD2 | A = 108.18 |
| 217N | 216CA | 216CD1 | A = 78.50 |
| 217N | 216CA | 217CA | A = 10.69 |
| 216CG | 216CA | 217CA | A = 102.67 |
| 216CD2 | 216CA | 217CA | A = 117.68 |
| 216CD1 | 216CA | 217CA | A = 84.94 |
| 216CG | 216CB | 217N | A = 93.95 |
| 216CA | 216CB | 217N | A = 44.07 |
| 216N | 216CB | 217N | A = 57.03 |
| 216C | 216CB | 217N | A = 21.81 |
| 216CD2 | 216CB | 217N | A = 107.73 |
| 216CD1 | 216CB | 217N | A = 83.39 |
| 216O | 216CB | 217N | A = 39.93 |
| 217N | 216CB | 216CE1 | A = 89.83 |
| 217N | 216CB | 216CE2 | A = 106.03 |
| 216CD2 | 216CG | 217N | A = 129.49 |
| 216CD1 | 216CG | 217N | A = 87.74 |
| 216CB | 216CG | 217N | A = 61.66 |
| 216CE1 | 216CG | 217N | A = 108.27 |
| 216CE2 | 216CG | 217N | A = 134.65 |
| 216CA | 216CG | 217N | A = 40.47 |
| 216CZ | 216CG | 217N | A = 125.90 |
| 216N | 216CG | 217N | A = 49.00 |
| 216C | 216CG | 217N | A = 20.78 |
| 216CE1 | 216CD1 | 217N | A = 138.03 |
| 216CG | 216CD1 | 217N | A = 71.23 |
| 216CD2 | 216CD1 | 217N | A = 93.79 |
| 216CZ | 216CD1 | 217N | A = 132.89 |
| 216CB | 216CD1 | 217N | A = 56.14 |
| 216CE2 | 216CD1 | 217N | A = 115.84 |
| 216CA | 216CD1 | 217N | A = 37.24 |
| 216O | 216C | 217N | A = 122.31 |
| 216O | 216C | 217CA | A = 89.58 |
| 216O | 216C | 217CB | A = 89.33 |
| 216O | 216C | 217C | A = 98.16 |
| 216O | 216C | 218N | A = 87.89 |
| 217N | 216C | 216CA | A = 117.72 |
| 217N | 216C | 217CA | A = 32.73 |
| 217N | 216C | 216N | A = 92.44 |
| 217N | 216C | 216CB | A = 112.49 |
| 217N | 216C | 217CB | A = 40.03 |
| 217N | 216C | 216CG | A = 89.28 |

TABLE III-continued

Middle

| Atom 1 | Atom 2 | Atom 3 | Angle° |
|---|---|---|---|
| 217N | 216C | 217C | A = 29.43 |
| 217N | 216C | 218N | A = 47.60 |
| 216CA | 216C | 217CA | A = 150.43 |
| 216CA | 216C | 217CB | A = 143.72 |
| 216CA | 216C | 217C | A = 137.49 |
| 216CA | 216C | 218N | A = 135.79 |
| 217CA | 216C | 216N | A = 122.09 |
| 217CA | 216C | 216CB | A = 136.80 |
| 217CA | 216C | 217CB | A = 24.20 |
| 217CA | 216C | 216CG | A = 116.56 |
| 217CA | 216C | 217C | A = 19.82 |
| 217CA | 216C | 218N | A = 34.59 |
| 216N | 216C | 217CB | A = 130.54 |
| 216N | 216C | 217C | A = 105.55 |
| 216N | 216C | 218N | A = 103.71 |
| 216CB | 216C | 217CB | A = 116.54 |
| 216CB | 216C | 217C | A = 141.86 |
| 216CB | 216C | 218N | A = 156.61 |
| 217CB | 216C | 216CG | A = 101.05 |
| 217CB | 216C | 217C | A = 42.91 |
| 217CB | 216C | 218N | A = 58.76 |
| 216CG | 216C | 217C | A = 118.52 |
| 216CG | 216C | 218N | A = 133.95 |
| 217C | 216C | 218N | A = 19.50 |
| 216C | 216O | 217N | A = 29.92 |
| 216C | 216O | 217CA | A = 62.89 |
| 216C | 216O | 217CB | A = 70.34 |
| 216C | 216O | 217C | A = 63.58 |
| 216C | 216O | 337NE | A = 131.52 |
| 216C | 216O | 217CG | A = 92.78 |
| 217N | 216O | 216CA | A = 63.29 |
| 217N | 216O | 217CA | A = 32.97 |
| 217N | 216O | 216CB | A = 70.39 |
| 217N | 216O | 216N | A = 54.43 |
| 217N | 216O | 217CB | A = 43.89 |
| 217N | 216O | 217C | A = 35.89 |
| 217N | 216O | 337NE | A = 159.88 |
| 217N | 216O | 217CG | A = 66.32 |
| 216CA | 216O | 217CA | A = 96.25 |
| 216CA | 216O | 216N | A = 18.49 |
| 216CA | 216O | 217CB | A = 101.39 |
| 216CA | 216O | 217C | A = 95.31 |
| 216CA | 216O | 337NB | A = 98.87 |
| 216CA | 216O | 217CG | A = 122.42 |
| 217CA | 216O | 216CB | A = 100.29 |
| 217CA | 216O | 216N | A = 85.83 |
| 217CA | 216O | 217CB | A = 23.38 |
| 217CA | 216O | 217C | A = 16.01 |
| 217CA | 216O | 337NE | A = 162.34 |
| 217CA | 216O | 217CG | A = 39.79 |
| 216CB | 216O | 217CB | A = 94.84 |
| 216CB | 216O | 217C | A = 106.26 |
| 216CB | 216O | 337NE | A = 89.50 |
| 216CB | 216O | 217CG | A = 110.18 |
| 216N | 216O | 217CB | A = 97.41 |
| 216N | 216O | 217C | A = 81.13 |
| 216N | 216O | 337NE | A = 111.11 |
| 216N | 216O | 217CG | A = 120.03 |
| 217CB | 216O | 217C | A = 39.18 |
| 217CB | 216O | 337NE | A = 142.07 |
| 217CB | 216O | 217CG | A = 22.64 |
| 217C | 216O | 337NE | A = 164.24 |
| 217C | 216O | 217CG | A = 52.47 |
| 337NE | 216O | 217CG | A = 122.91 |
| 216C | 217N | 218N | A = 114.66 |
| 217CA | 217N | 218N | A = 44.76 |
| 216O | 217N | 218N | A = 95.72 |
| 216CA | 217N | 218N | A = 131.08 |
| 217C | 217N | 218N | A = 22.69 |
| 217CB | 217N | 218N | A = 77.75 |

Mutants and Derivatives

The invention further provides homologues, co-complexes, mutants and derivatives of the *Staph aureus* tRNA synthetase crystal structure of the invention.

The term "homologue" means a protein having at least 30% amino acid sequence identity with synthetase or any functional domain of glycyl tRNA synthetase.

The term "co-complex" means glycyl tRNA synthetase or a mutant or homologue of glycyl tRNA synthetase in covalent or non-covalent association with a chemical entity or compound.

The term "mutant" refers to a glycyl tRNA synthetase polypeptide, i.e., a polypeptide displaying the biological activity of wild-type glycyl tRNA synthetase activity, characterized by the replacement of at least one amino acid from the wild-type synthetase sequence. Such a mutant may be prepared, for example, by expression of *Staph aureus* synthetase cDNA previously altered in its coding sequence by oligonucleotide-directed mutagenesis.

*Staph aureus* glycyl tRNA synthetase mutants may also be generated by site-specific incorporation of unnatural amino acids into glycyl tRNA synthetase proteins using the general biosynthetic method of C. J. Noren et al, *Science*, 244:182–188 (1989). In this method, the codon encoding the amino acid of interest in wild-type glycyl tRNA synthetase is replaced by a "blank" nonsense codon, TAG, using oligonucleotide-directed mutagenesis. A suppressor tRNA directed against this codon is then chemically aminoacylated in vitro with the desired unnatural amino acid. The aminoacylated tRNA is then added to an in vitro translation system to yield a mutant glycyl tRNA synthetase enzyme with the site-specific incorporated unnatural amino acid.

Selenocysteine or selenomethionine may be incorporated into wild-type or mutant tRNA glycyl synthetase by expression of *Staph aureus* glycyl tRNA synthetase-encoding cDNAs in auxotrophic *E. coli* strains [W. A. Hendrickson et al, *EMBO J.*, 9(5):1665–1672 (1990)]. In this method, the wild-type or mutagenized tRNA synthetase cDNA may be expressed in a host organism on a growth medium depleted of either natural cysteine or methionine (or both) but enriched in selenocysteine or selenomethionine (or both).

The term "heavy atom derivative" refers to derivates of glycyl tRNA synthetase produced by chemically modifying a crystal of glycyl tRNA synthetase. In practice, a crystal is soaked in a solution containing heavy metal atom salts, or organometallic compounds, e.g., lead chloride, gold thiomalate, thimerosal or uranyl acetate, which can diffuse through the crystal and bind to the surface of the protein. The location(s) of the bound heavy metal atom(s) can be determined by X-ray diffraction analysis of the soaked crystal. This information, in turn, is used to generate the phase information used to construct three-dimensional structure of the enzyme [T. L. Blundel and N. L. Johnson, *Protein Crystallography*, Academic Press (1976).

II. Methods of Identifying Inhibitors of the Novel Glycyl tRNA Synthetase Crystalline Structure Another aspect of this invention involves a method for identifying inhibitors of a Staph glycyl tRNA synthetase characterized by the crystal structure and novel active site described herein, and the inhibitors themselves. The novel synthetase crystalline structure of the invention permits the identification of inhibitors of synthetase activity. Such inhibitors may be competitive, binding to all or a portion of the active site of the glycyl tRNA synthetase; or non-competitive and bind to and inhibit glycl tRNA synthetase whether or not it is bound to another chemical entity.

One design approach is to probe the glycyl tRNA synthetase crystal of the invention with molecules composed of a variety of different chemical entities to determine optimal sites for interaction between candidate glycyl tRNA synthetase inhibitors and the enzyme. For example, high resolution X-ray diffraction data collected from crystals saturated with solvent allows the determination of where each type of solvent molecule sticks. Small molecules that bind tightly to those sites can then be designed and synthesized and tested for their glycyl tRNA synthetase inhibitor activity [J. Travis, *Science*, 262:1374 (1993)].

This invention also enables the development of compounds that can isomerize to short-lived reaction intermediates in the chemical reaction of a substrate or other compound that binds to or with glycyl tRNA synthetase. Thus, the time-dependent analysis of structural changes in glycyl tRNA synthetase during its interaction with other molecules is permitted. The reaction intermediates of glycyl tRNA synthetase can also be deduced from the reaction product in co-complex with glycyl tRNA synthetase. Such information is useful to design improved analogues of known glycyl tRNA synthetase inhibitors or to design novel classes of inhibitors based on the reaction intermediates of the glycyl tRNA synthetase enzyme and glycyl tRNA synthetase inhibitor co-complex. This provides a novel route for designing glycyl tRNA synthetase inhibitors with both high specificity and stability.

Another approach made possible by this invention, is to screen computationally small molecule data bases for chemical entities or compounds that can bind in whole, or in part, to the glycyl tRNA synthetase enzyme. In this screening, the quality of fit of such entities or compounds to the binding site may be judged either by shape complementarity or by estimated interaction energy [E. C. Meng et al, *J. Comp. Chem.*, 13:505–524 (1992)].

Because glycyl tRNA synthetase may crystallize in more than one crystal form, the structure coordinates of glycyl tRNA synthetase, or portions thereof, as provided by this invention are particularly useful to solve the structure of those other crystal forms of tRNA synthetase. They may also be used to solve the structure of glycyl tRNA synthetase mutant co-complexes, or of the crystalline form of any other protein with significant amino acid sequence homology to any functional domain of glycyl tRNA synthetase.

One method that may be employed for this purpose is molecular replacement. In this method, the unknown crystal structure, whether it is another crystal form of glycyl tRNA synthetase, a glycl tRNA synthetase mutant, or a glycyl tRNA synthetase co-complex, or the crystal of some other protein with significant amino acid sequence homology to any functional domain of glycyl tRNA synthetase, may be determined using the glycyl tRNA synthetase structure coordinates of this invention as provided in FIG. 1 and Tables I–III. This method will provide an accurate structural form for the unknown crystal more quickly and efficiently than attempting to determine such information ab initio.

Thus, the synthetase structure provided herein permits the screening of known molecules and/or the designing of new molecules which bind to the synthetase structure, particularly at the active site, via the use of computerized evaluation systems. For example, computer modelling systems are available in which the sequence of the synthetase, and the synthetase structure (i.e., the bond angles, dihedral angles, distances between atoms in the active site region, etc. as provided by FIG. 1 and Tables I–III herein) may be input. Thus, a machine readable medium may be encoded with data representing the coordinates of FIG. 1 and Tables I–III. The computer then generates structural details of the site into which a test compound should bind, thereby enabling the determination of the complementary structural details of said test compound.

More particularly, the design of compounds that bind to or inhibit glycyl tRNA synthetase according to this invention generally involves consideration of two factors. First, the compound must be capable of physically and structurally associating with glycyl tRNA synthetase. Non-covalent molecular interactions important in the association of glycyl tRNA synthetase with its substrate include hydrogen bonding, van der Waals and hydrophobic interactions.

Second, the compound must be able to assume a conformation that allows it to associate with glycyl tRNA synthetase. Although certain portions of the compound will not directly participate in this association with glycyl tRNA synthetase, those portions may still influence the overall conformation of the molecule. This, in turn, may have a significant impact on potency. Such conformational requirements include the overall three-dimensional structure and orientation of the chemical entity or compound in relation to all or a portion of the binding site, e.g., active site or accessory binding site of glycyl tRNA synthetase, or the spacing between functional groups of a compound comprising several chemical entities that directly interact with glycyl tRNA synthetase.

The potential inhibitory or binding effect of a chemical compound on glycyl tRNA synthetase may be analyzed prior to its actual synthesis and testing by the use of computer modelling techniques. If the theoretical structure of the given compound suggests insufficient interaction and association between it and glycyl tRNA synthetase, synthesis and testing of the compound is obviated. However, if computer modelling indicates a strong interaction, the molecule may then be synthesized and tested for its ability to bind to glycyl tRNA synthetase and inhibit using a suitable assay. In this manner, synthesis of inoperative compounds may be avoided.

An inhibitory or other binding compound of glycyl tRNA synthetase may be computationally evaluated and designed by means of a series of steps in which chemical entities or fragments are screened and selected for their ability to associate with the individual binding pockets or other areas of glycyl tRNA synthetase.

One skilled in the art may use one of several methods to screen chemical entities or fragments for their ability to associate with glycyl tRNA synthetase and more particularly with the individual binding pockets of the glycyl tRNA synthetase active site or accessory binding site. This process may begin by visual inspection of, for example, the active site on the computer screen based on the glycyl tRNA synthetase coordinates in FIG. 1 and Tables I–III. Selected fragments or chemical entities may then be positioned in a variety of orientations, or docked, within a binding pocket of glycyl tRNA synthetase. Docking may be accomplished using software such as Quanta and Sybyl, followed by energy minimization and molecular dynamics with standard molecular mechanics force fields, such as CHARMM and AMBER.

Specialized computer programs may also assist in the process of selecting fragments or chemical entities. These include:

1. GRID [P. J. Goodford, "A Computational Procedure for Determining Energetically Favorable Binding Sites on Biologically Important Macromolecules", *J. Med. Chem.*, 28:849–857 (1985)]. GRID is available from Oxford University, Oxford, UK.
2. MCSS [A. Miranker and M. Karplus, "Functionality Maps of Binding Sites: A Multiple Copy Simultaneous Search Method", *Proteins: Structure, Function and Genetics*, 11:29–34 (1991)]. MCSS is available from Molecular Simulations, Burlington, Mass.
3. AUTODOCK [D. S. Goodsell and A. J. Olsen, "Automated Docking of Substrates to Proteins by Simulated Annealing", *Proteins: Structure, Function, and Genetics,* 8:195–202 (1990)]. AUTODOCK is available from Scripps Research Institute, La Jolla, Calif.

4. DOCK [I. D. Kuntz et al, "A Geometric Approach to Macromolecule-Ligand Interactions", *J. Mol. Biol.,* 161:269–288 (1982)]. DOCK is available from University of California, San Francisco, Calif.

Once suitable chemical entities or fragments have been selected, they can be assembled into a single compound or inhibitor. Assembly may be proceed by visual inspection of the relationship of the fragments to each other on the three-dimensional image displayed on a computer screen in relation to the structure coordinates of glycyl tRNA synthetase. This would be followed by manual model building using software such as Quanta or Sybyl.

Useful programs to aid one of skill in the art in connecting the individual chemical entities or fragments include:

1. CAVEAT [P. A. Bartlett et al, "CAVEAT: A Program to Facilitate the Structure-Derived Design of Biologically Active Molecules", in *Molecular Recognition in Chemical and Biological Problems",* Special Pub., Royal Chem. Soc. 78, pp. 182–196 (1989)]. CAVEAT is available from the University of California, Berkeley, Calif.

2. 3D Database systems such as MACCS-3D (MDL Information Systems, San Leandro, Calif.). This area is reviewed in Y. C. Martin, "3D Database Searching in Drug Design", *J. Med. Chem.,* 35:2145–2154 (1992).

3. HOOK (available from Molecular Simulations, Burlington, Mass.).

Instead of proceeding to build a glycyl tRNA synthetase inhibitor in a step-wise fashion one fragment or chemical entity at a time as described above, inhibitory or other glycyl tRNA synthetase binding compounds may be designed as a whole or "de novo" using either an empty active site or optionally including some portion(s) of a known inhibitor (s). These methods include:

1. LUDI [H.-J. Bohm, "The Computer Program LUDI: A New Method for the De Novo Design of Enzyme Inhibitors", *J. Comp. Aid. Molec. Design,* 6:61–78 (1992)]. LUDI is available from Biosym Technologies, San Diego, Calif.

2. LEGEND [Y. Nishibata and A. Itai, *Tetrahedron,* 47:8985 (1991)].

LEGEND is available from Molecular Simulations, Burlington, Mass.

3. LeapFrog (available from Tripos Associates, St. Louis, Mo.).

Other molecular modelling techniques may also be employed in accordance with this invention. See, e.g., N. C. Cohen et al, "Molecular Modeling Software and Methods for Medicinal Chemistry", *J. Med. Chem.,* 33:883–894 (1990). See also, M. A. Navia and M. A. Murcko, "The Use of Structural Information in Drug Design", *Current Opinions in Structural Biology,* 2:202–210 (1992). For example, where the structures of test compounds are known, a model of the test compound may be superimposed over the model of the structure of the invention. Numerous methods and techniques are known in the art for performing this step, any of which may be used. See, e.g., P. S. Farmer, Drug Design, Ariens, E. J., ed., Vol. 10, pp 119–143 (Academic Press, New York, 1980); U.S. Pat. No. 5,331,573; U.S. Pat. No. 5,500,807; C. Verlinde, *Curr. Biol.,* 2:577–587 (1994); and I. D. Kuntz, *Science,* 257:1078–1082 (1992). The model building techniques and computer evaluation systems described herein are not a limitation on the present invention.

Thus, using these computer evaluation systems, a large number of compounds may be quickly and easily examined and expensive and lengthy testing avoided. Moreover, the need for actual synthesis of many compounds is effectively eliminated.

Once identified by the modelling techniques, the synthetase inhibitor may be tested for bioactivity using standard techniques. For example, structure of the invention may be used in binding assays using conventional formats to screen inhibitors. One particularly suitable assay format includes the enzyme-linked immunosorbent assay (ELISA). Other assay formats may be used; these assay formats are not a limitation on the present invention.

In another aspect, the synthetase structure of the invention permit the design and identification of synthetic compounds and/or other molecules which are characterized by the conformation of the synthetase of the invention. Using known computer systems, the coordinates of the synthetase structure of the invention may be provided in machine readable form, the test compounds designed and/or screened and their conformations superimposed on the structure of the synthetase of the invention. Subsequently, suitable candidates identified as above may be screened for the desired synthetase inhibitory bioactivity, stability, and the like.

Once identified and screened for biological activity, these inhibitors may be used therapeutically or prophylactically to block synthetase activity, and thus, bacterial replication.

III. Inhibitors of Glycyl tRNA Synthetase (GRS) Activity

The present invention also provides inhibitors of glycyl tRNA synthetase activity identified or designed by the methods of the invention. These inhibitors are useful as anti-bacterial agents.

One particularly desirable inhibitor is glycylsulfamoyladenosine. The structure of this compound is as follows.

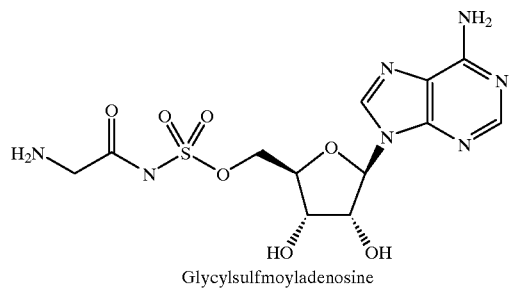

Glycylsulfmoyladenosine

Glycylsulfmoyladenosine is an analogue of the Gly-AMP reaction intermediate and inhibits GRS catalytic activity as measured by any of the techniques described in the examples below. Estimates of the potency of inhibition are obtained by performing enzyme assays in the presence of a range of inhibitor concentrations, and fitting the effect of inhibitor concentration on enzyme velocity to a four parameter logistic function that allows calculation of an $IC_{50}$ (the inhibitor concentration at which GRS activity is reduced by half). This parameter is directly related to the dissociation constant for inhibitor binding ($K_i$ or $K_d$) and has a value of around 2.4 mM for glycylsulfamoyladenosine when tested against the *S. aureus* GRS. Binding of glycylsulfamoyladenosine to GRS can also be measured directly using stopped-flow fluorescence techniques because enzyme:inhibitor binary complex has around 5% higher tryptophan fluorescence than the free enzyme. Experiments of this type yield the following elementary rate constants for inhibitor binding; $k_{on}=1.1\times10^6$ s$^{-1}$M$^{-1}$, $k_{off}=2.9$s$^{-1}$. The ratio of these yields an estimate for $K_d$ of 2.6 mM, almost identical to the result obtained in enzyme inhibition experiments.

The following examples illustrate various aspects of this invention. These examples do not limit the scope of this invention which is defined by the appended claims.

EXAMPLE 1

The Expression of the Glycyl t-RNA Synthetase from *Staphylococcus aureus* in *Escherichia coli*

The strategy for the expression of the glycyl t-RNA synthetase (GRS) from *Staphylococcus aureus,* using *Escherichia coli* as a host was based on the PCR amplification of the grs gene and the introduction of suitable restriction sites that allowed the cloning of the grs-containing DNA fragment in the pDB575 expression vector. After the PCR amplification the insert of the resultant recombinant plasmid, (pDBGRS hereafter), was sequenced to verify the absence of artefacts introduced by the Taq polymerase. Expression was monitored by SDS-polyacrylamide gel analysis.

A. Bacterial Strains, Plasmids and Medium

The *Escherichia coli* strains used were: DH5a (supE44, DlacU169 (f 80 lacZDM15), hsdR17, recA1, endA1, gyrA96, thi-1, relA1) and HB101 (thi-1, hsdS20($r^-_B,m^-_B$), supE44, recAl3, ara-14, leuB6, proA2, lacY1, rpsL20(str$^r$), xyl-5, mtl-1). *E. coli* cells were grown at 37° C. in Luria Bertani broth (LB). These strains may all be obtained from commercial sources.

The plasmids used were pBluescript SK-[Stratagene], pUC18 [J. Sambrook et al., *Molecular Cloning: A Laboratory Manual.* Cold Spring Harbor Laboratory Press, Cold Spring Harbor, N.Y. (1989)] and pDB575. A detailed description of pDB575 is provided in A. F. Chalker et al, *Gene,* 141:103–108 (1994). Briefly, pDB575 is a expression vector of *E. coli* based on pKK223–3 [Pharmacia] with the following modifications: (i) the polylinker between EcoRI and HindIII has been replaced with a longer one (EcoRI, NcoI, KpnI, NdeI, SstI, SstII, XbaI, ClaI, SmaI, BglII, XmaIII, HindIII); (ii) it has a lacI$^q$ gene inserted; (iii) it is non-mobilizable, the pBR322 portion of pKK223-3 has been replaced by the equivalent fragment from pATIS3. pDB575 allows the selection of the recombinant clones by ampicillin resistance and the gene expression is driven by the tac promoter.

LB Medium. Per liter:

| | |
|---|---|
| Bacto-tryptone | 10 g |
| Bacto-yeast extract | 5 g |
| NaCl | 5 g |

For plasmid propagation 0.1 mg/ml of ampicillin was added to the medium.

B. DNA Manipulations

Plasmid DNA was prepared by the rapid alkaline method (Sambrook et al, 1989). Transformations of *E. coli* cells were carried out using the RbCl methods (Sambrook et al, 1989). DNA fragments were purified using the Geneclean Kit [BIO 101 Inc., La Jolla, Calif., USA]. The plasmids for sequencing were purified using QIAGEN plasmid kit [QIAGEN]. DNA sequencing was carried out on supercoiled plasmid DNA by the dideoxy chain-termination method using the Thermo Sequenase cycle sequencing kit [Amersham Life Science, Inc. USA]. DNA was also sequenced by the Automated Sequencing Service of Pharmacy Faculty in the Complutense University of Madrid. Universal or synthetic oligonucleotides [MedProbe, Norway] were used as primers. Restriction enzymes and T4 DNA ligase were obtained from Promega and Boehringer respectively and the experiments were carried out following the instructions provided by the suppliers.

The grs gene from *S. aureus* cloned in the pBluescript SK- was amplified by PCR using the primers GRS1: (5'-GGGGTACCGCTAGCAGGAGAGGTAATTATGGCAAA AGATATG-3'; SEQ ID NO:2) and GRS2: (5'-GCTCTAGATTAGTCATTTAATTAGAATTTTGTTTTTT CAGTTAAG-3'; SEQ ID NO:3). Kpn I and Xba I restriction sites were incorporated at the 5' and 3' ends respectively of each primer to facilitate ligation of the amplified DNA into vectors. Plasmid DNA (100 ng) was amplified in 100 ml of PCR mixture containing 250 mM deoxynucleotide triphosphates (dNTPs), 0.9 mM oligonucleotide primers, the manufacturer's buffer and 2U of Taq polymerase (Promega). The following cycling parameters were used:

94° C. 5 min

94° C. 1 min, 55° C. 2 min, 72° C. 2 min (35 cycles)

72° C. 10 min Polymerase chain reaction (PCR) was performed using the DNA Thermal Cycler [Perkin Elmer Cetus]. PCR-amplified DNA fragments were purified using Wizard™ Preps DNA Purification System for Rapid Purification of DNA Fragments [Promega].

C. Cloning of the grs Gene of *S. aureus* in the Expression Vector pDB575 of *E. coli*

The cloning strategy is shown in FIG. 2. PCR amplification of the grs gene from *S. aureus* using the primers GRS 1 and GRS2 resulted in a DNA fragment of 1.4 kb. This fragment was purified and ligated to the KpnI, XbaI sites of pDB575 to obtain the recombinant plasmid pDBGRS and the ligation mix was used to transform *E. coli* DH5a competent cells. The construction of pDBGRS was initially confirmed by restriction analysis of the plasmid purified from the transformants. The amplification with Taq DNA polymerase made the sequencing of the grs of pDBGRS an obligatory step to confirm that no changes were introduced due to the low fidelity of this enzyme. Sequence analysis was accomplished by using grs gene introduced in the expression plasmid pDB575 and/or in pUC18. The sequencing of both strands showed that no artefacts had been introduced during the amplification process.

D. Small-scale Production of GRS from *S. aureus* in *E. coli*

Figure 3:
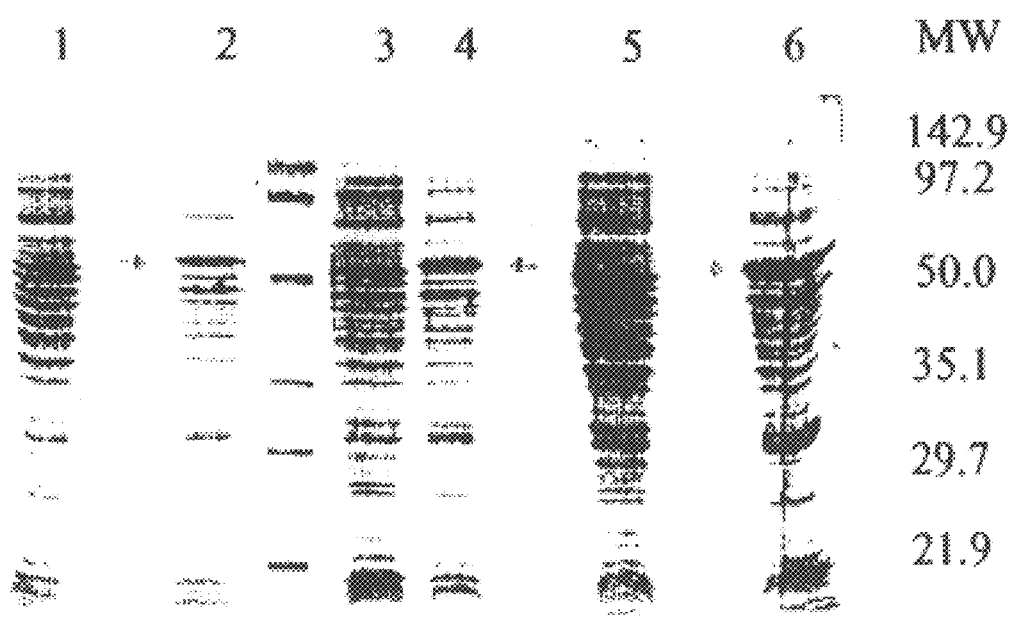
FIG. 3 illustrates the SDS-PAGE analysis of the GRS production by *E. coli. E. coli* HB101 cells, harboring either pDB575 or pDBGRS, were induced with 1 mM IPTG. Sonicated samples were electrophoresed through 0.1% SDS-15% polyacrylamide gels. The gel was stained with Coomassie brilliant blue. Lanes 1, 3 and 5 show the sonicated extracts of HB101:pDB575 at 2, 3 and 4 hours after the induction. Lanes 2, 4 and 6 show the corresponding samples of the recombinant clone HB101:pDBGRS.
Figure 4:
FIG. 4 provides a projection of the ribbon structure of the *Staphylococcus aureus* glycyl tRNA synthetase dimer. The two monomers are shaded in dark and light gray.
Figure 5:
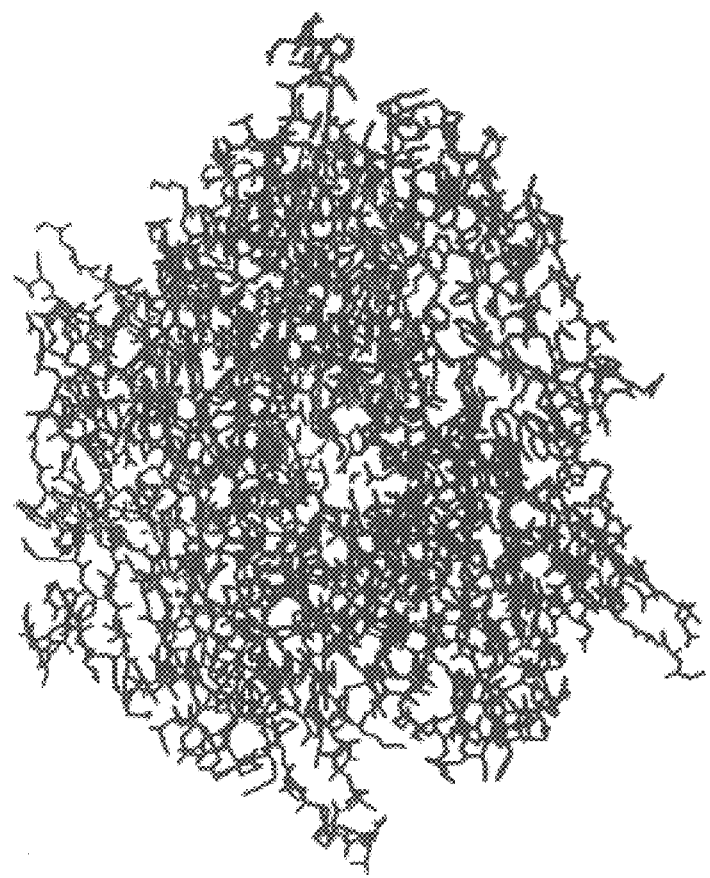
FIG. 5 provides a schematic drawing of the molecular structure of the *Staphylococcus aureus* glycyl tRNA synthetase dimer. The two monomers are shaded in dark and light gray.

The plasmid pDBGRS and the negative control pDB575 (vector without insert) were used to transform the *E. coli* HB101 host strain. Single clones of HB101:pDBGRS and HB101:pDB575 cells were grown overnight at 37° C. in 2 ml of LB medium in the presence of 0.1 mg/ml ampicillin. The cells were then diluted 100-fold in 30 ml LB with ampicillin. When the cultures reached a value of 0.5 at $OD_{600}$ the grs expression was induced by addition of isopropyl-thio-galactoside (IPTG) at 1 mM of final concentration. After this induction 2 ml samples were taken at different times (2, 3 and 4 hours). The cells were harvested in a microfuge for 3 min, the pellets were washed with 20 mM Tris-HCl pH 8/1 mM PMSF and resuspended in 300 ml of SDS-PAGE gel-loading buffer. The cells were broken by sonication (15 seconds). The samples were then boiled 10 minutes and after one spin, 10 ml fractions were analyzed by SDS-PAGE according to the methods of Laemmli [U. K. Laemmli, Nature 227, 680–685 (1970)]. The 12% polyacrylamide gels were stained with Coomassie blue. As shown in FIG. 3 good expression levels were detected from the early stages after induction with IPTG. The evidence was the presence of a prominent band (lanes 2, 4 and 6 in FIG. 3) that was in good agreement with the $M_r$ predicted from the primary sequence. The GRS protein has a theoretical molecular weight of about 53.7 kDa.

EXAMPLE 2

Fermentation and Purification of Glycyl tRNA Synthetase

A. Fermentation

A 300 liter fermentation of *E. coli* HB101:pDB575GRS was carried out in double strength Luria Bertani medium (LB), containing 50 ug/ml ampicillin. The vessel was inoculated at 2% (v/v) from a 15 hour secondary seed culture in single strength LB medium, containing 50 mg/ml ampicillin. The production vessel was incubated at 37° C., agitated at 1.5 msec$^{-1}$ and aerated at 1.0 VVM. The OD at 550 nm was monitored, and at 2.5 absorbance units, GRS expression was induced with the addition of isopropyl-thiogalactosidase to 1.0 mM and the cells harvested by centrifugation in a Westfalia CSA-19, 2 hours post induction. A total of 990 grams of cell paste was recovered.

LB Medium, per liter, contains the following components. The medium ingredients were supplied by Difco Laboratories, West Molesey, Surrey UK.

| Double strength | | Single strength | |
|---|---|---|---|
| Bacto Tryptone | 20 g | Bacto Tryptone | 10 g |
| Bacto Yeast Extract | 10 g | Bacto Yeast Extract | 5 g |
| Sodium Chloride | 5 g | Sodium Chloride | 5 g |

B. Purification

1) Lysis 125 g of cells of *E. coli* overexpressing *S. aureus* GRS obtained as described above, were resuspended in 600 ml of 20 mM Tris, 1 mM EDTA, 1 mM DTT, 5 mM MgCl$_2$ pH 7.5 (buffer A). Lysozyme (Sigma Chemicals: hen egg) was added to a final concentration of 2 mg/ml. Cells were incubated at 37° C. for 20 min. The cells were then frozen in an ethanol/dry ice water bath and thawed. Dnase (Sigma; bovine pancreas type 1) was added to a final concentration of 10 Kunitz units per ml and held at 37° C. for 5 minutes. The solution was centrifuged in a Beckman JA-HS centrifuge at 14,000 g for 60 minutes using a Beckman JA-14 rotor.

2) Anion Exchange

All chromatography was performed on a Waters 650E chromatography system, fitted with a UV detector (Pharmacia S2) and conductivity monitor (Pharmacia). UV (at 280 nm) and conductivity were monitored during all operations. All operations were performed at 4° C.

The supernatant from 1) was loaded onto a Q-Sepharose high performance (Pharmacia) column of 200 ml packed into a Pharmacia XK-50 column. The column was equilibrated with buffer A prior to loading. The column is then washed with buffer A (1000 ml) at 40 ml/min, and eluted with a linear gradient of buffer A to 1M NaCl in buffer A over 140 minutes at 10 ml/min. The eluate was fractionated into 5 minute fractions using a Pharmacia Superfrac.

The eluted fractions were assayed for GRS activity by measurement of aminoacylation of tRNA$^{Gly}$, and for protein by the Bradford method. Active fractions were analyzed by reducing SDS PAGE (Pharmacia Phast System 10–15% gradient gel)

3) Hydrophobic Interaction Chromatography

Two active fractions from 2) were pooled and the ammonium sulphate concentration adjusted to 1M by addition (1 to 1) of 2 M ammonium sulphate. The material was loaded onto a 50 ml column of butyl Toyopearl 650S (Tosohaas) equilibrated with buffer A plus 1M ammonium sulphate (column Pharmacia XK-26). The column was washed with 100 ml of the equilibration buffer and then eluted with a linear gradient of equilibration buffer to buffer A over 140 minutes at 5 ml/min.

4) Concentration/Buffer Exchange

Eluted fractions are collected (1 minute fraction) and assayed for GRS activity and protein. Active fractions are pooled and diafiltered against (1,000 fold buffer exchange) buffer A using an Amicon ultrafiltration cell (350 ml) under nitrogen. A final volume of 33 ml of protein was obtained containing 4.2 mg/ml of protein (by amino acid analysis). This product was greater than 95% purity by SDS PAGE and the activity showed an overall process yield of 60% from 1). N-terminal amino acid analysis confirmed identity.

C. Measurement of Glycyl tRNA Synthetase (GRS) Activity

The enzyme catalyses the aminoacylation of tRNA$^{Gly}$, which proceeds through a two step mechanism. The first step involves the formation of a stable enzyme:glycyl adenylate complex resulting from the specific binding and reaction of ATP and L-glycine. Subsequently, the 3' terminal adenosine of enzyme-bound tRNAGly reacts with the aminoacyladenylate, leading to the esterification of the tRNA and release of AMP. These steps are summarized below.

a) L-Gly+ATP.Mg+GRS $\check{p}$ GRS:Gly-AMP+PPi.Mg b) GRS:Gly-AMP+tRNA$^{Gly}$ $\check{p}$ GRS+Gly-tRNA$^{Gly}$+AMP This reaction can be assayed in order to characterize the enzyme or identify specific inhibitors of its activity in a number of ways:

(1) Measurement of the formation of Gly-tRNA$^{Gly}$ can be specifically determined using radiolabelled glycine and separating free glycine from Gly-tRNA using precipitation/filtration techniques (e.g. in cold trichloroacetic acid; see, Calender & Berg (1966) Biochemistry 5, 1681–1690; Toth M J & Schimmel P (1990) J. Biol. Chem. 265, 1000–1004].

(2) The full acylation reaction can also be measured by analyzing production of either PPi or AMP which are produced in stoichiometric ratio to the tRNA acylation. This may be achieved in a number of ways, for example using colorimetric [Hoenig (1989) J. Biochem. Biophys. Meth. 19, 249–252]; or enzyme coupled [Webb T M (1994) Anal. Biochem. 218, 449–454] measurement of Pi after addition of excess inorganic pyrophosphatase or using enzyme coupled assays to directly measure AMP or PPi production [Sigma Chemicals Catalogue, 1986].

(3) The partial reaction (a) can be assayed through radiolabel isotopic exchange between ATP and PPi, since each of the steps in this part of the reaction are freely reversible. This reaction is independent of tRNA binding, typically has a k$_{cat}$ around 20-fold higher than the full acylation reaction (a+b), and is readily measured using chromatographic principles which separate PPi from ATP (i.e. using activated charcoal; see, Calender & Berg, cited above; Toth & Schimmel, cited above).

D. Ligand Binding to GRS

It is also possible to define ligand interactions with GRS in experiments that are not dependent upon enzyme catalyzed turnover of substrates. This type of experiment can be done in a number of ways:

(1) Effects of ligand binding upon enzyme intrinsic fluorescence (e.g. of tryptophan). Binding of either natural ligands or inhibitors may result in enzyme conformational changes which alter enzyme fluorescence. Using stopped-flow fluorescence equipment, this can be used to define the microscopic rate constants that describe binding. Alternatively, steady-state fluorescence titration methods can yield the overall dissociation constant for binding in the same way that these are accessed through enzyme inhibition experiments.

(2) Spectral effects of ligands. Where the ligands themselves are either fluorescent or possess chromophores that overlap with enzyme tryptophan fluorescence, binding can be detected either via changes in the ligand fluorescence properties (e.g. intensity, lifetime or polarization) or fluorescence resonance energy transfer with enzyme tryptophans. The ligands could either be inhibitors or variants of the natural ligands (i.e. fluorescent ATP derivatives or tRNAGly labelled with a fluorophore).

(3) Thermal analysis of the enzyme:ligand complex. Using calorimetric techniques (e.g. Isothermal Calorimetry, Differential Scanning Calorimetry) it is possible to detect thermal changes, or shifts in the stability of GRS which reports and therefore allows the characterization of ligand binding.

E. Aminoacylation Assays for GRS Activity

Assays were performed either using purified *S. aureus* GRS overexpressed in *E. coli*, or using crude cell lysate from *E. coli* overexpressing GRS. The latter contained around 10% of total protein as GRS. Enzyme was stored at −70° C. in 50 mM Tris-HCl buffer (pH 7.8), 10 mM $MgCl_2$ and 10 mM B-mercaptoethanol after flash freezing in liquid $N_2$. In experiments to determine the activity of enzyme samples, these stocks were diluted over a wide range (100 fold to 10,000 fold) in 50 mM Tris pH 7.8, 10 mM $MgCl_2$, 1 mM Dithiothreitol and stored on ice prior to assay.

The assay procedure was as follows. 50 ml of enzyme prepared and diluted as described above was mixed with reaction mixture (100 ml), comprising: 0.15 mCi L-$[U-^{14}]$-Glycine (Amersham International), 4 mg/ml *E. coli* MRE600 mixed tRNA (Boehringer Manheim), 5 mM ATP, 15 mM $MgSO_4$, 3 mM DTT, 75 mM KCl and 50 mM Tris-HCl, pH 7.8. Unless otherwise states, all reagents were obtained from Sigma Chemical Company Ltd. Concentrations are given as in the final reaction mix. After addition of the enzyme to start the reaction, assay samples were incubated at 37° C. and, at the desired time, duplicate aliquots (50 ml) were removed and quenched with 7% trichloroacetic acid (100 ml) and left on ice for 30 min. The precipitates were harvested using a Packard Filtermate 196 Cell Harvester [Packard Instruments Ltd.] onto glass fibre filters which were washed successively with 7% trichloroacetic acid and ethanol. The filters were dried at 70° C. for 1 hour and the levels of radioactivity measured by scintillation counting (Packard Topcount).

EXAMPLE 3

Crystallization of *Staphylococcus aureus* Glycyl tRNA Synthetase

A. Crystallization

A large crystal (0.25×0.25×0.18 $mm^3$) was formed using the following conditions. The protein used for the crystallization was supplied @ 5.8 mg/ml in a solution of 20 mM tris, 5 mM $MgCl_2$, 1 mM DTT, 1 mM EDTA, 10% glycerol, pH 7.5). The crystal was obtained from a 1:1 mixture of the protein solution and a solution of 10% PEG 8000, 0.1M imidazole pH 8.0 and 0.2M calcium acetate using the hanging drop method, grown at room temperature.

B. X-ray Diffraction Characterization

Initially, the *Staph aureus* synthetase crystal was mounted in a sealed glass capillary with a small amount of mother liquor in each end of the capillary. The $CuK_a$ X-ray, having a wavelength of 1.54 Å, was generated by a Rigaku-RU200 rotating anode machine operating at 100 mA×50 kV electric power. The crystal was exposed to the $CuK_a$ X-ray, and the diffracted X-ray was collected by a Siemens multiwire area detector. The crystal diffracted to 3.5 Å.

By registering the position and intensity of many tens of thousands diffraction spots using the computer program XENGEN, the crystal has been determined to be an orthorhombic crystal system and $P2_12_12$, space group. The unit cell dimensions are a-81.5 Å, b=123.1 Å, c=127.5 Å. By established methods, an asymmetric unit was calculated to have one protein molecule. The crystal contains an estimated 60% solvent.

C. Structure Solution

It was determined that the amino acid sequences of *S. aureus* and *T. thermophilus* are 44% identical. Since the crystal structure of the *T. thermophilus* GRS has been published [D. T. Logan et al., *EMBO J.*, 14:4156–4167 (1995)], it served as a search model for structure solution using molecular replacement methods. The GRS dimer was used as the initial search model, the rotation search was carried out including all the data in 10.0–4.0 Å and the solution was evident from the 25s peak height. The subsequent translation search also yielded a pronounced solution at 15s and an R-factor of 49.4% using all the data to 3.5 Å resolution. Rigid body refinement reduced the R-factor to 47.8%. Solvent flattening and 2-fold non-crystallographic averaging was then used to improve the phases [Collaborative Computational Project, Number 4, *Acta Crystallogr.* D50, 760–763 (1994)], which introduced about 30° C. phase shifts and improved the averaged figure of merit from 0.4 to 0.8 and Rfree from 47% to 28%. An improved electron density map was then calculated.

D. Model Building and Refinement

Using the three-dimensional electron density map obtained from above experiments, the polypeptide chain of the *S. aureus* GRS can be traced without ambiguity. Three hundred ninety-five (395) residues (most with side chains) were built for each monomer in the 3-D computer graphics program XTALVIEW [McKee, D. E. in *Practical Protein Crystallography,* Academic Press, San Diego (1993)]. XTALVIEW was used in building models of the GRS structure. Using the initial model, a diffraction pattern was calculated and compared to the experimental data. The difference between the calculated and experimentally determined diffraction patterns was monitored by the value of R-factors. The refinement of the structural model was carried out by adjustments of atomic positions to minimizing the R-factor, where a value of about 20% is typical for a good quality protein structure.

The GRS model was subjected to one round of Xplor [A. Brunger et al., *Science,* 235:458–460 (1987) refinement using the standard positional, slowcool and overall B factor refining protocols. The GRS was refined as a tightly contained dimer without any solvent molecules. The R factor of the model is 23.9% with satisfactory geometry. The rms deviations are 0.017 Å for bond lengths, 2.0° for bond angles, 25.4 for dihedrals and 1.8° C. for impropers. The structure contains residues 1–86, 150–161, 164–352 and 356–463 [SEQ ID NO:1], while the other 68 residues (15%) are disordered in the crystal and not included in the model.

EXAMPLE 5

The Preparation of the Glycyl tRNA Synthetase Inhibitor, 5'-O-Glycylsulfamoyladenosine A solution of 2',3'-O-isopropylidene-5'-O-sulfamoyladenosine (J. Castro-Pichel et al, *Tetrahedron,*

1987, 43, 383) (0.50 g, 1.3 mmol) in dry tetrahydrofuran (THF) (3 ml) was added to a solution of N-t-butoxycarbonylglycine N-hydroxysuccinimide ester (Sigma Chemical Co.) in dry THF(2 ml), followed by 1,8-diazabicyclo[5.4.0]undec-7-ene (0.2 ml, 1.3 mmol), and the mixture stirred at room temperature for 1.5 h. The mixture was then partitioned between 10% aqueous citric acid (25 ml) and ethyl acetate (25ml) and the organic phase washed with saturated $NaHCO_3$, brine, dried ($MgSO_4$) and evaporated to an oil. This was chromatographed on Kieselgel 60 eluting with 0–20% methanol in dichloromethane to afford the protected product (200 mg).

This material (100 mg) was dissolved in trifluoroacetic acid (3 ml). After stirring for 15 min at room temperature, water (3 ml) was added and the mixture stirred at room temperature for a further hour. The solution was evaporated and the residue chromatographed on reverse-phase silica gel eluting with water. The product-containing fractions were combined and freeze-dried to afford the 5'-O-glycylsulfamoyladenosine as a white solid. (10 mg); d(ppm, $D_2O$) 3.78 (2H, $CH_2$), 4.49–4.52 (3H, m, 4'-H, 5'-$H_2$), 4.54 (1H, br.s. 3'-H), 4.63 (1H, t, J=4.84 Hz, 2'-H), 6.28 (1H, d, J=4.72 Hz, 1'-H) 8.51(1H, s, Ar-H), 8.63(1H, s, Ar-H); m/z (ESI) 404($MH^+$, 100%).

EXAMPLE 6

Characterization of Inhibition by Glycylsulfamoyladenosine

The characterization of the compound as an inhibitor of the catalytic activity of GRS was performed using a procedure similar to that described in Example 2E above, except that multiple assays were performed in the presence of inhibitor concentrations ranging (in two-fold dilution steps) from 100 mM down to 0.1 mM (final concentrations). These were added from stocks prepared at 10-fold higher concentrations and added to each reaction mix. The stock of inhibitor was prepared freshly from a solid sample and dissolved in dimethylsulfoxide. The enzyme concentration used for these assays was selected so that around 50% of the tRNA available was acylated during the reaction time course. Following harvesting and counting as described above, the acylation activity (relative to controls in the absence of inhibitor) were plotted as a function of inhibitor concentration and fitted to a four-parameter logistic function (using the Grafit package; Erithacus Software Ltd.) to yield $IC_{50}$, the inhibitor concentration required to inhibit half the enzyme activity.

EXAMPLE 7

Human Glycyl tRNA Synthetase

Figure 6:
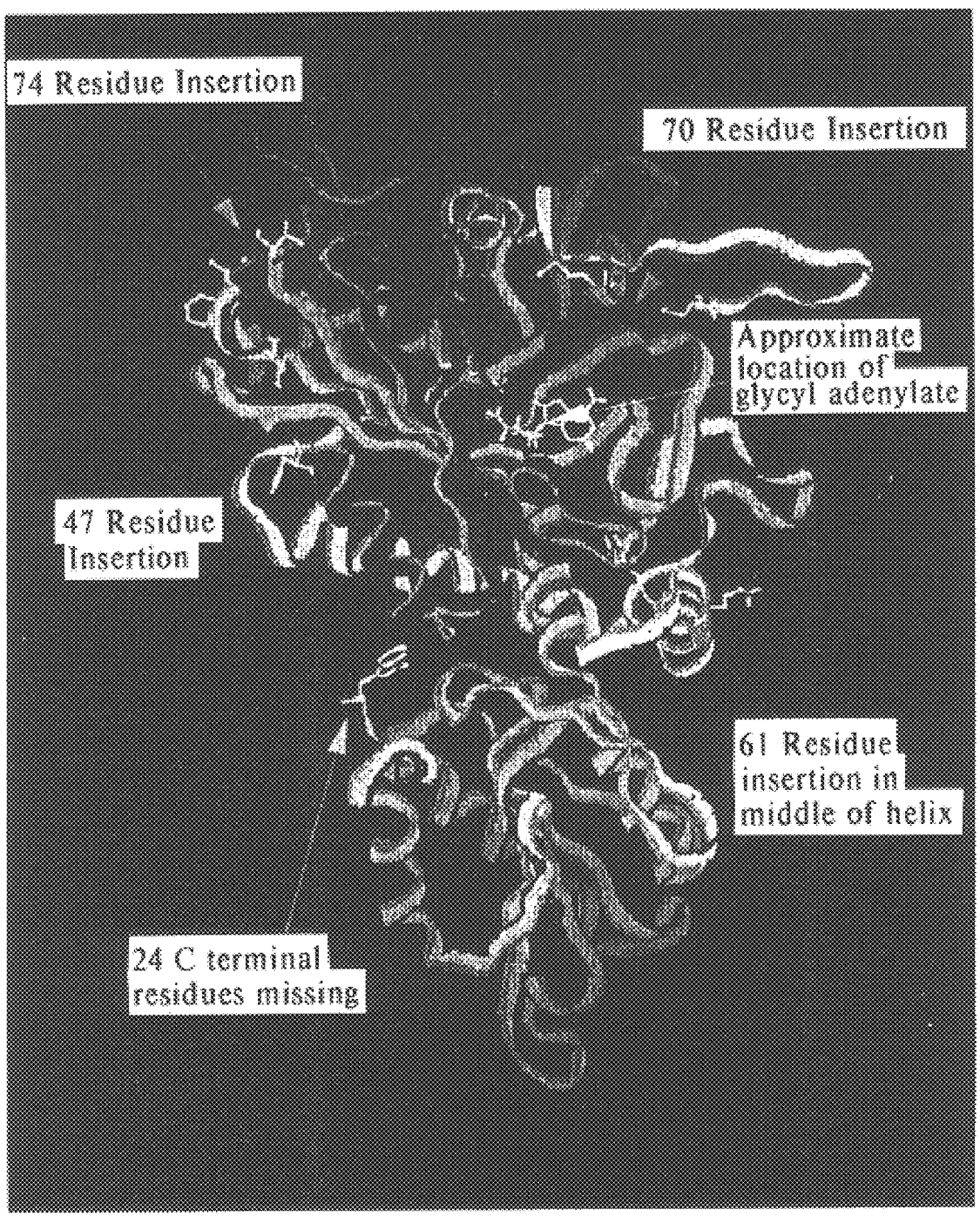
FIG. 6 provides the ribbon structure of the human glycyl tRNA synthetase monomer.
Figure 7:
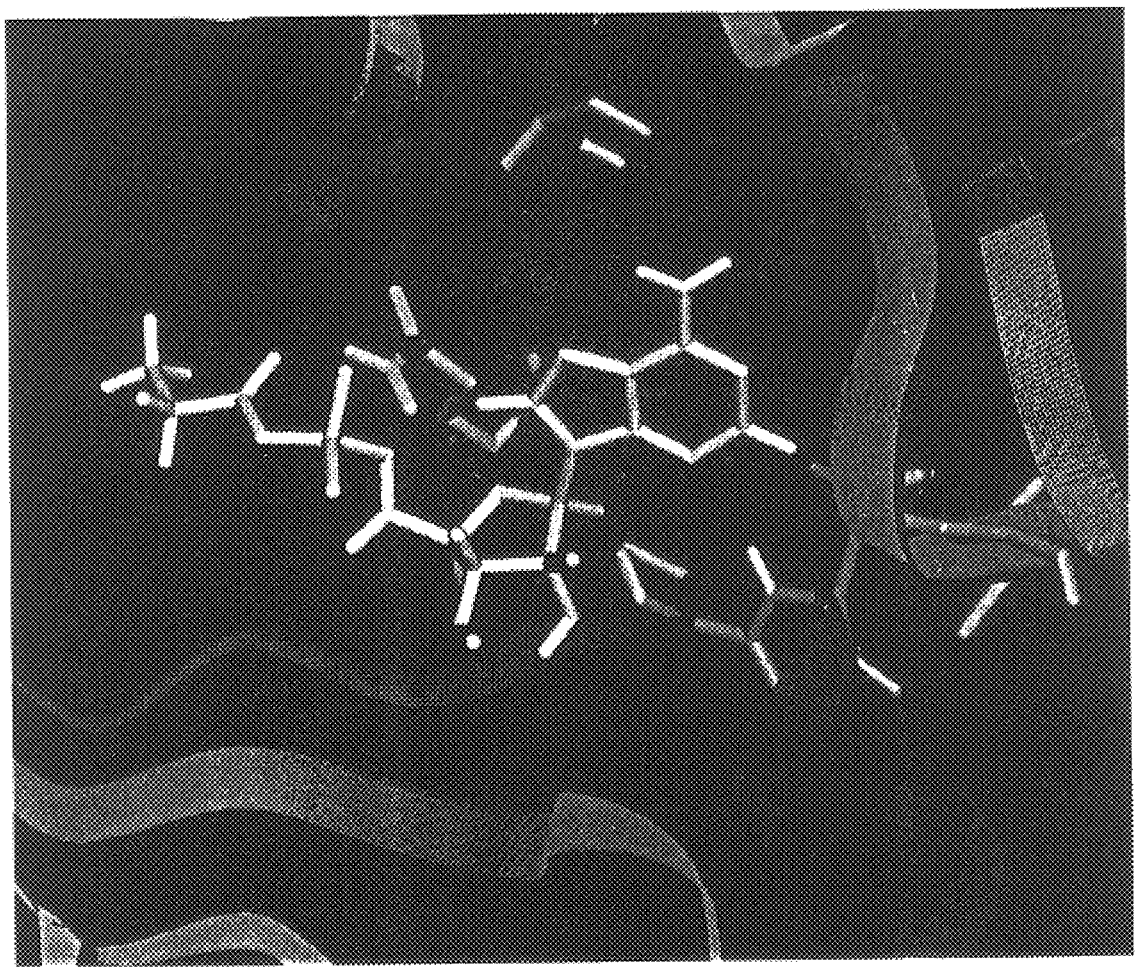
FIG. 7 provides a schematic drawing comparing the active sites of the human and *Staph aureus* glycyl tRNA synthetase enzymes.

A model of the human glycyl tRNA synthetase was constructed using Quanta version 4.1 [Molecular Simulations Inc, Burlington, Mass.]. The human enzyme contains a number of large surface loops (see FIG. 6). A comparison of the human and Staph enzyme aminoacylation sites is shown in FIG. 7. One of the most significant differences is that a glutamine in the prokaryotic enzyme is replaced by a methionine. The glutamine is believed to be capable of hydrogen bonding to the acyl phosphage moiety of glycyl adenylate.

This invention is not to be limited in scope by the specific embodiments described herein. Indeed, various modifications of the invention in addition to those described herein will become apparent to those skilled in the art from the foregoing description. Such modifications are intended to fall within the scope of the appended claims. The disclosures of the patents, patent applications and publications cited herein are incorporated by reference in their entireties.

What is claimed is:

1. A method of drug design comprising the step of using the structural coordinates of a Staphylococcus glycyl tRNA synthetase crystal comprising the coordinates of FIG. 1, to computationally evaluate a chemical entity for associating with the active site of a Staphylococcus glycyl tRNA synthetase.

2. The method according to claim 1, wherein said entity is a competitive or non-competitive inhibitor of a *Staphylococcus aureus* synthetase.

3. The method of drug design according to claim 1 comprising the step of using the structure coordinates of *Staphylococcus aureus* glycyl tRNA synthetase to identify an intermediate in a chemical reaction between said synthetase and a compound which is a substrate or inhibitor of said synthetase.

* * * * *